United States Patent
Allen et al.

(10) Patent No.: US 10,946,022 B2
(45) Date of Patent: Mar. 16, 2021

(54) IMIPRIDONES FOR GLIOMAS

(71) Applicant: Oncoceutics, Inc., Philadelphia, PA (US)

(72) Inventors: Joshua E. Allen, New Haven, CT (US); Martin Stogniew, Lakewood Ranch, FL (US); Varun Vijay Prabhu, Philadelphia, PA (US)

(73) Assignee: ONCOCEUTICS, INC., Philadelphia, PA (US)

( * ) Notice: Subject to any disclaimer, the term of this patent is extended or adjusted under 35 U.S.C. 154(b) by 0 days.

(21) Appl. No.: 16/526,444

(22) Filed: Jul. 30, 2019

(65) Prior Publication Data

US 2020/0022982 A1    Jan. 23, 2020

Related U.S. Application Data

(60) Division of application No. 16/204,964, filed on Nov. 29, 2018, now Pat. No. 10,369,154, which is a division of application No. 15/947,840, filed on Apr. 8, 2018, now Pat. No. 10,172,862, which is a continuation-in-part of application No. PCT/US2017/015608, filed on Jan. 30, 2017.

(60) Provisional application No. 62/581,478, filed on Nov. 3, 2017.

(51) Int. Cl.
*A61K 31/519* (2006.01)
*A61P 35/00* (2006.01)

(52) U.S. Cl.
CPC ............ *A61K 31/519* (2013.01); *A61P 35/00* (2018.01)

(58) Field of Classification Search
CPC .............................. A61K 31/519; A61P 35/00
See application file for complete search history.

(56) References Cited

U.S. PATENT DOCUMENTS

| | | | |
|---|---|---|---|
| 4,867,973 | A | 9/1989 | Goers et al. |
| 8,463,365 | B2 | 6/2013 | Luiken |
| 9,265,765 | B2 | 2/2016 | Stogniew et al. |
| 9,376,437 | B2 | 6/2016 | Stogniew et al. |
| RE46,290 | E | 1/2017 | El-deiry et al. |
| 9,688,679 | B2 | 6/2017 | Stogniew et al. |
| 10,172,862 | B2 | 1/2019 | Allen et al. |
| 2007/0026402 | A1 | 2/2007 | Noble et al. |
| 2009/0022717 | A1 | 1/2009 | Premack et al. |
| 2013/0065887 | A1 | 3/2013 | Bhatia et al. |
| 2014/0335048 | A1* | 11/2014 | Stogniew ............ A61K 31/337 424/85.2 |

FOREIGN PATENT DOCUMENTS

| | | |
|---|---|---|
| CN | 104860948 | 8/2015 |
| WO | WO 2004/082570 | 9/2004 |
| WO | WO 2015/073072 | 5/2015 |
| WO | WO 2015/073109 | 5/2015 |
| WO | WO 2015/153468 | 10/2015 |

OTHER PUBLICATIONS

Allen et al. "Discovery and clinical introduction of first-in-class imipridone ONC201" Oncotarget. Nov. 8, 2016;7(45):74380.
Allen et al. "Dual inactivation of Akt and ERK by TIC10 signals Foxo3a nuclear translocation, TRAIL gene induction, and potent antitumor effects" Science translational medicine. Feb. 6, 2013;5(171):171ra17.
Allen et al. "First-In-Class Small Molecule ONC201 Induces Drs and Cell Death in Tumor but Not Normal Cells to Provide a Wide Therapeutic Index as an Anti-Cancer Agent" PloS one. Nov. 18, 2015;10(11):e0143082.
Allen et al. "Correction: First-In-Class Small Molecule ONC201 Induces DR5 and Cell Death in Tumor but Not Normal Cells to Provide a Wide Therapeutic Index as an Anti-Cancer Agent" PloS one. Feb. 10, 2016;11(2):e0149365.
Allen et al. "Identification of TRAIL-inducing compounds highlights small molecule ONC201/TIC10 as a unique anti-cancer agent that activates the TRAIL. pathway" Molecular Cancer. 2015;14.
Allen et al. "Genetic and Pharmacological Screens Converge in Identifying FLIP, BCL2. and IAP Proteins as Key Regulators of Sensitivity to the TRAIL-Inducing Anticancer Agent ONC201/TIC10" Cancer research. Apr. 15, 2015;75(8):1668.
Alvarado et al. "Glioblastoma cancer stem cells evade innate immune suppression of self-renewal through reduced TLR4 expression" Cell stem cell. Apr. 6, 2017;20(4):450-61.
Anastassiadis et al. "Comprehensive assay of kinase catalytic activity reveals features of kinase inhibitor selectivity" Nature biotechnology. Nov. 2011;29(11):1039.
Arrillaga-Romany et al "Actr-51. Clinical Evaluation of the Imipridone Onc201 in Recurrent Glioblastoma: Predictive and Pharmacodynamic Biomarker Analyses" Neuro-oncology. Nov. 6, 2017;19(suppl_6):vi11-2, Abstract.
Arrillaga-Romany et al. "A phase 2 study of the first inn pridorie ONC201, a selective DRD2 antagonist for oncology, administered every three weeks in recurrent glioblastoma". Oncotarget. Oct. 3, 2017;8(45):79298.
Bajaj et al. "Parkinson's disease and cancer risk: a systematic review and meta-analysis" Cancer Causes & Control. May 1, 2010;21(5):697-707.

(Continued)

*Primary Examiner* — Jared Barsky
(74) *Attorney, Agent, or Firm* — Pearl Cohen Zedek Latzer Baratz LLP

(57) ABSTRACT

Imipridones selectively modulate Class A G protein-coupled receptors (GPCRs), such as the D2-like subfamily of dopamine receptors, and are useful for treating conditions and disorders in need of such modulation, such as cancers. Specifically, the cancer is a midline glioma, a cancer having a histone H3 mutation, or both. In addition, methods of identifying whether a subject having these conditions, is likely to be responsive to a treatment regimen, such as imipridone administration, are provided. Furthermore, methods of assessing the effectiveness of a treatment regimen, such as imipridone administration, monitoring, or providing a prognosis for a subject with these condition are also provided.

28 Claims, 20 Drawing Sheets

(56) References Cited

OTHER PUBLICATIONS

Bartek et al. "Dopamine signaling: target inglioblastoma" Oncotarget, Mar. 2014;5(5):1116.
Cheng et al. "Identification of DNA-PKcs as a primary resistance factor of TIC10 in hepatocellular carcinoma cells" Oncotarget. Apr. 25, 2017;8(17)28385.
Chi et al. "Exth-42. H3 K27m Mutant Gliomas are Selectively Killed by Onc201, A Small Molecule Inhibitor of Dopamine Receptor D2" Neuro-oncology. Nov. 6, 2017;19(suppl_6):vi81-. Abstract.
Dalton et al. "Cancer risk among users of neuroleptic medication: a population-based cohort study" British journal of cancer, Oct. 2006;95(7):934.
Ding et al. "Divergent angiocrine signals Irom vascular niche balance liver regeneration and fibrosis" Nature, Jan. 2014;505(7481):97.
Dowling et al. "Quantifyinc the association and dissociation rates of unlabelled antagonists at the muscarinic M3 receptor" British journal of pharmacology. Aug. 1, 2006;148(7):927-37
Edwards et al. "ONC201 Shows Promise in AML Treatment. Cell Cycle" Dec. 21, 2017(just-accepted):1-4. •.
Feng et a. "Small Molecular TRAIL Inducer ONC201 Induces Death in Lung Cancer Cells: A Preclinical Study" PLoS ONE. 2016;11(9).
Gont et al. "PREX1 integrates G protein-coupled receptor and phosphoinositide 3-kinase signaling to promote glioblastoma invasion" Oncotarget. Jan. 31, 2017;8(5):8559.
Greene et al. "Probenecid inhibits the human bitter taste receptor TAS2R 6 and suppresses bitter perception of salicin" PLoS One, May 24, 2011;6(5):e20123.
Greer et al. "ONC201 kills breast cancer cells in vitro by tarceting mitochondria". Oncotarget. Apr. 6, 2018;9(26):18454.
Greer et al, "TIC10/ONC201: a bend in the road to clinical development" Oncoscience. Feb. 20, 2015;2(2);75.
Greer et al. "ONC201; Stressing tumors to death". Science signaling. Feb. 16, 2016;9(415):fs1.
Hayes-Jordan et al. "Efficacy of ONC201 in Desmoplastic Small Round Cell Tumor" Neoplasia. May 31, 2018;20(5):524-32.
Ishizawa et al. "ATF4 induction through an atypical integrated stress response to ONC201 triggers p53-independent apoptosis in hematological malignancies". Science signaling, 2016;9(415):ra17.
Jacob et al. "Pharmacophore reassignment for induction of the immunosurveillance cytokine TRAIL"Angew Chem Int Ed Engl. Jun. 23, 2014;53(26):6628-31.
Jin et al. "mTOR inhibition sensitizes ONC201-induced anti-colorectal cancer cell activity" Biochemical and biophysical research communications. Sep. 30, 2016;478(4)1515.
Jung et al. "Ddis-06. Onc206, An Imipridone Family Member, Suppresses Glioma Stem Cell Maintenance" Neuro-oncology. Nov. 6, 2017;19(suppl_6):vi60. Abstract.
Karpel-Massler et al. "TIC10/ONC201 synergizes with Bcl-2/Bcl-xL inhibition in glioblastoma by suppression of Mcl-1 and its binding partners in vitro and in vivo" Oncotarget. Nov. 3, 2015;6(34):36456.
Khuong-Quang et al. "K27M mutation in histone H3. 3 defines clinically and biologically distinct subgroups of pediatric diffuse intrinsic pontine gliomas" Acta neuropathologica. Sep. 1, 2012;124(3):439-47.
Kline et al. "ONC201 kills solid tumor cells by triggering an integrated stress response dependent on ATF4 activation by specific eIF2α kinases" Sci. Signal.. Feb. 16, 2016;9(415):ra18.
Kline et al. "Role of Dopamine Receptors in the Anticancer Activity of ONC201". Neoplasia. Jan. 1, 2018;20(1):80-91.
Lev et al. "Anti-pancreatic cancer activity of ONC212 involves the unfolded protein response (UPR) and is reduced by IGF1-R and GRP78/BIP" Oncotarget. Oct. 10, 2017:8(47):81776.
Lev et al. "ONC201 Targets AR and AR-V7 Signaling, Reduces PSA, and Synergizes with Everolirnus in Prostate Cancer" Molecular Cancer Research. May 1, 2018;16(5):754-66.

Li et al. "Genome-wide shRNA screen revealed integrated mitogenic signaling between dopamine receptor D2 (DRD2) and epidermal growth factor receptor (EGFR) in glioblastoma" Oncotarget. Feb. 2014;5(4):882.
Lin et al. "Cancer incidence in patients with hizophrenia or bipolar disorder: a nationwide population-based study in Taiwan, 1997-2009" Schizophrenia bulletin. Nov. 1, 2011;39(2):407-16.
Madhukar et al. "Exth-43. Differentiated Pharmacology of the Imipridone Onc201, The First Selective Drd2/3 Antagonist" In Clinical Neuro-oncology. Neuro-oncology. Nov. 6, 2017;19(suppl_6):vi81-2. Abstract.
Madhukar et al. "The small molecule imipridone ONC201 is active in tumor types with dysregulation of the DRD2 pathway" AACR (2017): 2792-2792. Abstract.
Madhukar et al. "Abstract LB-209; D2-like dopamine receptor antagonism by ONC201 identified by confluence of computational, receptor binding, and clinical studies" AACR (2016); LB-209. Abstract.
McGuinness et al. "Characterizing Cannabinoid CB2 Receptor Ligands Using DiscoveRx PathHunter™ β-Arrestin Assay" Journal of biomolecular screening. Jan. 2009;14(1):49-58.
Meredith et al. "Dopamine targets cycling B cells independent of receptors/transporter for oxidative attack: Implications for non-Hodgkin's lymphoma" Proceedings of the National Academy of Sciences. Sep. 5, 2006;103(36);13485-90.
Michaelis et al. "Enzastaurin inhibits ABCB1-mediated drug efflux independently of effects on protein kinase C signalling and the cellular p53 status" Oncotarget. Jul. 10, 2015;6(19)17605.
Motulsky et al. "The kinetics of competitive radioligand binding predicted by the law of mass action" Molecular pharmacology. Jan. 1, 1984;25(1):1-9.
Ni et al. "ONC201 selectively induces apoptosis in cutaneous T-cell lymphoma cells via activating pro-apoptotic integrated stress response and inactivating JAK/STAT and NF-κB pathways" Oncotarget. Sep. 22, 2017;8(37):61761.
Prabhu et al. "ONC201 Depletes Cancer Stem Cells in Refractory Cancer Patient Samples" Blood. 2014:124:5219-5219.
Prabhu et al. "Small-molecule ONC201/TIC10 targets chemotherapy-resistant colorectal cancer stem-like cells in an Akt/Foxo3a/TRAIL-dependent manner" Cancer research. Apr. 1, 2015;75(7):1423-32.
Prabhu et al. "Single agent and synergistic combinatorial efficacy of first-in-class small molecule imipridone ONC201 in hematological maiignancies". Cell Cycle. Feb. 16, 2018;17(4);468-78.
Prabhu el al. Cancer stem cell-related gene expression as a potentia. biomarker of response for first-in-class imipridone ONC201 in solid tumors. PloS one. Aug. 2, 2017;12(8):e0180541.
Ralff et al, "ONC201 demonstrates antitumor effects in both triple-negative and non--triple-negative breast cancers through TRAIL-Dependent and TRAIL independent mechanisms. Molecular cancer therapeutics" Jul. 1, 2017;16(7):1290-8.
Razavi et al. "Gholamin S, Li G. Immune evasion strategies of glioblastoma" Frontiers in surgery, Mar. 2, 2016;3:11.
Romaguera et al. "Integrated Stress Response and Immune Cell Infiltration in an Ibrutinib-Refractory Mantle Cell Lymphoma Patient Following ONC201 Treatment" 2018 Epub ahead of print.
Rubio et al. "Triggering the succinate receptor GPR91 on dendritic cells enhances immunity" Nature immunology. Nov. 2008;9(11):1261.
Sachlos et al. "Identification of drugs including a dopamine receptor antagonist that selectiveiy target cancer stem cells" Cell. Jun. 8, 2012;149(6):1284-97.
Stein et al. "First-m-hurnan clinical trial of orai ONC201 in patients with refractory solid tumors". Clinical Cancer Research. Mar. 22, 2017; 23(15):4163-416.
Talekar et al. "ONC201 induces cell death in pediatric non-Hodgkin's lymphoma cells" Cell cycle (Georgetown, Tex.). Aug. 3, 2015;14(15):2422.
Tu et al. "The imipridone ONC201 induces apoptosis and overcomes chemotherapy resistance by up-regulation of Bim in multiple myeloma" Neoplasia. Oct. 1, 2017;19(10):772-80.
Wagner et ai. "Dose-intensified ONC201 to exert anti-metastatic efficacy and to promote intra-tumoral recruitment of NK-cells in mice" Journal of Clinical Oncology, 2016 :11550-11550.

(56) References Cited

OTHER PUBLICATIONS

Wagner et la. "The angular structure of ONC201, a TRAIL pathway-inducing compound, determines its potent anti-cancer activity" Oncotarget. Dec. 2014;5(24):12728.

Wagner et al. "Dose intensification of TRAIL-inducing ONC201 inhibits metastasis and promotes intratumora NK cell recruitment" The Journal of clinical investigation. Mar. 13, 2018;128(6).

Wagner et al. "Anti-tumor effects of ONC201 in combination with VEGF-inhibitors significantly impacts colorectal cancer growth and survival in vivo through complementary non-overlapping mechanisms" Journal of Experimental & Clinical Cancer Research. Dec. 2018;37(1):11.

Wagner et ai "Preclinical evaluation of the imipridone lamily, analogs of clinical stage anti-cancer small molecule ONC201, reveals potent anti-cancer effects of ONC212" Cell Cycle. Oct. 2, 2017;16(19):1790-9.

Wang et al. "Silencing the epigenetic silencer KDM4A for TRAIl and DR5 simultaneous induction and antitumor therapy" Cell death and differentiation, Nov. 1, 2016;23(11):1886.

Wang M. "Newkid ora the block: ONC201 in NHL" Cell Cycle. 2015;14(22):3526.

Yamaji et al. "Novel ATP-competitive Akt inhibitor afuresertib suppresses the proliferation of malignant pleural mesothelioma cells" Cancer medicine. Nov. 1, 2017;6(11)2646-59.

Yuan et al. "ONC201 activates ER stress to inhibit the growth of triple-negative breast cancer cells". Oncotarget. Mar. 28, 2017;8(13)21626.

Zhang et al. "The preclinical evaluation of TIC/ONC201 as an anti-pancreatic cancer agent" Biochemical and biophysical research communications. Aug. 5, 2016;476(4):260.

Zhao et al. "Dopamine receptors modulate cytotoxicity of natural killer cells via. cAMP-PKA-CREB signaling pathway" PLoS One. Jun. 14, 2013;8(6):e65860.

Cohen et al., "Temozolomide in the treatment of children with newly diagnosed diffuse intrinsic pontine gliomas: a report from the Children's Oncology Group", Neuro-Oncology 13(4):410-416, 2011.

Vanan et al., "DIPG in children—what can we learn from the past?", Front. Oncol. 5:237. doi:10.3389/fonc.2015.00237.

International Search Report and Written Opinion, dated Dec. 28, 2018, from corresponding International Application No. PCT/US18/59209.

Laburthe et al., "The orexin receptor $OX_1R$ in colon cancer: a promising therapeutic target and a new paradigm in G protein-coupled receptor signalling through ITIMs", British Journal of Pharmacology, (2012) 165, pp. 1678-1687.

Lutz et al., "Opioid receptors: distinct roles in mood disorders", Trends Neurosci. Mar. 2013; 36(3): 195-206.

Yung et al., "Host Chemokines Bind to *Staphylococcus aureus* and Stimulate Protein A Release", The Journal of Biological Chemistry, vol. 286, No. 7, pp. 5069-5077, Feb. 18, 2011.

Pollard, "A Guide to Simple and Informative Binding Assays", Molecular Biology of the Cell, vol. 21, 4061-4067, Dec. 1, 2010.

Fowler et al., "Receptor conformations involved in dopamine $D_{2L}$ receptor functional selectivity induced by selected transmembrane-5 serine mutations", Molecular Pharmacology Fast Forward, Mar. 13, 2012, 46 pages.

Jully et al., "Potential molecular targets for Ewing's sarcoma therapy", Indian J. Med. Paediatr. Oncol. Oct.-Dec. 2012; 33(4): 195-202.

Zhao et al., "p53 loss promotes acute myeloid leukemia by enabling aberrant self-renewal", Genes & Development (2010) 24:1389-1402.

Aihara et al., "H3F3A K27M mutations in thalamic gliomas from young adult patients", Neuro-Oncology 16(1), 140-146, 2014.

Soejima et al., "Epigenetic silencing of the MGMT gene in cancer", Biochem. Cell Biol. 83:429-437 (2005).

Soares et al., "Role of the platelet-activating factor (PAF) receptor during pulmonary infection with gram negative bacteria", British Journal of Pharmacology (2002) 137, 621-628.

Shah et al., "Real-time imaging of TRAIL-induced apoptosis of glioma tumors in vivo", Oncogene (2003) 22, 6865-6872.

Allen et al., "ONC201 Possesses a Benign Safety Profile at Highly Efficacious Does in Normal Human Cells and Animal Toxicology Studies", Blood (2014) 124:4812.

Peters et al., "Dopamine and serotonin regulate tumor behavior by affecting angiogenesis", Drug Resistance Updates 17 (2014) 96-104.

\* cited by examiner

A

B

HCT116, 48h
ONC201: 5µM
ONC212: 500nM

A

B

C

A

B

Figure 18
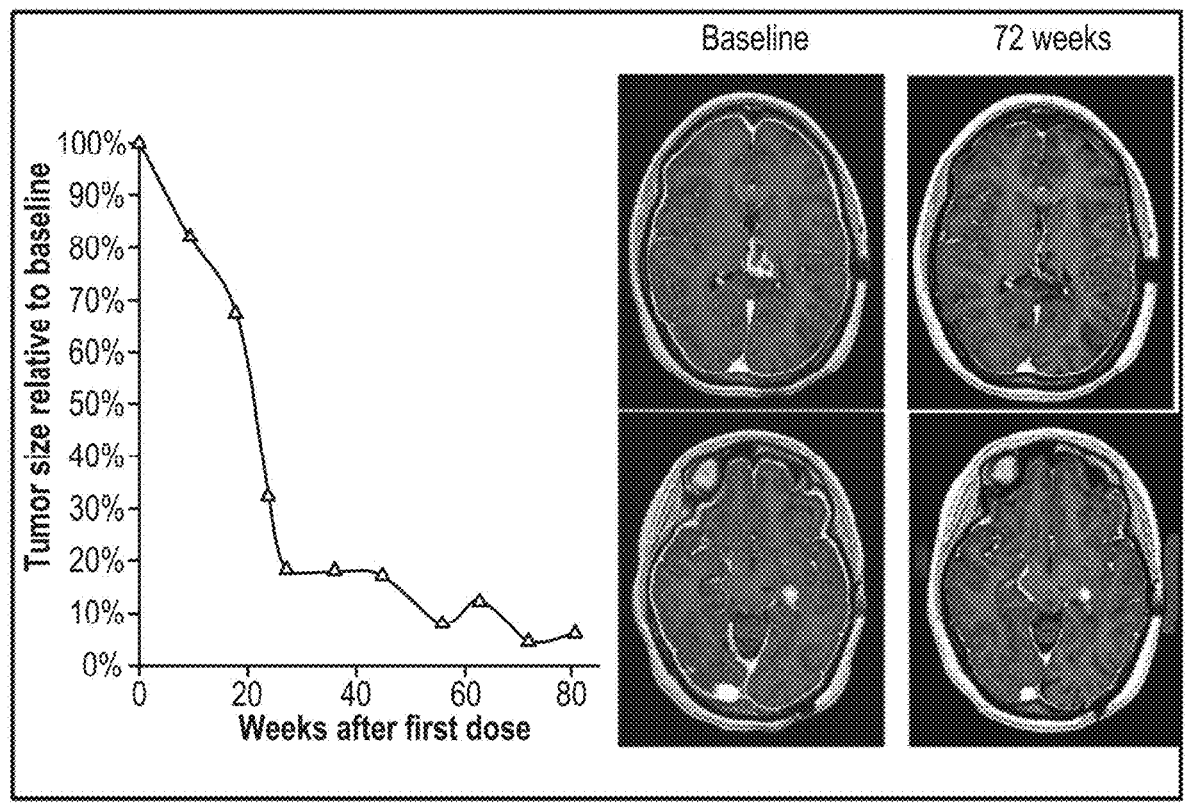
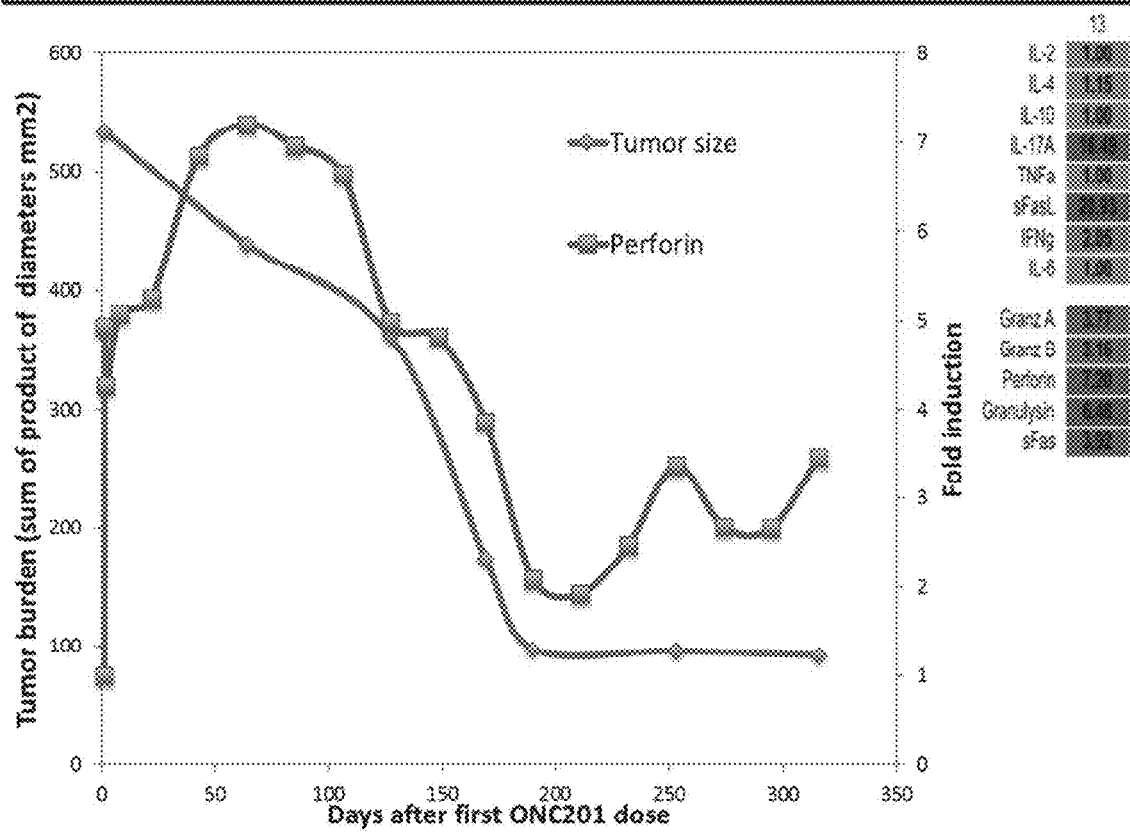
Figure 19

IMIPRIDONES FOR GLIOMAS

CROSS-REFERENCE TO RELATED APPLICATIONS

This application is a divisional application of U.S. patent application Ser. No. 16/204,964, filed Nov. 29, 2018, which is a divisional application of U.S. patent application Ser. No. 15/947,840, filed Apr. 8, 2018, which is claims benefit of U.S. Provisional Application No. 62/581,478, filed Nov. 3, 2017, and which also is a continuation-in-part of International Application No. PCT/US17/15608, filed Jan. 30, 2017, which are hereby incorporated by reference.

BACKGROUND OF THE INVENTION

ONC201 (7-benzyl-4-(2-methylbenzyl)-1,2,6,7,8,9-hexahydroimidazo [1,2-a]pyrido [3,4-e]pyrimidin-5(1H)-one) is the founding member of a class of anti-cancer compounds called imipridones that is in Phase II clinical trials in multiple advanced cancers. Since the discovery of ONC201 as a p53-independent inducer of TRAIL gene transcription, preclinical studies have determined that ONC201 has anti-proliferative and pro-apoptotic effects against a broad range of tumor cells but not normal cells. The mechanism of action of ONC201 involves engagement of PERK-independent activation of the integrated stress response, leading to tumor upregulation of DR5 and dual Akt/ERK inactivation, and consequent Foxo3a activation leading to upregulation of the death ligand TRAIL. ONC201 is orally active with infrequent dosing in animal models, causes sustained pharmacodynamic effects, and is not genotoxic. The first-in-human ONC201 clinical trial in advanced aggressive refractory solid tumors confirmed that it is well-tolerated.

The discovery of H3 K27M as an oncogenic mutation occurred in the context of midline gliomas that involve the thalamus, pons, or spinal cord. H3 K27M refers to a specific mutation in histone H3 proteins. Due to the location of these tumors, areas of the brain involved in critical physiological functions, these tumors have historically been inoperable (especially in the brain stem where the pons is located). This means that until recently, midline gliomas such as diffuse intrinsic pontine glioma (DIPG) were diagnosed solely on a radiographic basis. Advances in neurosurgical techniques and increased parental consent to post-mortem tumor tissue retrieval led to the availability of sufficient biospecimens that enabled systematic genomic evaluations of DIPG and other midline gliomas. Gliomas in the midline of the brain belong to the most aggressive types of primary malignant brain cancers. The disease arises from glial cells, which are cells that form the tissue that surrounds and protects other nerve cells found within the brain and spinal cord.

Standard therapy for midline gliomas involves neurosurgery, when feasible, followed by fractionated external beam radiotherapy. Due to location in the brain, aggressiveness and low survival time, gliomas in the midline of the brain are considered as part of the most lethal forms of cancer.

No medical therapies have been shown to prolong survival in H3 K27M mutant adult and pediatric glioma patients. Standard-of-care treatment for DIPG, 55 Gy focal radiation fractionated over 6 weeks, is associated with a 9-11-month overall survival. For adult H3 K27M glioma, the disease is often treated with the same regimen as glioblastoma that involves radiation with concomitant and maintenance temozolomide. Despite its use to treat this newly defined disease in adults, the efficacy of this regimen has not been evaluated specifically in adult mutant H3 K27M glioma patients.

The functions of histones are predominantly protein-DNA and protein-protein interactions and they do not function as enzymes, which have represented the bulk of targeted cancer therapy (kinases, HDAC inhibitors, etc.). Thus, no therapies directly target the mutant H3 proteins itself (such as the case for mutant BRAF); instead, therapeutic efforts have focused on targeting features of tumor cells with H3 K27M mutations, such as their epigenetic- and transcription-dependency. Inhibition of proteins involved in epigenetics such as histone de-acetylates, histone de-methylases, or bromodomains have yielded efficacy in preclinical models, however their ability to improve clinical outcome has not been shown.

A major challenge for effective H3 K27M glioma treatments is that therapeutics must penetrate the blood-brain barrier, a rare feature of current cancer therapies. This requirement is further enhanced by the location of these tumors in midline brain structures, which have been shown to be more difficult to penetrate than other brain locations. The H3 K27M mutation also tends to occur in midline gliomas where dopamine is present and DRD2 expression is prevalent in the tumor environment.

The lack of treatments for H3 K27M glioma leave a large unmet medical need with respect to disease control, symptom relief, and survival rates. Patients with recurrent disease following radiation, are left with no treatment options with a demonstrated survival benefit.

BRIEF SUMMARY OF THE INVENTION

In one aspect, provided herein are compounds of formula (10):

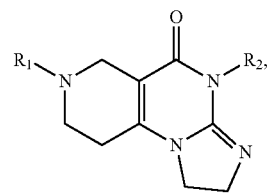

wherein $R_1$ and $R_2$ are independently selected from H, alkyl, cycloalkyl, cycloalkylalkyl, heterocycloalkyl, heterocycloalkylalkyl, aryl, heteroaryl, arylalkyl, heteroarylalkyl, alkoxyalkyl, alkoxycarbonyl, aralkoxy, aralkylthio, and acyl radicals. In one embodiment, when $R_1$ is $CH_2Ph$, $R_2$ is not $CH_2$-(2-$CH_3$-Ph). In one embodiment, $R_1$ is $CH_2Ph$ and $R_2$ is $CH_2$-(2-$CH_3$-Ph) (ONC201). In one embodiment, $R_1$ is $CH_2Ph$ and $R_2$ is $CH_2$-(2,4-di F-Ph) (ONC206). In one embodiment, $R_1$ is $CH_2Ph$ and $R_2$ is $CH_2$-(4-$CF_3$-Ph) (ONC212). In one embodiment, $R_1$ is $CH_2Ph$ and $R_2$ is $CH_2$-(3,4-di F-Ph) (ONC213). In one embodiment, $R_1$ is $CH_2$-(3,4-di-Cl-Ph) and $R_2$ is $CH_2$-(4-$CF_3$-Ph) (ONC234). In one embodiment, $R_1$ is $CH_2$-3-thienyl and $R_2$ is $CH_2$-(4-$CF_3$-Ph) (ONC236).

In another aspect, provided herein are methods of treating or preventing cancer in a subject in need thereof, comprising: administering to the subject in need of such treatment a pharmaceutical composition comprising a therapeutically effective amount compound (1)

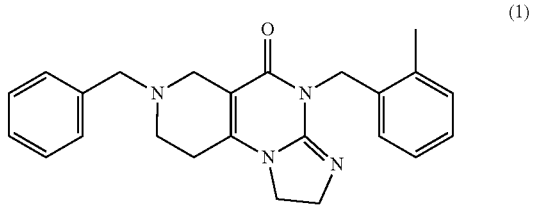 [SMILES: Cc1ccccc1CN1C(=O)C2=C(CCN(Cc3ccccc3)C2)N2CCN=C12]

(1)

or a pharmaceutically acceptable salt thereof, wherein the cancer is a midline glioma having a histone H3 K27M mutation.

In another aspect, provided herein are methods of treating or preventing cancer in a subject in need thereof, comprising: administering to the subject in need of such treatment a pharmaceutical composition comprising a therapeutically effective amount a compound of formula (10) or an analog thereof, or a pharmaceutically acceptable salt thereof, wherein the cancer has a histone H3 mutation.

In another aspect, provided herein are methods of treating or preventing cancer in a subject in need thereof, comprising: administering to the subject in need of such treatment a pharmaceutical composition comprising a therapeutically effective amount a compound of formula (10) or an analog thereof, or a pharmaceutically acceptable salt thereof, wherein the cancer is a midline glioma.

BRIEF DESCRIPTION OF THE DRAWINGS

The above summary, as well as the following detailed description of embodiments of the invention, will be better understood when read in conjunction with the appended drawings. It should be understood, however, that the invention is not limited to the precise arrangements and instrumentalities shown. In the drawings:

FIG. 18. The subject with recurrent H3 K27M thalamic glioblastoma of Example 14 has a durable objective response. (A) Relative overall tumor size (%) in the subject. (B) Contrast MRI scans at baseline, and 17 months of treatment with ONC201.

FIG. 19. Immune induction correlates with tumor shrinkage in glioblastoma.

DETAILED DESCRIPTION OF THE INVENTION

Figure 1:
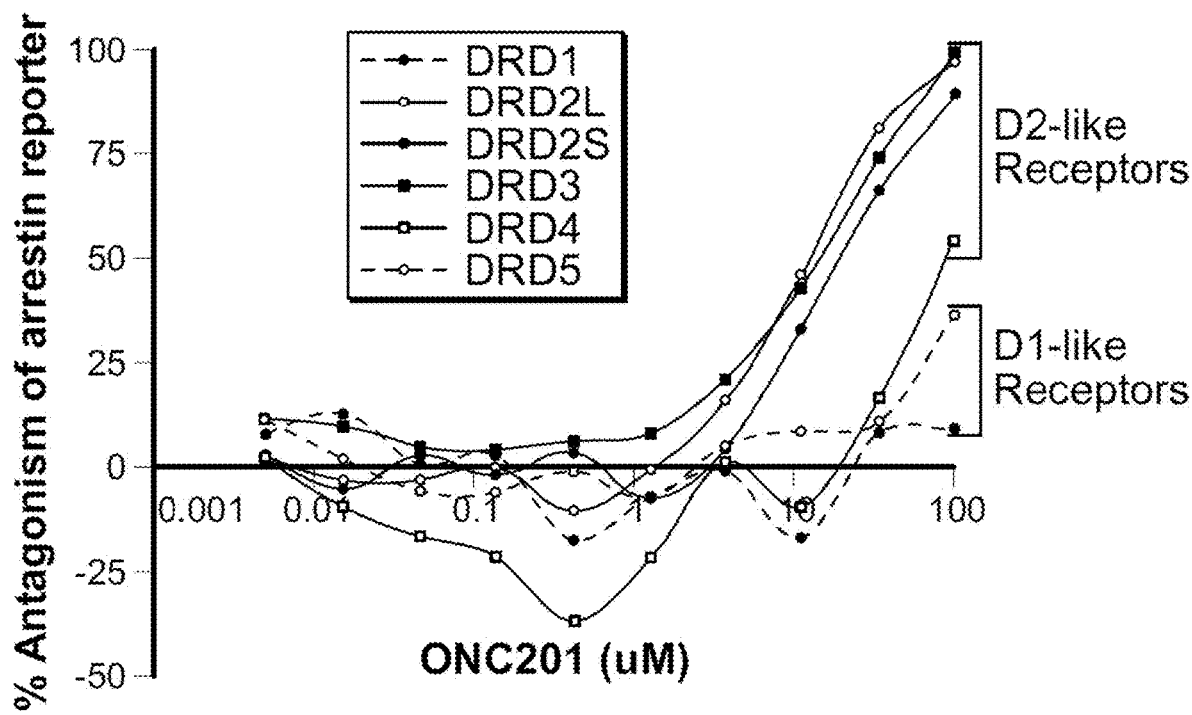
FIG. 1. Antagonism of dopamine receptors (DRD1, DRD2S, DRD2L, DRD3, DRD4, and DRD5) by ONC201.

Scientific and technical terms used here are intended to have the meanings commonly understood by those of ordinary skill in the art. Such terms are found and used in context in various standard references illustratively including J. Sambrook and D. W. Russell, Molecular Cloning: A Laboratory Manual, Cold Spring Harbor Laboratory Press; 3$^{rd}$ Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Engelke, D. R., RNA Interference (RNAi): Nuts and Bolts of RNAi Technology, DNA Press LLC, Eagleville, P A, 2003; Herdewijn, P. (Ed.), Oligonucleotide Synthesis: Methods and Applications, Methods in Molecular Biology, Humana Press, 2004; A. Nagy, M. Gertsenstein, K. Vintersten, R. Behringer, Manipulating the Mouse Embryo: A Laboratory Manual, 3$^{rd}$ edition, Cold Spring Harbor Laboratory Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN: 9780470151808, as well as U.S. Pat. No. 8,673,923. The content of each of the references above is hereby incorporated by reference in its entirety.

The term "substituted" means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds are double bonds that are formed between two adjacent ring atoms (e.g., C=C, C=N, or N=N).

When a variable (e.g., $R^4$) occurs more than one time in a constituent or formula for a compound, its definition at each occurrence is independent of its definition at every other occurrence. Thus, for example, if a group is shown to be substituted with 0-3 $R^4$ moieties, then the group may optionally be substituted with up to three $R^4$ moieties and $R^4$ at each occurrence is selected independently from the definition of $R^4$. Also, combinations of substituents and/or variables are permissible, but only if such combinations result in stable compounds.

When an atom or chemical moiety is followed by a subscripted numeric range (e.g., $C_{1-6}$), it will be appreciated that this is meant to encompass each number within the range, as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" includes both branched and straight-chain saturated aliphatic hydrocarbon groups having the specified number of carbon atoms. For example, $C_{1-6}$ alkyl includes $C_1$, $C_2$, $C_3$, $C_4$, $C_5$, and $C_6$ alkyl groups. Non-limiting examples of alkyl include methyl, ethyl, n-propyl, i-propyl, n-butyl, isobutyl s-butyl, t-butyl, n-pentyl, s-pentyl, neopentyl and n-hexyl. In certain cases, a straight or branched chain alkyl has six or fewer carbon atoms in its backbone (e.g., $C_1$-$C_6$ for a straight chain, $C_3$-$C_6$ for a branched chain); in other cases, a straight or branched chain alkyl has four or fewer carbon atoms. Likewise, cycloalkyls may have from three to eight carbon atoms in their ring structure; in some cases, cycloalkyls have five or six carbons in the ring structure. Most preferred is $C_{1-6}$ alkyl, particularly ethyl, methyl, isopropyl, isobutyl, n-pentyl, n-hexyl and cyclopropylmethyl.

The term "substituted alkyl" means alkyl as defined above, substituted by one, two or three substituents selected from halogen, —OH, alkoxy, —NH$_2$, —N(CH$_3$)$_2$, —C(=O)OH, trifluoromethyl, —C—N, —C(=O)O(C$_1$-C$_4$)alkyl, —C(=O)NH$_2$, —SO$_2$NH$_2$, —C(=NH)NH$_2$, and —NO$_2$, preferably containing one or two substituents selected from halogen, —OH, alkoxy, —NH$_2$, trifluoromethyl, —N(CH$_3$)$_2$, and —C(=O)OH, more preferably selected from halogen, alkoxy and —OH. Non-limiting examples of substituted alkyls include 2,2-difluoropropyl, 2-carboxycyclopentyl and 3-chloropropyl.

Unless the number of carbons is otherwise specified, "lower alkyl" is an alkyl group, as defined above, but having from one to six carbon atoms, preferably one to four, in its backbone structure. "Lower alkenyl" and "lower alkynyl" have chain lengths of 2-6 carbon atoms and preferably 2-4 carbon atoms.

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain cases, a straight or branched chain alkenyl group has six or fewer carbon atoms in its backbone (e.g., $C_2$-$C_6$ for a straight chain, $C_3$-$C_6$ for a branched chain). Likewise, cycloalkenyl groups may have from three to eight carbon atoms in their ring structure; in some cases, cycloalkenyl groups have five or six carbons in the ring structure. The terms "$C_2$-$C_6$" and "$C_3$-$C_6$" includes alkenyl groups containing two to six carbon atoms and three to six carbon atoms, respectively.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups. In certain cases, a straight or branched chain alkynyl group has six or fewer carbon atoms in its backbone (e.g., $C_2$-$C_6$ for a straight chain, $C_3$-$C_6$ for a branched chain). The terms "$C_2$-$C_6$" and "$C_3$-$C_6$" includes alkynyl groups containing two to six carbon atoms and three to six carbon atoms, respectively.

The term "cycloalkyl" refers to a monocyclic or polycyclic non-aromatic radical, where each of the atoms forming the ring (i.e. skeletal atoms) is a carbon atom. In some cases, the cycloalkyl group is saturated or partially unsaturated. In other cases, the cycloalkyl group is fused with an aromatic ring. Cycloalkyl groups include groups with from 3 to 10 ring atoms. Examples of cycloalkyl groups include, but are not limited to, the following moieties:

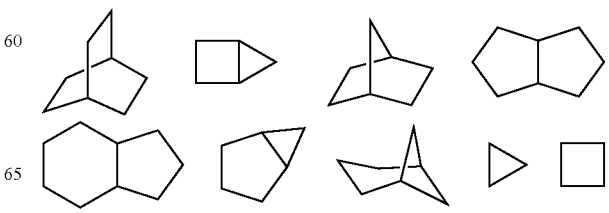

-continued

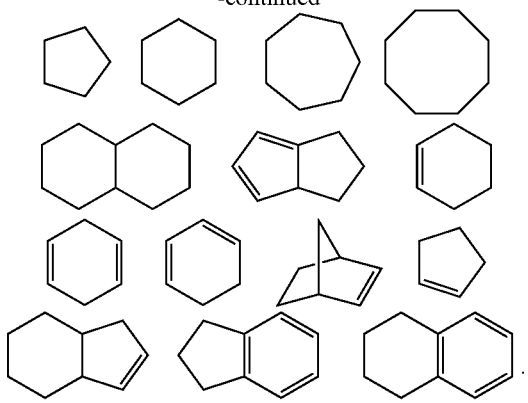

Monocyclic cycloalkyls include cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

The term "cycloalkylalkyl" refers to an alkyl group substituted by a cycloalkyl group. Example cycloalkylalkyl groups include cyclopropylalkyl, cyclohexylalkyl.

The term "heterocycloalkyl" refers to a non-aromatic heterocycle where one or more of the ring-forming atoms is a heteroatom such as an r, N, or S atom. Heterocycloalkyl groups include mono- or polycyclic (e.g., having 2, 3 or 4 fused rings) ring systems, as well as spirocycles. Example heterocycloalkyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, and imidazolidinyl. Also included in the definition of heterocycloalkyl can be moieties that have one or more aromatic rings fused (i.e., having a bond in common with) to the nonaromatic heterocyclic ring, for example, quinolyl, isoquinolyl, and benzo derivatives of heterocycles. A heterocycloalkyl group having one or more fused aromatic rings are attached though either the aromatic or non-aromatic portion. Also included in the definition of heterocycloalkyl are moieties where one or more ring-forming atoms can be substituted by 1 or 2 oxo or sulfido groups. In some cases, the heterocycloalkyl group has from 1 to about 20 carbon atoms, and in further case from about 3 to about 20 carbon atoms. In some cases, a heterocycloalkyl group contains 3 to about 20, 3 to about 14, 3 to about 7, or 5 to 6 ring-forming atoms. In some cases, a heterocycloalkyl group has 1 to about 4, 1 to about 3, or 1 to 2 heteroatoms. In some cases, a heterocycloalkyl group contains 0 to 3 double bonds. In some cases, a heterocycloalkyl group contains 0 to 2 triple bonds.

The term "heterocycloalkylalkyl" refers to an alkyl group substituted by a heterocycloalkyl. Example heterocycloalkylalkyls include morpholinoalkyl and piperazinylalkyl.

The term "aryl" refers to monocyclic or polycyclic (e.g., having 2, 3 or 4 fused rings) aromatic hydrocarbons, such as phenyl, naphthyl, anthracenyl, phenanthrenyl. In some cases, an aryl group has from 6 to about 20 carbon atoms.

The term "arylalkyl" refers to an alkyl group substituted by an aryl group. Example arylalkyl groups include benzyl and phenylethyl.

The term "heteroaryl" refers to an aromatic heterocycle having at least one heteroatom ring member such as an O, S, or N atom. Heteroaryl groups include monocyclic and polycyclic (e.g., having 2, 3 or 4 fused rings) systems. A ring-forming N atom in a heteroaryl group can also be oxidized to form an N-oxo moiety. Examples of heteroaryl groups include pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl. In some cases, a heteroaryl group has from 1 to about 20 carbon atoms, and in some cases from about 3 to 20 carbon atoms. In some cases, a heteroaryl group contains 3 to about 14, 3 to about 7, or 5-6 ring-forming atoms. In some cases, a heteroaryl group has 1 to about 4, 1 to about 3, or 1-2 heteroatoms.

A "heteroarylalkyl" group refers to an alkyl group substituted by a heteroaryl group. An example of a heteroarylalkyl group is pyridylmethyl.

The terms "halo" or "halogen" refer to a fluorine (F), chlorine (Cl), bromine (Br), or iodine (I) atom; preferably, F, Cl, or Br; more preferably, F or Cl. The term "perhalogenated" refers to a moiety where all hydrogens are replaced by halogens. The term "haloalkyl" refers to alkyl groups with a halogen replacing a hydrogen on one or more carbons of the hydrocarbon backbone. $C_1$-$C_6$ haloalkyl includes a straight chain or branched alkyl with six or fewer backbone carbon atoms and a halogen replaces a hydrogen on one or more backbone carbons.

The term "alkoxy" or "alkoxyl" includes substituted and unsubstituted alkyl, alkenyl, and alkynyl groups covalently linked to an oxygen atom. $C_1$-$C_6$ alkoxy refers to moieties having six or fewer carbon atoms in the hydrocarbon backbone. Examples of alkoxy groups (or alkoxyl radicals) include methoxy, ethoxy, isopropyloxy, propoxy, butoxy, and pentoxy groups. Preferred are ($C_1$-$C_3$) alkoxy, particularly ethoxy and methoxy. Examples of substituted alkoxy groups include halogenated alkoxy groups.

The term "hydroxy" or "hydroxyl" includes groups with an —OH or —O—.

The term "pharmaceutically acceptable salts" refers to derivatives of compounds that are modified by converting an existing acid or base moiety to its salt form. Non-limiting examples of pharmaceutically acceptable salts include mineral or organic acid salts of basic residues such as amines; alkali or organic salts of acidic residues such as carboxylic acids. Pharmaceutically acceptable salts include conventional non-toxic salts of a parent compound formed, for example, from non-toxic inorganic or organic acids. Pharmaceutically acceptable salts may be synthesized by conventional chemical methods from a parent compound that contains a basic or acidic moiety. Generally, such salts can be prepared by reacting a free acid or base form of these compounds with a stoichiometric amount of an appropriate base or acid in water or an organic solvent, or in a mixture of the two; generally, nonaqueous media like ether, ethyl acetate, ethanol, isopropanol, or acetonitrile are preferred. Lists of suitable salts can be found in *Remington's Pharmaceutical Sciences*, 17th ed., Mack Publishing Company, Easton, Pa., 1985, p. 1418, *Journal of Pharmaceutical Science*, 66, 2 (1977), and P. Stahl and C. Wermuth, editors, *Handbook of Pharmaceutical Salts: Properties, Selection* and Use, 2$^{nd}$ Revised ed., Weinheim/Zürich:Wiley-VCH/VHCA (2011), each of which is incorporated herein by reference in its entirety.

Examples of suitable inorganic acids include hydrochloric acid, sulphuric acid, phosphoric acid, or hydrobromic acid, while examples of suitable organic acids include carboxylic acid, sulpho acid, or sulphonic acid, such as acetic acid, tartaric acid, lactic acid, propionic acid, glycolic acid, malonic acid, maleic acid, fumaric acid, tannic acid, succinic acid, alginic acid, benzoic acid, 2-phenoxybenzoic acid, 2-acetoxybenzoic acid, cinnamic acid, mandelic acid, citric acid, maleic acid, salicylic acid, trifluoroacetic acid, 3-aminosalicylic acid, ascorbic acid, embonic acid, nicotinic acid, isonicotinic acid, oxalic acid, gluconic acid, amino acids, methanesulphonic acid, ethanesulphonic acid, 2-hydroxyethanesulphonic acid, ethane-1,2-disulphonic acid, benzenesulphonic acid, 4-methylbenzenesulphonic acid or naphthalene-2-sulphonic acid. Examples of suitable inorganic bases include sodium hydroxide, potassium hydroxide and ammonia, while examples of suitable organic bases include amines, e.g., tertiary amines, such as trimethylamine, triethylamine, pyridine, N,N-dimethylaniline, quinoline, isoquinoline, α-picoline, β-picoline, γ-picoline, quinaldine, or pyrimidine.

The term "antibody" encompasses the structure that constitutes the natural biological form of an antibody. In most mammals, including humans, and mice, this form is a tetramer and consists of two identical pairs of two immunoglobulin chains, each pair having one light and one heavy chain, each light chain comprising immunoglobulin domains $V_L$ and $C_L$, and each heavy chain comprising immunoglobulin domains $V_H$, Cγ1, Cγ2, and Cγ3. In each pair, the light and heavy chain variable regions ($V_L$ and $V_H$) are together responsible for binding to an antigen, and the constant regions ($C_L$, Cγ1, Cγ2, and Cγ3, particularly Cγ2, and Cγ3) are responsible for antibody effector functions. In some mammals, for example in camels and llamas, full-length antibodies may consist of only two heavy chains, each heavy chain comprising immunoglobulin domains $V_H$, Cγ2, and Cγ3. By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including full-length antibodies, antibody fragments, and individual immunoglobulin domains including $V_H$, Cγ1, Cγ2, Cγ3, $V_L$, and $C_L$.

Based on the heavy-chain constant domain amino acid sequence, intact antibodies can be assigned to different "classes." There are five-major classes (isotypes) of intact antibodies: IgA, IgD, IgE, IgG, and IgM, and several of these may be further divided into "subclasses," e.g., IgG1, IgG2, IgG3, IgG4, IgA, and IgA2. The heavy-chain constant domains that correspond to the different antibody classes are called alpha, delta, epsilon, gamma, and mu, respectively. The subunit structures and three-dimensional configurations of different classes of immunoglobulins are well known to one skilled in the art.

The terms "antibody" or "antigen-binding fragment," respectively, refer to intact molecules as well as functional fragments thereof, such as Fab, a scFv-Fc bivalent molecule, F(ab')$_2$, and Fv that can specifically interact with a desired target. In some cases, the antigen-binding fragments comprise:

(1) Fab, the fragment which contains a monovalent antigen-binding fragment of an antibody molecule, which can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the variable region of the light chain and the variable region of the heavy chain expressed as two chains;

(5) Single chain antibody ("SCA"), a genetically engineered molecule containing the variable region of the light chain and the variable region of the heavy chain, linked by a suitable polypeptide linker as a genetically fused single chain molecule; and (6) scFv-Fc, is produced by fusing single-chain Fv (scFv) with a hinge region from an immunoglobulin (Ig) such as an IgG, and Fc regions.

In one embodiment, an antibody provided herein is a monoclonal antibody. In one embodiment, the antigen-binding fragment provided herein is a single chain Fv (scFv), a diabody, a tandem scFv, a scFv-Fc bivalent molecule, an Fab, Fab', Fv, F(ab')$_2$ or an antigen binding scaffold (e.g., affibody, monobody, anticalin, DARPin, Knottin).

The terms "binds," "binding" or grammatical equivalents, refer to compositions, directly or indirectly, having affinity for each other. "Specific binding" refers to selective binding between two molecules. For example, specific binding occurs between an antibody and an antigen. Typically, specific binding can be distinguished from non-specific when the dissociation constant ($K_D$) is less than about $1\times10^{-5}$ M or less than about $1\times10^{-6}$ M or $1\times10^{-7}$ M. Specific binding can be detected, e.g., by ELISA, immunoprecipitation, coprecipitation, with or without chemical crosslinking, and two-hybrid assays. Use of appropriate controls can distinguish between "specific" and "non-specific" binding. "Affinity" is the strength of the binding interaction of two molecules, such as an antigen and its antibody, which is defined for antibodies and other molecules with more than one binding site as the strength of binding of the ligand at one specified binding site. Although noncovalent attachment of a ligand to an antibody or other molecule is typically not as strong as a covalent attachment, a "high affinity" ligand binds to an antibody or other molecule with an affinity constant ($K_a$) greater than $10^4$ M$^{-1}$, typically $10^5$-$10^{11}$ M$^{-1}$; as determined by inhibition ELISA or an equivalent affinity determined by comparable techniques, such as Scatchard plots or using $K_d$/dissociation constant, which is the reciprocal of the $K_a$.

The term "selective" with respect to binding, inhibition, stimulation, or modulation means preferential binding, inhibition, stimulation, or modulation, respectively, of a first activity relative to a second activity (e.g., preferential binding of one receptor to another receptor; preferential inhibition relative to other receptors; or preferential inhibition of a mutant to a wild-type or vice versa). In some cases, binding is greater than two times, greater than five times, greater than ten times, greater than fifty times, greater than 100 times, or greater than 1000 times more selective for the desired molecular target or pathway versus an undesired molecular target or pathway. In some cases, a compound will bind a first molecular target or affect a pathway by at least 2-fold, at least 5-fold, at least 10-fold, at least 20-fold, at least 50-fold, at least 100-fold relative to a second target or pathway under the same conditions. It will be appreciated that in preferred embodiments, binding to the D2-like family of dopamine receptors or a member thereof, will be selective with respect to the D1-like family of dopamine receptors or a member thereof by one of the foregoing amounts. The in vitro or in vivo activity of a molecular target or pathway may be measured by any suitable reproducible means.

The term "modulating" refers to "stimulating" or "inhibiting" an activity of a molecular target or pathway. For example, a composition modulates the activity of a molecular target or pathway if it stimulates or inhibits that activity by at least 10%, at least about 20%, at least about 25%, at least about 30%, at least about 40%, at least about 50%, at least about 60%, at least about 70%, at least about 75%, at least about 80%, at least about 90%, at least about 95%, at least about 98%, or about 99% or more relative to the activity of that molecular target or pathway under the same conditions but lacking the presence of the composition. In another example, a composition modulates the activity of a molecular target or pathway if it stimulates or inhibits that activity by at least 2-fold, at least 5-fold, at least 10-fold, at least 20-fold, at least 50-fold, at least 100-fold relative to the activity of that target or pathway under the same conditions but lacking the presence of the composition. The activity of a molecular target or pathway may be measured by any reproducible means. For example, the activity of a molecular target or pathway may be measured in vitro or in vivo by a suitable assay known in the art for measuring the activity. Control samples (untreated with the composition) can be assigned a relative activity value of 100%.

In one embodiment, an antibody, antigen-binding fragment, or affinity tag binds its target with a $K_D$ of 0.1 nM-10 mM, 0.1 nM-1 mM, or within the 0.1 nM range. In one embodiment, an antibody, antigen-binding fragment, or affinity tag binds its target with a $K_D$ of 0.1-2 nM, 0.1-1 nM, 0.05-1 nM, 0.1-0.5 nM, or 0.1-0.2 nM. In one embodiment, an antibody, antigen-binding fragment, or affinity tag bind its target directly. In one embodiment, an antibody, antigen-binding fragment, or affinity tag bind its target indirectly, for example, binding as a secondary antibody that binds to an antibody bound to the target.

The word "label" refers to a compound or composition which is conjugated or fused directly or indirectly to a reagent such as a nucleic acid probe or an antibody and facilitates detection of the reagent to which it is conjugated or fused. The label may itself be detectable (e.g., radioisotopes or fluorescent labels) or, in the case of an enzymatic label, may catalyze chemical alteration of a substrate compound or composition, which is detectable.

The term "probe" refers to synthetic or biologically produced nucleic acids that contain specific nucleotide sequences which hybridize under stringent conditions to target nucleic acid sequences. The terms "labeled probe," "nucleic acid probe operably linked to a detectable label," or "nucleic acid strand operably linked to a detectable label" refer to a probe which is prepared with a marker group or "detectable label" for detection. The marker group is attached at either the 5' end, the 3' end, internally, or a combination thereof. That is, one probe may be attached to multiple markers. A preferred group is an identifying label such as a fluorophore. A labeled probe may also comprise a plurality of different nucleic acid sequences each labeled with one or more markers. Each marker may be the same or different. It may be beneficial to label different probes (e.g., nucleic acid sequences) each with a different marker. This can be achieved by having a single distinguishable group on each probe. For example, probe A is attached to group X and probe B is attached to group Y. Alternatively, probe A is attached to groups X and Y while probe B is attached to groups Z and W. Alternatively, probe A is attached to groups X and Y, while probe B is attached to groups Y and Z. All probes "A" and "B" above would be distinguishable and uniquely labeled.

By "tissue sample" is meant a collection of similar cells obtained from tissue of a subject or patient, preferably containing nucleated cells with chromosomal material. The four main human tissues are (1) epithelium; (2) connective tissues, including blood vessels, bone and cartilage; (3) muscle tissue; and (4) nerve tissue. A tissue sample source may be solid tissue as from a fresh, frozen and/or preserved organ or tissue sample or biopsy or aspirate; blood or a blood constituent; bodily fluids such as cerebral spinal fluid, amniotic fluid, peritoneal fluid, or interstitial fluid; cells from a time in gestation or development of the subject. A tissue sample may be primary or cultured cells or cell lines. A tissue sample may contain compounds that are not naturally intermixed with the tissue in nature such as preservatives, anticoagulants, buffers, fixatives, nutrients, or antibiotics. By a tissue sample "section" is meant a single part or piece of a tissue sample, e.g., a thin slice of tissue or cells cut from a tissue sample. Multiple sections of tissue samples may be taken and subjected to analysis. A "cell line" refers to a permanently established cell culture that will proliferate given appropriate fresh medium and space.

Detection Methods

In various aspects, provided herein are methods of detecting or measuring a target receptor (e.g., a dopamine receptor or a GPCR) in a biological sample. Targets are detected by contacting a sample with a target detection reagent, e.g., an antibody or fragment thereof, and a labeling reagent. The presence or absence of targets are detected by the presence or absence of the labeling reagent. In some cases, a sample is contacted with the target detection and the labeling reagents concurrently e.g., the detection reagent is a primary antibody and the labeling reagent is a fluorescent dye conjugated to it. Alternatively, the biological sample is contacted with the target detection and labeling reagents sequentially, e.g., the detection reagent is a primary antibody and the labeling reagent includes a secondary antibody. For example, a sample is incubated with a detection reagent, in some cases together with a labeling reagent, under conditions that allow a complex between the detection reagent (and labeling reagent) and target to form. After complex formation the sample is optionally washed one or more times to remove unbound detection reagent (and labeling reagent). When the sample is further contacted with a labeling reagent that specifically binds the detection reagent bound to the target, the sample can optionally be washed one or more times to remove unbound labeling reagent. The presence or absence of the target in the sample is then determined by detecting the labeling reagent.

The methods described here provide for detecting multiple targets in a sample. Multiple targets are identified by contacting the biological sample with additional detection reagents followed by additional labeling reagent specific for the additional detection reagents using the methods described.

A detection moiety, i.e., detectable label, is a substance used to facilitate identification and/or quantitation of a target. Detection moieties are directly observed or measured or indirectly observed or measured. Non-limiting examples of detection moieties include radiolabels that can be measured with radiation-counting devices; pigments, dyes or other chromogens that can be visually observed or measured with a spectrophotometer; spin labels that can be measured with a spin label analyzer; and fluorescent moieties, where the output signal is generated by the excitation of a suitable molecular adduct and can be visualized by excitation with light that is absorbed by the dye or can be measured with standard fluorometers or imaging systems. A detection moiety can be a luminescent substance such as a phosphor or fluorogen; a bioluminescent substance; a chemiluminescent substance, where the output signal is generated by chemical modification of the signal compound; a metal-containing substance; or an enzyme, where an enzyme-dependent secondary generation of signal occurs, such as formation of a colored product from a colorless substrate. The detection moiety may also take the form of a chemical or biochemical, or an inert particle, including colloidal gold, microspheres, quantum dots, or inorganic crystals, such as nanocrystals or phosphors. The term "detection moiety" or "detectable label" can also refer to a "tag" or hapten that can bind selectively to a labeled molecule, such that the labeled molecule, when added subsequently, is used to generate a detectable signal. For instance, one can use biotin, iminobiotin or desthiobiotin as a tag and then use an avidin or streptavidin conjugate of horseradish peroxidase (HRP) to bind to the tag, and then use a chromogenic substrate (e.g., tetramethylbenzidine) or a fluorogenic substrate, such as Amplex Red or Amplex Gold (Molecular Probes, Inc.) to detect the presence of HRP. Similarly, the tag can be a hapten or antigen (e.g., digoxigenin), and an enzymatically, fluorescently, or radioactively labeled antibody can be used to bind to the tag. Numerous labels are known by those of skill in the art and non-limiting examples include particles, fluorescent dyes, haptens, enzymes and their chromogenic, fluorogenic, and chemiluminescent substrates.

A fluorophore is a chemical group that exhibits an absorption maximum beyond 280 nm, and when covalently attached in a labeling reagent retains its spectral properties. Fluorophores include pyrene, anthracene, naphthalene, acridine, stilbene, indole or benzindole, oxazole or benzoxazole, thiazole or benzothiazole, porphyrin, cyanine, perylene, 4-amino-7-nitrobenz-2-oxa-1,3-diazole (NBD), carbocyanine, carbostyryl, salicylate, anthranilate, azulene, pyridine, quinoline, borapolyazaindacene, xanthene, oxazine or benzoxazine, carbazine, phenalenone, coumarin, benzofuran and benzphenalenone and derivatives thereof. Oxazines include resorufins, aminooxazinones, diaminooxazines, and their benzo-substituted analogs.

For a xanthene fluorophore, the fluorophore may be a fluorescein, a rhodol, or a rhodamine. Fluorescein includes benzo- or dibenzofluoresceins, seminaphthofluoresceins, or naphthofluoresceins. Similarly, rhodol includes seminaphthorhodafluors. Alternatively, the fluorophore is a xanthene that is bound via a single covalent bond at the 9-position of the xanthene. Preferred xanthenes include derivatives of 3H-xanthen-6-ol-3-one, 6-amino-3H-xanthen-3-one, or of 6-amino-3H-xanthen-3-imine. Fluorophores include xanthene (rhodol, rhodamine, fluorescein and derivatives thereof) coumarin, cyanine, pyrene, oxazine and borapolyazaindacene. In addition, the fluorophore can be sulfonated xanthenes, fluorinated xanthenes, sulfonated coumarins, fluorinated coumarins and sulfonated cyanines. The choice of fluorophore in the labeling reagent will determine the absorption and fluorescence emission properties of the labeling reagent. Physical properties of a fluorophore label include spectral characteristics (absorption, emission and stokes shift), fluorescence intensity, lifetime, polarization and photo-bleaching rate can all be used to distinguish one fluorophore from another.

Typically, a fluorophore contains one or more aromatic or heteroaromatic rings that are optionally substituted by one or more substituents, including halogen, nitro, cyano, alkyl, perfluoroalkyl, alkoxy, alkenyl, alkynyl, cycloalkyl, arylalkyl, acyl, aryl or heteroaryl ring system, benzo, or other substituents typically found on fluorophores known in the art.

Preferably, the detection moiety is a fluorescent dye. Fluorescent dyes include, for example, Fluorescein, Rhodamine, Texas Red, Cy2, Cy3, Cy5, Cy0, Cy0.5, Cy1, Cy1.5, Cy3.5, Cy7, VECTOR Red, ELF™ (Enzyme-Labeled Fluorescence), FluorX, Calcein, Calcein-AM, CRYPTOFLUOR™'S, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-(6-(7-nitrobenz-2-oxa-1,3-diazol-4-yl)amino)caproyl) (NBD), BODIPY™, boron dipyrromethene difluoride, Oregon Green, MITOTRACKER™ Red, DiOC7 (3), DilC18, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Tyrosine and Tryptophan. Many fluorophores can also function as chromophores and thus they are also preferred chromophores.

In addition to fluorophores, enzymes also find use as detectable moieties. Enzymes are desirable detectable moieties because amplification of a detectable signal can be achieved resulting in increased assay sensitivity. The enzyme itself does not produce a detectable response but breaks down a substrate when it is contacted by an appropriate substrate such that the converted substrate produces a fluorescent, colorimetric or luminescent signal. Enzymes amplify a detectable signal because one enzyme on a labeling reagent can result in multiple substrates being converted to a detectable signal. This is advantageous where there is a low quantity of target present in the sample or a fluorophore does not exist that will give comparable or stronger signal than the enzyme. However, fluorophores are preferred because they do not require additional assay steps, and thus reduce the overall time to complete an assay. The enzyme substrate is selected to yield the preferred measurable product, e.g. colorimetric, fluorescent or chemiluminescence. Such substrates are extensively used in the art.

A preferred colorimetric or fluorogenic substrate and enzyme combination uses oxidoreductases, such as horseradish peroxidase and a substrate such as 3,3'-diaminobenzidine (DAB) and 3-amino-9-ethylcarbazol-e (AEC), which yield a distinguishing color (brown and red, respectively). Other non-limiting examples of colorimetric oxidoreductase substrates that yield detectable products include: 2,2-azinobis(3-ethylbenzothiaz-oline-6-sulfonic acid) (ABTS), o-phenylenediamine (OPD), 3,3',5,5'-tetramethylbenzidine (TMB), o-dianisidine, 5-aminosalicylic acid, 4-chloro-1-naphthol. Non-limiting examples of fluorogenic substrates include: homovanillic acid or 4-hydroxy-3-methoxyphenylacetic acid, reduced phenoxazines and reduced benzothiazines, including Amplexe Red reagent and its variants and reduced dihydroxanthenes, including dihydrofluoresceins and dihydrorhodamines including dihydrorhodamine 123. Peroxidase substrates that are tyramides represent a class of peroxidase substrates that can be intrinsically detectable before action of the enzyme but are "fixed in place" by the action of a peroxidase in the process described as tyramide signal amplification (TSA). These substrates are extensively utilized to label targets in samples that are cells, tissues or arrays for their subsequent detection by microscopy, flow cytometry, optical scanning and fluorometry.

Additional colorimetric (and in some cases fluorogenic) substrate and enzyme combinations use a phosphatase enzyme such as an acid phosphatase, an alkaline phosphatase or a recombinant version of such a phosphatase in combination with a colorimetric substrate such as 5-bromo-6-chloro-3-indolyl phosphate (BCIP), 6-chloro-3-indolyl phosphate, 5-bromo-6-chloro-3-indolyl phosphate, p-nitrophenyl phosphate, or o-nitrophenyl phosphate or with a fluorogenic substrate such as 4-methylumbelliferyl phosphate, 6,8-difluoro-7-hydroxy4-methylcoumarinyl phosphate (DiFMUP) fluorescein diphosphate, 3-0-methylfluorescein phosphate, resorufin phosphate, 9H-(1,3-dichloro-9, 9-dimethylacridin-2-one-7-yl) phosphate (DDAO phosphate), or ELF 97, ELF 39 or related phosphates.

Glycosidases, in particular β-galactosidase, β-glucuronidase and β-glucosidase, are additional suitable enzymes. Non-limiting examples of appropriate colorimetric substrates include: 5-bromo4-chloro-3-indolyl β-D-galactopyranoside (X-gal) and similar indolyl galactosides, glucosides, and glucuronides, o-nitrophenyl β-D-galactopyranoside (ONPG) and p-nitrophenyl β-D-galactopyranoside. Preferred fluorogenic substrates include resorufin β-D-galactopyranoside, fluorescein digalactoside (FDG), fluorescein diglucuronide and their structural variants, 4-methylumbelliferyl β-D-galactopyranoside, carboxyumbelliferyl β-D-galactopyranoside and fluorinated coumarin β-D-galactopyranosides. Additional enzymes include hydrolases, such as cholinesterases and peptidases; oxidases, such as glucose oxidase; and cytochrome oxidases and reductases for which suitable substrates are known.

Enzymes and their substrates that produce chemiluminescence are preferred for some assays. These include, for example, natural and recombinant forms of luciferases and aequorins. Chemiluminescence-producing substrates for phosphatases, glycosidases and oxidases such as those containing stable dioxetanes, luminol, isoluminol and acridinium esters are additionally useful. For example, the enzyme is luciferase or aequorin, and the substrates are luciferine, ATP, $Ca^{++}$ and coelenterazine.

In addition to enzymes, haptens such as biotin are useful detectable moieties. Biotin is useful as it is in an enzyme system that can further amplify a detectable signal, and it can serve as a tag in affinity chromatography for isolation purposes. For detection, an enzyme conjugate that has affinity for biotin is used, such as avidin-HRP. Subsequently, a peroxidase substrate is added to produce a detectable signal. Haptens also include hormones, naturally occurring and synthetic drugs, pollutants, allergens, affector molecules, growth factors, chemokines, cytokines, lymphokines, amino acids, peptides, chemical intermediates, or nucleotides.

In some cases, a detectable moiety is a fluorescent protein. Exemplary fluorescent proteins include green fluorescent protein (GFP), phycobiliproteins and their derivatives, luciferase or aequorin. Fluorescent proteins, especially phycobiliprotein, are particularly useful for creating tandem dye labeled labeling reagents. These tandem dyes comprise a fluorescent protein and a fluorophore to obtain a larger stokes shift where the emission spectra is farther shifted from the fluorescent protein's absorption spectra. This is particularly advantageous to detect a low amount of target in a sample where the emitted fluorescent light is maximally optimized, in other words the fluorescent protein reabsorbs little to none of the emitted light. The fluorescent protein and fluorophore function as an energy transfer pair where the fluorescent protein emits at a wavelength the fluorophore absorbs, and the fluorphore then emits at a wavelength farther from the fluorescent protein than could be obtained with only the fluorescent protein. A particularly useful combination is phycobiliproteins and sulforhodamine fluorophores, or sulfonated cyanine fluorophores; or sulfonated xanthene derivatives. Alternatively, the fluorophore is an energy donor and the fluorescent protein is an energy acceptor.

Methods of Visualizing the Detection Moiety Depend on the Label.

In some cases, a sample is illuminated with a light wavelength selected to give a detectable optical response, and observed with a means for detecting that response. Equipment useful for illuminating fluorescent compounds include hand-held ultraviolet lamps, mercury arc lamps, xenon lamps, lasers and laser diodes. These illumination sources are optically integrated into laser scanners, fluorescent microplate readers or standard or microfluorometers. The degree or location of signal, compared to a standard or expected response, indicates whether and to what degree the sample possesses a given characteristic or desired target.

An optical response is detected by visual inspection, or by using one of the following devices: CCD camera, video camera, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. When a sample is examined using a flow cytometer, examination of it optionally includes sorting portions of it according to their fluorescence response.

When an indirectly detectable label is used, then illuminating typically includes adding a reagent to produce a detectable signal such as a colorimetric enzyme substrate. Radioisotopes are also considered indirectly detectable where an additional reagent is not needed, rather the radioisotope is exposed to X-ray film or other mechanism to record and measure the signal. This is true for some chemiluminescent signals that are observed after exposure to film.

I. ONC201 (COMPOUND (1)), SALTS THEREOF AND SYNTHESES THEREOF

ONC201 (compound (1))

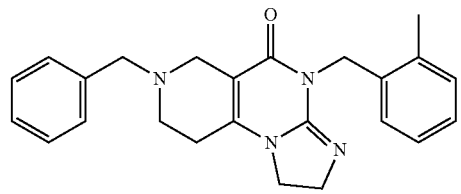 [SMILES: Cc1ccccc1CN1C(=O)C2=C(CCN(Cc3ccccc3)C2)N2CCN=C12]

and its analogs, and their pharmaceutically acceptable salts, as well as syntheses for them, are provided herein. In in vitro models, animal models, and human clinical trials, ONC201 has broad anti-cancer activity, low toxicity including few, if any, adverse effects, low genotoxicity, and high bioavailability including orally. These features allow ONC 201 and various analogs to be well suited for a variety of applications. ONC201 can be synthesized as shown in Scheme 1.

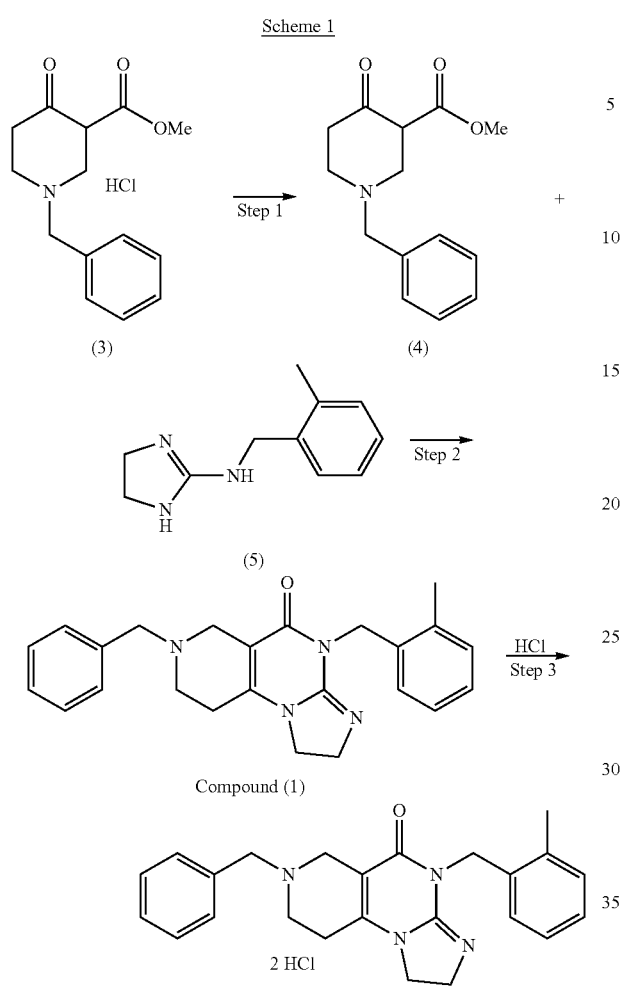

Scheme 1

Compound (1)

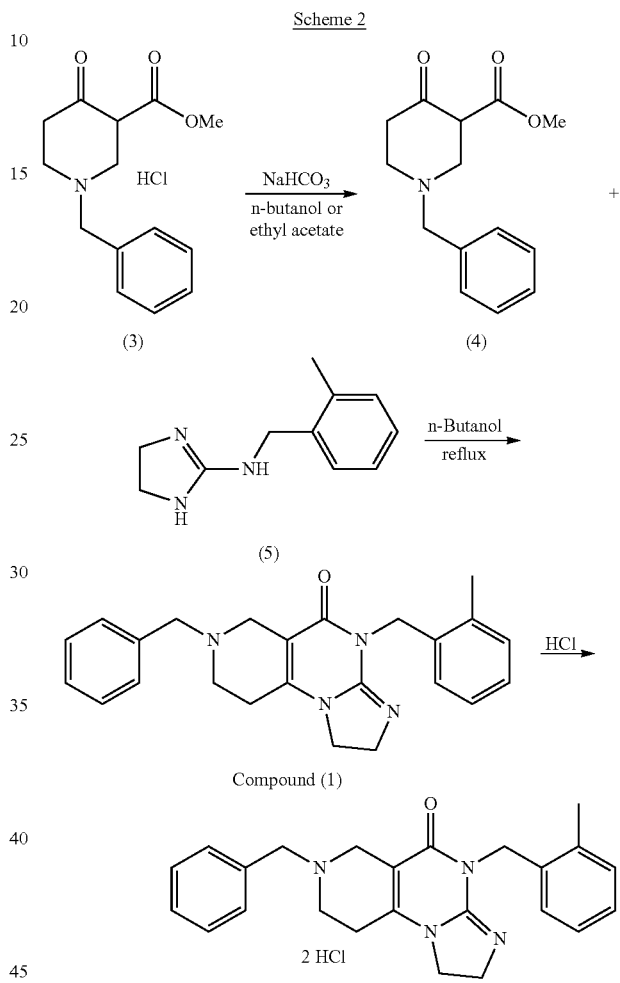

Scheme 2

Compound (1)

Synthesis of an ONC201 dihydrochloride salt starts with commercially available intermediary N-Benzyl-3-carbomethoxy-4-piperidone hydrochloride, compound (3). In some embodiments, the synthesis includes neutralizing compound (3) with a base (Step 1) to produce compound (4), a free base. For example, compound (3) is neutralized with an inorganic base to produce compound (4). Alternatively, compound (3) is neutralized with an organic base to produce compound (4). In some embodiments, compound (3) is neutralized in the presence of an alcohol, for example, n-butanol. In some embodiments, compound (3) is neutralized in the presence of at least one organic solvent (e.g., n-butanol, ethyl acetate or both). In some embodiments, compound (3) is neutralized in the presence of a base and at least one organic solvent (e.g., NaHCO$_3$ and n-butanol). In one embodiment, compound (3) is neutralized in the presence of n-butanol and triethyl amine (Et$_3$N).

In some embodiments, the synthesis includes reacting compounds (4) with (5) (Step 2) to produce intermediary compound (1). In some embodiments, Step 2 includes heating compounds (4) with (5). In some embodiments, Step 2 includes refluxing heating compounds (4) with (5) in the presence of a solvent. In some embodiments, Step 2 includes use of Dean-stark trap to remove water and/or methanol (MeOH) formed in the reaction.

In some embodiments, an ONC201 dihydrochloride salt is synthesized (Step 3). In some embodiments, Step 3 includes treating ONC201 with HCl in dioxane. In some embodiments, Step 3 includes treating ONC201 with 4N HCl in dioxane. In some embodiments, the synthesis optionally includes recrystallizing the ONC201 di-salt. Preferably, the ONC201 di-hydrochloride salt is synthesized as shown in Scheme 2.

II. TNF-RELATED APOPTOSIS-INDUCING LIGAND ("TRAIL")

TRAIL protein can be assayed in a sample obtained from a subject to detect TRAIL expression induced by compounds and their salts described herein. Immunoassays can be used to assay TRAIL, including enzyme-linked immunosorbent assay (ELISA), enzyme-linked immunofiltration assay (ELIFA), flow cytometry, immunoblot, immunoprecipitation, immunohistochemistry, immunocytochemistry, luminescent immunoassay (LIA), fluorescent immunoassay (FIA), and radioimmunoassay. Qualitative and/or quantitative results may be obtained. Suitable methods for qualitative and quantitative assays are described in standard references, including Harlow & Lane, Antibodies: A Laboratory Manual, Cold Spring Harbor Laboratory Press, 1988; Breitling & Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; B. K. C. Lo, Antibody Engineering: Methods and Protocols, Methods in Molecular Biology, Humana Press, 2003; Ausubel et al., Eds., Short Protocols in Molecular Biology, Current Protocols, Wiley, 2002; S. Klussman, Ed., The Aptamer Handbook: Functional Oligonucleotides and Their Applications, Wiley, 2006; Ormerod, M. G., Flow Cytometry: a practical approach, Oxford University Press, 2000; Givan, A. L., Flow Cytometry: first principles, Wiley, New York, 2001; Gorczyca, W., Flow Cytometry in Neoplastic Hematology: morphologic-immunophenotypic correlation, Taylor & Francis, 2006; Crowther, J. R., The ELISA Guidebook (Methods in Molecular Biology), Humana Press, 2000; Wild, D., The Immunoassay Handbook, 3$^{rd}$ Edition, Elsevier Science, 2005; and Sambrook & Russell, Molecular Cloning: A Laboratory Manual, Cold Spring Harbor Laboratory Press, 3$^{rd}$ ed., 2001.

Assays to analyze a sample for TRAIL to detect an effect of a pharmaceutical composition are described in U.S. Pat. No. 8,673,923, incorporated by reference herein in its entirety.

In some embodiments, TRAIL assays are used to monitor a subject. For example, a sample is obtained from a subject before treatment with a pharmaceutical agent and at one or more times during and/or following treatment to assess treatment effectiveness. In another example, a sample is obtained from a subject at various times to assess the course or progress of disease or healing. In one embodiment, death receptors from circulating tumor cells are assayed to see if a treatment described here increases the amount or type of death receptors.

Cancers treated using methods and compositions described herein are characterized by abnormal cell proliferation including pre-neoplastic hyperproliferation, cancer in-situ, neoplasms and metastasis. Methods and compositions described herein can be used for prophylaxis, as well as amelioration of cancer signs or symptoms. Cancer"treatment" in a subject includes: preventing, inhibiting or ameliorating cancer in the subject, such as slowing cancer progression or reducing or ameliorating a cancer sign or symptom. Examples of cancers treated using methods and compositions described herein include breast cancer, CNS cancers, colon cancer, ovarian cancer, prostate cancer, leukemia, lung cancer, and lymphoma.

III. COMPOUNDS OF FORMULA (10) AND SALTS THEREOF

In one aspect, provided herein are compounds and salts of formula (10) and methods of making them. Those skilled in the art will understand that the general principles and concepts described here in conjunction with ONC201 (compound (1)) and its salts, including principles and concepts related to methods and pharmaceutical compositions, apply with equal force to compounds of formula (10) and salts thereof.

In one embodiment, provided herein are compounds of formula (10):

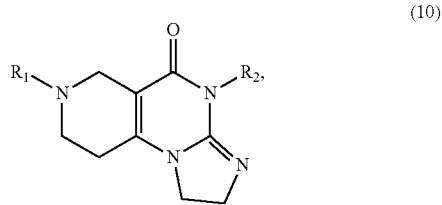

(10)

wherein $R_1$ and $R_2$ are independently selected from H, alkyl, aryl, cycloalkyl, cycloalkylalkyl, heterocycloalkyl, heterocycloalkylalkyl, heteroaryl, arylalkyl, heteroarylalkyl, alkoxyalkyl, alkoxycarbonyl, aralkoxy, aralkylthio, and acyl radicals. In one embodiment, $R_1$ is $CH_2Ph$ and $R_2$ is $CH_2$-(2-$CH_3$-Ph) (ONC201). In one embodiment, $R_1$ is $CH_2Ph$ and $R_2$ is $CH_2$-(2,4-di F-Ph) (ONC206). In one embodiment, $R_1$ is $CH_2Ph$ and $R_2$ is $CH_2$-(4-$CF_3$-Ph) (ONC212). In one embodiment, $R_1$ is $CH_2Ph$ and $R_2$ is $CH_2$-(3,4-di F-Ph) (ONC213). In one embodiment, $R_1$ is $CH_2$-(3,4-di-Cl-Ph) and $R_2$ is $CH_2$-(4-$CF_3$-Ph) (ONC234). In one embodiment, $R_1$ is $CH_2$-3-thienyl and $R_2$ is $CH_2$-(4-$CF_3$-Ph) (ONC236).

In one embodiment, $R_1$ and $R_2$ are independently selected from H, $C_{1-4}$alkyl, $C_{1-4}$alkylphenyl, $C_{1-4}$alkylphenylketone, $C_{1-4}$benzyl-piperazine, $C_{1-4}$alkylthienyl, $C_{1-4}$alkylpyridinyl, $C_{1-4}$alkylisoxazolidinyl, $C_{1-4}$alkylmorpholinyl, $C_{1-4}$alkylthiazolyl, and $C_{1-4}$alkylpyrazinyl wherein $C_{1-4}$alkyl, $C_{1-4}$alkylphenyl, $C_{1-4}$alkylphenylketone, $C_{1-4}$benzyl-piperazine, $C_{1-4}$alkylthienyl, $C_{1-4}$alkylpyridinyl, $C_{1-4}$alkylisoxazolidinyl, $C_{1-4}$alkylthiazolyl, $C_{1-4}$alkylmorpholinyl, and $C_{1-4}$alkylpyrazinyl are optionally substituted with $C_{1-4}$alkyl, $C_{1-4}$alkoxyl, hydroxyl, perhalogenated $C_{1-4}$alkyl, or halo. In one embodiment, $R_1$ and/or $R_2$ is a substituted or unsubstituted, arylalkyl or heteroarylalkyl. In one embodiment, the heteroarylalkyl is selected from $C_{1-4}$alkylpyrrolyl, $C_{1-4}$alkylfuryl, $C_{1-4}$alkylpyridyl, $C_{1-4}$alkyl-1,2,4-thiadiazolyl, $C_{1-4}$alkylthienyl, $C_{1-4}$alkylisothiazolyl, $C_{1-4}$alkylimidazolyl, $C_{1-4}$alkyltetrazolyl, $C_{1-4}$alkylpyrazinyl, $C_{1-4}$alkylpyrimidyl, $C_{1-4}$alkylquinolyl, $C_{1-4}$alkylpyrazolyl, $C_{1-4}$alkylisoquinolyl, $C_{1-4}$alkylthiophenyl, $C_{1-4}$alkylbenzothienyl, $C_{1-4}$alkylisobenzofuryl, $C_{1-4}$alkylindolyl, $C_{1-4}$alkylpurinyl, $C_{1-4}$alkylcarbazolyl, $C_{1-4}$alkylbenzimidazolyl, and $C_{1-4}$alkylisoxazolyl.

In one embodiment, $R_1$ and/or $R_2$ is a benzyl optionally substituted with one or more of the following substituents on the benzyl ring: X, —$CH_3$, —$NO_2$, —$OCH_3$, —CN, —$CXH_2$, —$CX_2H$, $C_2$-$C_4$ alkyl, —$CX_3$, —$CH_2(CX_3)$, —$CH(CX_3)_2$, —$C(CX_3)_3$, —$C_pX_{2p+1}$, —$OCX_3$, —$OC_pH_{2p+1}$, —$OC_pX_{2p+1}$, $OR'''$, $SR'''$, $NR'''R''$, $NR'''C(O)R''$, $SOR'''$, $SO_2R'''$, $C(O)R'''$, and $C(O)OR'''$; $R'''$ and $R''$ are independently selected from H or a $C_1$-$C_4$ alkyl; and where p is an integer from 2 to 20 and X is halogen, including F, Cl, Br, or I; preferably, F, Cl, or Br; more preferably, F or Cl.

In one embodiment, $R_1$ is selected from H, $CH_3$, $CH_2Ph$, $CH_2$-(4-$CF_3$-Ph), $CH_2$-(4-F-Ph), $CH_2$-(4-Cl-Ph), $CH_2$—(O$CH_3$-Ph), $CH_2$-((2-Cl)-Ph), $CH_2$-(2-thienyl), $CH_2$-(3-thienyl), $CH_{2-2}$-pyridinyl, $CH_2$-4-methyl-2-thiazolyl, $CH_2$-2-pyrazinyl, $CH_2CH_2Ph$, $CH_2CH_2$(4-N-benzyl-piperazine), $CH_2$-(2,4-di F-Ph), $CH_2$-(3,4-di Cl-Ph), $CH_2$-(3,4-di F-Ph), $CH_2$-(3,5-di F-Ph), $CH_2$-((2-$CH_3$)-Ph), $CH_2CH(OH)Ph$, (4-F-Ph)-4-oxobutyl, CH$_2$CH$_2$NHCOOC(CH$_3$)$_3$, CH$_2$CH$_2$CH$_2$NH$_2$, and CD$_2$C$_6$D$_5$. In one embodiment, R$_2$ is selected from H, CH$_3$, CH$_2$Ph, CH$_2$-(4-CF$_3$-Ph), CH$_2$-((2-Cl)-Ph), CH$_2$-((2-F)-Ph), CH$_2$-(2-thienyl), CH$_2$CH$_2$Ph, CH$_2$CH$_2$(4-N-benzyl-piperazine), CH$_2$-(2,4-di F-Ph), CH$_2$-(2,4-di Cl-Ph), CH$_2$-(3,4-di Cl-Ph), CH$_2$-(3,4-di F-Ph), CH$_2$-(3,5-di F-Ph), CH$_2$-((2-CH$_3$)-Ph), CH$_2$(2-CH$_3$, 4-F-Ph), CH$_2$-((4-OCH$_3$)-Ph), CH$_2$-(3-pyridinyl), CH$_2$-(3-isoxazolidinyl), CH$_2$CH$_2$-(4-morpholinyl), CH$_2$-(2-F, 4-CF$_3$-Ph), CH$_2$CH(OH)Ph, (CH$_2$)$_3$CO-4F-Ph, (4-F-Ph)-4-oxobutyl, CH$_2$CH$_2$NHCOOC(CH$_3$)$_3$, CH$_2$CH$_2$CH$_2$NH$_2$, and CD$_2$C$_6$D$_5$.

In one embodiment, R$_1$ is H. In one embodiment, R$_1$ is an unsubstituted or substituted arylalkyl, e.g., a benzyl (CH$_2$Ph) or phenylethyl (CH$_2$CH$_2$Ph) group. In one embodiment, the arylalkyl is substituted with C$_{1-4}$alkyl, C$_{1-4}$alkoxyl, hydroxyl, perhalogenated C$_{1-4}$alkyl, or halo.

In one embodiment, R$_2$ is a substituted or an unsubstituted arylalkyl, e.g., benzyl or phenylethyl. In one embodiment, the arylalkyl is substituted with C$_{1-4}$alkyl, C$_{1-4}$alkoxyl, hydroxyl, perhalogenated C$_{1-4}$alkyl, or halo. In one embodiment, the arylalkyl is substituted with one or more substituents selected from halo, CH$_3$, CF$_3$ or OCH$_3$. In one embodiment, R$_2$ is a substituted or an unsubstituted heterocycloalkylalkyl, e.g., piperazinylalkyl or morpholinoalkyl. In one embodiment, R$_2$ is a substituted or an unsubstituted heteroarylalkyl, e.g., pyridylmethyl or isoxazolidinylmethyl. In one embodiment, the heterocycloalkylalkyl or heteroarylalkyl is substituted with C$_{1-4}$alkyl, C$_{1-4}$alkoxyl, hydroxyl, perhalogenated C$_{1-4}$alkyl, or halo. In one embodiment, the heterocycloalkylalkyl or heteroarylalkyl is substituted with at least one substituent selected from halo, CH$_3$, CF$_3$ or OCH$_3$.

In one embodiment, compound (10) has the structure of formula (80):

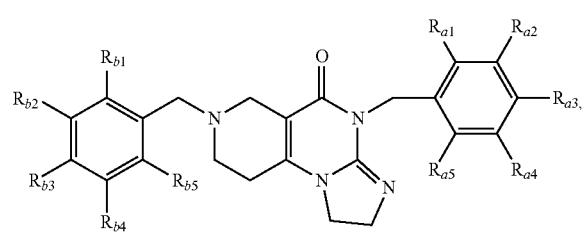

(80)

wherein R$_{a1}$, R$_{a2}$, R$_{a3}$, R$_{a4}$, R$_{a5}$, R$_{b1}$, R$_{b2}$, R$_{b3}$, R$_{b4}$, and R$_{b5}$ are each independently selected from the group consisting of H, X, —CH$_3$, —NO$_2$, —OCH$_3$, —CN, —CXH$_2$, —CX$_2$H, C$_2$-C$_4$ alkyl, —CX$_3$, —CH$_2$(CX$_3$), —CH(CX$_3$)$_2$, —C(CX$_3$)$_3$, —C$_p$X$_{2p+1}$, —OCX$_3$, —OC$_p$H$_{2p+1}$, —OC$_p$X$_{2p+1}$, OR$'''$, SR$'''$, NR$'''$R$''$, NR$'''$C(O)R$''$, SOR$'''$, SO$_2$R$'''$, C(O)R$'''$, and C(O)OR$'''$; R$'''$ and R$''$ are independently selected from H or a C$_1$-C$_4$ alkyl; and where p is an integer from 2 to 20 and X is a halogen.

In one embodiment, compound (10) has the structure of formula (90)

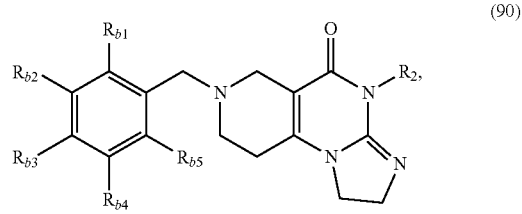

(90)

wherein R$_2$ is as defined above, and wherein R$_{b1}$, R$_{b2}$, R$_{b3}$, R$_{b4}$, and R$_{b5}$ are each independently selected from the group consisting of H, X, —CH$_3$, —NO$_2$, —OCH$_3$, —CN, —CXH$_2$, —CX$_2$H, C$_{2-4}$ alkyl, —CX$_3$, —CH$_2$(CX$_3$), —CH(CX$_3$)$_2$, —C(CX$_3$)$_3$, —C$_p$X$_{2p+1}$, —OCX$_3$, —OC$_p$H$_{2p+1}$, —OC$_p$X$_{2p+1}$, OR$'''$, SR$'''$, NR$'''$R$''$, NR$'''$C(O)R$''$, SOR$'''$, SO$_2$R$'''$, C(O)R$'''$, and C(O)OR$'''$; R$'''$ and R$''$ are independently selected from H or a C$_{1-4}$alkyl; and where p is an integer from 2 to 20 and X is a halogen.

In one embodiment, compound (10) has the structure of formula (40)

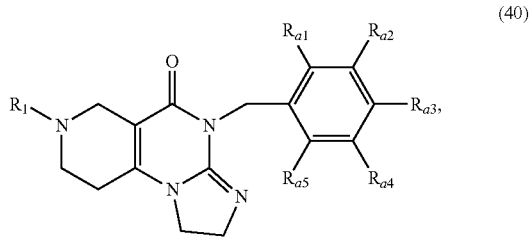

(40)

where R$_1$ is as defined above, and where R$_{a1}$, R$_{a2}$, R$_{a3}$, R$_{a4}$, and R$_{a5}$ are each independently selected from H, X, —CH$_3$, —NO$_2$, —OCH$_3$, —CN, —CXH$_2$, —CX$_2$H, C$_{2-4}$alkyl, —CX$_3$, —CH$_2$(CX$_3$), —CH(CX$_3$)$_2$, —C(CX$_3$)$_3$, —C$_p$X$_{2p+1}$, —OCX$_3$, —OC$_p$H$_{2p+1}$, —OC$_p$X$_{2p+1}$, OR$'''$, SR$'''$, NR$'''$R$''$, NR$'''$C(O)R$''$, SOR$'''$, SO$_2$R$'''$, C(O)R$'''$, and C(O)OR$'''$; R$'''$ and R$''$ are independently selected from H or a C$_{1-4}$ alkyl; p is an integer from 2 to 20; and X is a halogen. In one embodiment, R$_1$ is H. In one embodiment, R$_1$ is a substituted or unsubstituted arylalkyl, such as benzyl or phenylethyl. In one embodiment, the arylalkyl is substituted with C$_{1-4}$alkyl, C$_{1-4}$alkoxyl, hydroxyl, perhalogenated C$_{1-4}$alkyl, or halo. In one embodiment, the benzyl is substituted with one or more halo. In one embodiment, the benzyl is substituted with one or more substituents selected from halo, CH$_3$, CF$_3$, and OCH$_3$. In one embodiment, the benzyl is substituted with one halo, e.g., F at an ortho or para position. In one embodiment, the benzyl is substituted with two halogen, e.g., F at both meta positions.

In one embodiment, compound (40) has the structure of compound (45):

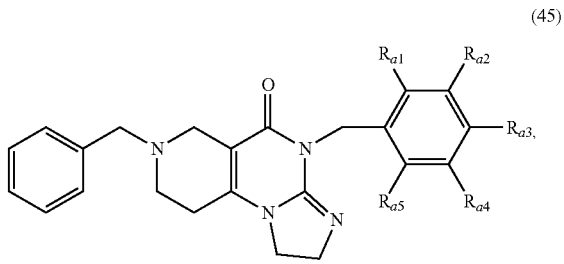

(45)

where $R_{a1}$, $R_{a2}$, $R_{a3}$, $R_{a4}$, and $R_{a5}$ are as defined above. In one embodiment, the benzyl is substituted with one or more halogens. In one embodiment, the benzyl is substituted with one or more substituents selected from halo, $CH_3$, $CF_3$, and $OCH_3$. In one embodiment, $R_{a1}$ or $R_{a5}$ is a halo, e.g., F. In one embodiment, both $R_{a2}$ and $R_{a3}$ are halo, e.g., F.

In one embodiment, compound (10) has the structure of compound (50)

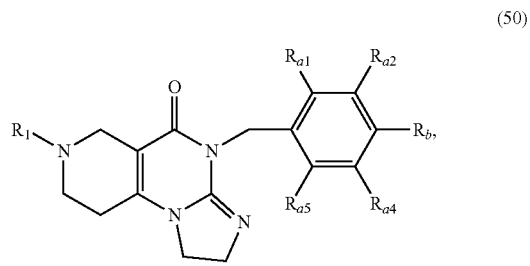

(50)

wherein $R_1$ is as defined above, and wherein Rb is selected from H, X, —$CH_3$, —$NO_2$, —$OCH_3$, —CN, —$CXH_2$, —$CX_2H$, $C_{2-4}$alkyl, —$CX_3$, —$CH_2(CX_3)$, —$CH(CX_3)_2$, —$C(CX_3)_3$, —$C_pX_{2p+1}$, —$OCX_3$, —$OC_pH_{2p+1}$, —$OC_pX_{2p+1}$, $OR'''$, $SR'''$, $NR'''R''$, $NR'''C(O)R''$, $SOR'''$, $SO_2R'''$, $C(O)R'''$, and $C(O)OR'''$; $R'''$ and $R''$ are independently selected from H or $C_{1-4}$alkyl; and where p is an integer from 2 to 20 and X is a halogen, and wherein $R_{a1}$, $R_{a2}$, $R_{a4}$, and $R_{a5}$ are each independently selected from H, X, —$CH_3$, —$NO_2$, —$OCH_3$, —CN, —$CXH_2$, —$CX_2H$, $C_{2-4}$alkyl, —$CX_3$, —$CH_2(CX_3)$, —$CH(CX_3)_2$, —$C(CX_3)_3$, —$C_pX_{2p+1}$, —$OCX_3$, —$OC_pH_{2p+1}$, —$OC_pX_{2p+1}$, $OR'''$, $SR'''$, $NR'''R''$, $NR'''C(O)R''$, $SOR'''$, $SO_2R'''$, $C(O)R'''$, and $C(O)OR'''$; $R'''$ and $R''$ are independently selected from H or $C_{1-4}$alkyl; and where p is an integer from 2 to 20 and X is a halogen. In one embodiment, $R_1$ is H. In one embodiment, $R_1$ is a substituted or unsubstituted arylalkyl, such as a benzyl or phenylethyl group. In one embodiment, the arylalkyl is substituted with $C_{1-4}$alkyl, $C_{1-4}$alkoxyl, hydroxyl, perhalogenated $C_{1-4}$alkyl, or halo. In one embodiment, $R_b$ is selected from halo, $CH_3$, $CF_3$, and $OCH_3$. In one embodiment, one or more of $R_{a1}$, $R_{a2}$, $R_{a4}$, and $R_{a5}$ is selected from halo, $CH_3$, $CF_3$, and $OCH_3$. In one embodiment, $R_{a1}$, $R_{a2}$, $R_{a4}$, and $R_{a5}$ are H, and $R_b$ is selected from halo, $CH_3$, $CF_3$, and $OCH_3$. In one embodiment, $R_b$ is halogen, e.g., F, and $R_{a1}$ is $CH_3$. In one embodiment, $R_b$ is F or Cl, and $R_{a2}$ is F or Cl. In one embodiment, $R_b$ is $CF_3$. In one embodiment, $R_b$ is $OCH_3$. In one embodiment, $R_b$ and $R_{a1}$ are Cl.

In one embodiment, compound (50) has the structure of compound (55):

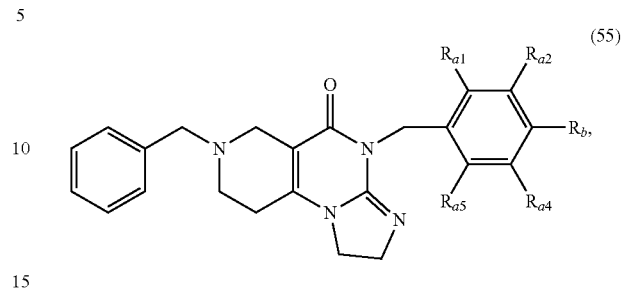

(55)

where $R_{a1}$, $R_{a2}$, $R_{a4}$, $R_{a5}$, and $R_b$ are as defined above. In one embodiment, $R_b$ is selected from halo, $CH_3$, $CF_3$, and $OCH_3$. In one embodiment, one or more of $R_{a1}$, $R_{a2}$, $R_{a4}$, and $R_{a5}$ is selected from halo, $CH_3$, $CF_3$, and $OCH_3$. In one embodiment, $R_{a1}$, $R_{a2}$, $R_{a4}$, and $R_{a5}$ are H, and $R_b$ is selected from halo, $CH_3$, $CF_3$, and $OCH_3$. In one embodiment, $R_b$ is halo, e.g., F, and $R_{a1}$ is $CH_3$. In one embodiment, $R_b$ is F or Cl, and $R_{a2}$ is F or Cl. In one embodiment, $R_b$ is $CF_3$. In one embodiment, $R_b$ is $OCH_3$. In one embodiment, $R_b$ and $R_{a1}$ are Cl.

In one embodiment, compound (10) has the structure of compound (60)

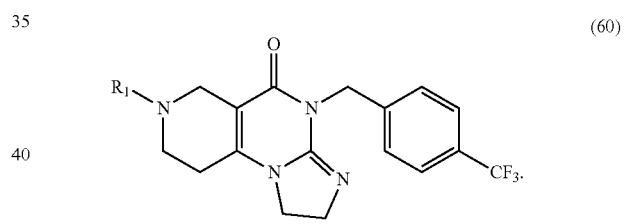

(60)

In one embodiment, $R_1$ is H. In one embodiment, $R_1$ is a substituted or unsubstituted arylalkyl, such as benzyl or phenylethyl. In one embodiment, $R_1$ is a substituted or unsubstituted heterocycloalkylalkyl or a substituted or unsubstituted heteroarylalkyl, such as $CH_2$-(2-thienyl), $CH_2$-(3-thienyl), $CH_2$-4-methyl-2-thiazolyl, $CH_2$-2-pyrazinyl, $CH_2CH_2$(4-N-benzyl-piperazine), $CH_2$-(3-isoxazolidinyl), $CH_2$-2-pyridinyl, $CH_2$-3-pyridinyl, and $CH_2CH_2$-(4-morpholinyl). In one embodiment, the arylalkyl is substituted with $C_{1-4}$alkyl, $C_{1-4}$alkoxyl, hydroxyl, perhalogenated $C_{1-4}$alkyl, or halo. In one embodiment, the benzyl is substituted with one or more halogens. In one embodiment, the benzyl is substituted with one or more substituents selected from halo (e.g., F), $CH_3$, $CF_3$, and $OCH_3$. In one embodiment, the benzyl is substituted at the para position with a halo, $CH_3$, $CF_3$, or $OCH_3$ substituent. In one embodiment, $R_1$ is fluorophenyloxobutyl or hydroxyphenylethyl.

Scheme 3

Scheme 3 illustrates the synthesis of compounds of formula (10):

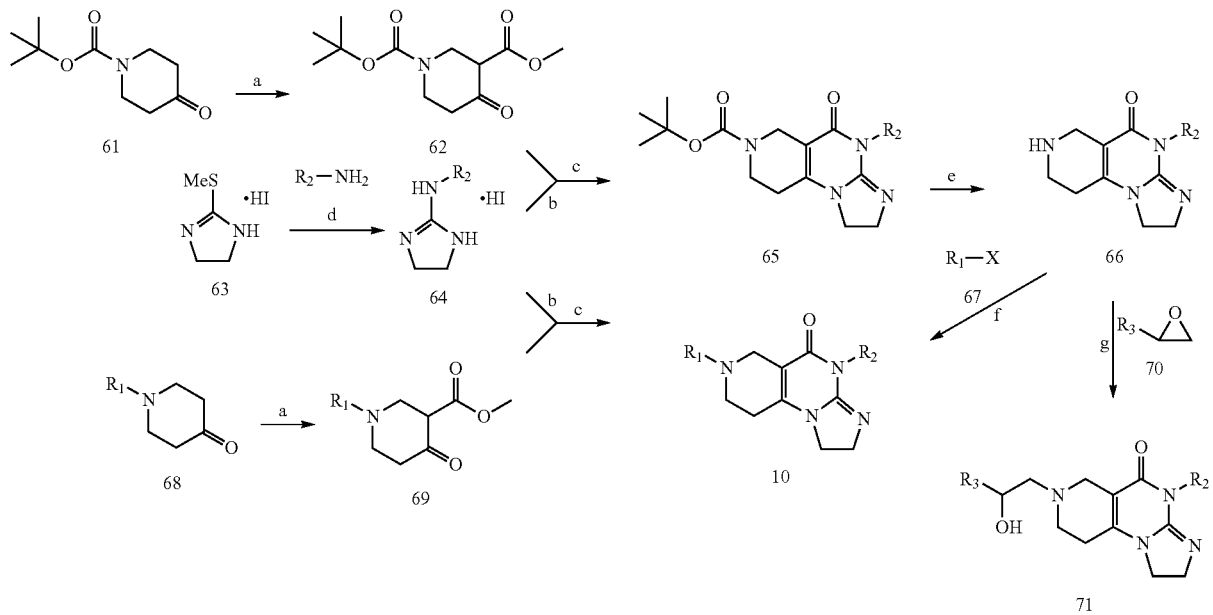

Methods: a. NaH, dimethyl carbonate, toluene, 80° C. 4 h; b. 1N NaOH/CH$_2$Cl$_2$ to convert to free base, then heat in dioxane 70° C.; c. 1-butanol/reflux 3-6 h (Dean-Stark trap) PPTS; d. dioxane 70° C.; e. HCl in dioxane -25° C.-RT to give HCl salt; f. Na$_2$CO$_3$, DIEA 80° C.; g. NaOH/CH$_2$Cl$_2$ to make free base, then MeOH reflux, 3.5 h Compounds of formula (10) (imipridones) are synthesized starting from a substituted piperidone, which is converted by reaction with a substituted aminoimidazoline to give the core compound (10). There are two routes, one in which the $R_1$ substituent is present in the piperidone (e.g., 68). In that route, (68) is acylated with dimethyl carbonate using sodium hydride in toluene at 80° C. to form piperidone ester (69). Commercially available methylthioimidazoline HI salt (63) is reacted with an amine in dioxane at 70° C. to afford the $R_2$-substituted aminoimidazoline (64) as its HI salt. Direct reaction of (64) with piperidone ester (69) in 1-butanol at reflux with removal of water via a Dean-Stark trap over 3-6 h gives the tricyclic compound (10). In a variant of this scheme, N—BOC protected piperidone (61) is converted by the same methods to BOC protected compound (65), which is treated with HCl in dioxane to remove the BOC group and then converted to the free base of (66) with 1N NaOH with extraction with methylene chloride. Subsequent treatment of (66) with a halide (67) or epoxide (70) affords desired compound (10).

Crude products may be purified by column chromatography eluting with methylene chloride:methanol or by HPLC using acetonitrile:TFA:H$_2$O to produce either free bases or TFA salts as final products. Treatment of free bases with HCl in dioxane or lyophilization of TFA salts generates products (10) as HCl or TFA salts. Alternatively, the free base may be treated with another inorganic or organic acid to form other salts, generally selected from those known to be pharmaceutically acceptable. Salts of compound (10) are usually solids and examples have been crystallized from ethanol or other solvents to give high quality crystals. The tricyclic structure of compound (1) has been definitively confirmed by an X-ray crystal structure and NMR.

Compounds described herein can be used, with or without an aminoalkyl linker (e.g., compound (33)), to identify molecules (e.g., proteins) that interact with them in a cellular context. Expression of these binding targets may be used to predict response to imipridones or analogs thereof (i.e. serve as biomarkers). These compounds can also be used to screen for structurally unrelated molecules using competition assays known in the art to identify drugs able to outcompete the target interaction with a higher affinity. In addition, these molecules may have improved drug properties or allow additional applications by altering drug properties including safety, potency, pharmacokinetics, biodistribution, or metabolism.

TABLE 1

EXAMPLES OF COMPOUNDS OF FORMULA (10)

| No. | ONC Number | $R_1$ | $R_2$ |
|---|---|---|---|
| 1 | ONC201 | CH$_2$Ph | CH$_2$-((2-CH$_3$)—Ph) |
| 13 |  | CH$_2$Ph | CH$_3$ |
| 14 | ONC202 | CH$_2$Ph | CH$_2$-((2-Cl)—Ph) |
| 15 | ONC203 | CH$_2$Ph | CH$_2$-(2-thienyl) |
| 16 | ONC204 | CH$_2$Ph | CH$_2$CH$_2$Ph |

TABLE 1-continued

EXAMPLES OF COMPOUNDS OF FORMULA (10)

| No. | ONC Number | $R_1$ | $R_2$ |
|---|---|---|---|
| 17 | ONC205 | $CH_2Ph$ | $CH_2CH_2$(4-N-benzyl-piperazine) |
| 18 | ONC206 | $CH_2Ph$ | $CH_2$-(2,4-di F—Ph) |
| 19 | ONC207 | H | $CH_2$-((2-$CH_3$)—Ph) |
| 20 | ONC208 | $CH_3$ | $CH_2$-((2-$CH_3$)—Ph) |
| 21 | ONC209 | $CH_2CH_2Ph$ | $CH_2$-((2-$CH_3$)—Ph) |
| 22 | | $CH_2CH_2$-(4-N-benzyl-piperizine) | $CH_2$-((2-$CH_3$)—Ph) |
| 23 | | $CH_2CHOHPh$ | $CH_2$-((2-$CH_3$)—Ph) |
| 24 | | $(CH_2)_3CO$—4F—Ph | $CH_2$-((2-$CH_3$)—Ph) |
| 32 | ONC215 | $CH_2CH_2NHCOOC(CH_3)_3$ | $CH_2$-((2-$CH_3$)—Ph) |
| 33 | ONC216 | $CH_2CH_2CH_2NH_2$ | $CH_2$-((2-$CH_3$)—Ph) |
| 41 | ONC210 | $CH_2Ph$ | $CH_2$-(3,5-di F—Ph) |
| 51 | ONC211 | $CH_2Ph$ | $CH_2$-(3,4-di Cl—Ph) |
| 52 | ONC212 | $CH_2Ph$ | $CH_2$-(4-$CF_3$—Ph) |
| 53 | ONC213 | $CH_2Ph$ | $CH_2$-(3,4-di F—Ph) |
| 54 | ONC214 | $CD_2C_6D_5$ | $CH_2$-((2-$CH_3$)—Ph) |
| 43 | ONC217 | $CH_2Ph$ | $CH_2$-(2-F—Ph) |
| 55 | ONC218 | $CH_2Ph$ | $CH_2$(2-$CH_3$, 4-F—Ph) |
| 56 | ONC219 | $CH_2Ph$ | $CH_2$-(2,4-di Cl—Ph) |
| 57 | ONC220 | $CH_2Ph$ | $CH_2$-((4-$OCH_3$)—Ph) |
| 34 | ONC226 | $CH_2Ph$ | $CH_2$-(3-pyridinyl) |
| 35 | ONC222 | $CH_2Ph$ | $CH_2$-(3-isoxazolidinyl) |
| 36 | ONC224 | $CH_2Ph$ | $CH_2CH_2$-(4-morpholinyl) |
| 37 | ONC223 | $CH_2Ph$ | $CH_2$-(4-$CH_3$—Ph) |
| 38 | ONC221 | H | $CH_2$-(4-$CF_3$—Ph) |
| 73 | ONC227 | $CH_2$-(4-$CF_3$—Ph) | $CH_2$-(4-$CF_3$—Ph) |
| 72 | ONC225 | $CH_2Ph$ | $CH_2$-(2-F, 4-$CF_3$—Ph) |
| 74 | ONC228 | $CH_2$-(4-F—Ph) | $CH_2$-(4-$CF_3$—Ph) |
| 75 | ONC229 | $CH_2$—($OCH_3$—Ph) | $CH_2$-(4-$CF_3$—Ph) |
| 76 | ONC230 | (4-F—Ph)-4-oxobutyl | $CH_2$-(4-$CF_3$—Ph) |
| 77 | ONC231 | $CH_2$-3-pyridyl | $CH_2$-(4-$CF_3$—Ph) |
| 78 | ONC232 | $CH_2$-4-methyl-2-thiazolyl | $CH_2$-(4-$CF_3$—Ph) |
| 79 | ONC233 | $CH_2$-2-pyrazinyl | $CH_2$-(4-$CF_3$—Ph) |
| 81 | ONC234 | $CH_2$-(3,4-di Cl—Ph) | $CH_2$-(4-$CF_3$—Ph) |
| 82 | ONC235 | $CH_2$-(4-Cl—Ph) | $CH_2$-(4-$CF_3$—Ph) |
| 83 | ONC236 | $CH_2$-3-thienyl | $CH_2$-(4-$CF_3$—Ph) |
| 84 | ONC237 | $CH_2CH(OH)Ph$ | $CH_2$-(4-$CF_3$—Ph) |

IV. ASSESSING SENSITIVITY AND EFFICACY OF TREATMENT REGIMENS

Measuring expression, gene mutation, or gene copy number of a dopamine receptor or other G protein-coupled receptor (GPCR) may be used to predict response or sensitivity to methods of treatment described herein or to identify subjects likely to be responsive to methods of treatment described herein, such as treatment with a compound of formula (10), a pharmaceutically acceptable salt thereof, or an analog thereof. In one aspect, provided herein are methods of identifying whether a subject having a condition is likely to be responsive to a treatment regimen described herein. In one embodiment, the methods comprises (i) obtaining a biological sample from the subject; (ii) measuring expression levels of at least one dopamine receptor or GPCR in the sample; (iii) comparing the levels measured in the sample to those for a pre-determined standard; and (iv) determining whether the subject is likely to be responsive to the treatment regimen, based on the levels measured in the sample to those for the pre-determined standard. In one embodiment, the step of measuring an expression level in the sample include the steps of (i) contacting the sample with an antibody or antigen-binding fragment that specifically binds to the receptor to form a complex of the antibody or antigen-binding fragment with the receptor; and (ii) measuring the amount of the complex. In one embodiment, the subject has, or is at risk of having, cancer. In one embodiment, the cancer is a neuro-oncology disease. In one embodiment, the cancer is a neuroendocrine tumor. In one embodiment, the cancer is selected from the group consisting of meningioma, ependymoma, glioma, neuroblastoma, and diffuse intrinsic pontine glioma. In one embodiment, the subject has, or is at risk of having, a psychiatric disorder. For example, the psychiatric disorder is selected from psychosis, bipolar disorder, and major depressive disorder. In one embodiment, the subject has, or is at risk of having, an infection, such as a bacterial infection. In one embodiment, the infection is a gram-positive bacterial infection. In one embodiment, the infection is a gram-negative bacterial infection. In one embodiment, the infection is an infection of a bacteria selected from *Enterococcus faecium, Staphylococcus aureus, Klebsiella pneumoniae, Acinetobacter baumannii, Pseudomonas aeruginosa*, and *Enterobacter* species. In one embodiment, the gram-positive bacterial infection is a *Staphylococcus* infection. For example, the *Staphylococcus* infection is an *S. aureus* infection (e.g., a methicillin-resistant *S. aureus* (MRSA) infection). In one embodiment, the treatment regimen comprises administering an effective amount of a therapeutic, such as a compound of formula (10), a pharmaceutically acceptable salt thereof, or an analog thereof. In one embodiment, the dopamine receptor is from the D2-like family. In one embodiment, the dopamine receptor is DRD2, DRD3, or both. In one embodiment, the dopamine receptor is DRD4. In one embodiment, the GPCR is a Class A GPCR. In one embodiment, the GPCR is GPR132. In one embodiment, the GPCR is selected from GPR132, GPR91, MTNR1A, GPR162, GPR137, BAI3, LGR4, PTGIR, CXCR7, and combinations thereof. In one embodiment, the dopamine receptor is DRD5, the treatment regimen comprises administering an effective amount of a therapeutic, such as a compound of formula (10) or a pharmaceutically acceptable salt thereof, and an increased DRD5 expression level measured in the sample relative to the pre-determined standard indicates that the subject is or is not likely to be responsive to the treatment regimen.

In another aspect, provided herein are methods of assessing the effectiveness of a treatment regimen described herein, monitoring, or providing a prognosis for a subject with a condition. In one embodiment, the methods comprises (i) obtaining a biological sample from the subject; (ii) measuring expression levels of at least one dopamine receptor or GPCR in the sample; (iii) comparing the levels measured in the sample to those for a pre-determined standard; and (iv) determining a prognosis or whether the subject is responsive to the treatment regimen, based on the levels measured in the sample to those for the pre-determined standard. In one embodiment, the step of measuring an expression level of a dopamine receptor or GPCR in the sample include the steps of (i) contacting the sample with an antibody or antigen-binding fragment that specifically binds to the receptor to form a complex of the antibody or antigen-binding fragment with the receptor; and (ii) measuring the amount of the complex. In one embodiment, the methods comprise (i) obtaining a biological sample from the subject; (ii) measuring gene copy number or mutations in at least one dopamine receptor in the sample; (iii) comparing the copy number measured or mutations found in the sample to those for a pre-determined standard; and (iv) determining whether the subject is responsive to the treatment regimen, based on the copy number measured or mutations found in the sample to those for the pre-determined standard. In one embodiment, the subject has, or is at risk of having, cancer. In one embodiment, the cancer is a neuro-oncology disease. In one embodiment, the cancer is a neuroendocrine tumor. In one embodiment, the cancer is selected from the group consisting of meningioma, ependymoma, glioma, neuroblastoma, and diffuse intrinsic pontine glioma. In one embodiment, the subject has, or is at risk of having, a psychiatric disorder. For example, the psychiatric disorder is selected from psychosis, bipolar disorder, and major depressive disorder. In one embodiment, the subject has, or is at risk of having, an infection, such as a bacterial infection. In one embodiment, the infection is a gram-negative bacterial infection. In one embodiment, the infection is a gram-positive bacterial infection. In one embodiment, the infection is an infection of a bacteria selected from *Enterococcus faecium, Staphylococcus aureus, Klebsiella pneumoniae, Acinetobacter baumannii, Pseudomonas aeruginosa*, and *Enterobacter* species. In one embodiment, the gram-positive bacterial infection is a *Staphylococcus* infection. For example, the *Staphylococcus* infection is an *S. aureus* infection (e.g., a methicillin-resistant *S. aureus* (MRSA) infection). In one embodiment, the treatment regimen comprises administering an effective amount of a therapeutic, such as a compound of formula (10), a pharmaceutically acceptable salt thereof, or an analog thereof. In one embodiment, the dopamine receptor is selected from DRD2, DRD2S, DRD2L, and DRD3. In one embodiment, the dopamine receptor is from the D2-like family. In one embodiment, the dopamine receptor is from the D1-like family. In one embodiment, the dopamine receptor is DRD1. In one embodiment, the dopamine receptor is DRD2. In one embodiment, the dopamine receptor is DRD3. In one embodiment, the dopamine receptor is DRD4. In one embodiment, the dopamine receptor is DRD5. In one embodiment, the dopamine receptor is DRD2, DRD3, or both. In one embodiment, the GPCR is a Class A GPCR. In one embodiment, the GPCR is GPR132. In one embodiment, the GPCR is selected from GPR132, GPR91, MTNR1A, GPR162, GPR137, BAI3, LGR4, PTGIR, CXCR7, and combinations thereof.

In one embodiment, the dopamine receptor is DRD5, the treatment regimen comprises administering an effective amount of a compound of formula (10) or a pharmaceutically acceptable salt thereof, and an increased DRD5 expression level measured in the sample relative to the pre-determined standard indicates that the treatment regimen is or is not effective. In one embodiment, the dopamine receptor is DRD5, the treatment regimen comprises administering an effective amount of a therapeutic, such as a compound of formula (10) or a pharmaceutically acceptable salt thereof, and mutation in the DRD5 gene measured in the sample indicates that the treatment regimen is or is not effective. In one embodiment, the dopamine receptor is DRD5, the treatment regimen comprises administering an effective amount of a therapeutic, such as a compound of formula (10) or a pharmaceutically acceptable salt thereof, and the missense mutation Q366R in the DRD5 gene measured in the sample indicates that the treatment regimen is or is not effective.

In another aspect, provided herein are methods of identifying whether a subject having a condition is likely to be responsive to a treatment regimen described herein. In one embodiment, the methods comprises (i) obtaining a biological sample from the subject; (ii) measuring gene copy number or mutations in at least one dopamine receptor in the sample; (iii) comparing the copy number measured or mutations found in the sample to those for a pre-determined standard; and (iv) determining whether the subject is likely to be responsive to the treatment regimen, based on the copy number measured or mutations found in the sample to those for the pre-determined standard. In one embodiment, the subject has, or is at risk of having, cancer. In one embodiment, the cancer is a neuro-oncology disease. In one embodiment, the cancer is a neuroendocrine tumor. In one embodiment, the cancer is selected from the group consisting of meningioma, ependymoma, glioma, neuroblastoma, and diffuse intrinsic pontine glioma. In one embodiment, the subject has, or is at risk of having, a psychiatric disorder. For example, the psychiatric disorder is selected from psychosis, schizophrenia, bipolar disorder, and major depressive disorder. In one embodiment, the subject has, or is at risk of having, an infection, such as a bacterial infection. In one embodiment, the infection is a gram-negative bacterial infection. In one embodiment, the infection is a gram-positive bacterial infection. In one embodiment, the infection is an infection of a bacteria selected from *Enterococcus faecium, Staphylococcus aureus, Klebsiella pneumoniae, Acinetobacter baumannii, Pseudomonas aeruginosa*, and *Enterobacter* species. In one embodiment, the gram-positive bacterial infection is a *Staphylococcus* infection. For example, the *Staphylococcus* infection is an *S. aureus* infection (e.g., a methicillin-resistant *S. aureus* (MRSA) infection). In one embodiment, the treatment regimen comprises administering an effective amount of a therapeutic, such as a compound of formula (10), a pharmaceutically acceptable salt thereof, or an analog thereof. In one embodiment, the dopamine receptor is from the D2-like family of dopamine receptors. In one embodiment, the dopamine receptor is DRD1. In one embodiment, the dopamine receptor is DRD2. In one embodiment, the dopamine receptor is DRD3. In one embodiment, the dopamine receptor is DRD4. In one embodiment, the dopamine receptor is DRD5. In one embodiment, the dopamine receptor is DRD2, DRD3, or both. In one embodiment, the dopamine receptor is DRD5, the treatment regimen comprises administering an effective amount of a therapeutic, such as a compound of formula (10) or a pharmaceutically acceptable salt thereof, and mutation in the DRD5 gene measured in the sample indicates that the subject is or is not likely to be responsive to the treatment regimen. In one embodiment, the dopamine receptor is DRD5, the treatment regimen comprises administering an effective amount of a therapeutic, such as a compound of formula (10) or a pharmaceutically acceptable salt thereof, and the misense mutation Q366R in the DRD5 gene measured in the sample indicates that the subject is or is not likely to be responsive to the treatment regimen.

In addition, measuring expression, post-translational modifications, or activity levels of or mutations in eIF2-α, ATF4, CHOP, DR5, or cleaved or total cytokeratin 18 may be used to predict response or sensitivity to a method of treatment described herein and to identify subjects likely to be responsive to a method of treatment described herein, such as treatment with a compound of formula (10), a pharmaceutically acceptable salt thereof, or an analog thereof. In addition, measuring expression, post-translational modifications, or activity levels of or mutations in eIF2-α, ATF4, CHOP, DR5, or cleaved or total cytokeratin 18 can be used to assess the effectiveness of or monitor a method of treatment described herein. Furthermore, measuring expression, post-translational modifications, or activity levels of or mutations in eIF2-α, ATF4, CHOP, DR5, or cleaved or total cytokeratin 18 can be used to screen in vivo, in vitro, or in silico for structurally unrelated anti-cancer molecules. For example, competition and other assays known in the art may be used to identify drugs able to outcompete the target interaction with a higher affinity to compare changes in those levels to the respective changes produced by a compound of formula (10) or an analog thereof. Assays can also be performed on living mammalian cells, which more closely approximate the effects of a particular serum drug level in the body, or on microsomal extracts prepared from cultured cell lines.

In one embodiment, the subject has, or is at risk of having, cancer. In one embodiment, the treatment regimen comprises administering an effective amount of an imipridone, such as ONC201, or an analog thereof. In one embodiment, the treatment regimen comprises administering an effective amount of ONC201. In one embodiment, the treatment regimen comprises administering an effective amount of a compound of formula (10). In one embodiment, the compound of formula (10) is a compound of formula (40), e.g., a compound of formula (45). In one embodiment, a compound of formula (10) is a compound of formula (50), e.g., a compound formula (55). In one embodiment, the compound of formula (10) is a compound of formula (80). In one embodiment, the compound of formula (10) is a compound of formula (90). In one embodiment, the compound of formula (10) is a compound of formula (60). In one embodiment, analogs of compound (1) have a structure selected from the structures of formula (25), formula (26), formula (27), formula (28), formula (29), formula (30), or formula (31).

Levels for a pre-determined standard can be, e.g., the average or median levels measured in samples from subjects. The levels for a pre-determined standard can be measured under the same or substantially similar experimental conditions as in measuring a sample from a subject. The levels for the pre-determined standard may be obtained from subjects who are responsive to treatment with an imipridone, such as ONC201, or an analog thereof. In one embodiment, the pre-determined standard is obtained from subjects who are responsive to treatment with the compound, and if the levels in a sample from a subject and in the standard are similar, then the subject can be classified as likely to be responsive to treatment. The levels for the pre-determined standard may be obtained from subjects who are not responsive to treatment with the compound. In one embodiment, the pre-determined standard is obtained from subjects who are not responsive to treatment with the compound, and if the levels in a sample from a subject and in the pre-determined standard are different (e.g., up- or down-regulated), then the subject can be classified as likely to be responsive to treatment. The levels for the pre-determined standard may be obtained from normal healthy subjects.

Immunoassays can be used to assay protein or methylation levels in a sample, including enzyme-linked immunosorbent assay (ELISA), enzyme-linked immunofiltration assay (ELIFA), flow cytometry, immunoblot, immunoprecipitation, immunohistochemistry, immunocytochemistry, luminescent immunoassay (LIA), fluorescent immunoassay (FIA), and radioimmunoassay. $m^6A$ mRNA methylation levels can be obtained by methylated RNA immunoprecipitation (Me-RIP)) or other quantitative biochemical assays known in the art.

Nucleic acid mutations can be determined by any of a number of procedures. For example, a biologic sample from a subject is be obtained. Non-limiting examples of biological samples include a bodily fluid (e.g., urine, saliva, plasma, or serum) or tissue sample (e.g., a buccal tissue sample or buccal cell). The biologic sample can then be sequenced or scanned using known methods. For example, DNA arrays can be used to analyze at least a portion of the subject's genomic sequence. Furthermore, whole or partial genome sequence information can be used. Such sequences can be determined using standard sequencing methods including chain-termination (Sanger dideoxynucleotide), dye-terminator sequencing, and SOLID™ sequencing (Applied Biosystems). Whole genome sequences can be cut by restriction enzymes or sheared (mechanically) into shorter fragments for sequencing. DNA sequences can also be amplified using methods such as PCR and vector-based cloning methods (e.g., *Escherichia coli*). In one embodiment, at least a portion of a subject's genetic material (e.g., DNA, RNA, mRNA, cDNA, other nucleotide bases or derivatives of these) is scanned or sequenced using, e.g., conventional DNA sequencers or chip-based technologies, to identify the presence or absence of mutations or copy number variations.

In one aspect, provided herein are methods of identifying and treating a subject having a condition and who is likely to be responsive to a treatment regimen described herein. In one embodiment, the method comprises (i) identifying whether a subject having a condition is likely to be responsive to a treatment regimen described herein; and (ii) treating with the treatment regimen a subject determined likely to be responsive to that treatment regimen. In one embodiment, the subject has, or is at risk of having, cancer. In one embodiment, the treatment regimen comprises administering an effective amount an imipridone, e.g., ONC201, or an analog thereof. In one embodiment, the treatment regimen comprises administering an effective amount of compound (1). In one embodiment, the treatment regimen comprises administering an effective amount of a compound of formula (10). In one embodiment, the compound of formula (10) is a compound of formula (40), e.g., a compound of formula (45). In one embodiment, a compound of formula (10) is a compound of formula (50), e.g., a compound formula (55). In one embodiment, the compound of formula (10) is a compound of formula (80). In one embodiment, the compound of formula (10) is a compound of formula (90). In one embodiment, the compound of formula (10) is a compound of formula (60). In one embodiment, analogs of compound (1) have a structure selected from the structures of formula (25), formula (26), formula (27), formula (28), formula (29), formula (30), or formula (31).

Levels for a pre-determined standard can be, e.g., the average or median levels measured in samples from subjects. The levels for a pre-determined standard can be measured under the same or substantially similar experimental conditions as in measuring a sample from a subject. The levels for the pre-determined standard may be obtained from subjects who are responsive to treatment with an imipridone, such as ONC201, or an analog thereof. In one embodiment, the pre-determined standard is obtained from subjects who are responsive to treatment with the compound, and if the levels in a sample from a subject are similar to those in the standard, then the subject can be classified as likely to be responsive to treatment. The levels for the pre-determined standard may be obtained from subjects who are not responsive to treatment with the compound. In one embodiment, the pre-determined standard is obtained from subjects who are not responsive to treatment with the compound, and if the levels in a sample from a subject are different (e.g., up- or down-regulated) than those in the pre-determined standard, then the subject can be classified as likely to be responsive to treatment. The levels for the pre-determined standard may be obtained from normal healthy subjects. Immunoassays can be used to assay protein levels in a sample.

In one aspect, provided herein are methods of treating and assessing the effectiveness of a treatment in a subject having a condition. In one embodiment, the method comprises (i) treating the subject according to a method of treatment described herein (ii) assessing as described herein the effectiveness of the treatment. In one embodiment, the subject has, or is at risk of having, cancer. In one embodiment, the treatment regimen comprises administering an effective amount of an imipridone, such as ONC201, or an analog thereof. In one embodiment, the treatment regimen comprises administering an effective amount of compound (1). In one embodiment, the treatment regimen comprises administering an effective amount of a compound of formula (10). In one embodiment, the compound of formula (10) is a compound of formula (40), e.g., a compound of formula (45). In one embodiment, a compound of formula (10) is a compound of formula (50), e.g., a compound formula (55). In one embodiment, the compound of formula (10) is a compound of formula (80). In one embodiment, the compound of formula (10) is a compound of formula (90). In one embodiment, the compound of formula (10) is a compound of formula (60). In one embodiment, analogs of compound (1) have a structure selected from the structures of formula (25), formula (26), formula (27), formula (28), formula (29), formula (30), or formula (31).

Other conditions that may be suitable for the methods described herein include Attention Deficit Disorder; Addiction; Epilepsy; Viral infection; Inflammation; Neurodegenerative diseases such as Alzheimer's disease, Parkinson's disease, Huntington's disease, Amyotrophic lateral sclerosis; Cardiovascular diseases such as coronary artery disease, cardiomyopathy, hypertensive heart disease, heart failure, pulmonary heart disease, cardiac dysrhythmias, inflammatory heart disease, endocarditis, inflammatory cardiomegaly, myocarditis, valvular heart disease, cerebrovascular disease, peripheral arterial disease, congenital heart disease, rheumatic heart disease; Diabetes; and light chain amyloidosis.

V. COMPOSITIONS

In one aspect, pharmaceutical compositions are provided, comprising compounds of formula (10):

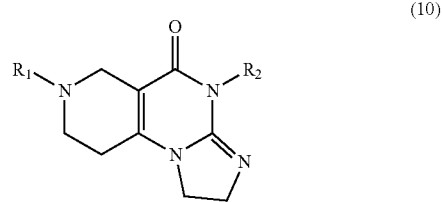

(10)

or of formula (1):

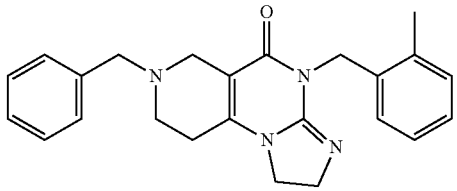 [SMILES: Cc1ccccc1CN1C(=O)C2=C(CCN(Cc3ccccc3)C2)N2CCN=C12]

and their pharmaceutically acceptable salts In one embodiment, the salt is a pharmaceutically acceptable mono-salt of the compound. In one embodiment, the salt is a pharmaceutically acceptable di-salt of the compound. In one embodiment, the salt is a pharmaceutically acceptable mono- or multi-salt (e.g., a di-salt or tri-salt) thereof selected from hydrochloride, hydrobromide, hydrogensulphate, sulfates, phosphates, fumarates, succinates, oxalates and lactates, bisulfates, hydroxyl, tartrate, nitrate, citrate, bitartrate, carbonate, malate, maleate, fumarate sulfonate, methylsulfonate, formate, acetate, and carboxylate. In one embodiment, the salt is a salt selected from the group consisting of p-toluene-sulfonate, benzenesulfonate, citrate, methanesulfonate, oxalate, succinate, tartrate, fumarate and maleate. In one embodiment, the salt is a salt selected from the group consisting of ammonium, sodium, potassium, calcium, magnesium, zinc, lithium, and/or with counter-ions such as methylamino, dimethylamino, diethylamino and triethylamino counter-ions. In one embodiment, the salt is a. di-hydrochloride salt or a di-hydrobromide salt.

Compound (1) (ONC201) has the same chemical structure that would be revealed by structural analysis (e.g., NMR, X-ray diffraction) of compound NSC 350625, available from the National Cancer Institute's Developmental Therapeutics Program Repository.

In one embodiment, the pharmaceutical composition includes a di-salt (e.g., a di-hydrochloride salt) of ONC201 or an analog thereof (e.g., an imipridone). Salts (e.g., di-salts or tri-salts) of an ONC201 analog can be prepared from an ONC201 analog, which can be synthesized as described herein, or using standard chemical synthetic methodology known to one of ordinary skill in the art.

In one embodiment, the pharmaceutical composition includes at least one pharmaceutically acceptable carrier. Non-limiting examples of suitable pharmaceutically acceptable carriers include, those in Handbook of Pharmaceutical Excipients, 7$^{th}$ ed., edited by Raymond C. Rowe et al., American Pharmaceutical Association, Washington, USA and Pharmaceutical Press, London; and earlier editions. Exemplary pharmaceutically acceptable carriers, methods for making pharmaceutical compositions and various dosage forms, as well as administration modes are well-known in the art, for example as detailed in Pharmaceutical Dosage Forms: Tablets, edited by Larry L. Augsburger & Stephen W. Hoag., London: Informa Healthcare, 2008; and in L. V. Allen, Jr. et al., Ansel's Pharmaceutical Dosage Forms and Drug Delivery Systems, 8$^{th}$ ed., Philadelphia, Pa.: Lippincott, Williams & Wilkins, 2004; A. R. Gennaro, Remington: The Science and Practice of Pharmacy, Lippincott Williams & Wilkins, 21$^{st}$ ed., 2005, particularly chapter 89; and J. Hardman et al., Goodman & Gilman's The Pharmacological Basis of Therapeutics, McGraw-Hill Professional, 10$^{th}$ ed., 2001.

In one embodiment, pharmaceutical compositions are formulated for ocular administration. In one embodiment, pharmaceutical compositions are formulated for topical administration. In one embodiment, pharmaceutical compositions are formulated as drops, ointments, or liquids. In one embodiment, pharmaceutical compositions include conventional pharmaceutical carriers such as aqueous, powdery or oily bases, thickeners.

In one embodiment, a pharmaceutical composition is a formulation for intravenous administration. In one embodiment, the intravenous formulation comprises a compound of formula (10) or a pharmaceutically acceptable salt thereof dissolved in a solvent. In one embodiment, the solvent comprises water. In one embodiment, the intravenous formulation includes the compound or its salt in a concentration of about 0.05, about 0.25, about 0.5, about 2.5, about 5, about 25, or about 50 mg/mL. In one embodiment, the intravenous formulation includes the compound or its salt in a concentration of from about 0.05, 0.5, or 5 mg/mL to about 1, 10, or 100 mg/mL. In one embodiment, the intravenous formulation includes from about 0.005% 0.05%, or 0.5% to about 0.1%, 1%, or 10% of the compound or its salt. In one embodiment, the intravenous formulation includes about 0.05%, 0.5%, or 5% of the compound or its salt. In one embodiment, the intravenous formulation includes a higher or a lower concentration of the compound or its salt.

In one embodiment, the intravenous formulation has a pH of about 3. In one embodiment, the formulation is adjusted to pH 3 with a phosphate buffer. In one embodiment, the intravenous formulation includes dextrose or sodium chloride. In one embodiment, the intravenous formulation includes the compound or its salt in a concentration of about 5 mg/mL and pH 3 and forms a stable solution. In one embodiment, the intravenous formulation includes the compound or its salt in a concentration of about 5 mg/mL and pH <5 and forms a stable solution. In one embodiment, the intravenous formulation includes the compound or its salt and one or more antioxidants. In one embodiment, the intravenous formulation includes a mixture of mono- and di-hydrochloride salts of the compound. In one embodiment, the intravenous formulation includes the compound or its salt as a 1% solution in a concentration of about 10 mg/mL. For example, the intravenous formulation is a solution with a pH of about 3.3. In one embodiment, the pH is less than 4.0.

In one embodiment, a suitable pharmaceutically acceptable carrier includes an aqueous carrier. In one embodiment, the aqueous carrier includes sterile water. In one embodiment, the formulation includes dextrose, sodium chloride or both. In one embodiment, the pharmaceutically acceptable carrier includes an oil.

In one embodiment, an intravenous formulation comprises ONC201 or an analog thereof or a di-hydrochloride salt thereof dissolved in water at 25 mg/mL. In one embodiment, the formulation is adjusted to pH 3 with phosphate buffer. In one embodiment, the formulation includes dextrose, sodium chloride or both. In one embodiment, the formulation includes a higher or a lower concentration of the di-hydrochloride salt of ONC201 or an analog thereof. In one embodiment, the formulation includes ONC201 or an analog thereof or a di-hydrochloride salt thereof in a concentration of about 5 mg/mL. In one embodiment, the formulation of about 5 mg/mL forms a stable solution and pH 3. In one embodiment, the formulation of about 5 mg/mL has a pH <5 and forms a stable solution. In one embodiment, the intravenous formulation includes ONC201 or an analog thereof or a di-hydrochloride salt thereof and one or more antioxidants. In one embodiment, the intravenous formulation includes a mixture of mono- and di-hydrochloride salts of ONC201 or an analog thereof. In one embodiment, the intravenous formulation includes ONC201 or an analog thereof or a di-hydrochloride salt thereof as a 1% solution in a concentration of about 10 mg/mL. For example, the intravenous formulation is a solution having a pH of about 3.3. In one embodiment, the pH is less than 4.0.

In one embodiment, the intravenous formulation includes from about 0.5% to about 10% (or from about 5 mg/mL to about 100 mg/mL) of ONC201 or an analog thereof or a di-salt thereof. In one embodiment, the formulation includes from about 5% (or about 50 mg/mL) of ONC201 or an analog thereof or a di-salt thereof. In one embodiment, the intravenous infusion rate may be slowed to decrease side effects of ONC201 or an analog thereof or a di-salt thereof.

In one embodiment, the pharmaceutical composition comprises about 0.1-99% of an ONC201 salt or an analog thereof; and a pharmaceutically acceptable carrier, e.g., an oil or sterile water or other aqueous carrier. In one embodiment, the composition comprises a mono or di-salt of ONC201 or an analog thereof in a range of from about 5% to about 50% for oral dosage forms.

In one embodiment, a pharmaceutical composition includes an antioxidant. Suitable antioxidants include: ascorbic acid derivatives such as ascorbic acid, erythorbic acid, sodium ascorbate, thiol derivatives such as thioglycerol, cysteine, acetylcysteine, cystine, dithioerythreitol, dithiothreitol, glutathione, tocopherols, butylated hydroxyanisole (BHA), butylated hydroxytoluene (BHT), sulfurous acid salts such as sodium sulfate, sodium bisulfite, acetone sodium bisulfite, sodium formaldehyde sulfoxylate, sodium metabisulfite, sodium sulfite, and sodium thiosulfate, nordihydroguaiaretic acid. It should be noted that antioxidants used for aqueous formulations typically include: sodium sulphite, sodium metabisulphite, sodium formaldehyde sulphoxylate or ascorbic acid and combinations thereof, whereas antioxidants used in oil-based solutions, organic solvents, include BHT, BHA or propyl gallate and combinations thereof. In yet other embodiments, an antioxidant can be one or more of a flavanoid, an isoflavone, monothioglycerol, L-cysteine, thioglycolic acid, α-tocopherol, ascorbic acid 6-palmitate, dihydrolipoic acid, BHT, BHA, vitamin E, propyl gallate, β-carotene, and ascorbic acid. Antioxidants can typically be used in about 0.1% to 1.0% by weight, more typically about 0.2%.

In one embodiment, the pharmaceutical composition includes an imipridone, such as ONC201 or an analog thereof, or a pharmaceutically acceptable salt thereof and at least one other therapeutic agent. For example, the other therapeutic agent is selected from the group consisting of hormone analogs and antihormones, aromatase inhibitors, LHRH agonists and antagonists, inhibitors of growth factors, growth factor antibodies, growth factor receptor antibodies, tyrosine kinase inhibitors; antimetabolites; antitumour antibiotics; platinum derivatives; alkylation agents; antimitotic agents; tubuline inhibitors; PARP inhibitors, topoisomerase inhibitors, serine/threonine kinase inhibitors, tyrosine kinase inhibitors, protein protein interaction inhibitors, RAF inhibitors, MEK inhibitors, ERK inhibitors, IGF-1R inhibitors, ErbB receptor inhibitors, rapamycin analogs, BTK inhibitors, CRM1 inhibitors (e.g., KPT185), P53 modulators (e.g., Nutlins), antiangiogenics (e.g., axitinib, aflibercept, sorafenib, and regorafenib), amifostin, anagrelid, clodronat, filgrastin, interferon, interferon α, leucovorin, rituximab, procarbazine, levamisole, mesna, mitotane, pamidronate and porfimer, 2-chlorodesoxyadenosine, 2-fluorodesoxy-cytidine, 2-methoxyoestradiol, 2C4,3-alethine, 131-1-TM-601, 3CPA, 7-ethyl-10-hydroxycamptothecin, 16-aza-epothilone B, A 105972, A 204197, abiraterone, aldesleukin, alitretinoin, allovectin-7, altretamine, alvocidib, amonafide, anthrapyrazole, AG-2037, AP-5280, apaziquone, apomine, aranose, arglabin, arzoxifene, atamestane, atrasentan, auristatin PE, ABT-199 (Venetoclax), ABT-263 (Navitoclax), AVLB, AZ10992, ABX-EGF, AMG-479 (ganitumab), ARRY 162, ARRY 438162, ARRY-300, ARRY-142886/AZD-6244 (selumetinib), ARRY-704/AZD-8330, AR-12, AR-42, AS-703988, AXL-1717, AZD-8055, AZD-5363, AZD-6244, ARQ-736, ARQ 680, AS-703026 (primasertib), avastin, AZD-2014, azacytidine, azaepothilone B, azonafide, BAY-43-9006, BAY 80-6946, BBR-3464, BBR-3576, bevacizumab, BEZ-235, biricodar dicitrate, BCX-1777, BKM-120, bleocin, BLP-25, BMS-184476, BMS-247550, BMS-188797, BMS-275291, BMS-663513, BMS-754807, BNP-1350, BNP-7787, BIBW 2992 (afatinib, tomtovok), BIBF 1120 (vargatef), BI 836845, BI 2536, BI 6727, BI 836845, BI 847325, BI 853520, BUB-022, bleomycinic acid, bleomycin A, bleomycin B, brivanib, bryostatin-1, bortezomib, brostallicin, busulphan, BYL-719, CA-4 prodrug, CA-4, CapCell, calcitriol, canertinib, canfosfamide, capecitabine, carboxyphthalatoplatin, CC1-779, CC-115, CC-223, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, CKI-27, clofarabin, colchicin, combretastatin A4, COT inhibitors, CHS-828, CH-5132799, CLL-Thera, CMT-3 cryptophycin 52, CTP-37, CTLA-4 monoclonal antibodies, CP-461, CV-247, cyanomorpholinodoxorubicin, cytarabine, D 24851, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, DS-7423, E7010, E-6201, edatrexat, edotreotide, efaproxiral, eflornithine, EGFR inhibitors, EKB-569, EKB-509, enzastaurin, enzalutamide, elsamitrucin, epothilone B, epratuzumab, ER-86526, erlotinib, ET-18-0CH3, ethynylcytidine, ethynyloestradiol, exatecan, exatecan mesylate, exemestane, exisulind, fenretinide, figitumumab, floxuridine, folic acid, FOLFOX, FOLFOX4, FOLFIRI, formestane, fotemustine, galarubicin, gallium maltolate, gefinitib, gemtuzumab, gimatecan, glufosfamide, GCS-100, GDC-0623, GDC-0941 (pictrelisib), GDC-0980, GDC-0032, GDC-0068, GDC-0349, GDC-0879, G17DT immunogen, GMK, GPX-100, gp100-peptide vaccines, GSK-5126766, GSK-690693, GSK-1120212 (trametinib), GSK-2118436 (dabrafenib), GSK-2126458, GSK-2132231A, GSK-2334470, GSK-2110183, GSK-2141795, GW2016, granisetron, herceptine, hexamethylmelamine, histamine, homoharringtonine, hyaluronic acid, hydroxyurea, hydroxyprogesterone caproate, ibandronate, ibrutinib, ibritumomab, idatrexate, idenestrol, IDN-5109, IGF-1R inhibitors, IMC-1C11, IMC-A12 (cixutumumab), immunol, indisulam, interferon α-2a, interferon α-2b, pegylated interferon α-2b, interleukin-2, INK-1117, INK-128, INSM-18, ionafarnib, ipilimumab, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, KW-2450, lobaplatin, leflunomide, lenograstim, leuprolide, leuporelin, lexidronam, LGD-1550, linezolid, lutetium texaphyrin, lometrexol, losoxantrone, LU 223651, lurtotecan, LY-S6AKT1, LY-2780301, mafosfamide, marimastat, mechloroethamine, MEK inhibitors, MEK-162, methyltestosteron, methylprednisolone, MEDI-573, MEN-10755, MDX-H210, MDX-447, MDX-1379, MGV, midostaurin, minodronic acid, mitomycin, mivobulin, MK-2206, MK-0646 (dalotuzumab), MLN518, motexaf in gadolinium, MS-209, MS-275, MX6, neridronate, neratinib, Nexavar, neovastat, nilotinib, nimesulide, nitroglycerin, nolatrexed, norelin, N-acetylcysteine, 06-benzylguanine, oblimersen, omeprazole, oncophage, oncoVEXGM-CSF, ormiplatin, ortataxel, OX44 antibodies, OSI-027, OSI-906 (linsitinib), 4-1BB antibodies, oxantrazole, oestrogen, panitumumab, patupilone, pegfilgrastim, PCK-3145, pegfilgrastim, PBI-1402, PBI-05204, PD0325901, PD-1 antibodies, PEG-paclitaxel, albumin-stabilized paclitaxel, PEP-005, PF-05197281, PF-05212384, PF-04691502, PHT-427, P-04, PKC412, P54, PI-88, pelitinib, pemetrexed, pentrix, perifosine, perillylalcohol, pertuzumab, PI3K inhibitors, PI3K/mTOR inhibitors, PG-TXL, PG2, PLX-4032/RO-5185426 (vemurafenib), PLX-3603/RO-5212054, PT-100, PWT-33597, PX-866, picoplatin, pivaloyloxymethylbutyrate, pixantrone, phenoxodiol O, PKI166, plevitrexed, plicamycin, polyprenic acid, porfiromycin, prednisone, prednisolone, quinamed, quinupristin, R115777, RAF-265, ramosetron, ranpirnase, RDEA-119/BAY 869766, RDEA-436, rebeccamycin analogs, receptor tyrosine kinase (RTK) inhibitors, regorafenib, revimid, RG-7167, RG-7304, RG-7421, RG-7321, RG 7440, rhizoxin, rhu-MAb, rinfabate, risedronate, rituximab, robatumumab, rofecoxib, RO-31-7453, RO-5126766, RO-5068760, RPR 109881A, rubidazone, rubitecan, R-flurbiprofen, RX-0201, S-9788, sabarubicin, SAHA, sargramostim, satraplatin, SB 408075, Se-015/Ve-015, SU5416, SU6668, SDX-101, semustin, seocalcitol, SM-11355, SN-38, SN-4071, SR-27897, SR-31747, SR-13668, SRL-172, sorafenib, spiroplatin, squalamine, suberanilohydroxamic acid, sutent, T 900607, T 138067, TAK-733, TAS-103, tacedinaline, talaporf in, Tarceva, tariquitar, tasisulam, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymalfasin, thymectacin, tiazofurin, tipifarnib, tirapazamine, tocladesine, tomudex, toremofin, trabectedin, TransMID-107, transretinic acid, traszutumab, tremelimumab, tretinoin, triacetyluridine, triapine, triciribine, trimetrexate, TLK-286TXD 258, tykerb/tyverb, urocidin, valrubicin, vatalanib, vincristine, vinflunine, virulizin, WX-UK1, WX-554, vectibix, xeloda, XELOX, XL-147, XL-228, XL-281, XL-518/R-7420/GDC-0973, XL-765, YM-511, YM-598, ZD-4190, ZD-6474, ZD-4054, ZD-0473, ZD-6126, ZD-9331, ZD1839, ZSTK-474, zoledronat, zosuquidar, and combinations thereof.

In one embodiment, the other therapeutic agent comprises a hormone analog, an antihormone or both selected from tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxy-progesterone, octreotide, and combinations thereof. In one embodiment, the other therapeutic agent comprises one or more LHRH agonists are selected from goserelin acetate, luprolide acetate, triptorelin pamoate and combinations thereof and wherein the LHRH antagonists are selected from Degarelix, Cetrorelix, Abarelix, Ozarelix, Degarelix combinations thereof. In one embodiment, the other therapeutic agent comprises one or more growth factor inhibitors selected from inhibitors of: platelet derived growth factor (PDGF), fibroblast growth factor (FGF), vascular endothelial growth factor (VEGF), epidermal growth factor (EGF), insuline-like growth factors (IGF), human epidermal growth factor (HER) and hepatocyte growth factor (HGF). In one embodiment, the other therapeutic agent comprises one or more inhibitors of the human epidermal growth factor selected from HER2, HER3, and HER4. In one embodiment, the other therapeutic agent comprises one or more tyrosine kinase inhibitors selected from cetuximab, gefitinib, imatinib, lapatinib and trastuzumab, and combinations thereof. In one embodiment, the other therapeutic agent comprises one or more aromatase inhibitors selected from anastrozole, letrozole, liarozole, vorozole, exemestane, atamestane, and combinations thereof. In one embodiment, the other therapeutic agent comprises one or more antimetabolites which are antifolates selected from methotrexate, raltitrexed, and pyrimidine analogs. In one embodiment, the other therapeutic agent comprises one or more antimetabolites which are pyrimidine analogs selected from 5-fluorouracil, capecitabin and gemcitabin. In one embodiment, the other therapeutic agent comprises one or more antimetabolites which are purine and/or adenosine analogs selected from mercaptopurine, thioguanine, cladribine and pentostatin, cytarabine, fludarabine, and combinations thereof. In one embodiment, the other therapeutic agent comprises one or more antitumour antibiotics selected from anthracyclins, doxorubicin, daunorubicin, epirubicin and idarubicin, mitomycin-C, bleomycin, dactinomycin, plicamycin, streptozocin and combinations thereof. In one embodiment, the other therapeutic agent comprises one or more platinum derivatives selected from cisplatin, oxaliplatin, carboplatin and combinations thereof. In one embodiment, the other therapeutic agent comprises one or more alkylation agents selected from estramustin, meclorethamine, melphalan, chlorambucil, busulphan, dacarbazin, cyclophosphamide, ifosfamide, temozolomide, nitrosoureas, and combinations thereof. In one embodiment, the other therapeutic agent comprises nitrosoureas selected from carmustin, lomustin, thiotepa, and combinations thereof. In one embodiment, the other therapeutic agent comprises antimitotic agents selected from Vinca alkaloids and taxanes. In one embodiment, the other therapeutic agent comprises one or more taxanes selected from paclitaxel, docetaxel, and combinations thereof. In one embodiment, the other therapeutic agent comprises one or more Vinca alkaloids selected from vinblastine, vindesin, vinorelbin, vincristine, and combinations thereof. In one embodiment, the other therapeutic agent comprises one or more topoisomerase inhibitors which are epipodophyllotoxins. In one embodiment, the other therapeutic agent comprises one or more epipodophyllotoxins selected from etoposide and etopophos, teniposide, amsacrin, topotecan, irinotecan, mitoxantron, and combinations thereof. In one embodiment, the other therapeutic agent comprises one or more serine/threonine kinase inhibitors selected from PDK 1 inhibitors, B-Raf inhibitors, mTOR inhibitors, mTORC1 inhibitors, PI3K inhibitors, dual mTOR/PI3K inhibitors, STK 33 inhibitors, AKT inhibitors, PLK 1 inhibitors, inhibitors of CDKs, Aurora kinase inhibitors, and combinations thereof. In one embodiment, the other therapeutic agent comprises one or more tyrosine kinase inhibitors which are PTK2/FAK inhibitors. In one embodiment, the other therapeutic agent comprises one or more protein protein interaction inhibitors selected from IAP, Mcl-1, MDM2/MDMX and combinations thereof. In one embodiment, the other therapeutic agent comprises one or more rapamycin analogs selected from everolimus, temsirolimus, ridaforolimus, sirolimus, and combinations thereof. In one embodiment, the other therapeutic agent comprises one or more therapeutic agents selected from amifostin, anagrelid, clodronat, filgrastin, interferon, interferon α, leucovorin, rituximab, procarbazine, levamisole, mesna, mitotane, pamidronate and porfimer, and combinations thereof. In one embodiment, the other therapeutic agent comprises one or more therapeutic agents selected from 2-chlorodesoxyadenosine, 2-fluorodesoxy-cytidine, 2-methoxyoestradiol, 2C4,3-alethine, 131-1-TM-601, 3CPA, 7-ethyl-10-hydroxycamptothecin, 16-aza-epothilone B, A 105972, A 204197, abiraterone, aldesleukin, alitretinoin, allovectin-7, altretamine, alvocidib, amonafide, anthrapyrazole, AG-2037, AP-5280, apaziquone, apomine, aranose, arglabin, arzoxifene, atamestane, atrasentan, auristatin PE, ABT-199 (Venetoclax), ABT-263 (Navitoclax), AVLB, AZ10992, ABX-EGF, AMG-479 (ganitumab), ARRY 162, ARRY 438162, ARRY-300, ARRY-142886/AZD-6244 (selumetinib), ARRY-704/AZD-8330, AR-12, AR-42, AS-703988, AXL-1717, AZD-8055, AZD-5363, AZD-6244, ARQ-736, ARQ 680, AS-703026 (primasertib), avastin, AZD-2014, azacytidine, azaepothilone B, azonafide, BAY-43-9006, BAY 80-6946, BBR-3464, BBR-3576, bevacizumab, BEZ-235, biricodar dicitrate, BCX-1777, BKM-120, bleocin, BLP-25, BMS-184476, BMS-247550, BMS-188797, BMS-275291, BMS-663513, BMS-754807, BNP-1350, BNP-7787, BIBW 2992 (afatinib, tomtovok), BIBF 1120 (vargatef), BI 836845, BI 2536, BI 6727, BI 836845, BI 847325, BI 853520, BUB-022, bleomycinic acid, bleomycin A, bleomycin B, brivanib, bryostatin-1, bortezomib, brostallicin, busulphan, BYL-719, CA-4 prodrug, CA-4, CapCell, calcitriol, canertinib, canfosfamide, capecitabine, carboxyphthalatoplatin, CC1-779, CC-115, CC-223, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, CKI-27, clofarabin, colchicin, combretastatin A4, COT inhibitors, CHS-828, CH-5132799, CLL-Thera, CMT-3 cryptophycin 52, CTP-37, CTLA-4 monoclonal antibodies, CP-461, CV-247, cyanomorpholinodoxorubicin, cytarabine, D 24851, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, DS-7423, E7010, E-6201, edatrexat, edotreotide, efaproxiral, eflornithine, EGFR inhibitors, EKB-569, EKB-509, enzastaurin, enzalutamide, elsamitrucin, epothilone B, epratuzumab, ER-86526, erlotinib, ET-18-0CH3, ethynylcytidine, ethynyloestradiol, exatecan, exatecan mesylate, exemestane, exisulind, fenretinide, figitumumab, floxuridine, folic acid, FOLFOX, FOLFOX4, FOLFIRI, formestane, fotemustine, galarubicin, gallium maltolate, gefinitib, gemtuzumab, gimatecan, glufosfamide, GCS-100, GDC-0623, GDC-0941 (pictrelisib), GDC-0980, GDC-0032, GDC-0068, GDC-0349, GDC-0879, G17DT immunogen, GMK, GPX-100, gp100-peptide vaccines, GSK-5126766, GSK-690693, GSK-1120212 (trametinib), GSK-2118436 (dabrafenib), GSK-2126458, GSK-2132231A, GSK-2334470, GSK-2110183, GSK-2141795, GW2016, granisetron, herceptine, hexamethylmelamine, histamine, homoharringtonine, hyaluronic acid, hydroxyurea, hydroxyprogesterone caproate, ibandronate, ibrutinib, ibritumomab, idatrexate, idenestrol, IDN-5109, IGF-1R inhibitors, IMC-1C11, IMC-A12 (cixutumumab), immunol, indisulam, interferon α-2a, interferon α-2b, pegylated interferon α-2b, interleukin-2, INK-1117, INK-128, INSM-18, ionafarnib, ipilimumab, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, KW-2450, lobaplatin, leflunomide, lenograstim, leuprolide, leuporelin, lexidronam, LGD-1550, linezolid, lutetium texaphyrin, lometrexol, losoxantrone, LU 223651, lurtotecan, LY-S6AKT1, LY-2780301, mafosfamide, marimastat, mechloroethamine, MEK inhibitors, MEK-162, methyltestosteron, methylprednisolone, MEDI-573, MEN-10755, MDX-H210, MDX-447, MDX-1379, MGV, midostaurin, minodronic acid, mitomycin, mivobulin, MK-2206, MK-0646 (dalotuzumab), MLN518, motexaf in gadolinium, MS-209, MS-275, MX6, neridronate, neratinib, Nexavar, neovastat, nilotinib, nimesulide, nitroglycerin, nolatrexed, norelin, N-acetylcysteine, 06-benzylguanine, oblimersen, omeprazole, oncophage, oncoVEXGM-CSF, ormiplatin, ortataxel, OX44 antibodies, OSI-027, OSI-906 (linsitinib), 4-1BB antibodies, oxantrazole, oestrogen, panitumumab, patupilone, pegfilgrastim, PCK-3145, pegfilgrastim, PBI-1402, PBI-05204, PD0325901, PD-1 antibodies, PEG-paclitaxel, albumin-stabilized paclitaxel, PEP-005, PF-05197281, PF-05212384, PF-04691502, PHT-427, P-04, PKC412, P54, PI-88, pelitinib, pemetrexed, pentrix, perifosine, perillylalcohol, pertuzumab, PI3K inhibitors, PI3K/mTOR inhibitors, PG-TXL, PG2, PLX-4032/RO-5185426 (vemurafenib), PLX-3603/RO-5212054, PT-100, PWT-33597, PX-866, picoplatin, pivaloyloxymethylbutyrate, pixantrone, phenoxodiol O, PKI166, plevitrexed, plicamycin, polyprenic acid, porfiromycin, prednisone, prednisolone, quinamed, quinupristin, R115777, RAF-265, ramosetron, ranpirnase, RDEA-119/BAY 869766, RDEA-436, rebeccamycin analogs, receptor tyrosine kinase (RTK) inhibitors, revimid, RG-7167, RG-7304, RG-7421, RG-7321, RG 7440, rhizoxin, rhuMAb, rinfabate, risedronate, rituximab, robatumumab, rofecoxib, RO-31-7453, RO-5126766, RO-5068760, RPR 109881A, rubidazone, rubitecan, R-flurbiprofen, RX-0201, S-9788, sabarubicin, SAHA, sargramostim, satraplatin, SB 408075, Se-015/Ve-015, SU5416, SU6668, SDX-101, semustin, seocalcitol, SM-11355, SN-38, SN-4071, SR-27897, SR-31747, SR-13668, SRL-172, sorafenib, spiroplatin, squalamine, suberanilohydroxamic acid, sutent, T 900607, T 138067, TAK-733, TAS-103, tacedinaline, talaporf in, Tarceva, tariquitar, tasisulam, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymalfasin, thymectacin, tiazofurin, tipifarnib, tirapazamine, tocladesine, tomudex, toremofin, trabectedin, TransMID-107, transretinic acid, traszutumab, tremelimumab, tretinoin, triacetyluridine, triapine, triciribine, trimetrexate, TLK-286TXD 258, tykerb/tyverb, urocidin, valrubicin, vatalanib, vincristine, vinflunine, virulizin, WX—UK1, WX-554, vectibix, xeloda, XELOX, XL-147, XL-228, XL-281, XL-518/R-7420/GDC-0973, XL-765, YM-511, YM-598, ZD-4190, ZD-6474, ZD-4054, ZD-0473, ZD-6126, ZD-9331, ZD1839, ZSTK-474, zoledronat, zosuquidar, and combinations thereof.

In one embodiment, the other therapeutic agent comprises a steroid, including dexamethasone, prednisolone, methyl prednisolone, prednisone, hydrocortisone, triamcinolone, betamethasone, and cortivazol. In one embodiment, the other therapeutic agent comprises an anti-emetic, Antiemetics include, but are not limited to, 5-HT3 receptor agonists (e.g., dolasetron, granisetron, ondansetron, tropisetron, palonosetron, and mirtazapine), dopamine agonists (e.g., domperidone, olanzapine, droperidol, haloperidol, chlorpromazine, prochlorperazine, alizapride, prochlorperazine, and metoclopramide), NK1 receptor antagonists (e.g., aprepitant and casopitant), antihistamines (such as cyclizine, diphenhydramine, dimenhydrinate, doxylamine, meclizine, promethazine, hydroxyzine), cannabinoids (e.g., cannabis, dronabinol, nabilone, and sativex), benzodiazepines (e.g., midazolam and lorazepam), anticholinergics (e.g., hyoscine), trimethobenzamide, ginger, emetrol, propofol, peppermint, muscimol, and ajwain.

In one embodiment, the other therapeutic agent comprises an anti-cancer agent, which includes a mitotic inhibitor. In one embodiment, the mitotic inhibitor includes a taxane. In one embodiment, the mitotic inhibitor includes a taxane selected from paclitaxel and docetaxel.

In one embodiment, the pharmaceutical composition includes an imipridone, such as ONC201, or an analog thereof, or a pharmaceutically acceptable salt thereof; and at least one anti-cancer agent, which includes one or more of acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bevacizumab, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflornithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, flurocitabine, fosquidone, fostriecin, fulvestrant, gemcitabine, hydroxyurea, idarubicin, ifosfamide, ilmofosine, interleukin II (IL-2, including recombinant interleukin II or rIL2), interferon α-2a, interferon α-2b, interferon α-n1, interferon α-n3, interferon β-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, zorubicin and combinations thereof.

Examples of suitable anti-cancer agents include those described Goodman and Gilman's The Pharmacological Basis of Therapeutics, 12$^{th}$ Ed., edited by Laurence Brunton, Bruce Chabner, Bjorn Knollman, McGraw Hill Professional, 2010.

In some exemplary embodiments, the pharmaceutical composition includes a salt (e.g., a mono- or di-salt) of an imipridone, e.g., ONC201, or an analog thereof and at least one other therapeutic agent, where the other therapeutic agent comprises an anti-angiogenic agent, for example, bevacizumab. In one embodiment, the anti-angiogenic agent is selected from aflibercept, axitinib, angiostatin, endostatin, 16 kDa prolactin fragment, laminin peptides, fibronectin peptides, tissue metalloproteinase inhibitors (TIMP 1, 2, 3, 4), plasminogen activator inhibitors (PAI-1, -2), tumor necrosis factor α, (high dose, invitro), TGF-β1, interferons (IFN-α, -β, γ), ELR-CXC chemokines, IL-12; SDF-1; MIG; platelet factor 4 (PF-4); IP-10, thrombospondin (TSP), SPARC, 2-methoxyoestradiol, proliferin-related protein, suramin, sorafenib, regorafenib, thalidomide, cortisone, linomide, fumagillin (AGM-1470; TNP-470), tamoxifen, retinoids, CM101, dexamethasone, leukemia inhibitory factor (LIF), hedgehog inhibitor and combinations thereof.

A pharmaceutical combination can include first and second therapeutic agents in any desired proportions provided that the synergistic or cooperative effect still occurs. A synergistic pharmaceutical combination preferably contains the first and second therapeutic agents in a ratio of from about 1:9 to about 9:1. In one embodiment, a synergistic combination contains the first and second therapeutic agents in a ratio of from about 1:8 to about 8:1, from about 1:7 to about 7:1, from about 1:6 to about 6:1, from about 1:5 to about 5:1, from about 1:4 to about 4:1, from about 1:3 to about 3:1, or from about 1:2 to about 2:1. In one embodiment, the synergistic combination contains the therapeutic agents in a ratio of approximately 1:1.

In one embodiment, the second therapeutic agent is selected from Allopurinol, Arsenic Trioxide, Azacitidine, Bortezomib, Bevacizumab, Capecitabine, Carboplatin, Celecoxib, Chlorambucil, Clofarabine, Cytarabine, Dacarbazine, Daunorubicin HCl, Docetaxel, Doxorubicin HCl, Floxuridine, Gemcitabine HCl, Hydroxyurea, Ifosfamide, Imatinib Mesylate, Ixabepilone, Lenalidomide, Megestrol acetate, Methotrexate, Mitotane, Mitoxantrone HCl, Oxaliplatin, Paclitaxel, Pralatrexate, Romidepsin, Sorafenib, Streptozocin, Tamoxifen Citrate, Topotecan HCl, Tretinoin, Vandetanib, Vismodegib, Vorinostat, and combinations thereof.

In one embodiment, the second therapeutic agent comprises a small molecule multi-kinase inhibitor, e.g., sorafenib or regorafenib. In one embodiment, the second therapeutic agent comprises a Hedgehog Pathway Inhibitor, e.g., vismodegib. In one embodiment, the second therapeutic agent includes a drug selected from Table 2 below.

TABLE 2

Classes Of Drugs

| Classes of drugs | Examples |
| --- | --- |
| Purine analogs | allopurinol, oxypurinol, clofarabine, and tisopurine |
| Pyrimidine analogs | 5-fluorouracil, Floxuridine (FUDR), capecitabine, cytarabine, 6-azauracil (6-AU), and gemcitabine (Gemzar) |
| Proteasome inhibitors | bortezomib, carfilzomib, cediranib, disulfiram, epigallocatechin-3-gallate, salinosporamide A, ONCX 0912, CEP-18770, MLN9708, epoxomicin, and MG132. |
| Anti-angiogenic | bevacizumab, aflibercept, sunitinib, sorafenib, pazopanib, vandetanib, cabozantinib, axitinib, ponatinib, regorafenib, ranibizumab, lapatinib, and vandetanib. |
| Platinum-based antineoplastic drugs | cisplatin, carboplatin, oxaliplatin, satraplatin, picoplatin, nedaplatin, and triplatin. |
| COX-2 inhibitors | celecoxib, valdecoxib (Bextra), parecoxib (Dynastat), lumiracoxib, etoricoxib, and rofecoxib. |
| Nitrogen mustards | cyclophosphamide, chlorambucil, uramustine, ifosfamide, melphalan, bendamustine, and mustine. |
| Alkylating agents | cyclophosphamide, mechlorethamine or mustine (HN2) (trade name Mustardgen), uramustine or uracil mustard, melphalan, chlorambucil, ifosfamide, bendamustine, carmustine, lomustine, streptozocin, and busulfan. |
| Anthracyclines | Daunorubicin (Daunomycin), Daunorubicin (liposomal), Doxorubicin (Adriamycin), Doxorubicin (liposomal), Epirubicin, Idarubicin, Valrubicin, and Mitoxantrone. |
| Taxanes | Paclitaxel (Taxol), Docetaxel (Taxotere), and albumin-bound paclitaxel (Abraxane). |
| Nucleotide synthesis inhibitor | methotrexate, pralatrexate, hydroxyurea, and 5-fluorodeoxyuridine, 3,4-dihydroxybenzylamine. |
| Bcr-abl inhibitors | imatinib, nilotinib, dasatinib, bosutinib and ponatinib. |
| Other | arsenic trioxide, thalidomide, revlimid, and mitotane. |
| Topoisomerase inhibitor | amsacrine, etoposide, etoposide phosphate, teniposide, doxorubicin, Topotecan (Hycamtin), Irinotecan (CPT-11, Camptosar), Exatecan, Lurtotecan, ST 1481, CKD 602, ICRF-193, and genistein. |

TABLE 2-continued

Classes Of Drugs

| Classes of drugs | Examples |
| --- | --- |
| HDAC inhibitors | Vorinostat (SAHA), Romidepsin (Istodax), Panobinostat (LBH589), Valproic acid (as Mg valproate), Belinostat (PXD101), Mocetinostat (MGCD0103), Abexinostat (PCI-24781), Entinostat (MS-275), SB939, Resminostat (4SC-201), Givinostat, Quisinostat (JNJ-26481585), CUDC-101, AR-42, CHR-2845, CHR-3996, 4SC-202, CG200745, ACY-1215, ME-344, sulforaphane, Kevetrin, and ATRA. |
| Multi-kinase inhibitors | sorafenib, regorafenib, and vandetanib. |
| Hormone therapies | tamoxifen, toremifene, Arimidex (anastrozole), Aromasin (exemestane), Femara (letrozole), and Fulvestrant (Faslodex). |
| Hedgehog signaling Inhibitors | vismodegib, BMS-833923, IPI-926, LDE-225, PF-04449913, LEQ 506, and TAK-441. |
| Checkpoint Inhibitors | Opdivo (nivolumab), Durvalumab (Medi4736), Keytruda (pembrolizumab, MK3475), BGB-A317, AMP-224, PDR001, REGN 281, Atezolizumab (MPDL3280A), Pidilizumab (BMS-936559, CT-011, ONO-4538), Avelumab (MSB0010718 C), Yervoy (ipilimumab), tremelimumab |
| BCL2 Inhibitors | AT-101, Bcl-2/xL inhibitor, Navitoclax (ABT-263), Venetoclax (ABT-199), Apogossypol, PTN1258, obatoclax, G3139 |

In one embodiment, the second therapeutic agent includes drugs that target tumor necrosis factor-related apoptosis-inducing ligand (TRAIL) receptors. In one embodiment, the second therapeutic agent includes recombinant TRAIL or an agonistic antibody that activates one or more TRAIL receptors. In one embodiment, the second therapeutic agent includes one or more antibodies or recombinant TRAIL that activate signaling by DR4, DR5 or both. In one embodiment, the second therapeutic agent includes one or more of AMG-655, LBY-135, mapatumumab, lexatumumab, Apomab, and rhApo2L/TRAIL. In one embodiment, the second therapeutic agent includes an active agent selected from Camptothecin, 5-FU, capecitabine, cisplatin, doxorubicin, irinotecan, paclitaxel, cisplatin, bortezomib, BH3I-2, rituximab, radiation, triterpenoids, sorafenib, gemcitabine, HDAC inhibitors, carboplatin, T-101 (a gossypol derivate), ABT-263, ABT-737, and GX-15-070 (obatoclax), vorinostat, cetuximab, panitumumab, bevacizumab, ganitumab, interferon gamma, sorafenib, XIAP antagonists, Bcl-2 antagonists, and Smac mimetics.

VI. DOSE

In one embodiment, a pharmaceutical composition comprises an imipridone, such as ONC201, or an analog thereof, or a pharmaceutically acceptable salt thereof in a dose ranging from about 40, 50, 60, or 100 mg to about 2000 mg; from about 4, 5, 6, or 10 mg to about 200 mg; or from about 0.4, 0.5, 0.6, or 1 mg to about 20 mg where the weight can be based on the compound in its free base form. In one embodiment, a pharmaceutical composition comprises an imipridone, such as ONC201, or an analog thereof, or a pharmaceutically acceptable salt thereof in a dose level ranging from about 50 mg to about 200, 300, 400, 500, 600, 700, 800, 900, 1000, 1100, 1200, 1300, 1400, 1500, 1600, 1700, 1800, 1900, or 2000 mg; from about 5 mg to about 20, 30, 40, 50, 60, 70, 80, 90, 100, 110, 120, 130, 140, 150, 160, 170, 180, 190, and 200 mg; or from about 0.5 mg to about 2, 3, 4, 5, 6, 7, 8, 9, 10, 11, 12, 13, 14, 15, 16, 17, 18, 19, and 20 mg. In one embodiment, a pharmaceutical composition comprises an imipridone, such as ONC201, or an analog thereof, or a pharmaceutically acceptable salt thereof in a dose level ranging from about 40 mg to about 200, 300, 400, 500, 600, 700, 800, 900, 1000, 1100, 1200, 1300, 1400, 1500, 1600, 1700, 1800, 1900, or 2000 mg; from about 4 mg to about 20, 30, 40, 50, 60, 70, 80, 90, 100, 110, 120, 130, 140, 150, 160, 170, 180, 190, or 200 mg; or from about 0.4 mg to about 2, 3, 4, 5, 6, 7, 8, 9, 10, 11, 12, 13, 14, 15, 16, 17, 18, 19, and 20 mg. In one embodiment, a pharmaceutical composition comprises an imipridone, such as ONC201, or an analog thereof, or a pharmaceutically acceptable salt thereof in a dose level ranging from about 60 mg to about 200, 300, 400, 500, 600, 700, 800, 900, 1000, 1100, 1200, 1300, 1400, 1500, 1600, 1700, 1800, 1900, or 2000 mg; from about 6 mg to about 20, 30, 40, 50, 60, 70, 80, 90, 100, 110, 120, 130, 140, 150, 160, 170, 180, 190, or 200 mg; or from about 0.6 mg to about 2, 3, 4, 5, 6, 7, 8, 9, 10, 11, 12, 13, 14, 15, 16, 17, 18, 19, or 20 mg. In one embodiment, a pharmaceutical composition comprises an imipridone, such as ONC201, or an analog thereof, or a pharmaceutically acceptable salt thereof in a dose level ranging from about 100 mg to about 200, 300, 400, 500, 600, 700, 800, 900, 1000, 1100, 1200, 1300, 1400, 1500, 1600, 1700, 1800, 1900 mg, or 2000 mg; from about 10 mg to about 20, 30, 40, 50, 60, 70, 80, 90, 100, 110, 120, 130, 140, 150, 160, 170, 180, 190, or 200 mg; or from about 1 mg to about 2, 3, 4, 5, 6, 7, 8, 9, 10, 11, 12, 13, 14, 15, 16, 17, 18, 19, or 20 mg. In one embodiment, a pharmaceutical composition comprises an imipridone, such as ONC201, or an analog thereof, or a pharmaceutically acceptable salt thereof in a dose level ranging from about 200 mg to about 300, 400, 500, 600, 700, 800, 900, 1000, 1100, 1200, 1300, 1400, 1500, 1600, 1700, 1800, 1900, or 2000 mg; from about 20 mg to about 30, 40, 50, 60, 70, 80, 90, 100, 110, 120, 130, 140, 150, 160, 170, 180, 190, or 200 mg; or from about 2 mg to about 3, 4, 5, 6, 7, 8, 9, 10, 11, 12, 13, 14, 15, 16, 17, 18, 19, or 20 mg, based on the compound in its free base form. In one embodiment, a pharmaceutical composition comprises an imipridone, such as ONC201, or an analog thereof, or a pharmaceutically acceptable salt thereof in a dose level ranging from about 400 mg to about 500, 600, 700, 800, 900, 1000, 1100, 1200, 1300, 1400, 1500, 1600, 1700, 1800, 1900, or 2000 mg; from about 40 mg to about 50, 60, 70, 80, 90, 100, 110, 120, 130, 140, 150, 160, 170, 180, 190, or 200 mg; or from about 4 mg to about 5, 6, 7, 8, 9, 10, 11, 12, 13, 14, 15, 16, 17, 18, 19, or 20 mg based on the compound in its free base form. In one embodiment, a pharmaceutical composition comprises an imipridone, such as ONC201, or an analog thereof, or a pharmaceutically acceptable salt thereof thereof in a dose level ranging from about 50 mg to about 60, 70, 80, 90, or 100 mg; from about 60 mg to about 70, 80, 90, or 100 mg; from about 70 mg to about 80, 90 or 100 mg, from about 80 mg to about 90 or 100 mg; from about 90 mg to about 100 mg; from about 5 mg to about 6, 7, 8, 9, or 10 mg; from about 6 mg to about 7, 8, 9, or 10 mg; from about 7 mg to about 8, 9 or 10 mg, from about 8 mg to about 9 or 10 mg; from about 9 mg to about 10 mg; from about 0.5 mg to about 0.6, 0.7, 0.8, 0.9, or 1 mg; from about 0.6 mg to about 0.7, 0.8, 0.9, or 1 mg; from about 0.7 mg to about 0.8, 0.9 or 1 mg, from about 0.8 mg to about 0.9 or 1 mg; or from about 0.9 mg to about 1 mg.

In one embodiment, a pharmaceutical composition comprises an imipridone, such as ONC201, or an analog thereof, or a pharmaceutically acceptable salt thereof in a dose ranging from about 1 to about 40 mg/kg; about 0.1 to about 4 mg/kg; or about 0.01 to about 0.40 mg/kg. In one embodiment, a pharmaceutical composition comprises an imipridone, such as ONC201, or an analog thereof, or a pharmaceutically acceptable salt thereof in a dose level ranging from about 1, 2, 3, 4, 5, 6, 7, 8, or 9 mg/kg to about 10, 20, 30, or 40 mg/kg; from about 10, 11, 12, 13, 14, 15, 16, 17, 18, or 19 mg/kg to about 20, 30, or 40 mg/kg; from about 20, 21, 22, 23, 24, 25, 26, 27, 28, or 29 mg/kg to about 30 or 40 mg/kg; from about 30, 31, 32, 33, 34, 35, 36, 37, 38, or 39 mg/kg to about 40 mg/kg; from about 0.1, 0.2, 0.3, 0.4, 0.5, 0.6, 0.7, 0.8, or 0.9 mg/kg to about 1, 2, 3, or 4 mg/kg; from about 1.0, 1.1, 1.2, 1.3, 1.4, 1.5, 1.6, 1.7, 1.8, or 1.9 mg/kg to about 2, 3, or 4 mg/kg; from about 2.0, 2.1, 2.2, 2.3, 2.4, 2.5, 2.6, 2.7, 2.8, or 2.9 mg/kg to about 3 or 4 mg/kg; or from about 3.0, 3.1, 3.2, 3.3, 3.4, 3.5, 3.6, 3.7, 3.8, or 3.9 mg/kg to about 4 mg/kg; from about 0.01, 0.02, 0.03, 0.04, 0.05, 0.06, 0.07, 0.08, 0.09 mg/kg to about 0.10, 0.20, 0.30, or 0.40 mg/kg; from about 0.10, 0.11, 0.12, 0.13, 0.14, 0.15, 0.16, 0.17, 0.18, or 0.19 mg/kg to about 0.20, 0.30, or 0.40 mg/kg; from about 0.20, 0.21, 0.22, 0.23, 0.24, 0.25, 0.26, 0.27, 0.28, or 0.29 mg/kg to about 0.30 or 0.40 0. mg/kg; or from about 0.30, 0.31, 0.32, 0.33, 0.34, 0.35, 0.36, 0.37, 0.38, or 0.39 mg/kg to about 0.40 mg/kg.

In one embodiment, a pharmaceutical composition comprises an imipridone, such as ONC201, or an analog thereof, or a pharmaceutically acceptable salt thereof in a dose ranging from about 37.5 mg/m$^2$ to about 1500 mg/m$^2$; from about 3.75 mg/m$^2$ to about 150 mg/m$^2$; or from about 0.4 mg/m$^2$ to about 15 mg/m$^2$ In one embodiment, a pharmaceutical composition comprises comprises an imipridone, such as ONC201, or an analog thereof, or a pharmaceutically acceptable salt thereof in a dose ranging from about 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000, 1005, 1010, 1015, 1020, 1025, 1030, 1035, 1040, 1045, 1050, 1055, 1060, 1065, 1070, 1075, 1080, 1085, 1090, 1095, 1100, 1105, 1110, 1115, 1120, 1125, 1130, 1135, 1140, 1145, 1150, 1155, 1160, 1165, 1170, 1175, 1180, 1185, 1190, 1195, 1200, 1205, 1210, 1215, 1220, 1225, 1230, 1235, 1240, 1245, 1250, 1255, 1260, 1265, 1270, 1275, 1280, 1285, 1290, 1295, 1300, 1305, 1310, 1315, 1320, 1325, 1330, 1335, 1340, 1345, 1350, 1355, 1360, 1365, 1370, 1375, 1380, 1385, 1390, 1395, 1400, 1405, 1410, 1415, 1420, 1425, 1430, 1435, 1440, 1445, 1450, 1455, 1460, 1465, 1470, 1475, 1480, 1485, 1490, 1495 mg/m$^2$ to about 1500 mg/m$^2$; from about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or 149 mg/m$^2$ to about 150 mg/m$^2$; or from about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 111, 11.5, 12, 12.5, 13, 13.5, 14, or 14.5 mg/m$^2$ to about 15 mg/m$^2$.

VII. DOSAGE FORMS

Pharmaceutical compositions for use in the methods described herein can be formulated into a dosage form that can be administered to a patient. In some embodiments, the composition is in the form of an oral or parenteral dosage unit. In some embodiments, the composition is in the form of an oral dosage unit. In some embodiments, the oral dosage unit is fractionated into several, smaller doses, which are administered to a subject over a predetermined period of time in order to reduce toxicity of a therapeutic agent being administered. In some embodiments, an oral dosage unit is administered as a tablet or capsule comprising a controlled release formulation that can include a plurality of particles, granules, pellets, minitablets or tablets. In some embodiments, the composition is in the form of a parenteral dosage unit. In some embodiments, the parenteral dosage unit is selected from intravenous (IV), subcutaneous (SC), and intramuscular (M), rectal (PR) or transdermal dosage units. In some embodiments, the composition is in a dosage form selected from sterile solutions, suspensions, suppositories, tablets and capsules. In some embodiments, the composition is an oral dosage form selected from a tablet, caplet, capsule, lozenge, syrup, liquid, suspension and elixir. In some embodiments, the composition is in an oral dosage form selected from tablets, hard shell capsules, soft gelatin capsules, beads, granules, aggregates, powders, gels, solids and semi-solids.

In some embodiments, suitable forms of pharmaceutical compositions for use in the methods described herein include dermatological compositions adapted for cutaneous topical administration. For example, dermatological compositions include a cosmetically or pharmaceutically acceptable medium. Dermatological compositions for topical administration can include ointments, lotions, creams, gels, drops, suppositories, sprays, liquids and powders. In some embodiments, conventional pharmaceutical carriers, aqueous, powder or oily bases, thickeners, skin enhancers can be necessary or desirable and therefore used. Examples of suitable enhancers include ethers, such as diethylene glycol monoethyl ether (available commercially as TRANSCUTOL®) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80), and lecithin; alcohols such as ethanol, propanol, octanol, benzyl alcohol; polyethylene glycol and esters thereof such as polyethylene glycol monolaurate; amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly citric acid and succinic acid. AZONE® and sulfoxides such as DMSO and CtOMSO may also be used, but are less preferred.

In some embodiments, the composition is in a dosage form selected from sustained release, controlled release, delayed release and response release forms.

VIII. METHODS OF USE

The compositions and methods described herein have utility in treating many disease conditions, including cancer (e.g., colorectal, brain, and glioblastoma). In one embodiment, the compositions and methods described herein are used to treat diseases such as ocular melanoma, desmoplastic round cell tumor, chondrosarcoma, leptomengial disease, diffuse large B-cell lymphoma, Acute Lymphoblastic Leukemia, Acute Myeloid Leukemia, Adrenocortical Carcinoma, AIDS-Related Cancers, AIDS-Related Lymphoma, Anal or Rectal Cancer, Appendix Cancer, Astrocytomas, and Atypical Teratoid/Rhabdoid Tumor. In one embodiment, the compositions and methods described herein are used to treat diseases such as Basal Cell Carcinoma, Basal Cell Nevus Syndrome, Gorlin-Nevus Syndrome, Bile Duct Cancer, Bladder Cancer, Bone Cancer, Osteosarcoma and Malignant Fibrous Histiocytoma, Brain Tumor, Breast Cancer, Bronchial Tumors, Burkitt Lymphoma, and Spinal Cord Tumors. In one embodiment, the compositions and methods described herein are used to treat diseases such as Carcinoid Tumor, Carcinoma of Unknown Primary, Central Nervous System Atypical Teratoid/Rhabdoid Tumor, Leptomeningeal Disease, Central Nervous System Embryonal Tumors, Central Nervous System Lymphoma, Cervical Cancer, Chordoma, Chronic Lymphocytic Leukemia, Chronic Myelogenous Leukemia, Chronic Myeloproliferative Disorders, Colon Cancer, Colorectal Cancer, Craniopharyngioma, and Cutaneous T-Cell Lymphoma (including Sezary syndrome and mycosis fungoides (MF)). In one embodiment, the compositions and methods described herein are used to treat diseases such as Embryonal Tumors of Central Nervous System, Endometrial Cancer, Ependymoblastoma, Ependymoma, Esophageal Cancer, Ewing Sarcoma Family of Tumors, Extracranial Germ Cell Tumor, Extragonadal Germ Cell Tumor, Extrahepatic Bile Duct Cancer, and Eye Cancer, including Intraocular Melanoma and Retinoblastoma. In one embodiment, the compositions and methods described herein are used to treat diseases such as Gallbladder Cancer, Gastric (Stomach) Cancer, Gastrointestinal Carcinoid Tumor, Gastrointestinal Stromal Tumor (GIST), Germ Cell Tumor, Gestational Trophoblastic Tumor, and Glioma. In one embodiment, the compositions and methods described herein are used to treat a cancer selected from the group consisting of Hairy Cell Leukemia, Head and Neck Cancer, Hepatocellular (Liver) Cancer, Histiocytosis, Hodgkin Lymphoma, and Hypopharyngeal Cancer. In one embodiment, the compositions and methods described herein are used to treat diseases such as Kaposi Sarcoma and Kidney (Renal Cell) Cancer. In one embodiment, the compositions and methods described herein are used to treat diseases such as Langerhans Cell Histiocytosis, Laryngeal Cancer, Lip and Oral Cavity Cancer, Liver Cancer, Lung Cancer, including Non-Small Cell Lung Cancer, and Small Cell Lung Cancer, Non-Hodgkin Lymphoma, and Primary Central Nervous System Lymphoma. In one embodiment, the compositions and methods described herein are used to treat diseases such as Waldenström's macroglobulinemia (lymphoplasmacytic lymphoma), Malignant Fibrous Histiocytoma of Bone and Osteosarcoma, Medulloblastoma, Medulloepithelioma, Melanoma, Merkel Cell Carcinoma, Mesothelioma, Metastatic Squamous Neck Cancer with Occult Primary, Multiple Endocrine Neoplasia Syndrome, Mouth Cancer, Multiple Myeloma/Plasma Cell Neoplasm, Mycosis Fungoides, Myelodysplastic Syndromes, complex karyotype, blastic phase leukemia, Myelodysplastic/Myeloproliferative Neoplasms, Multiple Myeloma, and Myeloproliferative Disorders. In one embodiment, the compositions and methods described herein are used to treat cancer. In one embodiment, the compositions and methods described herein are used to treat diseases such as Nasal Cavity and Paranasal Sinus Cancer, Nasopharyngeal Cancer, and Neuroblastoma. In one embodiment, the compositions and methods described herein are used to treat diseases such as Oral Cancer, Lip and Oral Cavity Cancer, Oropharyngeal Cancer, Osteosarcoma and Malignant Fibrous Histiocytoma of Bone, Ovarian Cancer, Ovarian Germ Cell Tumor, Ovarian Epithelial Cancer, and Ovarian Low Malignant Potential Tumor. In one embodiment, the compositions and methods described herein are used to treat diseases such as Pancreatic Cancer, Papillomatosis, Paranasal Sinus and Nasal Cavity Cancer, Parathyroid Cancer, Penile Cancer, Pharyngeal Cancer, Pineal Parenchymal Tumors of Intermediate Differentiation, Pineoblastoma and Supratentorial Primitive Neuroectodermal Tumors, Pituitary Tumor, Pleuropulmonary Blastoma, Pregnancy and Breast Cancer, Primary Central Nervous System Lymphoma, and Prostate Cancer. In one embodiment, the compositions and methods described herein are used to treat a cancer selected from the group consisting of Rectal Cancer, Renal Cell (Kidney) Cancer, Renal Pelvis and Ureter, Respiratory Tract Carcinoma Involving the NUT Gene on Chromosome 15, Retinoblastoma, and Rhabdomyosarcoma. In one embodiment, the compositions and methods described herein are used to treat high grade prostate cancer. In one embodiment, the compositions and methods described herein are used to treat medium grade prostate cancer. In one embodiment, the compositions and methods described herein are used to treat low grade prostate cancer. In one embodiment, the compositions and methods described herein are used to treat castration-resistant prostate cancer. In one embodiment, the compositions and methods described herein are used to treat a nervous system tumor. In one embodiment, the compositions and methods described herein are used to treat a central nervous system tumor. In one embodiment, the compositions and methods described herein are used to treat a peripheral nervous system tumor. In one embodiment, the compositions and methods described herein are used to treat a paraganglioma. In one embodiment, the compositions and methods described herein are used to treat a pheochromocytoma.

In in vitro models, in animal models, and in human clinical trials compound (1) (ONC201) has broad anti-cancer activity, low toxicity including few, if any, adverse effects, low genotoxicity, and high bioavailability including oral bioavailability. These features allow ONC 201 and various analogs to be particularly well suited for pediatric patients. These features also make ONC 201 and various analogs particularly well suited for chronic therapy, for high risk patients, and to ensure long-lasting responses or stable disease or to prevent disease recurrence.

In another aspect, provided herein are methods of treating or preventing cancer in a subject in need thereof, comprising: administering to the subject in need of such treatment a pharmaceutical composition comprising a therapeutically effective amount compound (1)

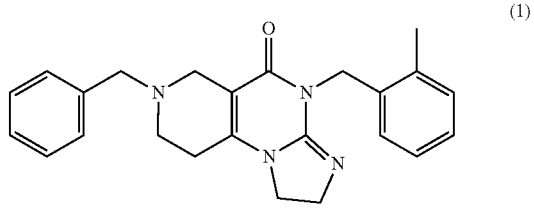 [SMILES: Cc1ccccc1CN1C(=O)C2=C(CCN(Cc3ccccc3)C2)N2CCN=C12]

(1)

or a pharmaceutically acceptable salt thereof, wherein the cancer is a midline glioma having a histone H3 K27M mutation. In some embodiments, the cancer is selected from the group consisting of a diffuse intrinsic pontine glioma, a diffuse midline glioma, a spinal cord glioma, a thalamic glioma, a brainstem glioma, and a cerebellar glioma. In some embodiments, the cancer is not a spinal cord tumor. In some embodiments, the histone H3 K27M mutation is H3.3 K27M or H3.1 K27M. In some embodiments, the histone H3 K27M mutation is in one or more histone genes selected from H3F3A, H3F3B, HIST1H3A, HIST1H3B, HIST1H3C, HIST1H3D, HIST1H3E, HIST1H3F, HIST1H3G, HIST1H3H, HIST1H3I, or HIST1H3J. In some embodiments, DRD2 is overexpressed in cancerous tissue. In some embodiments, DRD5 is underexpressed in cancerous tissue. In some embodiments, DRD2 is overexpressed and DRD5 is underexpressed in cancerous tissue. In some embodiments, the subject is a human. In some embodiments, the subject is a domesticated pet. In some embodiments, the subject is a pediatric subject.

In another aspect, provided herein are methods of treating or preventing cancer in a subject in need thereof, comprising: administering to the subject in need of such treatment a pharmaceutical composition comprising a therapeutically effective amount a compound of formula (10) or an analog thereof, or a pharmaceutically acceptable salt thereof, wherein the cancer has a histone H3 mutation. In some embodiments, the cancer is selected from the group consisting of a central nervous system tumor, a brain tumor, a peripheral nervous system tumor, a pheochromocytoma, a paraganglioma, an adrenal cortical carcinoma, an adrenal tumor, and a neuroendocrine tumor. In some embodiments, the cancer is selected from the group consisting of meningioma, ependymoma, glioma, neuroblastoma, and diffuse intrinsic pontine glioma. In some embodiments, the cancer is selected from the group consisting of a diffuse midline glioma, a spinal cord glioma, a thalamic glioma, a brainstem glioma, and a cerebellar glioma. In some embodiments, the histone H3 mutation is H3.3 K27M or H3.1 K27. In some embodiments, the cancer has a K27M mutation in one or more histone genes selected from H3F3A, H3F3B, HIST1H3A, HIST1H3B, HIST1H3C, HIST1H3D, HIST1H3E, HIST1H3F, HIST1H3G, HIST1H3H, HIST1H3I, or HIST1H3J. In some embodiments, DRD2 is overexpressed in cancerous tissue. In some embodiments, DRD5 is underexpressed in cancerous tissue. In some embodiments, DRD2 is overexpressed and DRD5 is underexpressed in cancerous tissue. In some embodiments, the compound is ONC201. In some embodiments, the subject is a human. In some embodiments, the subject is a domesticated pet. In some embodiments, the subject is a pediatric subject.

In another aspect, provided herein are methods of treating or preventing cancer in a subject in need thereof, comprising: administering to the subject in need of such treatment a pharmaceutical composition comprising a therapeutically effective amount a compound of formula (10) or an analog thereof, or a pharmaceutically acceptable salt thereof, wherein the cancer is a midline glioma. In some embodiments, the cancer is selected from the group consisting of a diffuse intrinsic pontine glioma, a diffuse midline glioma, a spinal cord glioma, a thalamic glioma, a brainstem glioma, and a cerebellar glioma. In some embodiments, the cancer is not a spinal cord tumor. In some embodiments, the cancer has a histone H3 mutation, wherein the histone H3 mutation is H3.3 K27M or H3.1 K27M. In some embodiments, the cancer has a histone H3 K27M mutation in one or more histone genes selected from H3F3A, H3F3B, HIST1H3A, HIST1H3B, HIST1H3C, HIST1H3D, HIST1H3E, HIST1H3F, HIST1H3G, HIST1H3H, HIST1H3I, or HIST1H3J. In some embodiments, DRD2 is overexpressed in cancerous tissue. In some embodiments, DRD5 is underexpressed in cancerous tissue. In some embodiments, DRD2 is overexpressed and DRD5 is underexpressed in cancerous tissue. In some embodiments, the compound is ONC201. In some embodiments, the subject is a human. In some embodiments, the subject is a domesticated pet. In some embodiments, the subject is a pediatric subject.

In one embodiment, the compositions and methods described herein are used to treat a pediatric cancer (e.g., pediatric solid tumors, pediatric sarcomas, pediatric Ewing's sarcomas, pediatric gliomas, pediatric central nervous system cancers, pediatric neuroblastoma, pediatric leukemia and pediatric lymphoma).

In one embodiment, the compositions and methods described herein are used to treat a proliferative skin disorder such as psoriasis. In one embodiment, the compositions and methods described herein are used to treat a cancer selected from the group consisting of Salivary Gland Cancer, Sarcoma, Sezary Syndrome, Skin Cancer, Ocular Cancer, Skin Carcinoma, Small Intestine Cancer, Soft Tissue Sarcoma, Squamous Cell Carcinoma, Squamous Neck Cancer with Occult Primary, and Supratentorial Primitive Neuroectodermal Tumors. In one embodiment, the compositions and methods described herein are used to treat a cancer selected from the group consisting of T-Cell Lymphoma, Testicular Cancer, Throat Cancer, Thymoma and Thymic Carcinoma, Thyroid Cancer, Transitional Cell Cancer of the Renal Pelvis and Ureter, and Gestational Trophoblastic Tumor. In one embodiment, the compositions and methods described herein are used to treat a cancer selected from the group consisting of Carcinoma of Unknown Primary Site, Cancer of Unknown Primary Site, Unusual Cancers of Childhood, Transitional Cell Cancer of the Renal Pelvis and Ureter, Urethral Cancer, and Uterine Sarcoma. In one embodiment, the compositions and methods described herein are used to treat cancer selected from the group consisting of Vaginal Cancer and Vulvar Cancer. In one embodiment, the compositions and methods described herein are used to treat a cancer selected from the group consisting of Wilms Tumor and Women's Cancers.

In one embodiment, the compositions and methods described herein are used as a first-line therapy (sometimes called primary therapy). In one embodiment, the compositions and methods described herein are used as a second-line therapy. In one embodiment, the compositions and methods described herein are used as a third-line therapy. In one embodiment, the compositions and methods described herein are used as a salvage therapy. The term "salvage therapy" means a therapeutic agent that can be taken with any regimen after a subject's initial treatment regimen has failed or after the subject's condition has not responded to an initial treatment. In one embodiment, the compositions and methods described herein are used as a rescue therapy. In some embodiments, the compositions are used as a rescue agent to counteract the action of an initial treatment. In some embodiments, the compositions are used as rescue agent which is administered to a subject who has developed resistance to a standard or an initial treatment. In one embodiment, the compositions and methods described herein are used as a neoadjuvant therapy. In some embodiments, a neoadjuvant therapy comprises administration of one or more of the therapeutic agents described herein to a subject before a main or first line treatment. In one embodiment, a neoadjuvant therapy reduces the size or extent of the cancer being treated before a main or first line treatment is administered to the subject undergoing treatment. In one embodiment, the compositions and methods described herein are used as an adjuvant therapy. In one embodiment, an adjuvant therapy comprises administration of one or more therapeutic agents described herein to a subject, wherein the one or more therapeutic agent that modify the effect of other therapeutic agents that are already administered to the subject or are concurrently administered to the subject or subsequently administered to the subject.

In one embodiment, the compositions and methods described herein exhibit reduced chance of drug-drug interactions. In one embodiment, an imipridone, such as ONC201, or an analog thereof are eliminated from the patient's body before it can interact with another pharmaceutically active agent.

In one embodiment, the compositions and methods of described herein exhibit toxicity levels that facilitates combinations with other pharmaceutical agents.

The methods and compositions described herein are not limited to a particular animal species. In one embodiment, a subject treated according to methods and using compositions described herein, can be mammalian or non-mammalian. In one embodiment, a mammalian subject includes, but is not limited to, a human; a non-human primate; a rodent such as a mouse, rat, or guinea pig; a domesticated pet such as a cat or dog; a horse, cow, pig, sheep, goat, or rabbit. In one embodiment, a non-mammalian subject includes, but is not limited to, a bird such as a duck, goose, chicken, or turkey. In one embodiment, the subject is a human. In one embodiment, subjects can be either gender and any age. The composition and methods can also be used to prevent cancer. The composition and methods can also be used to stimulate the immune system.

The methods and compositions described herein are not limited to a particular age of the subject. In one embodiment, a subject treated according to methods and using compositions described herein is over 50 years old, over 55 years old, over 60 years old, or over 65 years old. In one embodiment, a subject treated according to methods and using compositions described herein is under 50 years old, under 55 years old, under 60 years old, or under 65 years old.

In one embodiment, a subject treated according to methods and using compositions described herein is a pediatric patient. In one embodiment, the pediatric patient is younger than 18 years old, younger than 17 years old, younger than 16 years old, younger than 15 years old, younger than 14 years old, is younger than 13 years old, younger than 12 years old, younger than 11 years old, younger than 10 years old, younger than 9 years old, younger than 8 years old, younger than 7 years old, younger than 6 years old, younger than 5 years old, younger than 4 years old, younger than 3 years old, younger than 2 years old, younger than 1 year old. In one embodiment, the pediatric patient is younger than 12 months old, younger than 11 months old, younger than 10 months old, younger than 9 months old, younger than 8 months old, younger than 7 months old, younger than 6 months old, is younger than 5 months old, younger than 4 months old, younger than 3 months old, younger than 2 months old, younger than 1 month old. In one embodiment, the pediatric patient younger than 4 weeks old, younger than 3 weeks old, younger than 2 weeks old, younger than 1 weeks old. In one embodiment, the pediatric patient is younger than 7 days old, younger than 6 days old, younger than 5 days old, younger than 4 days old, younger than 3 days old, younger than 2 days old, or younger than 1 day old. In one embodiment, the pediatric patient is a neonate. In one embodiment, the pediatric patient is prematurely born.

In some embodiments, the patient is less than 45 kg in weight, less than 40 kg in weight, less than 35 kg in weight, less than 30 kg in weight, less than 25 kg in weight, less than 20 kg in weight, less than 15 kg in weight, less than 14 kg in weight, less than 10 kg in weight, less than 5 kg in weight, less than 4 kg in weight, less than 3 kg in weight, less than 2 kg in weight, or less than 1 kg in weight.

In one embodiment, the subject has received at least one prior therapeutic agent. In one embodiment the subject has received at least two, at least three, or at least four prior therapeutic agents. In one embodiment the prior therapeutic agent is ibrutinib, bortezomib, carfilzomib, temozolomide, bevacizumab, cyclophosphamide, hydroxydaunorubicin, vincristine, prednisone, cytarabine, cisplatin, rituximab, 5-fluorouracil, oxaliplatin, leucovorin, or lenalidomide.

In one embodiment, the subject has been treated with radiation. In one embodiment, the subject has been treated with surgery. In one embodiment, the subject has been treated with adoptive T-cell therapy.

In one embodiment, the cancer no longer responds to treatment with ibrutinib, bortezomib, carfilzomib, temozolomide, bevacizumab, cyclophosphamide, hydroxydaunorubicin, vincristine, prednisone, cytarabine, cisplatin, rituximab, 5-fluorouracil, oxaliplatin, leucovorin, lenalidomide, radiation, surgery, or a combination thereof.

In one embodiment, the compositions and methods described herein have a dose response relation in cancer cells that is different from the dose response relation of the same compositions and methods in normal cells. The dose response relation of ONC201 on proliferation and cell death in normal and tumor cells was determined by measuring cell viability following treatment with ONC201 at various concentrations for 72 hours. The tumors tested included a human colon cancer cell line (HCT116), breast tumor cell line (MDA-MB-231), and a human primary glioblastoma cell line (U87). And the normal cells tested included human foreskin fibroblasts (HFF), human fetal lung fibroblast (MRC-5) cells, and a human lung fibroblast cell line (WI-38). Doxorubicin was used as a positive control at 1 µg/mL in normal fibroblasts. Cell viability of normal cells tested was at least about 75% at about 1-5 mg/mL of ONC201, whereas viability of tumor cells was significantly lower (e.g., at or below 50%) at the same ONC201 concentration. Moreover, as ONC201 concentration increased beyond about 5 mg/mL viability of tumor cells fell to below 25%, whereas viability of normal cells remained at about 75%.

Cell viability assays in human fetal lung fibroblast (MRC-5) cells were performed following 72 hour treatment with compound (1) (5 µM) or DMSO and a recovery period in complete drug-free media after treatment. Cell recovery was seen with ONC201, but not with DMSO.

In some embodiments, the compositions and methods described herein are useful for treating cancer in a subject. In some embodiments, the compositions and methods described herein are useful for treating cancer in a human subject. In some embodiments, the treatment method comprises administering to a subject in need of such treatment, a pharmaceutically effective amount of an imipridone, such as ONC201, or an analog thereof, or a pharmaceutically acceptable salt thereof and a pharmaceutically acceptable carrier.

In one embodiment, the treatment method comprises administering to a subject in need of such treatment: (i) a first therapeutic agent including an imipridone, such as ONC201, or an analog thereof, or a pharmaceutically acceptable salt thereof in combination with (ii) a second therapeutic agent, wherein the first and the second therapeutic agents are administered either simultaneously or sequentially. The second therapeutic agent can be any suitable therapeutic agent, including a pharmaceutically active agent disclosed herein. A pharmaceutically acceptable ONC201 salt includes the di-hydrochloride salt below:

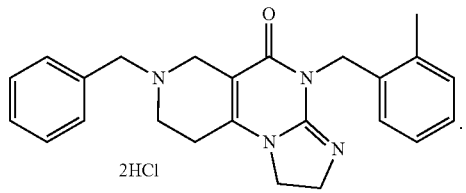 [SMILES: Cc1ccccc1CN1C(=O)C2=C(CCN(Cc3ccccc3)C2)N2CCN=C12]

It is understood that a di-hydrochloride salt of ONC201 or an analog thereof (including a compound of formula (10)), or an alternative di-salt thereof apparent from the teaching of this disclosure, can be substituted for ONC201 or an analog thereof in a composition or dosing regimen described herein.

In one embodiment, the treatment method comprises administering a synergistic pharmaceutical combination, either simultaneously or sequentially, to a subject in need of such treatment, wherein the synergistic pharmaceutical combination comprises (i) a first therapeutic agent comprising an imipridone, such as ONC201, or an analog thereof, or a pharmaceutically acceptable salt thereof; and (ii) a second therapeutic agent. In one embodiment, the treatment method comprises administering to a subject in need of such treatment, either simultaneously or sequentially, therapeutically synergistic effective amounts of the first therapeutic agent in combination with the second therapeutic agent. In one embodiment, the treatment method comprises administering to a subject in need of such treatment, an effective amount of the first therapeutic agent in combination with an effective amount of the second therapeutic agent, wherein the combination provides a synergistic effect in the in vivo treatment of a cancer sensitive to the combination, and wherein the first and the second therapeutic agents are administered either simultaneously or sequentially. In one embodiment, the treatment method comprises administering to a subject in need of such treatment, an effective amount of the first therapeutic agent in combination with an effective amount of a second therapeutic agent, wherein the combination provides a synergistic effect in the in vivo treatment of a minimal residual disease sensitive to the combination, and wherein the first and second therapeutic agents are administered either simultaneously or sequentially. In one embodiment, the second therapeutic agent is given before or prior to the first therapeutic agent.

In one embodiment, the treatment method targets a cancer selected from the group consisting of solid tumors, liquid tumors, lymphomas, leukemias, or myelomas.

In one embodiment, the treatment method targets a solid tumor, wherein the solid tumor is selected from the group consisting of: Cervical Cancer, Endometrial Cancer, Extracranial Germ Cell Tumor; Extragonadal Germ Cell Tumor; Germ Cell Tumor; Gestational Trophoblastic Tumor; Ovarian Cancer, Ovarian Germ Cell Tumor, Ovarian Epithelial Cancer, and Ovarian Low Malignant Potential Tumor; Penile Cancer, Prostate Cancer; Pregnancy and Breast Cancer; high grade prostate cancer; medium grade prostate cancer; low grade prostate cancer; castration-resistant prostate cancer; Breast Cancer; Bile Duct Cancer; Extrahepatic Bile Duct Cancer; Gallbladder Cancer; Hepatocellular (Liver) Cancer; Kidney (Renal Cell) Cancer; Liver Cancer, Renal Cell (Kidney) Cancer, Renal Pelvis and Ureter; Basal Cell Carcinoma; Basal Cell Nevus Syndrome, Gorlin-Nevus Syndrome, Melanoma, Merkel Cell Carcinoma, Papillomatosis, Multiple Endocrine Neoplasia Syndrome; Pancreatic Cancer, Parathyroid Cancer, ocular melanoma; Eye Cancer; Retinoblastoma; Malignant Fibrous Histiocytoma; Ewing Sarcoma Family of Tumors; desmoplastic round cell tumor; chondrosarcoma, Kaposi Sarcoma, Rhabdomyosarcoma; Spinal Cord Tumors, Leptomeningeal Disease, Central Nervous System Embryonal Tumors, Chordoma, Embryonal Tumors of Central Nervous System, Ependymoblastoma, Ependymoma, Neuroblastoma; Pineal Parenchymal Tumors of Intermediate Differentiation, Pineoblastoma; Adrenocortical Carcinoma; Bone Cancer, Osteosarcoma; Malignant Fibrous Histiocytoma of Bone and Osteosarcoma; Osteosarcoma and Malignant Fibrous Histiocytoma of Bone; Carcinoid Tumor, Carcinoma of Unknown Primary, Bronchial Tumors, Lung Cancer, Pleuropulmonary Blastoma; Respiratory Tract Carcinoma Involving the NUT Gene on Chromosome 15, Astrocytomas, Atypical Teratoid/Rhabdoid Tumor; Central Nervous System Atypical Teratoid/Rhabdoid Tumor, Craniopharyngioma, Glioma, Brain cancer, Medulloblastoma, Medulloepithelioma, Supratentorial Primitive Neuroectodermal Tumors; Pituitary Tumor; Gastric (Stomach) Cancer, Gastrointestinal Carcinoid Tumor, Gastrointestinal Stromal Tumor (GIST), Bladder Cancer, Anal or Rectal Cancer, Appendix Cancer, Esophageal Cancer, Hypopharyngeal Cancer; Laryngeal Cancer, Lip and Oral Cavity Cancer, Metastatic Squamous Neck Cancer with Occult Primary, Mouth Cancer, Nasal Cavity and Paranasal Sinus Cancer, Nasopharyngeal Cancer, Oral Cancer, Lip and Oral Cavity Cancer, Oropharyngeal Cancer, Paranasal Sinus and Nasal Cavity Cancer, Pharyngeal Cancer; Head and Neck Cancer, and Mesothelioma.

In one embodiment, the treatment method targets a lymphoma selected from the group consisting of: diffuse large B-cell lymphoma, AIDS-Related Lymphoma, Cutaneous T-Cell Lymphoma, Sezary syndrome, mycosis fungoides (MF); Histiocytosis; Burkitt Lymphoma, and Central Nervous System Lymphoma; Non-Hodgkin Lymphoma, and Primary Central Nervous System Lymphoma, Hodgkin Lymphoma, Waldenström's macroglobulinemia; Mycosis Fungoides; Primary Central Nervous System Lymphoma; lymphoplasmacytic lymphoma, and Primary Central Nervous System Lymphoma.

In one embodiment, the treatment method targets a Non-Hodgkin's lymphoma (NHL) selected from the group consisting of: mantle cell lymphoma, diffuse large B-cell lymphoma, follicular lymphoma, marginal zone lymphoma, small lymphocytic lymphoma, lyphoplasmacytic NHL, Waldenstrom's macroglobulinaemia, and skin lymphomas.

In one embodiment, the treatment method targets a leukemia selected from the group consisting of: Acute Lymphoblastic Leukemia (ALL), Chronic Lymphocytic Leukemia (CLL), Chronic Myeloproliferative Disorders; Hairy Cell Leukemia; Acute Myeloid Leukemia (AML); Chronic Myelogenous Leukemia (CML); and Langerhans Cell Histiocytosis.

In one embodiment, the treatment method targets an acute leukemia selected from the group consisting of: acute lymphotyte leukemia, acute myeloid leukemia, chronic lymphoblasitc leukemia, chronic myeloid leukemia, myelodysplastic syndrome, and myeloproliferative disease.

In one embodiment, the treatment method targets a myeloma selected from the group consisting of: IgA myeloma; IgG myeloma; IgM myeloma; IgD myeloma; IgE myeloma; light chain myeloma; non secretory myeloma; complex karyotype, blastic phase leukemia; Multiple Myeloma/Plasma Cell Neoplasm, Multiple Myeloma, Myelodysplastic Syndromes, Myelodysplastic/Myeloproliferative Neoplasms, and Myeloproliferative Disorders.

In one embodiment, the treatment method targets a peripheral nervous system tumor. In one embodiment, the treatment method targets a paraganglioma. In one embodiment, the treatment method targets a pheochromocytoma.

In one embodiment, treatment of cancer comprises prevention of tumor growth in a cancer subject. In one embodiment, treatment of cancer comprises prevention of formation of cancer metastases in a cancer subject. In one embodiment, treatment of cancer comprises targeted treatment of minimal residual disease in a cancer subject known to have the minimal residual disease in a cancer or a subject at risk for having minimal residual disease.

This might be indicated after treatment of the primary tumor by surgery and/or after chemotherapy (radiotherapy) has been initiated or determined to be efficacious. Disseminated tumor cells may be in their dormant state and often cannot be attacked by chemotherapy (radiotherapy). A thus treated patient seemingly is in a healed state, and referred to as "minimal residual disease." Nevertheless, the dormant tumor cells have a potential to form metastases if they become metastasising cells due to a growth stimulus after a longer dormant state.

The term "minimal residual disease" denotes a small number of cancer cells that remain in a subject during or after treatment when the subject is in remission (exhibiting no symptoms or signs of the disease). The methods described herein are preferably applied to a form of the diseases listed herein, including adult and childhood forms of these diseases.

In one embodiment, the treatment method is useful for treating an autoimmune disease. Autoimmune diseases include, but are not limited to alopecia areata, antiphospholipid, autoimmune hepatits, celiac disease, diabetes type 1, Graves' disease, Guillain-Barre syndrome, Hashimoto's disease, hemolytic anemia, idiopathic thrombocytopenic purpura, inflammatory bowel disease, inflammatory myopathies, multiple sclerosis, primary biliary cirrhosis, psoriasis, rheumatoid arthritis, scleroderma, Sjögren's syndrome, systemic lupus erythematosus, and vitiligo.

In one embodiment, the treatment method is useful for treating autoimmune and inflammatory disorders of the peripheral nerve system such as amyotrophic lateral sclerosis (Lou Gehrig's disease), based on various causes such as metabolic disorders that include diabetes, B12 and folate vitamin deficiencies, chemotherapy medications and medicines used to treat HIV, poisons that cause peripheral nerve damage, cancers that develop peripheral neuropathies as well as paraneoplastic syndromes, alcohol abuse, chronic kidney disease, injuries that cause compression on nerves and other lesions, infections such as Lyme disease, Guillain Barre syndrome, connective tissue disease, rheumatoid arthritis, Sjogren's syndrome, systemic lupus erythematosus, certain inflammatory conditions such as sarcoidosis, coeliac disease, hereditary diseases such as charcot marie tooth syndrome, Friedreich's ataxia, and/or idiopathic where no specific cause is found but inflammatory and/or autoimmune mechanisms are the cause of onset.

In one embodiment, the treatment method is useful for treating autoimmune and inflammatory disorders with ocular manifestations. Such ocular manifestations include, but are not limited to, ocular cicatricial pemphigoid, Mooren's corneal ulcer, various forms of uveitis, rheumatoid arthritis, systemic lupus erythematosus, polyarteritis nodosa, relapsing polychondritis, Wegener's granulomatosis, scleroderma, Behcet's disease, Reiter's disease, inflammatory bowel disease (ulcerative colitis and Crohn's disease) and ankylosing spondylitis, retinitis pigmentosa, macular degeneration, keratoconjunctivitis sicca, scleritis, episcleritis, keratitis, peripheral corneal ulceration, and less common entities such as choroiditis, retinal vasculitis, episcleral nodules, retinal detachments, and/or macular edema.

In one embodiment, the treatment method is useful for treating acute allograft rejection in transplant patients. In one embodiment, the treatment method is useful for treating ischemic stroke. In one embodiment, the treatment method is useful for treating inflammatory diseases including arthritis, psoriasis, asthma, and colitis.

In one embodiment, a therapeutic agent includes a pharmaceutically acceptable mono-salt of ONC201 or an analog thereof (e.g., a compound of formula (10)). In one embodiment, a therapeutic agent includes a pharmaceutically acceptable ONC201 di-salt or an analog thereof (e.g., a compound of formula (10)). As described herein, some of the analogs can be tri-salts In one embodiment, a therapeutic agent includes ONC201 or an analog thereof (e.g., a compound of formula (10)) in the form of a pharmaceutically acceptable mono- or di-salt selected from the group consisting of hydrochloride, hydrobromide, hydrogensulphate, sulfates, phosphates, fumarates, succinates, oxalates and lactates, bisulfates, hydroxyl, tartrate, nitrate, citrate, bitartrate, carbonate, malate, maleate, fumarate sulfonate, methylsulfonate, formate, acetate, and carboxylate. In one embodiment, a therapeutic agent includes ONC201 or an analog thereof in the form of a pharmaceutically acceptable mono- or di-salt selected from p-toluene-sulfonate, benzenesulfonate, methanesulfonate, oxalate, succinate, tartrate, citrate, fumarate and maleate. In one embodiment, a therapeutic agent includes ONC201 or an analog thereof in the form of a pharmaceutically acceptable mono- or di-salt having a counter ion selected from the group consisting of ammonium, sodium, potassium, calcium, magnesium, zinc, lithium, and/or with counter-ions such as methylamino, dimethylamino, diethylamino, triethylamino counter-ions, and combinations thereof. In one embodiment, a therapeutic agent includes a compound described herein in the form of a halide di-salt, such as a di-hydrochloride salt or a di-hydrobromide salt.

In some embodiments, the second therapeutic agent includes an anti-cancer agent. In some embodiments, the second therapeutic agent is selected from acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bevacizumab, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflomithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, flurocitabine, fosquidone, fostriecin, fulvestrant, gemcitabine, hydroxyurea, idarubicin, ifosfamide, ilmofosine, interleukin II (IL-2, including recombinant interleukin II or rIL2), interferon α-2a, interferon α-2b, interferon α-n1, interferon α-n3, interferon β-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, zorubicin and combinations thereof.

In some embodiments, the second therapeutic agent is selected, from hormone analogs and antihormones, aromatase inhibitors, LHRH agonists and antagonists, inhibitors of growth factors, growth factor antibodies, growth factor receptor antibodies, tyrosine kinase inhibitors; antimetabolites; antitumour antibiotics; platinum derivatives; alkylation agents; antimitotic agents; tubuline inhibitors; PARP inhibitors, topoisomerase inhibitors, serine/threonine kinase inhibitors, tyrosine kinase inhibitors, protein protein interaction inhibitors, MEK inhibitors, ERK inhibitors, IGF-1R inhibitors, ErbB receptor inhibitors, rapamycin analogs, amifostin, anagrelid, clodronat, filgrastin, interferon, interferon α, leucovorin, rituximab, procarbazine, levamisole, mesna, mitotane, pamidronate and porfimer, 2-chlorodesoxyadenosine, 2-fluorodesoxy-cytidine, 2-methoxyoestradiol, 2C4,3-alethine, 131-1-TM-601, 3CPA, 7-ethyl-10-hydroxycamptothecin, 16-aza-epothilone B, A 105972, A 204197, abiraterone, aldesleukin, alitretinoin, allovectin-7, altretamine, alvocidib, amonafide, anthrapyrazole, AG-2037, AP-5280, apaziquone, apomine, aranose, arglabin, arzoxifene, atamestane, atrasentan, auristatin PE, ABT-199 (Venetoclax), ABT-263 (Navitoclax), AVLB, AZ10992, ABX-EGF, AMG-479 (ganitumab), ARRY 162, ARRY 438162, ARRY-300, ARRY-142886/AZD-6244 (selumetinib), ARRY-704/AZD-8330, AR-12, AR-42, AS-703988, AXL-1717, AZD-8055, AZD-5363, AZD-6244, ARQ-736, ARQ 680, AS-703026 (primasertib), avastin, AZD-2014, azacytidine, azaepothilone B, azonafide, BAY-43-9006, BAY 80-6946, BBR-3464, BBR-3576, bevacizumab, BEZ-235, biricodar dicitrate, BCX-1777, BKM-120, bleocin, BLP-25, BMS-184476, BMS-247550, BMS-188797, BMS-275291, BMS-663513, BMS-754807, BNP-1350, BNP-7787, BIBW 2992 (afatinib, tomtovok), BIBF 1120 (vargatef), BI 836845, BI 2536, BI 6727, BI 836845, BI 847325, BI 853520, BUB-022, bleomycinic acid, bleomycin A, bleomycin B, brivanib, bryostatin-1, bortezomib, brostallicin, busulphan, BYL-719, CA-4 prodrug, CA-4, CapCell, calcitriol, canertinib, canfosfamide, capecitabine, carboxyphthalatoplatin, CC1-779, CC-115, CC-223, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, CKI-27, clofarabin, colchicin, combretastatin A4, COT inhibitors, CHS-828, CH-5132799, CLL-Thera, CMT-3 cryptophycin 52, CTP-37, CTLA-4 monoclonal antibodies, CP-461, CV-247, cyanomorpholinodoxorubicin, cytarabine, D 24851, decitabine, deoxirubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, DS-7423, E7010, E-6201, edatrexat, edotreotide, efaproxiral, eflornithine, EGFR inhibitors, EKB-569, EKB-509, enzastaurin, enzalutamide, elsamitrucin, epothilone B, epratuzumab, ER-86526, erlotinib, ET-18-0CH3, ethynylcytidine, ethynyloestradiol, exatecan, exatecan mesylate, exemestane, exisulind, fenretinide, figitumumab, floxuridine, folic acid, FOLFOX, FOLFOX4, FOLFIRI, formestane, fotemustine, galarubicin, gallium maltolate, gefinitib, gemtuzumab, gimatecan, glufosfamide, GCS-100, GDC-0623, GDC-0941 (pictrelisib), GDC-0980, GDC-0032, GDC-0068, GDC-0349, GDC-0879, G17DT immunogen, GMK, GPX-100, gp100-peptide vaccines, GSK-5126766, GSK-690693, GSK-1120212 (trametinib), GSK-2118436 (dabrafenib), GSK-2126458, GSK-2132231A, GSK-2334470, GSK-2110183, GSK-2141795, GW2016, granisetron, herceptin, hexamethylmelamine, histamine, homoharringtonine, hyaluronic acid, hydroxyurea, hydroxyprogesterone caproate, ibandronate, ibritumomab, idatrexate, idenestrol, IDN-5109, IGF-1R inhibitors, IMC-1C11, IMC-A12 (cixutumumab), immunol, indisulam, interferon α-2a, interferon α-2b, pegylated interferon α-2b, interleukin-2, INK-1117, INK-128, INSM-18, ionafarnib, ipilimumab, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, KW-2450, lobaplatin, leflunomide, lenograstim, leuprolide, leuporelin, lexidronam, LGD-1550, linezolid, lutetium texaphyrin, lometrexol, losoxantrone, LU 223651, lurtotecan, LY-S6AKT1, LY-2780301, mafosamide, marimastat, mechloroethamine, MEK inhibitors, MEK-162, methyltestosteron, methylprednisolone, MEDI-573, MEN-10755, MDX-H210, MDX-447, MDX-1379, MGV, midostaurin, minodronic acid, mitomycin, mivobulin, MK-2206, MK-0646 (dalotuzumab), MLN518, motexaf in gadolinium, MS-209, MS-275, MX6, neridronate, neratinib, Nexavar, neovastat, nilotinib, nimesulide, nitroglycerin, nolatrexed, norelin, N-acetylcysteine, 06-benzylguanine, oblimersen, omeprazole, oncophage, oncoVEXGM-CSF, ormiplatin, ortataxel, OX44 antibodies, OSI-027, OSI-906 (linsitinib), 4-1BB antibodies, oxantrazole, oestrogen, panitumumab, patupilone, pegfilgrastim, PCK-3145, pegfilgrastim, PBI-1402, PBI-05204, PD0325901, PD-1 antibodies, PEG-paclitaxel, albumin-stabilized paclitaxel, PEP-005, PF-05197281, PF-05212384, PF-04691502, PHT-427, P-04, PKC412, P54, PI-88, pelitinib, pemetrexed, pentrix, perifosine, perillylalcohol, pertuzumab, PI3K inhibitors, PI3K/mTOR inhibitors, PG-TXL, PG2, PLX-4032/RO-5185426 (vemurafenib), PLX-3603/RO-5212054, PT-100, PWT-33597, PX-866, picoplatin, pivaloyloxymethylbutyrate, pixantrone, phenoxodiol O, PKI166, plevitrexed, plicamycin, polyprenic acid, porfiromycin, prednisone, prednisolone, quinamed, quinupristin, R115777, RAF-265, ramosetron, ranpirnase, RDEA-119/BAY 869766, RDEA-436, rebeccamycin analogs, receptor tyrosine kinase (RTK) inhibitors, revimid, RG-7167, RG-7304, RG-7421, RG-7321, RG 7440, rhizoxin, rhu-MAb, rinfabate, risedronate, rituximab, robatumumab, rofecoxib, RO-31-7453, RO-5126766, RO-5068760, RPR 109881A, rubidazone, rubitecan, R-flurbiprofen, RX-0201, S-9788, sabarubicin, SAHA, sargramostim, satraplatin, SB 408075, Se-015/Ve-015, SU5416, SU6668, SDX-101, semustin, seocalcitol, SM-11355, SN-38, SN-4071, SR-27897, SR-31747, SR-13668, SRL-172, sorafenib, spiroplatin, squalamine, suberanilohydroxamic acid, sutent, T 900607, T 138067, TAK-733, TAS-103, tacedinaline, talaporf in, Tarceva, tariquitar, tasisulam, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymalfasin, thymectacin, tiazofurin, tipifarnib, tirapazamine, tocladesine, tomudex, toremofin, trabectedin, TransMID-107, transretinic acid, traszutumab, tremelimumab, tretinoin, triacetyluridine, triapine, triciribine, trimetrexate, TLK-286TXD 258, tykerb/tyverb, urocidin, valrubicin, vatalanib, vincristine, vinflunine, virulizin, WX—UK1, WX-554, vectibix, xeloda, XELOX, XL-147, XL-228, XL-281, XL-518/R-7420/GDC-0973, XL-765, YM-511, YM-598, ZD-4190, ZD-6474, ZD-4054, ZD-0473, ZD-6126, ZD-9331, ZD1839, ZSTK-474, zoledronat, zosuquidar, and combinations thereof.

In some embodiments, the second therapeutic agent is selected from tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxy-progesterone, octreotide, and combinations thereof. In some embodiments, the second therapeutic agent is selected from LHRH agonists and LHRH antagonists. In one embodiment, a LHRH agonist is selected from goserelin acetate, luprolide acetate, triptorelin pamoate and combinations thereof. In one embodiment, the second therapeutic agent includes a LHRH antagonist is selected from Degarelix, Cetrorelix, Abarelix, Ozarelix, Degarelix combinations thereof. In some embodiments, the second therapeutic agent includes an inhibitor of a growth factor. In one embodiment, the inhibitor of a growth factor is selected from inhibitors of: platelet derived growth factor (PDGF), fibroblast growth factor (FGF), vascular endothelial growth factor (VEGF), epidermal growth factor (EGF), insuline-like growth factors (IGF), human epidermal growth factor (HER), hepatocyte growth factor (HGF), and combinations thereof. In one embodiment, the human epidermal growth factor (HER) is selected from HER2, HER3, and HER4.

In some embodiments, the second therapeutic agent includes a tyrosine kinase inhibitor. In some embodiments, the tyrosine kinase inhibitor is selected from cetuximab, gefitinib, imatinib, lapatinib and trastuzumab, and combinations thereof. In some embodiments, the second therapeutic agent includes an aromatase inhibitor. In some embodiments, the aromatase inhibitor is selected from anastrozole, letrozole, liarozole, vorozole, exemestane, atamestane, and combinations thereof.

In some embodiments, the second therapeutic agent includes an antimetabolite. In some embodiments, the antimetabolite comprises an antifolate. In some embodiments, the antifolate is selected from methotrexate, raltitrexed, pyrimidine analogs, and combinations thereof. In some embodiments, the antimetabolite is a pyrimidine analog. In some embodiments, the pyrimidine analog is selected from 5-fluorouracil, capecitabin, gemcitabin, and combination thereof. In some embodiments, the antimetabolite is a purine analog or an adenosine analog. In some embodiments, the purine analog or adenosine analog is selected from mercaptopurine, thioguanine, cladribine and pentostatin, cytarabine, fludarabine, and combinations thereof. In some embodiments, the second therapeutic agent includes an antitumour antibiotic. In some embodiments, the antitumor antibiotic is selected from anthracyclins, doxorubicin, daunorubicin, epirubicin and idarubicin, mitomycin-C, bleomycin, dactinomycin, plicamycin, streptozocin and combinations thereof. In some embodiments, the second therapeutic agent includes a platinum derivative. In some embodiments, the platinum derivative is selected from cisplatin, oxaliplatin, carboplatin and combinations thereof. In some embodiments, the second therapeutic agent includes an alkylation agent. In some embodiments, the alkylation agent is selected from estramustin, meclorethamine, melphalan, chlorambucil, busulphan, dacarbazin, cyclophosphamide, ifosfamide, temozolomide, nitrosoureas, and combinations thereof. In some embodiments, the second therapeutic agent includes a nitrosourea. In some embodiments, the nitrosourea is selected from carmustin, lomustin, thiotepa, and combinations thereof. In some embodiments, the second therapeutic agent includes an antimitotic agent. In some embodiments, the antimitotic agent is selected from Vinca alkaloids and taxanes. In some embodiments, the taxane is selected from paclitaxel, docetaxel, and combinations thereof. In some embodiments, the Vinca alkaloids are selected from vinblastine, vindesin, vinorelbin, vincristine, and combinations thereof. In some embodiments, the second therapeutic agent includes a topoisomerase inhibitor. In some embodiments, the topoisomerase inhibitor is an epipodophyllotoxin. In some embodiments, the topoisomerase inhibitor, which is an epipodophyllotoxin selected from etoposide, etopophos, teniposide, amsacrin, topotecan, irinotecan, mitoxantron, and combinations thereof. In some embodiments, the second therapeutic agent includes a serine/threonine kinase inhibitor. In some embodiments, the serine/threonine kinase inhibitor is selected from PDK 1 inhibitors, B-Raf inhibitors, mTOR inhibitors, mTORC1 inhibitors, PI3K inhibitors, dual mTOR/PI3K inhibitors, STK 33 inhibitors, AKT inhibitors, PLK 1 inhibitors, inhibitors of CDKs, Aurora kinase inhibitors, and combinations thereof. In some embodiments, the second therapeutic agent includes a tyrosine kinase inhibitor. In some embodiments, the second therapeutic agent includes a PTK2/FAK inhibitor. In some embodiments, the second therapeutic agent includes a protein protein interaction inhibitor. In some embodiments, the protein protein interaction inhibitor is selected from IAP, Mcl-1, MDM2/MDMX and combinations thereof. In some embodiments, the second therapeutic agent includes a rapamycin analog. In some embodiments, the rapamycin analog is selected from everolimus, temsirolimus, ridaforolimus, sirolimus, and combinations thereof. In some embodiments, the second therapeutic agent is selected from amifostin, anagrelid, clodronat, filgrastin, interferon, interferon α, leucovorin, rituximab, procarbazine, levamisole, mesna, mitotane, pamidronate and porfimer, and combinations thereof. In some embodiments, the second therapeutic agent is selected from 2-chlorodesoxyadenosine, 2-fluorodesoxy-cytidine, 2-methoxyoestradiol, 2C4,3-alethine, 131-1-TM-601, 3CPA, 7-ethyl-10-hydroxycamptothecin, 16-aza-epothilone B, A 105972, A 204197, abiraterone, aldesleukin, alitretinoin, allovectin-7, altretamine, alvocidib, amonafide, anthrapyrazole, AG-2037, AP-5280, apaziquone, apomine, aranose, arglabin, arzoxifene, atamestane, atrasentan, auristatin PE, ABT-199 (Venetoclax), ABT-263 (Navitoclax), AVLB, AZ10992, ABX-EGF, AMG-479 (ganitumab), ARRY 162, ARRY 438162, ARRY-300, ARRY-142886/AZD-6244 (selumetinib), ARRY-704/AZD-8330, AR-12, AR-42, AS-703988, AXL-1717, AZD-8055, AZD-5363, AZD-6244, ARQ-736, ARQ 680, AS-703026 (primasertib), avastin, AZD-2014, azacytidine, azaepothilone B, azonafide, BAY-43-9006, BAY 80-6946, BBR-3464, BBR-3576, bevacizumab, BEZ-235, biricodar dicitrate, BCX-1777, BKM-120, bleocin, BLP-25, BMS-184476, BMS-247550, BMS-188797, BMS-275291, BMS-663513, BMS-754807, BNP-1350, BNP-7787, BIBW 2992 (afatinib, tomtovok), BIBF 1120 (vargatef), BI 836845, BI 2536, BI 6727, BI 836845, BI 847325, BI 853520, BUB-022, bleomycinic acid, bleomycin A, bleomycin B, brivanib, bryostatin-1, bortezomib, brostallicin, busulphan, BYL-719, CA-4 prodrug, CA-4, CapCell, calcitriol, canertinib, canfosfamide, capecitabine, carboxyphthalatoplatin, CC1-779, CC-115, CC-223, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, CKI-27, clofarabin, colchicin, combretastatin A4, COT inhibitors, CHS-828, CH-5132799, CLL-Thera, CMT-3 cryptophycin 52, CTP-37, CTLA-4 monoclonal antibodies, CP-461, CV-247, cyanomorpholino-doxorubicin, cytarabine, D 24851, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, DS-7423, E7010, E-6201, edatrexat, edotreotide, efaproxiral, eflornithine, EGFR inhibitors, EKB-569, EKB-509, enzastaurin, enzalutamide, elsamitrucin, epothilone B, epratuzumab, ER-86526, erlotinib, ET-18-OCH3, ethynylcytidine, ethynyloestradiol, exatecan, exatecan mesylate, exemestane, exisulind, fenretinide, figitumumab, floxuridine, folic acid, FOLFOX, FOLFOX4, FOLFIRI, formestane, fotemustine, galarubicin, gallium maltolate, gefinitib, gemtuzumab, gimatecan, glufosfamide, GCS-100, GDC-0623, GDC-0941 (pictrelisib), GDC-0980, GDC-0032, GDC-0068, GDC-0349, GDC-0879, G17DT immunogen, GMK, GPX-100, gp100-peptide vaccines, GSK-5126766, GSK-690693, GSK-1120212 (trametinib), GSK-2118436 (dabrafenib), GSK-2126458, GSK-2132231A, GSK-2334470, GSK-2110183, GSK-2141795, GW2016, granisetron, herceptine, hexamethylenamine, histamine, homoharringtonine, hyaluronic acid, hydroxyurea, hydroxyprogesterone caproate, ibandronate, ibritumomab, idatrexate, idenestrol, IDN-5109, IGF-1R inhibitors, IMC-1C11, IMC-A12 (cixutumumab), immunol, indisulam, interferon α-2a, interferon α-2b, pegylated interferon α-2b, interleukin-2, INK-1117, INK-128, INSM-18, ionafarnib, ipilimumab, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, KW-2450, lobaplatin, leflunomide, lenograstim, leuprolide, leuporelin, lexidronam, LGD-1550, linezolid, lutetium texaphyrin, lometrexol, losoxantrone, LU 223651, lurtotecan, LY-S6AKT1, LY-2780301, mafosfamide, marimastat, mechloroethamine, MEK inhibitors, MEK-162, methyltestosteron, methylprednisolone, MEDI-573, MEN-10755, MDX-H210, MDX-447, MDX-1379, MGV, midostaurin, minodronic acid, mitomycin, mivobulin, MK-2206, MK-0646 (dalotuzumab), MLN518, motexaf in gadolinium, MS-209, MS-275, MX6, neridronate, neratinib, Nexavar, neovastat, nilotinib, nimesulide, nitroglycerin, nolatrexed, norelin, N-acetylcysteine, 06-benzylguanine, oblimersen, omeprazole, oncophage, oncoVEXGM-CSF, ormiplatin, ortataxel, OX44 antibodies, OSI-027, OSI-906 (linsitinib), 4-1BB antibodies, oxantrazole, oestrogen, panitumumab, patupilone, pegfilgrastim, PCK-3145, pegfilgrastim, PBI-1402, PBI-05204, PD0325901, PD-1 antibodies, PEG-paclitaxel, albumin-stabilized paclitaxel, PEP-005, PF-05197281, PF-05212384, PF-04691502, PHT-427, P-04, PKC412, P54, PI-88, pelitinib, pemetrexed, pentrix, perifosine, perillylalcohol, pertuzumab, PI3K inhibitors, PI3K/mTOR inhibitors, PG-TXL, PG2, PLX-4032/RO-5185426 (vemurafenib), PLX-3603/RO-5212054, PT-100, PWT-33597, PX-866, picoplatin, pivaloyloxymethylbutyrate, pixantrone, phenoxodiol O, PKI166, plevitrexed, plicamycin, polyprenic acid, porfiromycin, prednisone, prednisolone, quinamed, quinupristin, R115777, RAF-265, ramosetron, ranpirnase, RDEA-119/BAY 869766, RDEA-436, rebeccamycin analogs, receptor tyrosine kinase (RTK) inhibitors, revimid, RG-7167, RG-7304, RG-7421, RG-7321, RG 7440, rhizoxin, rhu-MAb, rinfabate, risedronate, rituximab, robatumumab, rofecoxib, RO-31-7453, RO-5126766, RO-5068760, RPR 109881A, rubidazone, rubitecan, R-flurbiprofen, RX-0201, S-9788, sabarubicin, SAHA, sargramostim, satraplatin, SB 408075, Se-015/Ve-015, SU5416, SU6668, SDX-101, semustin, seocalcitol, SM-11355, SN-38, SN-4071, SR-27897, SR-31747, SR-13668, SRL-172, sorafenib, spiroplatin, squalamine, suberanilohydroxamic acid, sutent, T 900607, T 138067, TAK-733, TAS-103, tacedinaline, talaporf in, Tarceva, tariquitar, tasisulam, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymalfasin, thymectacin, tiazofurin, tipifarnib, tirapazamine, tocladesine, tomudex, toremofin, trabectedin, TransMID-107, transretinic acid, traszutumab, tremelimumab, tretinoin, triacetyluridine, triapine, triciribine, trimetrexate, TLK-286TXD 258, tykerb/tyverb, urocidin, valrubicin, vatalanib, vincristine, vinflunine, virulizin, WX—UK1, WX-554, vectibix, xeloda, XELOX, XL-147, XL-228, XL-281, XL-518/R-7420/GDC-0973, XL-765, YM-511, YM-598, ZD-4190, ZD-6474, ZD-4054, ZD-0473, ZD-6126, ZD-9331, ZD1839, ZSTK-474, zoledronat, zosuquidar, and combinations thereof.

In one embodiment, the other therapeutic agent comprises a steroid, including dexamethasone, prednisolone, methyl prednisolone, prednisone, hydrocortisone, triamcinolone, betamethasone, and cortivazol. In one embodiment, the other therapeutic agent comprises an anti-emetic. Anti-emetics include, but are not limited to, 5-HT3 receptor agonists (such as dolasetron, granisetron, ondansetron, tropisetron, palonosetron, and mirtazapine), dopamine agonists (such as domperidone, olanzapine, droperidol, haloperidol, chlorpromazine, prochlorperazine, alizapride, prochlorperazine, and metoclopramide), NK1 receptor antagonists (such as aprepitant and casopitant), antihistamines (such as cyclizine, diphenhydramine, dimenhydrinate, doxylamine, meclizine, promethazine, hydroxyzine), cannabinoids (such as cannabis, dronabinol, nabilone, and sativex), benzodiazepines (such as midazolam and lorazepam), anticholinergics (such as hyoscine), trimethobenzamide, ginger, emetrol, propofol, peppermint, muscimol, and ajwain.

Pharmaceutical compositions may be administered to a subject via any suitable administration route. In one embodiment, the pharmaceutical composition is administered to a subject orally, parenterally, transdermally or transmucosally. In one embodiment, the pharmaceutical composition is administered to a subject parenterally. In one embodiment, the pharmaceutical composition is administered to a subject via a parenteral administration route selected from intravenous (IV), subcutaneous (SC), and intramuscular (IM). In one embodiment, the pharmaceutical composition is administered to a subject via a route of administration selected from rectal and transdermal. In one embodiment, the pharmaceutical composition is administered to a subject in a dosage form selected from the group consisting of sterile solutions, suspensions, suppositories, tablets and capsules. In one embodiment, the pharmaceutical composition is administered to a subject in an oral dosage form selected from the group consisting of a tablet, caplet, capsule, lozenge, syrup, liquid, suspension and elixir. In one embodiment, the pharmaceutical composition is administered to a subject in an oral dosage form selected from the group consisting of tablets, hard shell capsules, soft gelatin capsules, beads, granules, aggregates, powders, gels, solids and semi-solids.

In some embodiments, the pharmaceutical composition is administered to a subject as a dosage form selected from sustained release, controlled release, delayed release and response release forms.

In one embodiment, the pharmaceutical composition is administered to a subject once daily. In one embodiment, the pharmaceutical composition is administered to a subject according to an infrequent dosing regimen (e.g., administered once per week or less frequently). In one embodiment, the pharmaceutical composition is administered to a subject according to a frequent dosing regimen (e.g., administered more than once per week). In one embodiment, the pharmaceutical composition is administered to a subject once weekly. In one embodiment, the pharmaceutical composition is administered to a subject once every four weeks. In one embodiment, the pharmaceutical composition is administered to a subject twice a week. In one embodiment, the pharmaceutical composition is administered to a subject once every two weeks. In one embodiment, the pharmaceutical composition is administered to a subject once every three weeks. In one embodiment, the pharmaceutical composition is administered to a subject in a repeated cycle of once weekly, once every two weeks, once every three weeks, once every four weeks or combinations thereof.

In one embodiment, the treatment method comprises administering to a subject in need of such treatment: (i) a first therapeutic agent including a compound comprising an imipridone, such as ONC201, or an analog thereof, or a pharmaceutically acceptable salt thereof in combination with (ii) a second therapeutic agent, wherein the first therapeutic agent and the second therapeutic agent are administered either simultaneously or sequentially; and further comprises assaying the expression of an endoplasmic reticulum (ER) stress response gene in a biological sample. In one embodiment, the endoplasmic reticulum stress response gene is selected from the group that includes, but is not limited to, C/EBP-Homologous Protein (CHOP), Activating Transcription Factor 3 (ATF3) and both CHOP and ATF3. In one embodiment, the endoplasmic reticulum stress response gene is selected from the group that includes, but is not limited to, ATF3, Activating Transcription Factor 4 (ATF4) CHOP, IRE1, Binding immunoglobulin protein (BiP), Eukaryotic translation initiation factor 2A (eIF2a), X-box binding protein 1 (XBP1). The biological sample may be tumor, peripheral blood mononuclear cells, or skin biopsy. The biological sample may be obtained before, during, or after drug administration. In one embodiment, the treatment method further comprises adjusting a dose of the first therapeutic agent to achieve induction of about 50%, 75%, 100%, 125%, 150%, 175%, 200%, 225%, 250%, 275%, 300%, 325%, 350%, 375%, 400%, 425%, 450%, 475%, 500%, 525%, 550%, 575%, 600%, or greater than 600% of one or more ER stress gene. In one embodiment, the treatment method further comprises adjusting a dose of the first therapeutic agent to achieve induction of about 50% to about 100%, about 100% to about 150%, about 150% to about 200%, about 200% to about 250%, about 250% to about 300%, about 300% to about 350%, about 350% to about 400%, about 400% to about 450%, about 450% to about 500%, about 500% to about 550%, about 550% to about 600%, or greater than 600% of ER stress genes. In one embodiment, the treatment method further comprises adjusting a dose of the first therapeutic agent to achieve induction of about 50% to about 100%, about 100% to about 200%, about 200% to about 300%, about 300% to about 400%, about 400% to about 500%, about 500% to about 600%, or greater than 600% of ER stress genes.

In one embodiment, the treatment method comprises administering to a subject in need of such treatment: (i) a first therapeutic agent including a compound comprising an imipridone, such as ONC201, an analog thereof, or a pharmaceutically acceptable salt thereof in combination with (ii) a second therapeutic agent, wherein the first therapeutic agent and the second therapeutic agent are administered either simultaneously or sequentially; and further comprises assaying the expression of proteasomal activity in a biological sample. In one embodiment the proteasomal activity may be chymotrypsin-like, trypsin-like, and/or caspase-like activity. In one embodiment, the biological sample may be tumor, peripheral blood mononuclear cells, or skin cells. The biological sample may be obtained before, during, or after drug administration. In one embodiment, the treatment method further comprises adjusting the dose to achieve inhibition of about 20%, about 25%, about 30%, about 35%, about 40%, about 45%, about 50%, about 55%, about 60%, about 65%, about 70%, about 75%, about 80%, about 85%, about 90%, about 95%, or about 100% of the proteasomal activity. In one embodiment, the treatment method further comprises adjusting the dose to achieve inhibition of at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of the proteasomal activity. In one embodiment, the treatment method further comprises adjusting the dose to achieve inhibition of about 20% to about 30%, about 30% to about 40%, about 40% to about 50%, about 50% to about 60%, about 60% to about 70%, about 70% to about 80%, about 80% to about 90%, or greater than 90% of the proteasomal activity.

In an aspect, provided herein are treatment methods, which comprise administering to a subject in need of such treatment a combination of a first therapeutic agent including an imipridone, such as ONC201, an analog thereof, or a pharmaceutically acceptable salt thereof (e.g., a di-salt or tri-salt) and a second therapeutic agent, the method comprising:

(i) administering to the subject the first therapeutic agent;

(ii) waiting until a predetermined waiting time has elapsed after the time of administration of the first therapeutic agent to the subject; and/or until adverse events are resolved or resolving; and (iii) administering the second therapeutic agent to the subject, wherein the predetermined waiting time is chosen so as to obtain a delayed therapeutic effect of the first therapeutic agent without an increased risk of possible combined toxic effects of the first and second therapeutic agents. In one embodiment, the predetermined waiting time is determined based on the clearance rate of the compound of the first therapeutic agent or a metabolite thereof. In one embodiment, the predetermined waiting time is determined by a quantitative assessment of renal function and parameters of renal. In one embodiment, the predetermined waiting time is determined by an assay for the determination of renal function, wherein the assay is selected from the group consisting of serum level the compound of the first therapeutic agent or a metabolite thereof; clearance rate of the compound of the first therapeutic agent or a metabolite thereof; 24-hour urinary clearance of the compound of the first therapeutic agent or a metabolite thereof.

In some embodiments, the predetermined waiting time substantially equals the time required for systemic clearance of the compound of the first therapeutic agent or a metabolite thereof from the subject's body. In some embodiments, the predetermined waiting time substantially equals the time required for renal clearance of the compound of the first therapeutic agent or a metabolite thereof from the subject's body. In some embodiments, the predetermined waiting time substantially equals the time required for hepatic clearance of the compound of the first therapeutic agent or a metabolite thereof from the subject's body. In some embodiments, the predetermined waiting time substantially equals the time required for total clearance of the compound of the first therapeutic agent or a metabolite thereof from the subject's body. In some embodiments, the predetermined waiting time is about 4 hours. In other embodiments the waiting time is 1 day. In one embodiment, the waiting time is until $C_{max}$ of the compound of the first therapeutic agent has passed. In other embodiments, the waiting time is after most of the adverse events are resolved or are resolving. In some embodiments, the predetermined waiting time is about 2 days, about 3 days, about 4 days, about 5 days, about 6 days, or about 7 days. In some embodiments, the predetermined waiting time is a range of about 1-7 days, about 1-6 days, about 1-5 days, about 1-4 days, about 1-3 days, or about 1 to 2 days. In one embodiment, the waiting time is up to 3 weeks. The preceeding are considered "therapeutic time periods."

When the order of administration is reversed, timing for the administration of the first therapeutic agent can be after the $C_{max}$ of the second therapeutic agent (i.e., the first administered drug) has passed. In one embodiment, administration of the first therapeutic agent can be after most or substantially all of the first administered drug has been eliminated from the body or the toxicity effects for the first administered drug are resolved or are resolving.

In one embodiment, the treatment method further comprises monitoring levels of the compound of the first therapeutic agent or a metabolite thereof in the subject using pharmacokinetic profiling. In some such embodiments, monitoring levels of the compound of the first therapeutic agent or a metabolite thereof in the subject using pharmacokinetic profiling comprises constructing a pharmacokinetic profile of the compound of the first therapeutic agent or a metabolite thereof for the subject using concentrations of the compound of the first therapeutic agent or a metabolite thereof in at least two samples obtained from the subject at time points suitable to construct a pharmacokinetic profile. In one embodiment, which include monitoring levels of the compound of the first therapeutic agent or a metabolite thereof in the subject using pharmacokinetic profiling, samples are collected from the subject at point-of-care or point of use by sampling or self-sampling on point-of-care devices or point of use devices or on matrices suitable for storage of the samples prior to quantitation in a laboratory. In one embodiment, each of the point-of-care devices or point of use devices is capable of quantitating the compound of the first therapeutic agent or a metabolite thereof. In one embodiment, which include monitoring levels of the compound of the first therapeutic agent or a metabolite thereof in the subject, one or more samples are collected from the subject at point-of-care or point of use by biopsy device for analysis at the point-of-care or point of use devices or for storage prior to analysis by a laboratory. In one embodiment, a biopsy is taken after a time interval of 3-8 hours following administration the first therapeutic agent to the subject. In one embodiment, a biopsy is taken after a time interval of 3-24 hours following administration of the first therapeutic agent to the subject. In one embodiment, a biopsy is taken after a time interval of 8-24 hours following administration of the first therapeutic agent thereof to the subject. In one embodiment, a biopsy is taken after a time interval of 2 days following administration of the first therapeutic agent to the subject. In one embodiment, a biopsy is taken after a time interval of 3 days following administration of the first therapeutic agent to the subject. In one embodiment, a biopsy is taken after a time interval of 4 days following administration of the first therapeutic agent to the subject. In one embodiment, a biopsy is taken after a time interval of 1-7 days following administration of the first therapeutic agent.

In one embodiment, the pharmacokinetic profile includes pharmacokinetic parameters suitable for guiding dosing of the first therapeutic agent for the subject being treated. In some embodiments, the $C_{max}$ of the first therapeutic agent following its administration to the subject ranges from about 1000 ng/dL to 1500 ng/dL for a therapeutic time period. In one embodiment, $C_{max}$ is less than 1500 ng/dL and greater than 85 ng/dL for a therapeutic time period. In one embodiment, the $C_{max}$ of the first therapeutic following its administration to the subject ranges from about 1000 ng/mL to 1500 ng/mL for a therapeutic time period. In one embodiment, $C_{max}$ is less than 1500 ng/mL and greater than 85 ng/mL for a therapeutic time period.

In one embodiment, maximum concentration of the first therapeutic agent in blood (whole blood, plasma, or serum) ("$C_{max}$") of a subject after administering it to the subject is a $C_{max}$ of from about 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, or 1490 ng/dL to about 1500 ng/dL; from about 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or 149 ng/dL to about 150 ng/dL; or from about 10, 10.5, 11, 11.5, 120, 12.5, 13, 13.5, 14, or 14.5 ng/dL to about 15 ng/dL.

In one embodiment, maximum concentration of the first therapeutic agent in blood (whole blood, plasma, or serum) ("$C_{max}$") of the subject following its administration is a $C_{max}$ of from about 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, or 1490 ng/mL to about 1500 ng/mL; from about 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or 149 ng/mL to about 150 ng/mL; or from about 10, 10.5, 11, 11.5, 120, 12.5, 13, 13.5, 14, or 14.5 ng/mL to about 15 ng/mL.

In one embodiment, maximum concentration of the first therapeutic agent in blood (whole blood, plasma, or serum) ("$C_{max}$") of a subject following its administration is selected from about 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, or 1490 ng/dL. In one embodiment, the $C_{max}$ of the first therapeutic agent in blood (whole blood, plasma, or serum) ("$C_{max}$") of a subject following its administration is selected from about 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or 149 ng/dL. In one embodiment, the $C_{max}$ of the first therapeutic agent following its administration is selected from about 10, 10.5, 11, 11.5, 120, 12.5, 13, 13.5, 14, or 14.5 ng/dL.

In one embodiment, the $C_{max}$ of the first therapeutic agent following its administration is selected from about 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, or 1490 ng/mL. In one embodiment, the $C_{max}$ of the first therapeutic agent following its administration is selected from about 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or 149 ng/mL. In one embodiment, the $C_{max}$ of the first therapeutic agent following its administration is selected from about 10, 10.5, 11, 11.5, 120, 12.5, 13, 13.5, 14, or 14.5 ng/mL.

In one embodiment, the $C_{max}$ of the first therapeutic agent following its administration is selected from about 85, 95, 105, 115, 125, 135, 145, 155, 165, 175, 185, 195, 205, 215, 225, 235, 245, 255, 265, 275, 285, 295, 305, 315, 325, 335, 345, 355, 365, 375, 385, 395, 405, 415, 425, 435, 445, 455, 465, 475, 485, 495, 505, 515, 525, 535, 545, 555, 565, 575, 585, 595, 605, 615, 625, 635, 645, 655, 665, 675, 685, 695, 705, 715, 725, 735, 745, 755, 765, 775, 785, 795, 805, 815, 825, 835, 845, 855, 865, 875, 885, 895, 905, 915, 925, 935, 945, 955, 965, 975, 985, 995, 1005, 1015, 1025, 1035, 1045, 1055, 1065, 1075, 1085, 1095, 1105, 1115, 1125, 1135, 1145, 1155, 1165, 1175, 1185, 1195, 1205, 1215, 1225, 1235, 1245, 1255, 1265, 1275, 1285, 1295, 1305, 1315, 1325, 1335, 1345, 1355, 1365, 1375, 1385, 1395, 1405, 1415, 1425, 1435, 1445, 1455, 1465, 1475, 1485, 1495, or 1500 ng/dL. In one embodiment, the $C_{max}$ of the first therapeutic agent following its administration is selected from about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or 149 ng/dL. In one embodiment, the $C_{max}$ of the first therapeutic agent following its administration is selected from about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, or 14.5 ng/dL.

In one embodiment, the $C_{max}$ of the first therapeutic agent following its administration is selected from about 85, 95, 105, 115, 125, 135, 145, 155, 165, 175, 185, 195, 205, 215, 225, 235, 245, 255, 265, 275, 285, 295, 305, 315, 325, 335, 345, 355, 365, 375, 385, 395, 405, 415, 425, 435, 445, 455, 465, 475, 485, 495, 505, 515, 525, 535, 545, 555, 565, 575, 585, 595, 605, 615, 625, 635, 645, 655, 665, 675, 685, 695, 705, 715, 725, 735, 745, 755, 765, 775, 785, 795, 805, 815, 825, 835, 845, 855, 865, 875, 885, 895, 905, 915, 925, 935, 945, 955, 965, 975, 985, 995, 1005, 1015, 1025, 1035, 1045, 1055, 1065, 1075, 1085, 1095, 1105, 1115, 1125, 1135, 1145, 1155, 1165, 1175, 1185, 1195, 1205, 1215, 1225, 1235, 1245, 1255, 1265, 1275, 1285, 1295, 1305, 1315, 1325, 1335, 1345, 1355, 1365, 1375, 1385, 1395, 1405, 1415, 1425, 1435, 1445, 1455, 1465, 1475, 1485, 1495, or 1500 ng/mL. In one embodiment, the $C_{max}$ of the first therapeutic following its administration is selected from about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or 149 ng/mL. In one embodiment, the $C_{max}$ of the first therapeutic agent following its administration is selected from about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, or 14.5 ng/mL.

In one embodiment, the $C_{max}$ of the first therapeutic agent after administering it to the subject ranges from about 85 ng/dL to 1500 ng/dL; from about 8.5 ng/dL to 150 ng/dL; or from about 0.85 ng/dL to 15 ng/dL. In one embodiment, the $C_{max}$ of the first therapeutic agent in a subject's blood (whole blood, plasma, or serum) after its administration is selected from about 85, 95, 105, 115, 125, 135, 145, 155, 165, 175, 185, 195, 205, 215, 225, 235, 245, 255, 265, 275, 285, 295, 305, 315, 325, 335, 345, 355, 365, 375, 385, 395, 405, 415, 425, 435, 445, 455, 465, 475, 485, 495, 505, 515, 525, 535, 545, 555, 565, 575, 585, 595, 605, 615, 625, 635, 645, 655, 665, 675, 685, 695, 705, 715, 725, 735, 745, 755, 765, 775, 785, 795, 805, 815, 825, 835, 845, 855, 865, 875, 885, 895, 905, 915, 925, 935, 945, 955, 965, 975, 985, 995, 1005, 1015, 1025, 1035, 1045, 1055, 1065, 1075, 1085, 1095, 1105, 1115, 1125, 1135, 1145, 1155, 1165, 1175, 1185, 1195, 1205, 1215, 1225, 1235, 1245, 1255, 1265, 1275, 1285, 1295, 1305, 1315, 1325, 1335, 1345, 1355, 1365, 1375, 1385, 1395, 1405, 1415, 1425, 1435, 1445, 1455, 1465, 1475, 1485, or 1495 ng/dL to about 1500 ng/dL; from about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or 149 ng/dL to about 150 ng/dL; or from about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, or 14.5 ng/dL to about 15 ng/dL.

In one embodiment, the $C_{max}$ of the first therapeutic agent following its administration ranges from about 85 ng/mL to 1500 ng/mL; from about 8.5 ng/mL to 150 ng/mL; or from about 0.85 ng/mL to 15 ng/mL. In one embodiment, the $C_{max}$ of the first therapeutic following its administration is selected from about 85, 95, 105, 115, 125, 135, 145, 155, 165, 175, 185, 195, 205, 215, 225, 235, 245, 255, 265, 275, 285, 295, 305, 315, 325, 335, 345, 355, 365, 375, 385, 395, 405, 415, 425, 435, 445, 455, 465, 475, 485, 495, 505, 515, 525, 535, 545, 555, 565, 575, 585, 595, 605, 615, 625, 635, 645, 655, 665, 675, 685, 695, 705, 715, 725, 735, 735, 745, 755, 765, 775, 785, 795, 805, 815, 825, 835, 845, 855, 865, 875, 885, 895, 905, 915, 925, 935, 945, 955, 965, 975, 985, 995, 1005, 1015, 1025, 1035, 1045, 1055, 1065, 1075, 1085, 1095, 1105, 1115, 1125, 1135, 1145, 1155, 1165, 1175, 1185, 1195, 1205, 1215, 1225, 1235, 1245, 1255, 1265, 1275, 1285, 1295, 1305, 1315, 1325, 1335, 1345, 1355, 1365, 1375, 1385, 1395, 1405, 1415, 1425, 1435, 1445, 1455, 1465, 1475, 1485, or 1495 ng/mL to about 1500 ng/mL; from about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, or 149 ng/mL to about 150 ng/mL; or from about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, or 14.5 ng/mL to about 15 ng/mL.

In one embodiment, the total drug exposure over time, measured as the area under the curve ("AUC") of a plot of the concentration of the drug in blood (whole blood, plasma, or serum) of a subject following administration of the drug against time after administration of the drug ranges from about 150 ng hr/mL to about 8000 ng hr/mL; from about 15 ng hr/mL to about 800 ng hr/mL; or from about 1.5 ng hr/mL to about 80 ng hr/mL. In one embodiment, AUC is less than 8000 ng hr/mL and is greater than or equal to 150 ng hr/mL. In one embodiment, AUC is less than 800 ng hr/mL and is greater than or equal to 15 ng hr/mL. In one embodiment, AUC is less than 80 ng hr/mL and is greater than or equal to 1.5 ng hr/mL.

In one embodiment, the total drug exposure over time is an AUC of from about 100 ng hr/mL to about 8000 ng hr/mL; from about 10 ng hr/mL to about 800 ng hr/mL; or from about 1 ng hr/mL to about 80 ng hr/mL. In one embodiment, the total drug exposure over time is an AUC of from about from about 150, 200, 400, 600, 800, 1000, 1200, 1400, 1600, 1800, 2000, 2200, 2400, 2600, 2800, 3000, 3200, 3400, 3600, 3800, 4000, 4200, 4400, 4600, 4800, 5000, 5200, 5400, 5600, 5800, 6000, 6200, 6400, 6600, 6800, 7000, 7200, 7400, 7600, or 7800 ng hr/mL to about 8000 ng hr/mL. In one embodiment, the total drug exposure over time is an AUC of from about 15, 20, 40, 60, 80, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 720, 740, 760, or 780 ng hr/mL to about 800 ng hr/mL. In one embodiment, the total drug exposure over time is an AUC of from about from about 1.5, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, or 78 ng hr/mL to about 80 ng hr/mL.

In one embodiment, the total drug exposure over time is an AUC of from about 100 ng hr/mL to about 8000 ng hr/mL, from about 10 ng hr/mL to about 800 ng hr/mL; or from about 1 ng hr/mL to about 80 ng hr/mL. In one embodiment, the total drug exposure over time is an AUC of from about from about 150 ng hr/mL to about 7800, 7600, 7400, 7200, 7000, 6800, 6600, 6400, 6200, 6000, 5800, 5600, 5400, 5200, 5000, 4800, 4600, 4400, 4200, 4000, 3800, 3600, 3400, 3200, 3000, 2800, 2600, 2400, 2200, 2000, 1800, 1600, 1400, 1200, 1000, 800, 600, 400, or 200 ng hr/mL. In one embodiment, the total drug exposure over time is an AUC of from about from about 15 ng hr/mL to about 780, 760, 740, 720, 700, 680, 660, 640, 620, 600, 580, 560, 540, 520, 500, 480, 460, 440, 420, 400, 380, 360, 340, 320, 300, 280, 260, 240, 220, 200, 180, 160, 140, 120, 100, 80, 60, 40, or 20 ng hr/mL. In one embodiment, the total drug exposure over time is an AUC of from about from about 1.5 ng hr/mL to about 78, 76, 74, 72, 70, 68, 66, 64, 62, 60, 58, 56, 54, 52, 50, 48, 46, 44, 42, 40, 38, 36, 34, 32, 30, 28, 26, 24, 22, 20, 18, 16, 14, 12, 10, 8, 6, 4, or 2 ng hr/mL. In one embodiment, the total drug exposure over time is an AUC of from about 100 ng hr/mL to about 200 ng hr/mL; from about 10 ng hr/mL to about 20 ng hr/mL; or from about 1 ng hr/mL to about 2 ng hr/mL.

In one embodiment, the total drug exposure over time is an AUC selected from about 100, 150, 200, 400, 600, 800, 1000, 1200, 1400, 1600, 1800, 2000, 2200, 2400, 2600, 2800, 3000, 3200, 3400, 3600, 3800, 4000, 4200, 4400, 46000, 4800, 5000, 5200, 5400, 5600, 5800, 6000, 6200, 6400, 6600, 6800, 7000, 7200, 7400, 7600, 7800, and 8000 ng hr/mL. In one embodiment, the total drug exposure over time is an AUC selected from about 10, 15, 20, 40, 60, 80, 100, 120, 140, 160, 180, 200, 220, 240, 260, 280, 300, 320, 340, 360, 380, 400, 420, 440, 4600, 480, 500, 520, 540, 560, 580, 600, 620, 640, 660, 680, 700, 720, 740, 760, 780, and 800 ng hr/mL. In one embodiment, the total drug exposure over time is an AUC selected from about 1, 15, 2, 4, 6, 8, 10, 12, 14, 16, 18, 20, 22, 24, 26, 28, 30, 32, 34, 36, 38, 40, 42, 44, 460, 48, 50, 52, 54, 56, 58, 60, 62, 64, 66, 68, 70, 72, 74, 76, 78, and 80 ng hr/mL.

In another aspect, provided herein are methods of treatment, or use of a composition to treat a disease state, which comprises administering to a subject in need of such treatment a combination of a first therapeutic agent and a second therapeutic agent, the method comprising:

(i) administering to the subject the first therapeutic agent including an imipridone, such as ONC201, an analog thereof, or a pharmaceutically acceptable salt thereof;

(ii) monitoring levels of the compound of the first therapeutic agent or a metabolite thereof in the subject using pharmacokinetic profiling; and (iii) administering the second therapeutic agent conditional on the level of the first therapeutic agent in the subject. In one embodiment, the monitoring step includes constructing a pharmacokinetic profile of the compound of the first therapeutic agent or a metabolite thereof for the subject using concentrations of the compound of the first therapeutic agent or a metabolite thereof in a plurality of samples obtained from the subject at time points suitable to construct a pharmacokinetic profile. In one embodiment, at least two samples are collected at point-of-care or point of use by sampling or self-sampling on point-of-care devices or point of use devices or on matrices suitable for storage of the samples prior to quantitation of the compound or a metabolite thereof by a laboratory. In one embodiment, each point-of-care devices or point of use devices is capable of quantitating the compound or a metabolite thereof. In one embodiment, the pharmacokinetic profile includes pharmacokinetic parameters suitable for guiding dosing of the compound or a salt thereof for the subject. In one embodiment, the samples include from 2-12 samples. In one embodiment, the samples are collected over a time period of up to 8 hours, up to 24 hours, up to 48 hours, or up to 72 hours. In one embodiment, the pharmacokinetic parameters include at least one parameter selected from the group consisting of AUC, $AUC_{inf}$, $T_{max}$, $C_{max}$, time above threshold, steady state concentration, absorption rate, clearance rate, distribution rate, terminal T-1/2 or parameters drawn from noncompartmental pharmacokinetic (PK) or compartmental PK analysis, including physiological model-based compartmental PK analysis. In one embodiment, the treatment method further comprises generating a report including the pharmacokinetic profile of the subject. In one embodiment, the report includes a recommendation regarding dosing based on the pharmacokinetic profile of the subject. In one embodiment, a reduction in dosage of ONC201, the analog thereof, or the pharmaceutically acceptable salt thereof is indicated to reduce risk of toxicity based on one or more pharmacokinetic parameters. In one embodiment, the reduction in dosage of the compound or salt thereof is indicated based on time above threshold, wherein the threshold is the drug concentration above which toxicity occurs, or one or more of AUC, $AUC_{inf}$, mean residence time (MRT), exponentials defining the pharmacokinetic profile, volume of distribution at steady state (Vss), volume of distribution during the terminal phase (Vz) or combination of a group of pharmacokinetic variable to adequately describe the pharmacokinetic profile. In one embodiment, a dose adjustment of the compound or salt thereof is indicated to increase efficacy based on one or more pharmacokinetic parameters. In one embodiment, an increase in dosage of the compound or salt thereof is indicated based on one or more of AUC, $AUC_{inf}$, MRT, exponentials defining the pharmacokinetic profile, steady state volume (Vss) of distribution, volume of distribution during the terminal phase (Vz) or combination of a group of pharmacokinetic variables to adequately describe the pharmacokinetic profile. In one embodiment, the dose of the compound or salt thereof is adjusted to within 5% to 25% of a desired target value. In one embodiment, each of the samples is applied to the point-of-care device or the point of use device for determining the concentration of the compound or a metabolite thereof, wherein the point-of-care device or the point of use device comprises a lateral flow strip having a construction and composition such that an application of one or more of the samples to the lateral flow strip causes a fraction of the drug in the sample to bind to with a component of the lateral flow strip such that a detectable signal proportional to the concentration of the drug in the applied sample is produced. In one embodiment, the samples are applied to matrices suitable for storage of the samples prior to quantitation by a laboratory. In one embodiment, the samples are stored as dried blood spots. In one embodiment, drug concentrations are measured by ELISA, LC MS MS, LC UV or LCMS. In one embodiment, the pharmacokinetic parameters include at least one of steady state concentration, absorption, and terminal $T_{1/2}$. In one embodiment, at least one of the samples is whole blood.

IX. MULTIMODAL THERAPEUTIC METHODS

In one aspect, provided herein are multimodal therapeutic methods in which administration of an imipridone, such as ONC201, an analog thereof, or a pharmaceutically acceptable salt thereof to a subject in need of such treatment is supplemented by administration of other therapeutic modalities. In one embodiment, the multimodal therapeutic method comprises administering to a subject a pharmaceutical composition comprising an imipridone, such as ONC201, an analog thereof, or a pharmaceutically acceptable salt thereof in conjunction with radiation therapy or after radiation is determined to not have been efficacious. In one embodiment, the multimodal therapeutic method comprises administering to a subject a pharmaceutical composition comprising an imipridone, such as ONC201, an analog thereof, or a pharmaceutically acceptable salt thereof in conjunction with radiation therapy, wherein the pharmaceutical composition comprising theimipridone, such as ONC201, the analog thereof, or pharmaceutically acceptable salt thereof and the radiation therapy are administered concurrently or sequentially in any order. In one embodiment, the multimodal therapeutic method comprises administering to a subject a pharmaceutical composition comprising an imipridone, such as ONC201, an analog thereof, or a pharmaceutically acceptable salt thereof in conjunction with radiation therapy in a sequential arrangement. In one embodiment, the multimodal therapeutic method comprises administering to a subject in need of such treatment a pharmaceutical composition comprising an imipridone, such as ONC201, an analog thereof, or a pharmaceutically acceptable salt thereof thereof concurrently with radiation therapy. In one embodiment, the multimodal therapeutic method is used for the treatment of cancer. In one embodiment, the multimodal therapeutic method includes administering to a cancer subject in need of such treatment a pharmaceutical composition comprising an imipridone, such as ONC201, an analog thereof, or a pharmaceutically acceptable salt thereof and irradiating cancer cells with a radiation beam. In one embodiment, the multimodal therapeutic method uses the technique of conformal radiotherapy (CRT) to deliver a dose volume histogram (DVH) prescribed to a cancer subject. In one embodiment, the multimodal therapeutic method uses the technique of intensity modulated radiation therapy (IMRT) to deliver radiation to cancer cells. In one embodiment, the multimodal therapeutic method uses techniques that compensate for motion of tumors in the subject during treatment (e.g., where doses of radiation must be administered to a thoracic tumor which moves as the patient breathes). For example, the multimodal therapeutic method use Four Dimensional Computed Tomography (4D CT) scanning techniques to adjust the delivered radiation field to compensate for tumor motion over the breathing cycle.

Any suitable type of radiation, including gamma radiation which is given fractionated, IMRT (intensity modulated radiation therapy), gamma knife, proton therapy and brachytherapy can be used with the multimodal therapeutic method. Radiation therapy and administering an imipridone, such as ONC201, an analog thereof, or a pharmaceutically acceptable salt thereof can be used to treat brain tumors such as glioblastoma or disease that has metastasized to the brain from lung cancer. The multimodal therapeutic method can be used to treat lung cancer, pancreatic cancer, rectal cancer, breast cancer, sarcoma, prostate cancer, gynecological malignancies, and lymphoma. The gamma knife is used frequently to treat brain metastases. In one embodiment, the multimodal therapeutic method includes use of proton therapy to treat cancer, including brain tumors, prostate cancer and any tumor proximate vital organs where it is very important to minimize toxicity to nearby normal tissue.

In one embodiment, a multimodal therapeutic method includes administering to a cancer subject in need of such treatment a pharmaceutical composition comprising an imipridone, such as ONC201, an analog thereof, or a pharmaceutically acceptable salt thereof in combination with adoptive cell therapy (e.g., CAR-T (JCAR 14, 15, 16, 17, KTE-C19, or CTL019); other T Cell (AFM13); or NK (CDNO-109 or NK-92)) either simultaneously or in combination.

In one embodiment, the multimodal therapeutic method eliminates minimal residual disease without adding to toxicity resulting from treatment by an imipridone, such as ONC201, an analog thereof, or a pharmaceutically acceptable salt thereof. In one embodiment, the multimodal therapeutic method improves prognosis and/or reduces adverse side-effects associated with a disease state or condition in a subject undergoing treatment.

X. ADDITIONAL IMIPRIDONE DERIVATIVES, ANALOGS, AND SALTS

In one aspect, provided herein are compounds that are analogs of the compounds of formula (10) and methods of making them. Persons skilled in the art will understand that the general principles and concepts described above in conjunction with ONC201 and compounds of formula (10) and their salts, including principles and concepts related to methods and pharmaceutical compositions, apply with equal force to the following analogs and salts thereof.

In one embodiment, the analogs have the structure of compound (25):

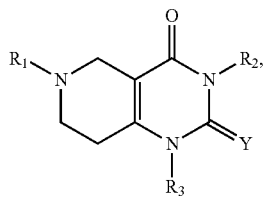

(25)

wherein Y is $NR_4$ or O, and wherein $R_1$, $R_2$, $R_3$, and $R_4$ independently represent H, alkyl, cycloalkyl, cycloalkylalkyl, carboxyl, haloalkyl, alkenyl, cycloalkenyl, alkynyl, aryl, aralkyl, hydroxyalkyl, alkoxy, aryloxy, alkoxyalkyl, alkoxycarbonyl, aralkoxy, aralkylthio, alkanoyl, mercapto, alkylthio, arylthio, alkylsulfinyl, arylsulfinyl, alkylsulfonyl, arylsulfonyl, heteroaryl, acyl, and heterocycle radicals. In one embodiment, $R_1$, $R_2$, $R_3$, and $R_4$ are optionally substituted. In one embodiment, some or all hydrogens in $R_1$, $R_2$, $R_3$, and $R_4$ are substituted by deuterium. In other embodiments, $R_1$, $R_2$, $R_3$, and $R_4$ are independently selected from the group consisting of H, $C_{1-4}$alkyl, $C_{1-4}$alkylphenyl, $C_{1-4}$alkylphenylketone, $C_{1-4}$benzyl-piperazine, and $C_{1-4}$alkylthienyl, wherein $C_{1-4}$alkyl, $C_{1-4}$alkylphenyl, $C_{1-4}$alkylphenylketone, and $C_{1-4}$benzyl-piperazine are optionally substituted with $C_{1-4}$alkyl, hydroxyl, or halo. In still other embodiments, $R_1$, $R_2$, $R_3$, and $R_4$ are independently selected from the group consisting of H, $CH_3$, $CH_2Ph$, $CH_2$-((2-Cl)-Ph), $CH_2$-(2-thienyl), $CH_2CH_2Ph$, $CH_2CH_2$(4-N-benzyl-piperazine), $CH_2$-(2,4-di F-Ph), $CH_2$-((2-$CH_3$)-Ph), $CH_2CHOHPh$, and $(CH_2)_3CO$-4F-Ph.

In one embodiment, the analogs have the structure of compound (26):

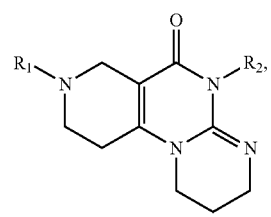

(26)

wherein $R_1$ and $R_2$ independently represent H, alkyl, cycloalkyl, cycloalkylalkyl, carboxyl, haloalkyl, alkenyl, cycloalkenyl, alkynyl, aryl, aralkyl, hydroxyalkyl, alkoxy, aryloxy, alkoxyalkyl, alkoxycarbonyl, aralkoxy, aralkylthio, alkanoyl, mercapto, alkylthio, arylthio, alkylsulfinyl, arylsulfinyl, alkylsulfonyl, arylsulfonyl, heteroaryl, acyl, and heterocycle radicals. In one embodiment, $R_1$ and $R_2$ are independently selected from the group consisting of H, $C_{1-4}$alkyl, $C_{1-4}$alkylphenyl, $C_{1-4}$alkylphenylketone, $C_{1-4}$benzyl-piperazine, and $C_{1-4}$alkylthienyl, wherein $C_{1-4}$alkyl, $C_{1-4}$alkylphenyl, $C_{1-4}$alkylphenylketone, and $C_{1-4}$benzyl-piperazine are optionally substituted with $C_{1-4}$alkyl, $C_{1-4}$alkoxyl, hydroxyl, perhalogenated $C_{1-4}$alkyl, or halo. In one embodiment, $R_1$ is selected from the group consisting of H, $CH_3$, $CH_2Ph$, $CH_2$-((2-Cl)-Ph), $CH_2$-(2-thienyl), $CH_2CH_2Ph$, $CH_2CH_2$(4-N-benzyl-piperazine), $CH_2$-(2,4-di F-Ph), $CH_2$-((2-$CH_3$)-Ph), $CH_2CHOHPh$, and $(CH_2)_3CO$-4F-Ph. In one embodiment, $R_2$ is selected from the group consisting of H, $CH_3$, $CH_2Ph$, $CH_2$-((2-Cl)-Ph), $CH_2$-(2-thienyl), $CH_2CH_2Ph$, $CH_2CH_2$(4-N-benzyl-piperazine), $CH_2$-(2,4-di F-Ph), $CH_2$-((2-$CH_3$)-Ph), $CH_2CHOHPh$, and $(CH_2)_3CO$-4F-Ph.

In one embodiment, $R_1$ is a benzyl optionally substituted with one or more of the following substituents alone or in combination in the ortho, meta, and/or para positions of the benzyl ring: —$CH_3$, —$NO_2$, —$OCH_3$, —$CXH_2$, —$CX_2H$, —$CX_3$, —$CH_2(CX_3)$, —$CH(CX_3)_2$, —$C(CX_3)_3$, —$C_pX_{2p+1}$, —$OCX_3$, or —$OC_pX_{2p+1}$, where p is an integer from 2 to 20 and where X is a halogen including F, Cl, Br, or I; preferably, F, Cl, or Br; more preferably, F or Cl. In one embodiment, $R_2$ is a benzyl substituted with one or more of the following substituents alone or in combination in the ortho, meta, and/or para positions of the benzyl ring: —$CH_3$, —$NO_2$, —$OCH_3$, —$CXH_2$, —$CX_2H$, —$CX_3$, —$CH_2(CX_3)$, —CH(CX$_3$)$_2$, —C(CX$_3$)$_3$, —C$_p$X$_{2p+1}$, —OCX$_3$, or —OC$_p$X$_{2p+1}$, where p is an integer from 2 to 20 and where X is a halogen.

In one embodiment, R1 is a H. In one embodiment, R$_1$ is a substituted or an unsubstituted arylalkyl, such as a benzyl or phenylethyl group. In one embodiment, the arylalkyl is substituted with C$_{1-4}$alkyl, C$_{1-4}$alkoxyl, hydroxyl, perhalogenated C$_{1-4}$alkyl, or halo.

In one embodiment, R$_2$ is a substituted or an unsubstituted arylalkyl, such as a benzyl or phenylethyl group. In one embodiment, the arylalkyl is substituted with C$_{1-4}$alkyl, C$_{1-4}$alkoxyl, hydroxyl, perhalogenated C$_{1-4}$alkyl, or halo. In one embodiment, the arylalkyl is substituted with one or more substituents selected from the group consisting of halo, —CH$_3$, —CF$_3$, and —OCH$_3$. In one embodiment, R$_2$ is a substituted or an unsubstituted heterocycloalkylalkyl, such as a morpholinoalkyl or piperazinylalkyl group. In one embodiment, R$_2$ is a substituted or an unsubstituted heteroarylalkyl, such as an isoxazolidinylmethyl or pyridylmethyl group. In one embodiment, the heterocycloalkylalkyl or heteroarylalkyl is substituted with C$_{1-4}$alkyl, C$_{1-4}$alkoxyl, hydroxyl, perhalogenated C$_{1-4}$alkyl, or halo. In one embodiment, the heterocycloalkylalkyl or heteroarylalkyl is substituted with one or more substituents selected from the group consisting of halo, —CH$_3$, —CF$_3$, and —OCH$_3$.

In one embodiment, the analogs have the structure of compound (27):

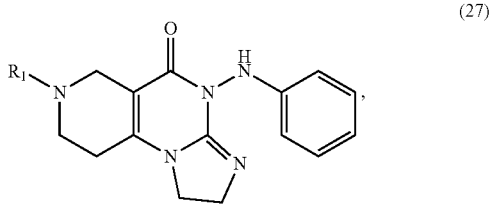

(27)

wherein R$_1$ is H, alkyl, cycloalkyl, cycloalkylalkyl, carboxyl, haloalkyl, alkenyl, cycloalkenyl, alkynyl, aryl, aralkyl, hydroxyalkyl, alkoxy, aryloxy, alkoxyalkyl, alkoxycarbonyl, aralkoxy, aralkylthio, alkanoyl, mercapto, alkylthio, arylthio, alkylsulfinyl, arylsulfinyl, alkylsulfonyl, arylsulfonyl, heteroaryl, acyl, and heterocycle radicals. In one embodiment, R$_1$ is selected from the group consisting of H, C$_{1-4}$alkyl, C$_{1-4}$alkylphenyl, C$_{1-4}$alkylphenylketone, C$_{1-4}$benzyl-piperazine, and C$_{1-4}$alkylthienyl, wherein C$_{1-4}$alkyl, C$_{1-4}$alkylphenyl, C$_{1-4}$alkylphenylketone, and C$_{1-4}$benzyl-piperazine are optionally substituted with C$_{1-4}$alkyl, C$_{1-4}$alkoxyl, hydroxyl, perhalogenated C$_{1-4}$alkyl, or halo. In one embodiment, R$_1$ is selected from the group consisting of H, CH$_3$, CH$_2$Ph, CH$_2$-((2-Cl)-Ph), CH$_2$-(2-thienyl), CH$_2$CH$_2$Ph, CH$_2$CH$_2$(4-N-benzyl-piperazine), CH$_2$-(2,4-di F-Ph), CH$_2$-((2-CH$_3$)-Ph), CH$_2$CHOHPh, and (CH$_2$)$_3$CO-4F-Ph.

In one embodiment, R$_1$ is a benzyl optionally substituted with one or more of the following substituents alone or in combination in the ortho, meta, and/or para positions of the benzyl ring: —CH$_3$, —NO$_2$, —OCH$_3$, —CXH$_2$, —CX$_2$H, —CX$_3$, —CH$_2$(CX$_3$), —CH(CX$_3$)$_2$, —C(CX$_3$)$_3$, —C$_p$X$_{2p+1}$, —OCX$_3$, or —OC$_p$X$_{2p+1}$, where p is an integer from 2 to 20 and where X is a halogen including F, Cl, Br, or I; preferably, F, Cl, or Br; more preferably, F or Cl. In one embodiment, R$_1$ is a H. In one embodiment, R$_1$ is a substituted or an unsubstituted arylalkyl, such as a benzyl or phenylethyl group. In one embodiment, the arylalkyl is substituted with C$_{1-4}$alkyl, C$_{1-4}$alkoxyl, hydroxyl, perhalogenated C$_{1-4}$alkyl, or halo.

In one embodiment, the analogs have the structure of compound (28):

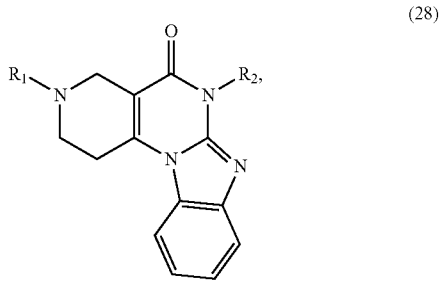

(28)

wherein R$_1$ and R$_2$ independently represent H, alkyl, cycloalkyl, cycloalkylalkyl, carboxyl, haloalkyl, alkenyl, cycloalkenyl, alkynyl, aryl, aralkyl, hydroxyalkyl, alkoxy, aryloxy, alkoxyalkyl, alkoxycarbonyl, aralkoxy, aralkylthio, alkanoyl, mercapto, alkylthio, arylthio, alkylsulfinyl, arylsulfinyl, alkylsulfonyl, arylsulfonyl, heteroaryl, acyl, and heterocycle radicals. In one embodiment, R$_1$ and R$_2$ are independently selected from the group consisting of H, C$_{1-4}$alkyl, C$_{1-4}$alkylphenyl, C$_{1-4}$alkylphenylketone, C$_{1-4}$benzyl-piperazine, and C$_{1-4}$alkylthienyl, wherein C$_{1-4}$alkyl, C$_{1-4}$alkylphenyl, C$_{1-4}$alkylphenylketone, and C$_{1-4}$benzyl-piperazine are optionally substituted with C$_{1-4}$alkyl, C$_{1-4}$alkoxyl, hydroxyl, perhalogenated C$_{1-4}$alkyl, or halo. In one embodiment, R$_1$ is selected from the group consisting of H, CH$_3$, CH$_2$Ph, CH$_2$-((2-Cl)-Ph), CH$_2$-(2-thienyl), CH$_2$CH$_2$Ph, CH$_2$-(2,4-di F-Ph), CH$_2$-((2-CH$_3$)-Ph), CH$_2$CHOHPh, CH$_2$CH$_2$(4-N-benzyl-piperazine), and (CH$_2$)$_3$CO-4F-Ph. In one embodiment, R$_2$ is selected from the group consisting of H, CH$_3$, CH$_2$Ph, CH$_2$-((2-Cl)-Ph), CH$_2$-(2-thienyl), CH$_2$CH$_2$Ph, CH$_2$CH$_2$(4-N-benzyl-piperazine), CH$_2$-(2,4-di F-Ph), CH$_2$-((2-CH$_3$)-Ph), CH$_2$CHOHPh, and (CH$_2$)$_3$CO-4F-Ph. In one embodiment, when R$_1$ is CH$_2$Ph, R$_2$ is not CH$_2$-(2-CH$_3$-Ph). In one embodiment, R$_1$ is CH$_2$Ph and R$_2$ is CH$_2$-(2-CH$_3$-Ph). In one embodiment, R$_1$ is CH$_2$Ph and R$_2$ is CH$_2$-(2,4-di F-Ph). In one embodiment, R$_1$ is CH$_2$Ph and R$_2$ is CH$_2$-(4-CF$_3$-Ph).

In one embodiment, R1 is a benzyl optionally substituted with one or more of the following substituents alone or in combination in the ortho, meta, and/or para positions of the benzyl ring: —CH$_3$, —NO$_2$, —OCH$_3$, —CXH$_2$, —CX$_2$H, —CX$_3$, —CH$_2$(CX$_3$), —CH(CX$_3$)$_2$, —C(CX$_3$)$_3$, —C$_p$X$_{2p+1}$, —OCX$_3$, or —OC$_p$X$_{2p+1}$, where p is an integer from 2 to 20 and where X is a halogen including F, Cl, Br, or I; preferably, F, Cl, or Br; more preferably, F or Cl. In one embodiment, R$_2$ is a benzyl substituted with one or more of the following substituents alone or in combination in the ortho, meta, and/or para positions of the benzyl ring: —CH$_3$, —NO$_2$, —OCH$_3$, —CXH$_2$, —CX$_2$H, —CX$_3$, —CH$_2$(CX$_3$), —CH(CX$_3$)$_2$, —C(CX$_3$)$_3$, —C$_p$X$_{2p+1}$, —OCX$_3$, or —OC$_p$X$_{2p+1}$, where p is an integer from 2 to 20 and where X is a halogen.

In one embodiment, R$_1$ is a H. In one embodiment, R$_1$ is a substituted or an unsubstituted arylalkyl, such as a benzyl or phenylethyl group. In one embodiment, the arylalkyl is substituted with C$_{1-4}$alkyl, C$_{1-4}$alkoxyl, hydroxyl, perhalogenated C$_{1-4}$alkyl, or halo.

In one embodiment, R$_2$ is a substituted or an unsubstituted arylalkyl, such as a benzyl or phenylethyl group. In one embodiment, the arylalkyl is substituted with $C_{1-4}$alkyl, $C_{1-4}$alkoxyl, hydroxyl, perhalogenated $C_{1-4}$alkyl, or halo. In one embodiment, the arylalkyl is substituted with one or more substituents selected from the group consisting of halo, —$CH_3$, —$CF_3$, and —$OCH_3$. In one embodiment, $R_2$ is a substituted or an unsubstituted heterocycloalkylalkyl, such as a morpholinoalkyl or piperazinylalkyl group. In one embodiment, $R_2$ is a substituted or an unsubstituted heteroarylalkyl, such as an isoxazolidinylmethyl or pyridylmethyl group. In one embodiment, the heterocycloalkylalkyl or heteroarylalkyl is substituted with $C_{1-4}$alkyl, $C_{1-4}$alkoxyl, hydroxyl, perhalogenated $C_{1-4}$alkyl, or halo. In one embodiment, the heterocycloalkylalkyl or heteroarylalkyl is substituted with one or more substituents selected from the group consisting of halo, —$CH_3$, —$CF_3$, and —$OCH_3$.

In one embodiment, the analogs have the structure of compound (29):

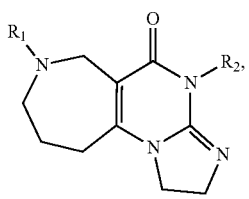

(29)

wherein $R_1$ and $R_2$ independently represent H, alkyl, cycloalkyl, cycloalkylalkyl, carboxyl, haloalkyl, alkenyl, cycloalkenyl, alkynyl, aryl, aralkyl, hydroxyalkyl, alkoxy, aryloxy, alkoxyalkyl, alkoxycarbonyl, aralkoxy, aralkylthio, alkanoyl, mercapto, alkylthio, arylthio, alkylsulfinyl, arylsulfinyl, alkylsulfonyl, arylsulfonyl, heteroaryl, acyl, and heterocycle radicals. In one embodiment, $R_1$ and $R_2$ are independently selected from the group consisting of H, $C_{1-4}$alkyl, $C_{1-4}$alkylphenyl, $C_{1-4}$alkylphenylketone, $C_{1-4}$benzyl-piperazine, and $C_{1-4}$alkylthienyl, wherein $C_{1-4}$alkyl, $C_{1-4}$alkylphenyl, $C_{1-4}$alkylphenylketone, and $C_{1-4}$benzyl-piperazine are optionally substituted with $C_{1-4}$alkyl, $C_{1-4}$alkoxyl, hydroxyl, perhalogenated $C_{1-4}$alkyl, or halo. In one embodiment, $R_1$ is selected from the group consisting of H, $CH_3$, $CH_2Ph$, $CH_2$-((2-Cl)-Ph), $CH_2$-(2-thienyl), $CH_2CH_2Ph$, $CH_2CH_2$(4-N-benzyl-piperazine), $CH_2$-(2,4-di F-Ph), $CH_2$-((2-$CH_3$)-Ph), $CH_2CHOHPh$, and $(CH_2)_3CO$-4F-Ph. In one embodiment, $R_2$ is selected from the group consisting of H, $CH_3$, $CH_2Ph$, $CH_2$-((2-Cl)-Ph), $CH_2$-(2-thienyl), $CH_2CH_2Ph$, $CH_2CH_2$(4-N-benzyl-piperazine), $CH_2$-(2,4-di F-Ph), $CH_2$-((2-$CH_3$)-Ph), $CH_2CHOHPh$, and $(CH_2)_3CO$-4F-Ph. In one embodiment, when $R_1$ is $CH_2Ph$, $R_2$ is not $CH_2$-(2-$CH_3$-Ph). In one embodiment, $R_1$ is $CH_2Ph$ and $R_2$ is $CH_2$-(2-$CH_3$-Ph). In one embodiment, $R_1$ is $CH_2Ph$ and $R_2$ is $CH_2$-(2,4-di F-Ph). In one embodiment, $R_1$ is $CH_2Ph$ and $R_2$ is $CH_2$-(4-$CF_3$-Ph).

In one embodiment, R1 is a benzyl optionally substituted with one or more of the following substituents alone or in combination in the ortho, meta, and/or para positions of the benzyl ring: —$CH_3$, —$NO_2$, —$OCH_3$, —$CXH_2$, —$CX_2H$, —$CX_3$, —$CH_2(CX_3)$, —$CH(CX_3)_2$, —$C(CX_3)_3$, —$C_pX_{2p+1}$, —$OCX_3$, or —$OC_pX_{2p+1}$, where p is an integer from 2 to 20 and where X is a halogen including refers to F, Cl, Br, or I; preferably, F, Cl, or Br; more preferably, F or Cl. In one embodiment, $R_2$ is a benzyl substituted with one or more of the following substituents alone or in combination in the ortho, meta, and/or para positions of the benzyl ring: —$CH_3$, —$NO_2$, —$OCH_3$, —$CXH_2$, —$CX_2H$, —$CX_3$, —$CH_2(CX_3)$, —$CH(CX_3)_2$, —$C(CX_3)_3$, —$C_pX_{2p+1}$, —$OCX_3$, or —$OC_pX_{2p+1}$, where p is an integer from 2 to 20 and where X is a halogen.

In one embodiment, $R_1$ is a H. In one embodiment, $R_1$ is a substituted or an unsubstituted arylalkyl, such as a benzyl or phenylethyl group. In one embodiment, the arylalkyl is substituted with $C_{1-4}$alkyl, $C_{1-4}$alkoxyl, hydroxyl, perhalogenated $C_{1-4}$alkyl, or halo.

In one embodiment, $R_2$ is a substituted or an unsubstituted arylalkyl, such as a benzyl or phenylethyl group. In one embodiment, the arylalkyl is substituted with $C_{1-4}$alkyl, $C_{1-4}$alkoxyl, hydroxyl, perhalogenated $C_{1-4}$alkyl, or halo. In one embodiment, the arylalkyl is substituted with one or more substituents selected from the group consisting of halo, —$CH_3$, —$CF_3$, and —$OCH_3$. In one embodiment, $R_2$ is a substituted or an unsubstituted heterocycloalkylalkyl, such as a morpholinoalkyl or piperazinylalkyl group. In one embodiment, $R_2$ is a substituted or an unsubstituted heteroarylalkyl, such as an isoxazolidinylmethyl or pyridylmethyl group. In one embodiment, the heterocycloalkylalkyl or heteroarylalkyl is substituted with $C_{1-4}$alkyl, $C_{1-4}$alkoxyl, hydroxyl, perhalogenated $C_{1-4}$alkyl, or halo. In one embodiment, the heterocycloalkylalkyl or heteroarylalkyl is substituted with one or more substituents selected from the group consisting of halo, —$CH_3$, —$CF_3$, and —$OCH_3$.

In one embodiment, the analogs have the structure of compound (30):

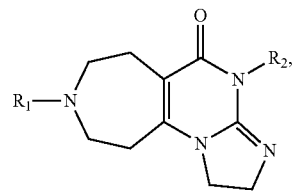

(30)

wherein $R_1$ and $R_2$ independently represent H, alkyl, cycloalkyl, cycloalkylalkyl, carboxyl, haloalkyl, alkenyl, cycloalkenyl, alkynyl, aryl, aralkyl, hydroxyalkyl, alkoxy, aryloxy, alkoxyalkyl, alkoxycarbonyl, aralkoxy, aralkylthio, alkanoyl, mercapto, alkylthio, arylthio, alkylsulfinyl, arylsulfinyl, alkylsulfonyl, arylsulfonyl, heteroaryl, acyl, and heterocycle radicals. In one embodiment, $R_1$ and $R_2$ are independently selected from the group consisting of H, $C_{1-4}$alkyl, $C_{1-4}$alkylphenyl, $C_{1-4}$alkylphenylketone, $C_{1-4}$benzyl-piperazine, and $C_{1-4}$alkylthienyl, wherein $C_{1-4}$alkyl, $C_{1-4}$alkylphenyl, $C_{1-4}$alkylphenylketone, and $C_{1-4}$benzyl-piperazine are optionally substituted with $C_{1-4}$alkyl, $C_{1-4}$alkoxyl, hydroxyl, perhalogenated $C_{1-4}$alkyl, or halo. In one embodiment, $R_1$ is selected from the group consisting of H, $CH_3$, $CH_2Ph$, $CH_2$-((2-Cl)-Ph), $CH_2$-(2-thienyl), $CH_2CH_2Ph$, $CH_2CH_2$(4-N-benzyl-piperazine), $CH_2$-(2,4-di F-Ph), $CH_2$-((2-$CH_3$)-Ph), $CH_2CHOHPh$, and $(CH_2)_3CO$-4F-Ph. In one embodiment, $R_2$ is selected from the group consisting of H, $CH_3$, $CH_2Ph$, $CH_2$-((2-Cl)-Ph), $CH_2$-(2-thienyl), $CH_2CH_2Ph$, $CH_2CH_2$(4-N-benzyl-piperazine), $CH_2$-(2,4-di F-Ph), $CH_2$-((2-$CH_3$)-Ph), $CH_2CHOHPh$, and $(CH_2)_3CO$-4F-Ph. In one embodiment, when $R_1$ is $CH_2Ph$, $R_2$ is not $CH_2$-(2-$CH_3$-Ph). In one embodiment, $R_1$ is $CH_2Ph$ and $R_2$ is $CH_2$-(2-$CH_3$-Ph). In one embodiment, $R_1$ is $CH_2Ph$ and $R_2$ is $CH_2$-(2,4-di F-Ph). In one embodiment, $R_1$ is $CH_2Ph$ and $R_2$ is $CH_2$-(4-$CF_3$-Ph).

In one embodiment, $R_1$ is a benzyl optionally substituted with one or more of the following substituents alone or in combination in the ortho, meta, and/or para positions of the benzyl ring: —CH$_3$, —NO$_2$, —OCH$_3$, —CXH$_2$, —CX$_2$H, —CX$_3$, —CH$_2$(CX$_3$), —CH(CX$_3$)$_2$, —C(CX$_3$)$_3$, —C$_p$X$_{2p+1}$, —OCX$_3$, or —OC$_p$X$_{2p+1}$, where p is an integer from 2 to 20 and where X is a halogen including refers to F, Cl, Br, or I, preferably, F, Cl, or Br, more preferably, F or Cl. In one embodiment, R$_2$ is a benzyl substituted with one or more of the following substituents alone or in combination in the ortho, meta, and/or para positions of the benzyl ring: —CH$_3$, —NO$_2$, —OCH$_3$, —CXH$_2$, —CX$_2$H, —CX$_3$, —CH$_2$(CX$_3$), —CH(CX$_3$)$_2$, —C(CX$_3$)$_3$, —C$_p$X$_{2p+1}$, —OCX$_3$, or —OC$_p$X$_{2p+1}$, where p is an integer from 2 to 20 and where X is a halogen.

In one embodiment, R$_1$ is a H. In one embodiment, R$_1$ is a substituted or an unsubstituted arylalkyl, such as a benzyl or phenylethyl group. In one embodiment, the arylalkyl is substituted with C$_{1-4}$alkyl, C$_{1-4}$alkoxyl, hydroxyl, perhalogenated C$_{1-4}$alkyl, or halo.

In one embodiment, R$_2$ is a substituted or an unsubstituted arylalkyl, such as a benzyl or phenylethyl group. In one embodiment, the arylalkyl is substituted with C$_{1-4}$alkyl, C$_{1-4}$alkoxyl, hydroxyl, perhalogenated C$_{1-4}$alkyl, or halo. In one embodiment, the arylalkyl is substituted with one or more substituents selected from the group consisting of halo, —CH$_3$, —CF$_3$, and —OCH$_3$. In one embodiment, R$_2$ is a substituted or an unsubstituted heterocycloalkylalkyl, such as a morpholinoalkyl or piperazinylalkyl group. In one embodiment, R$_2$ is a substituted or unsubstituted heteroarylalkyl, such as an isoxazolidinylmethyl or pyridylmethyl group. In one embodiment, the heterocycloalkylalkyl or heteroarylalkyl is substituted with C$_{1-4}$alkyl, C$_{1-4}$alkoxyl, hydroxyl, perhalogenated C$_{1-4}$alkyl, or halo. In one embodiment, the heterocycloalkylalkyl or heteroarylalkyl is substituted with one or more substituents selected from the group consisting of halo, —CH$_3$, —CF$_3$, and —OCH$_3$.

In one embodiment, the analogs have the structure of compound (31):

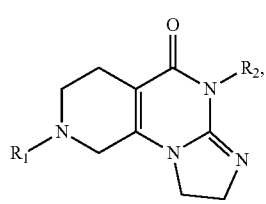

(31)

wherein R$_1$ and R$_2$ independently represent H, alkyl, cycloalkyl, cycloalkylalkyl, carboxyl, haloalkyl, alkenyl, cycloalkenyl, alkynyl, aryl, aralkyl, hydroxyalkyl, alkoxy, aryloxy, alkoxyalkyl, alkoxycarbonyl, aralkoxy, aralkylthio, alkanoyl, mercapto, alkylthio, arylthio, alkylsulfinyl, arylsulfinyl, alkylsulfonyl, arylsulfonyl, heteroaryl, acyl, and heterocycle radicals. In one embodiment, R$_1$ and R$_2$ are independently selected from the group consisting of H, C$_{1-4}$alkyl, C$_{1-4}$alkylphenyl, C$_{1-4}$alkylphenylketone, C$_{1-4}$benzyl-piperazine, and C$_{1-4}$alkylthienyl, wherein C$_{1-4}$alkyl, C$_{1-4}$alkylphenyl, C$_{1-4}$alkylphenylketone, and C$_{1-4}$benzyl-piperazine are optionally substituted with C$_{1-4}$alkyl, C$_{1-4}$alkoxyl, hydroxyl, perhalogenated C$_{1-4}$alkyl, or halo. In one embodiment, R$_1$ is selected from the group consisting of H, CH$_3$, CH$_2$Ph, CH$_2$-((2-Cl)-Ph), CH$_2$-(2-thienyl), CH$_2$CH$_2$Ph, CH$_2$CH$_2$(4-N-benzyl-piperazine), CH$_2$-(2,4-di F-Ph), CH$_2$-((2-CH$_3$)-Ph), CH$_2$CHOHPh, and (CH$_2$)$_3$CO-4F-Ph. In one embodiment, R$_2$ is selected from the group consisting of H, CH$_3$, CH$_2$Ph, CH$_2$-((2-Cl)-Ph), CH$_2$-(2-thienyl), CH$_2$CH$_2$Ph, CH$_2$CH$_2$(4-N-benzyl-piperazine), CH$_2$-(2,4-di F-Ph), CH$_2$-((2-CH$_3$)-Ph), CH$_2$CHOHPh, and (CH$_2$)$_3$CO-4F-Ph. In one embodiment, when R$_1$ is CH$_2$Ph, R$_2$ is not CH$_2$-(2-CH$_3$-Ph). In one embodiment, R$_1$ is CH$_2$Ph and R$_2$ is CH$_2$-(2-CH$_3$-Ph). In one embodiment, R$_1$ is CH$_2$Ph and R$_2$ is CH$_2$-(2,4-di F-Ph). In one embodiment, R$_1$ is CH$_2$Ph and R$_2$ is CH$_2$-(4-CF$_3$-Ph).

In one embodiment, R$_1$ is a benzyl optionally substituted with one or more of the following substituents alone or in combination in the ortho, meta, and/or para positions of the benzyl ring: —CH$_3$, —NO$_2$, —OCH$_3$, —CXH$_2$, —CX$_2$H, —CX$_3$, —CH$_2$(CX$_3$), —CH(CX$_3$)$_2$, —C(CX$_3$)$_3$, —C$_p$X$_{2p+1}$, —OCX$_3$, or —OC$_p$X$_{2p+1}$, where p is an integer from 2 to 20 and where X is a halogen including F, Cl, Br, or I; preferably, F, Cl, or Br; more preferably, F or Cl. In one embodiment, R$_2$ is a benzyl substituted with one or more of the following substituents alone or in combination in the ortho, meta, and/or para positions of the benzyl ring: —CH$_3$, —NO$_2$, —OCH$_3$, —CXH$_2$, —CX$_2$H, —CX$_3$, —CH$_2$(CX$_3$), —CH(CX$_3$)$_2$, —C(CX$_3$)$_3$, —C$_p$X$_{2p+1}$, —OCX$_3$, or —OC$_p$X$_{2p+1}$, where p is an integer from 2 to 20 and where X is a halogen.

In one embodiment, R$_1$ is a H. In one embodiment, R$_1$ is a substituted or an unsubstituted arylalkyl, such as a benzyl or phenylethyl group. In one embodiment, the arylalkyl is substituted with C$_{1-4}$alkyl, C$_{1-4}$alkoxyl, hydroxyl, perhalogenated C$_{1-4}$alkyl, or halo.

In one embodiment, R$_2$ is a substituted or an unsubstituted arylalkyl, such as a benzyl or phenylethyl group. In one embodiment, the arylalkyl is substituted with C$_{1-4}$alkyl, C$_{1-4}$alkoxyl, hydroxyl, perhalogenated C$_{1-4}$alkyl, or halo. In one embodiment, the arylalkyl is substituted with one or more substituents selected from the group consisting of halo, —CH$_3$, —CF$_3$, and —OCH$_3$. In one embodiment, R$_2$ is a substituted or an unsubstituted heterocycloalkylalkyl, such as a morpholinoalkyl or piperazinylalkyl group. In one embodiment, R$_2$ is a substituted or an unsubstituted heteroarylalkyl, such as an isoxazolidinylmethyl or pyridylmethyl group. In one embodiment, the heterocycloalkylalkyl or heteroarylalkyl is substituted with C$_{1-4}$alkyl, C$_{1-4}$alkoxyl, hydroxyl, perhalogenated C$_{1-4}$alkyl, or halo. In one embodiment, the heterocycloalkylalkyl or heteroarylalkyl is substituted with one or more substituents selected from the group consisting of halo, —CH$_3$, —CF$_3$, and —OCH$_3$.

In one embodiment, provided herein are compounds of formula (100):

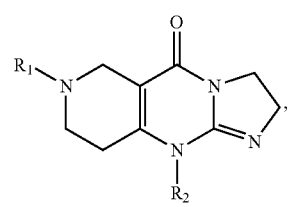

(100)

wherein R$_1$ and R$_2$ are independently selected from H, alkyl, cycloalkyl, cycloalkylalkyl, heterocycloalkyl, heterocycloalkylalkyl, aryl, heteroaryl, arylalkyl, heteroarylalkyl, alkoxyalkyl, alkoxycarbonyl, aralkoxy, aralkylthio, and acyl radicals. In one embodiment, R$_1$ is CH$_2$Ph and R$_2$ is CH$_2$-(2-CH$_3$-Ph), which is an ONC201 linear isomer

TIC-10

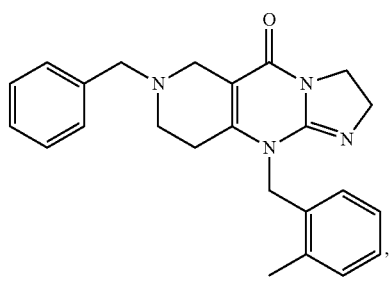

which lacks anti-cancer activity (Jacob et al., *Angew. Chem. Int. Ed.*, (2014) 53:6628; Wagner et al., *Oncotarget* (2015) 5(24):12728). TIC-10 is a CXCR7 agonist. CXCR7 agonists can be used for liver regeneration and to prevent or treat liver fibrosis.

In one embodiment, $R_1$ and $R_2$ are independently selected from the group consisting of H, $C_{1-4}$alkyl, $C_{1-4}$alkylphenyl, $C_{1-4}$alkylphenylketone, $C_{1-4}$benzyl-piperazine, $C_{1-4}$alkylthienyl, $C_{1-4}$alkylpyridinyl, $C_{1-4}$alkylisoxazolidinyl, $C_{1-4}$alkylmorpholinyl, $C_{1-4}$alkylthiazolyl, and $C_{1-4}$alkylpyrazinyl wherein $C_{1-4}$alkyl, $C_{1-4}$alkylphenyl, $C_{1-4}$alkylphenylketone, $C_{1-4}$benzyl-piperazine, $C_{1-4}$alkylthienyl, $C_{1-4}$alkylpyridinyl, $C_{1-4}$alkylisoxazolidinyl, $C_{1-4}$alkylmorpholinyl, $C_{1-4}$alkylthiazolyl, and $C_{1-4}$alkylpyrazinyl are optionally substituted with $C_{1-4}$alkyl, $C_{1-4}$alkoxyl, hydroxyl, perhalogenated $C_{1-4}$alkyl, or halo. In one embodiment, $R_1$ and/or $R_2$ is a substituted or unsubstituted, arylalkyl or heteroarylalkyl. In one embodiment, the heteroarylalkyl is selected from $C_{1-4}$alkylpyrrolyl, $C_{1-4}$alkylfuryl, $C_{1-4}$alkylpyridyl, $C_{1-4}$alkyl-1,2,4-thiadiazolyl, $C_{1-4}$alkylpyrimidyl, $C_{1-4}$alkylthienyl, $C_{1-4}$alkylisothiazolyl, $C_{1-4}$alkylimidazolyl, $C_{1-4}$alkyltetrazolyl, $C_{1-4}$alkylpyrazinyl, $C_{1-4}$alkylpyrimidyl, $C_{1-4}$alkylquinolyl, $C_{1-4}$alkylisoquinolyl, $C_{1-4}$alkylthiophenyl, $C_{1-4}$alkylbenzothienyl, $C_{1-4}$alkylisobenzofuryl, $C_{1-4}$alkylpyrazolyl, $C_{1-4}$alkylindolyl, $C_{1-4}$alkylpurinyl, $C_{1-4}$alkylcarbazolyl, $C_{1-4}$alkylbenzimidazolyl, and $C_{1-4}$alkylisoxazolyl.

In one embodiment, $R_1$ and/or $R_2$ is a benzyl optionally substituted with one or more of the following substituents on the benzyl ring: X, —$CH_3$, —$NO_2$, —$OCH_3$, —CN, —$CXH_2$, —$CX_2H$, $C_2$-$C_4$ alkyl, —$CX_3$, —$CH_2(CX_3)$, —$CH(CX_3)_2$, —$C(CX_3)_3$, —$C_pX_{2p+1}$, —$OCX_3$, —$OC_pH_{2p+1}$, —$OC_pX_{2p+1}$, $OR'''$, $SR'''$, $NR'''R''$, $NR'''C(O)R''$, $SOR'''$, $SO_2R'''$, $C(O)R$, and $C(O)OR$; $R'''$ and $R''$ are independently selected from H or a $C_1$-$C_4$ alkyl; and where p is an integer from 2 to 20 and X is a halogen, including F, Cl, Br, or I; preferably, F, Cl, or Br; more preferably, F or Cl.

XI. EXAMPLES

It should be understood that the description and examples below are meant only for illustration purposes and are not meant to limit the scope of this disclosure. The examples below are meant to illustrate the embodiments disclosed and are not to be construed as being limitations to them. Additional compounds, other than those described below, may be made by the following reaction schemes or appropriate variations or modifications thereof.

Example 1. Synthesis of 2-Chlorobenzylamino-2-imidazoline hydroiodide

To a stirred solution of 2-methylthio-2-imidazoline hydroiodide (244 mg, 1.00 mMol) in dry dioxane (2.0 mL) was added 2-chlorobenzylamine (141 mg, 1.0 mMol). The reaction mixture was stirred for 90 min at 70° C. under argon. The solution was cooled to room temperature, filtered on a sintered funnel, washed with cold dioxane (2 mL) and dried under vacuum. The white solid compound 4.HI ($R_2$=2-chlorobenzyl) was obtained (242 mg, 72%) and used without further purification.

Example 2. Synthesis of 2-Chlorobenzylamino-2-imidazoline

To a stirred solution of 2-chlorobenzylamino-2-imidazoline hydroiodide (242 mg, 0.72 mMol) in water (3 mL), was added 1.0 N sodium hydroxide (2 mL) at 7° C. The reaction mixture was stirred for 30 min at 7° C. under argon. After that methylene chloride (5 mL) was added and the mixture stirred for another 5 min. The reaction mixture was extracted with methylene chloride (2×2.5 mL). The organic layer was dried over anhydrous $Na_2SO_4$, filtered and evaporated. The resulting free base (150 mg, 100%) was obtained as a viscous liquid and was used for the next reaction without any further purification. MS(ESI) 210 (M+H).

Example 3. Synthesis of Methyl-1-benzyl 4-oxo-3-piperidine carboxylate (Compound (6))

To a stirred methyl-1-benzyl 4-oxo-3-piperidine carboxylate hydrochloride (5.7 g, 20 mMol) in ethyl acetate (50 mL), was added triethylamine (6 mL) at 7° C. The reaction mixture was stirred for 30 min at 7° C. under an argon atmosphere. The reaction mixture was extracted with ethyl acetate (2×50 mL) and washed with water (50 mL). The organic layer was dried over anhydrous $Na_2SO_4$, filtered and evaporated. The resulting free base residue (5, $R_1$=benzyl) as a viscous oil was used in the next reaction without any further purification MS(ESI) 248 (M+H)

Example 4. Synthesis of ONC202 (Compound (14))

To a solution of 2-chlorobenzylamino-2-imidazoline (150 mg, 0.72 mMol), methyl 1-benzyl 4-oxo-3-piperidine carboxylate (5, $R_1$=benzyl) (195 mg, 0.79 mMol) in 1-butanol (2 mL) was added PPTS (10 mg) and the mixture was stirred at room temperature for 48 h. After that the reaction mixture was refluxed at 125° C. to 130° C. for 2 h. The solvents were removed under vacuum, extracted with ethyl acetate (10 mL), and washed with saturated sodium bicarbonate solution (2×10 mL) and water (10 mL). The organic layer was dried over anhydrous $Na_2SO_4$, filtered and evaporated. The crude free base was purified by RP HPLC (10%-40% acetonitrile/water) to give ONC202 TFA salt as a white solid (228 mg, 50% yield) MS(ESI) 407 (M+H).

The same process was used starting with different benzylamines to prepare various analogs, e.g., ONC203, 204, 205, 206, 912, 210, 211, 212, 213, 214, 217, 218, 219, 220, 221, 222, 223, 224, 225, and 226.

Example 5. Synthesis of ONC207 (Compound (19))

To a suspension of 60% sodium hydride (3.5 g, 88 mMol) in dry toluene (50 mL), dimethyl carbonate (4.32 g, 48.0 mMol) was added dropwise in 0.5 h at room temperature under nitrogen. After addition of a few drops of methanol, 1-tert-butoxycarbonyl-4-piperidone (4.8 g, 24 mMol) dissolved in dry toluene (20 mL) was added dropwise to the reaction mixture while stirring at 80° C. over 1 h. The reaction mixture was stirred for 3 h at the same temperature and then cooled to 0° C. (ice bath) and adjusted to pH 6-6.5 with acetic acid. The resulting cold mixture was diluted with water (10 mL) and adjusted to pH 8 with 5% sodium hydroxide solution. The toluene layer was separated and the aqueous layer was extracted with toluene (20 mL). The combined organic layer was dried over anhydrous sodium sulfate, and concentrated under reduced pressure. The compound was dried in vacuum to give methyl-1-tert-butoxycarbonyl-4-oxo-3-piperidine carboxylate (5.0 g, 80%). The compound obtained was carried to the next reaction without any further purification.

2-methybenzylamino-2-imidazoline (190 mg, 1 mMol), methyl 1-tert-butoxycarbonyl-4-oxo-3-piperidine carboxylate (315 mg, 1.1 mMol) in 1-butanol (2 mL) was added PPTS (10.0 mg) and the mixture was stirred at room temperature for 48 h. After that the reaction mixture was refluxed at 125° C. to 130° C. for 2 h. The solvents were removed under vacuum, extracted with ethyl acetate (10 mL), washed with saturated sodium bicarbonate solution (2×10 mL) and water (10 mL). The organic layer was dried over anhydrous $Na_2SO_4$, filtered and evaporated. The crude free base was cleaved with 10% trifluoroacetic acid in dichloromethane, purified by RP HPLC (10%-40% acetonitrile/water) to give ONC207 (262 mg, 50%) TFA salt as a white solid MS(ESI) 297 (M+H).

Example 6. Synthesis of ONC209 (Compound (21))

A mixture of ONC207 (100 mg, 0.2 mMol), phenylethyl bromide (55.0 mg, 0.28 mMol) and potassium carbonate (150 mg, 1.0 mMol) in N,N-dimethylformamide (3 mL) was heated to 70° C. for 12 h. The solvents were removed under vacuum, extracted with ethyl acetate (10 mL), and washed with water (5 mL). The organic layer was dried over anhydrous $Na_2SO_4$, filtered and evaporated. The crude free base was purified by RP HPLC (10%-40% acetonitrile/water) to give ONC209 (62 mg, 50%) TFA salt as a white solid MS(ESI) 401 (M+H).

The same process was used starting with different halides to give ONC215 and 214. Compounds 227, 228, 229, 230, 231, 232, 233, 234, 235, and 236 were prepared using an analogous process from Examples 1 and 5 starting with different benzylamines. Then treating the intermediate compound where $R_1$ is H with different halides as above.

Compound ONC216 was prepared from ONC215 by treatment with TFA.

Compound (72) was prepared by reacting the precursor NH compound prepared in analogy to Example 5 and treating it with styrene oxide.

Example 7. Synthesis of ONC208 (Compound (20))

To a solution of 2-methylbenzylamino-2-imidazoline (190.0 mg, 1.0 mmol), methyl 1-methyl 4-oxo-3-piperidine carboxylate (185.0 mg, 1.0 mMol) in 1-butanol (2.0 mL) was added PPTS (10.0 mg) and the mixture was stirred at room temperature for 48 h. After that the reaction mixture was refluxed at 125° C. to 130° C. for 2 h. The solvents were removed under vacuum, extracted with ethyl acetate (10 mL), washed with saturated sodium bicarbonate solution (2×10 mL) and water (10 mL). The organic layer was dried over anhydrous $Na_2SO_4$, filtered and evaporated. The crude free base was purified by HPLC 10%-40% acetonitrile and water to give ONC208 (270.0 mg, 50%) TFA salt as a white solid MS(ESI) 311 (M+H).

Example 8. Synthesis of ONC201 (Compound (1))

To a stirred 800 mL saturated $NaHCO_3$ in a 2 L round bottom flask, compound (3) (239.7 g, 0.845 mol, 1.6 equiv) was added in portions. n-Butanol (500 mL) was added to the resulting mixture, which was stirred for 30 min and then transferred to a separating funnel. The organic phase, containing compound (4), was separated and transferred to a 2 L three-neck round bottom flask equipped with mechanical stirring, $N_2$ inlet, a thermocouple, a condenser and a Dean-Stark trap. To the contents of the flask, Compound (5) (100 g, 0.528 mol, 1 equiv) and pyridinium p-toluenesulfonate (PPTS) (6.63 gm 0.026 mol, 5 mol %) were added. The resulting mixture was heated to reflux for 6 hours. Water in the reaction mixture was separated into the Dean-Stark trap as necessary. Refluxing temperature increased from 93° C. to 118° C. Reaction progress was monitored by HPLC. When the peak area of compound (1) on HPLC remained constant with the reaction time, the reaction was stopped.

Example 9. Synthesis of Di-Salt of ONC201 (Compound (1)*2HCl)

Without isolation of the compound (1), the reaction mixture from Example 8 was washed with water (500 mL) and diluted with methyl tert-butyl ether (MTBE) (800 mL). The organic phase was washed with water (500 mL×2) and transferred to a 3 L three-neck round bottom flask equipped with mechanical stirring, $N_2$ inlet, a thermocouple, a condenser and a Dean-Stark trap. While agitating the reaction mixture, 1 N HCl in dioxane-MTBE solution was added dropwise (4 N HCl in dioxane: 300 mL, 1.2 mol, 2.27 equiv; MTBE: 1200 mL) until no more solid precipitated out of the reaction mixture upon addition of HCl. The reaction mixture was heated to reflux at 60-65° C. for 2 hours. Water was separated into the Dean-Stark trap as necessary. Upon cooling to room temperature, the solid precipitate was filtered through a sintered glass funnel and washed with n-butanol-MTBE (1:2, 600 mL) and MTBE (600 mL) respectively. The solid was dried in a vacuum oven at 65° C. overnight (16 hours) to afford 200 g yellow solid.

To a 2 L three-neck round bottom flask equipped with mechanical stirring, $N_2$ inlet, a thermocouple and a condenser, the above solid (200 g) was added, followed by ethanol (1000 mL). The mixture was heated to reflux at 78° C. for 2 hours. Upon cooling to room temperature, the solid was filtered through a sintered glass funnel and washed with ethanol (200 mL×3). The wet solid was dried in the vacuum oven at 85° C. for 3 days until the residual solvent met specification. 120 g of compound (2) was obtained as a white solid in a yield of 49%, with HPLC purity 99.7%.

Example 10. Activity of Imipridones

A number of imipridones were prepared based on the syntheses above. Viability of human cancer cells was measured at 72 hours post-treatment with each compound. The change in potency (relative to ONC201) was determined and shown in Table 3.

TABLE 3

RELATIVE POTENCY OF ONC201 ANALOGS

| No. | Identifier | $R_1$ | $R_2$ | Relative Potency* |
|---|---|---|---|---|
| 1 | ONC201 | $CH_2Ph$ | $CH_2$-((2-$CH_3$)—Ph) | N/A |
| 14 | ONC202 | $CH_2Ph$ | $CH_2$(2-Cl—Ph) | B |
| 15 | ONC203 | $CH_2Ph$ | $CH_2$-(2-thienyl) | C |
| 16 | ONC204 | $CH_2Ph$ | $CH_2CH_2Ph$ | C |
| 17 | ONC205 | $CH_2Ph$ | $CH_2CH_2$(4-N-benzyl-piperazine) | C |
| 18 | ONC206 | $CH_2Ph$ | $CH_2$-(2,4-di F—Ph) | A |
| 19 | ONC207 | H | $CH_2$-((2-$CH_3$)—Ph) | B |
| 20 | ONC208 | $CH_3$ | $CH_2$-((2-$CH_3$)—Ph) | B |
| 21 | ONC209 | $CH_2CH_2Ph$ | $CH_2$-((2-$CH_3$)—Ph) | B |
| 32 | ONC215 | $(CH_2)_3$—NH—BOC | $CH_2$-((2-$CH_3$)—Ph) | B |
| 33 | ONC216 | $(CH_2)_3$—$NH_2$ | $CH_2$-((2-$CH_3$)—Ph) | B |
| 41 | ONC210 | $CH_2Ph$ | $CH_2$-(3,5-di F—Ph) | B |
| 51 | ONC211 | $CH_2Ph$ | $CH_2$-(3,4-di Cl—Ph) | B |
| 52 | ONC212 | $CH_2Ph$ | $CH_2$-(4-$CF_3$—Ph) | A |
| 53 | ONC213 | $CH_2Ph$ | $CH_2$-(3,4-di F—Ph) | A |
| 54 | ONC214 | $CD_2C_6D_5$ | $CH_2$-((2-$CH_3$)—Ph) | B |
| 43 | ONC217 | $CH_2Ph$ | $CH_2$(2-F—Ph) | C |
| 55 | ONC218 | $CH_2Ph$ | $CH_2$(2-$CH_3$, 4-F—Ph) | A |
| 56 | ONC219 | $CH_2Ph$ | $CH_2$-(2,4-di Cl—Ph) | A |
| 57 | ONC220 | $CH_2Ph$ | $CH_2$-((4-$OCH_3$)—Ph) | A |
| 35 | ONC222 | $CH_2Ph$ | $CH_2$-(3-isoxazolidinyl) | C |
| 36 | ONC224 | $CH_2Ph$ | $CH_2CH_2$-(4-morpholinyl) | A |
| 38 | ONC221 | H | $CH_2$-(4-$CF_3$—Ph) | A |
| 72 | ONC225 | $CH_2Ph$ | $CH_2$-(2-F, 4-$CF_3$—Ph) | A |
| 37 | ONC223 | $CH_2Ph$ | $CH_2$-(4-$CH_3$—Ph) | A |
| 34 | ONC226 | $CH_2Ph$ | $CH_2$-(3-pyridinyl) | A |
| 77 | ONC231 | $CH_2$-3-pyridyl | $CH_2$-(4-$CF_3$—Ph) | A |
| 78 | ONC232 | $CH_2$-4-methyl-2-thiazolyl | $CH_2$-(4-$CF_3$—Ph) | B |
| 79 | ONC233 | $CH_2$-2-pyrazinyl | $CH_2$-(4-$CF_3$—Ph) | B |
| 81 | ONC234 | $CH_2$-(3,4-di Cl—Ph) | $CH_2$-(4-$CF_3$—Ph) | A |
| 83 | ONC236 | $CH_2$-3-thienyl | $CH_2$-(4-$CF_3$—Ph) | A |
| 84 | ONC237 | $CH_2CH(OH)Ph$ | $CH_2$-(4-$CF_3$—Ph) | C |
| 73 | ONC227 | $CH_2$-(4-$CF_3$—Ph) | $CH_2$-(4-$CF_3$—Ph) | B |
| 74 | ONC228 | $CH_2$-(4-F—Ph) | $CH_2$-(4-$CF_3$—Ph) | A |
| 75 | ONC229 | $CH_2$-(4-$OCH_3$—Ph) | $CH_2$-(4-$CF_3$—Ph) | B |
| 76 | ONC230 | 4-F—Ph-4-oxobutyl | $CH_2$-(4-$CF_3$—Ph) | A |

*Relative to the potency of ONC201; A Indicates a potency increase of >2-fold of ONC201; B Indicates potency that is within 2-fold of ONC201; and C Indicates a potency decrease of >2-fold of ONC201.

ONC212

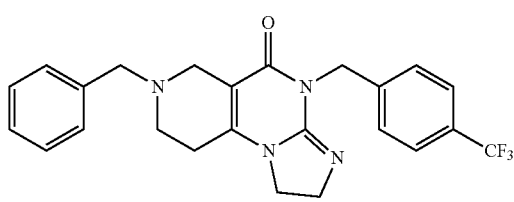

The $IC_{50}$ of ONC201 and ONC212 (5 nM-5 μM, 72 h) upon treatment of several acute myeloid leukemia (AML) cell lines (n=3) were determined and shown in Table 4.

TABLE 4

| AML cell line | ONC201 $IC_{50}$ (μM) | ONC212 $IC_{50}$ (μM) |
|---|---|---|
| MV411 | 3.25 | 0.01 |
| HL60 | >5 | 0.21 |
| MOLM14 | 3.92 | 0.01 |

Figure 14:
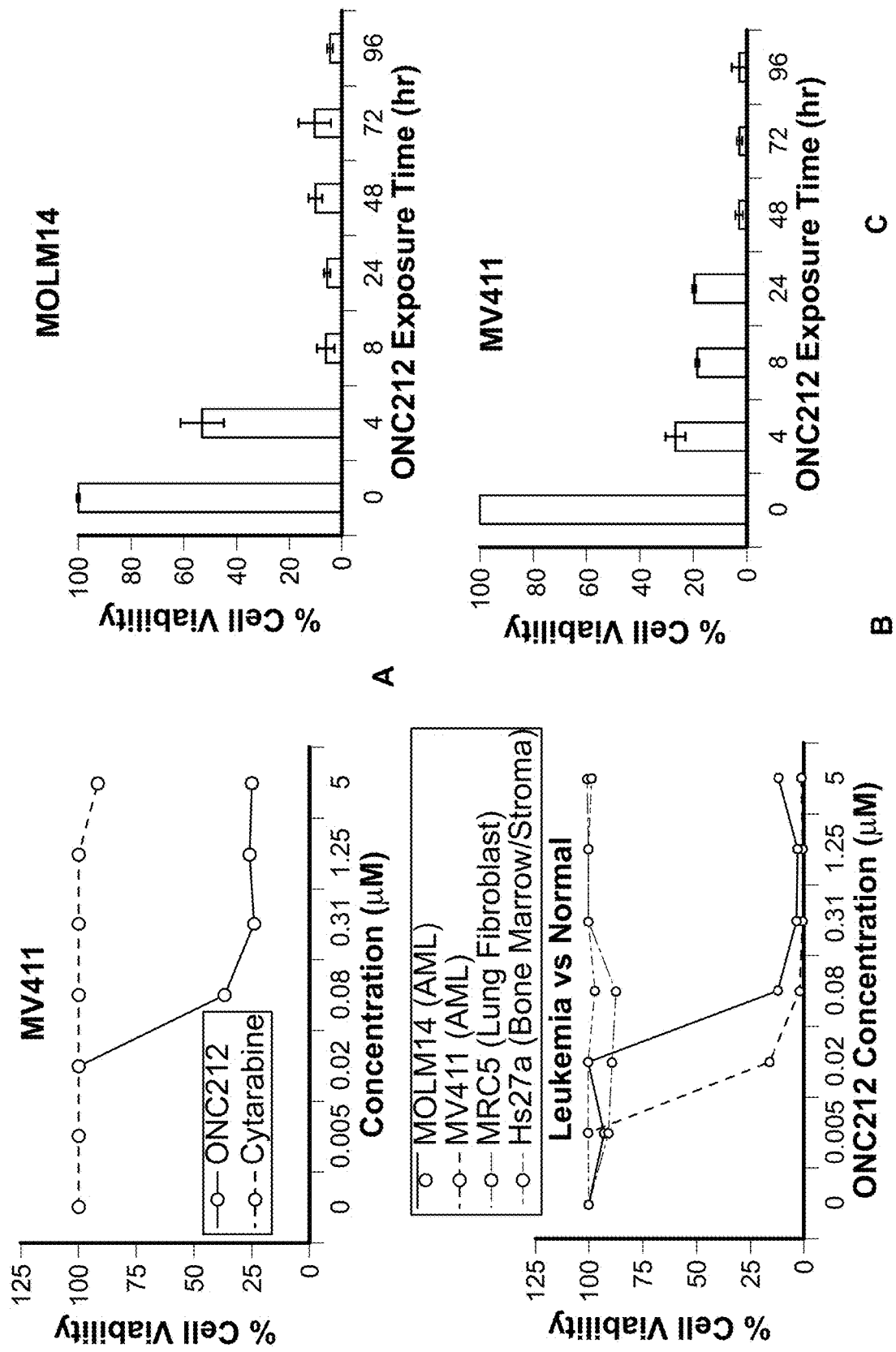
FIG. 14. Anti-cancer efficacy of ONC212 in acute myeloid leukemia (AML) cell lines. (A) Comparison of cell viability of MV411 AML cells treated with ONC212 or cytarabine. (B) Comparison of cell viability of MOLM14, MV411 AML cells, MRC5 lung fibroblasts and Hs27a bone marrow cells treated with ONC212. (C) Cell viability of MOLM14 and MV411 AML cells treated with ONC212 (250 nM) for 4, 8, 24, 48, 72 and 96 h.

Cell viability of MV411 AML cells treated with ONC212 and cytarabine (5 nM-5 μM, 24 h) (n=3) was measured (FIG. 14A). Furthermore, cell viability MOLM14, MV411 AML cells, MRC5 lung fibroblasts and Hs27a bone marrow cells treated with ONC212 (5 nM-5 μM, 72 h) (n=3) was measured (FIG. 14B). Cell viability of MOLM14 and MV411 AML cells treated with ONC212 (250 nM) for 4, 8, 24, 48, 72 and 96 h was measured. ONC212 medium was replaced by fresh medium at these time points and cell viability was determine at 96 h for all samples. (n=2) (FIG. 14C).

Figure 10:
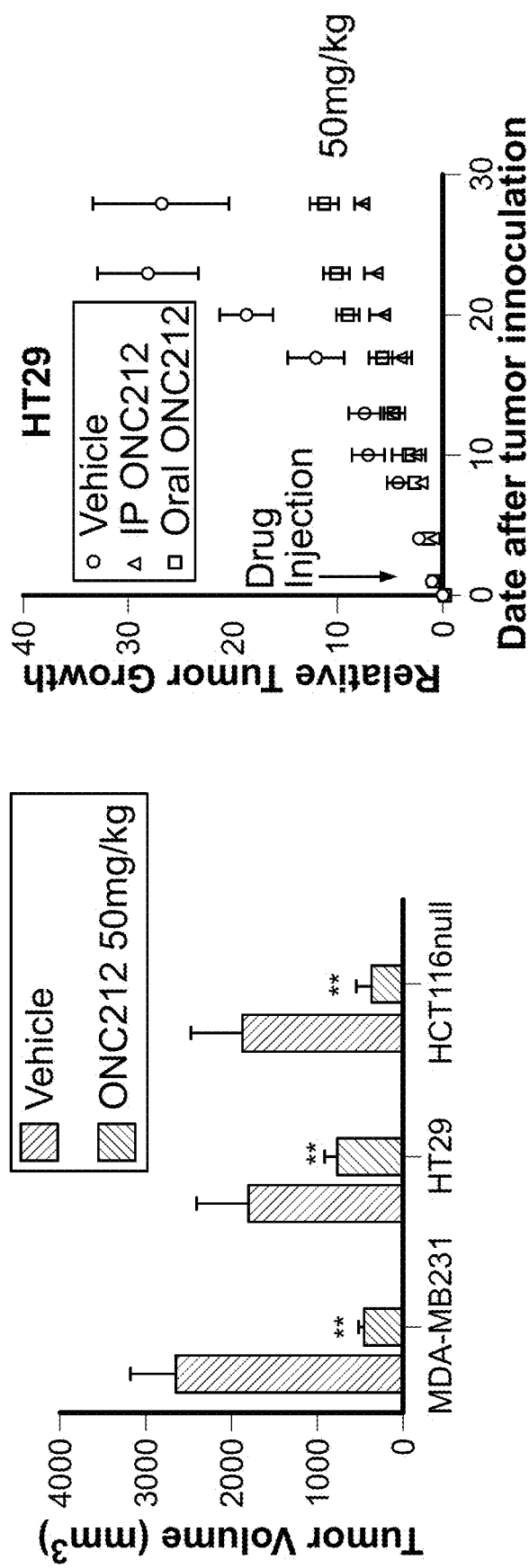
FIG. 10. ONC212 demonstrates oral and IP anti-cancer efficacy in xenograft mouse models of colorectal and breast cancer.
Figure 11:
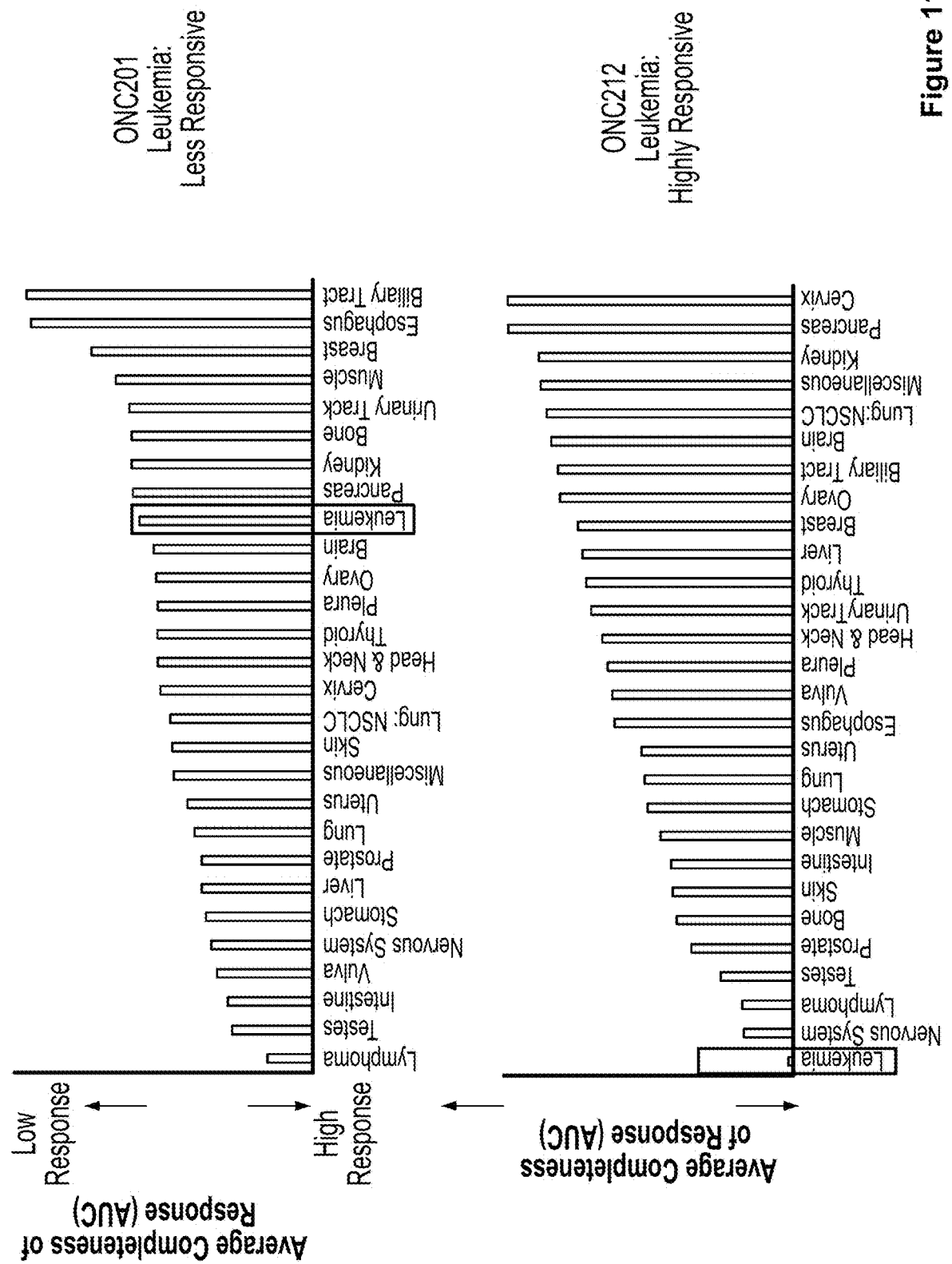
FIG. 11. Leukemia is more responsive to ONC212 than ONC201.
Figure 12:
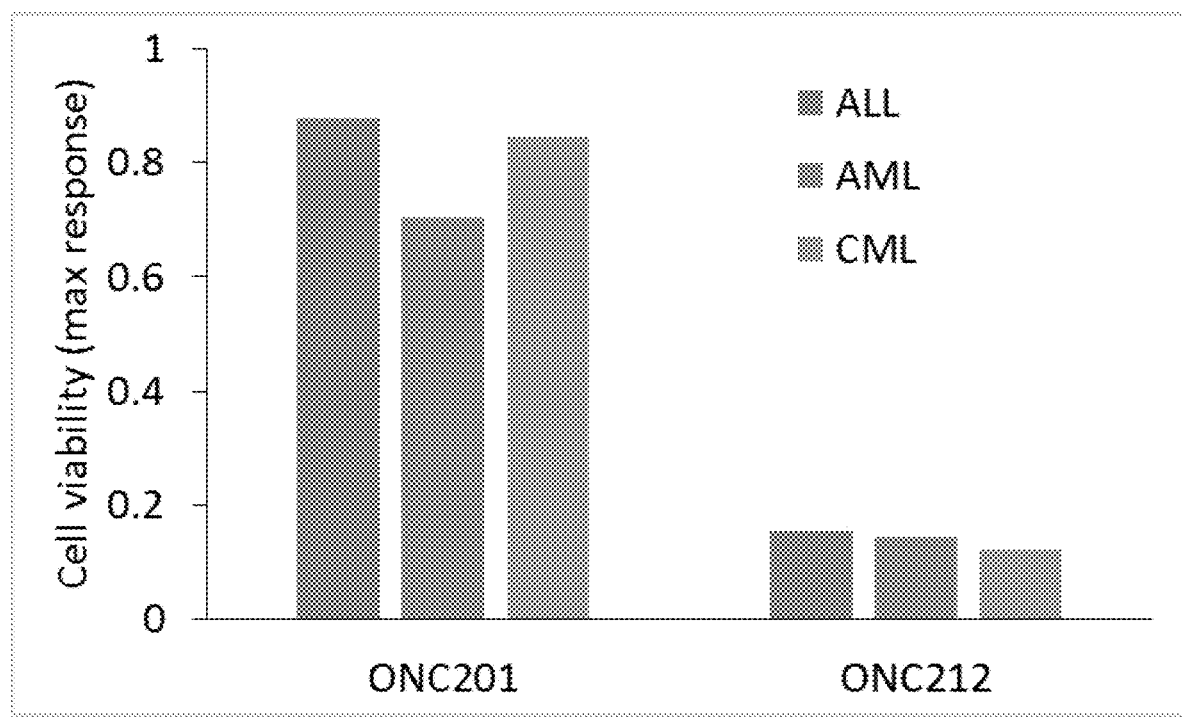
FIG. 12. ONC212 demonstrates anti-cancer efficacy (and superior efficacy compared to ONC201) in the nanomolar range in 55 leukemia cell lines regardless of subtype.

In addition, a single dose of ONC212 by oral or intraperitoneal administration to human colon cancer xenograft-bearing mice resulted in significant reduction of tumor volume compared to vehicle-treated control cohorts (FIG. 10). ONC212 has a wide therapeutic window, as it is well tolerated at doses at least up to 225 mg/kg in mice.

Figure 15:
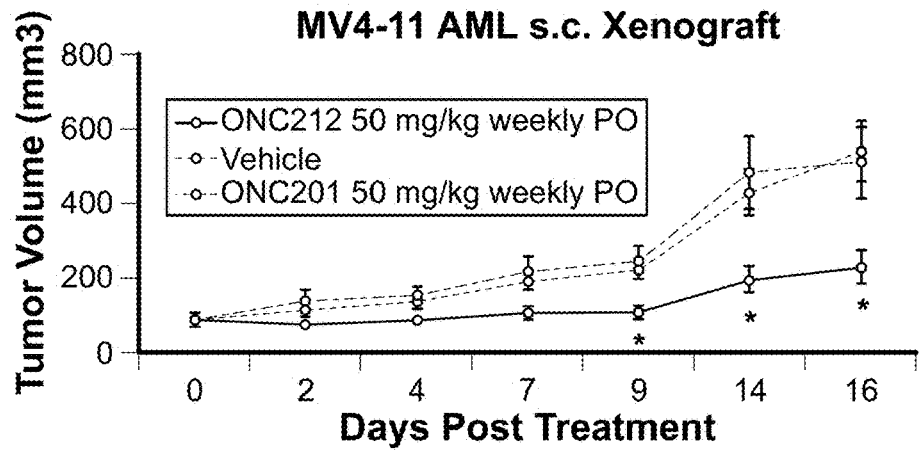
FIG. 15. ONC212 efficacy in ONC201-resistant AML xenograft model (MV411 AML cells ($5 \times 10^6$) subcutaneously implanted in the flanks of athymic nude mice). ONC212 and ONC201 were administered orally (PO) as indicated. Tumor volume (A and B) and body weight (C) (n=10) was measured on indicated days. * represents p<0.05 relative to vehicle.
Figure 15:
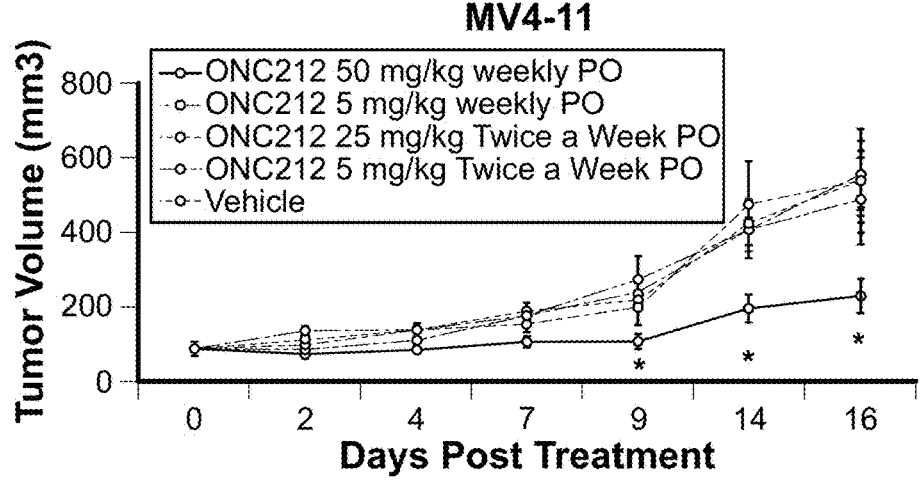
Figure 15:
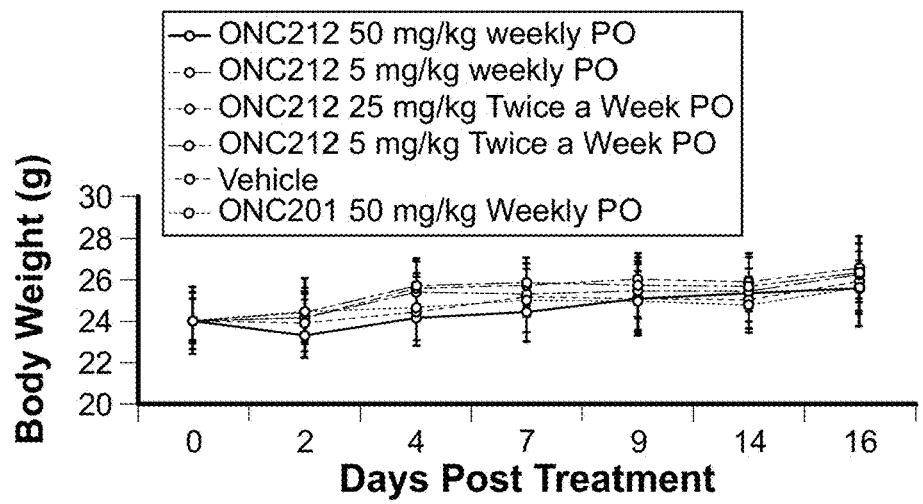

Furthermore, ONC212 demonstrated efficacy in ONC201-resistant AML xenograft model (FIG. 15). MV411 AML cells (5×10⁶) were subcutaneously implanted in the flanks of athymic nude. ONC212 and ONC201 were administered orally (PO) as indicated. Tumor volume (A and B) and body weight (C) (n=10) was measured on indicated days. * represents p<0.05 relative to vehicle.

ONC212 efficacy in AML was evaluated in vitro and was upto 400 fold more potent compared to ONC201 (Table 4). ONC212 was also efficacious in AML cells resistant to standard of care cytarabine (FIG. 14A). Despite robust improvement in efficacy ONC212 maintains a wide therapeutic window in vitro and is non-toxic to normal cells at efficacious concentrations (FIG. 14B). An 8 hr exposure of ONC212 at 250 nM was sufficient to cause robust reduction in cell viability in MOLM14 and MV411 AML cells (FIG. 14C). At least 24-48 h exposure was required with ONC201 for efficacy.

ONC212 efficacy was determined in a leukemia xenograft model with MV411 AML cells resistant to standard-of-care cytarabine (FIG. 15). ONC212 50 mg/kg significantly reduced leukemia xenograft tumor growth with oral weekly administration while ONC201 was not efficacious in this model at similar doses (FIG. 15A). Interesting, biweekly ONC212 dosing with 25 mg/kg and weekly/biweekly dosing with 5 mg/kg was not efficacious (FIG. 15B). None of these ONC212 administration regimens were associated with body weight loss (FIG. 15C) or gross observations.

ONC212 25 mg/kg represents NOAEL in mouse and rat non-GLP oral single dose studies which is also the efficacious dose in mouse xenograft studies. ONC212 is approximately 10 fold more toxic compared to ONC201 (NOAEL 225 mg/kg in rat non-GLP oral single dose study).

ONC206

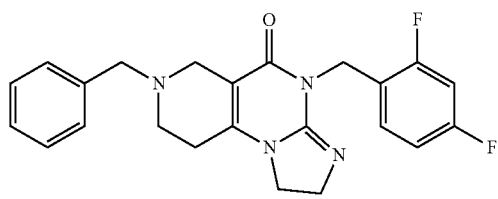

ONC206 demonstrated efficacy in a Ewing's sarcoma xenograft model. MHH-ES-1 Ewing's sarcoma cells ($5 \times 10^6$) were subcutaneously implanted in the flanks of athymic nude mice. ONC206 (PO) and methotrexate (IV) were administered on day 1 and day 13 as indicated. Tumor volume (FIG. 16A) and body weight (FIG. 16B) (n=4) was measured on indicated days.

In addition, the $IC_{50}$ of ONC201 and ONC206 (5 nM-5 µM, 72 h) upon treatment of several cell lines (n=3) were determined and shown below in Table 5.

TABLE 5

| Cell line | ONC201 $IC_{50}$ (µM) | ONC206 $IC_{50}$ (µM) |
|---|---|---|
| MV411 (AML) | 3.25 | 0.2 |
| K562 (CML) | >5 | 0.22 |
| MOLM14 (AML) | 3.92 | 0.27 |
| MHH-ES-1 (Ewing's sarcoma) | 5.65 | 0.61 |
| HFF (Normal Fibroblast) |  | >5 |

Figure 16:
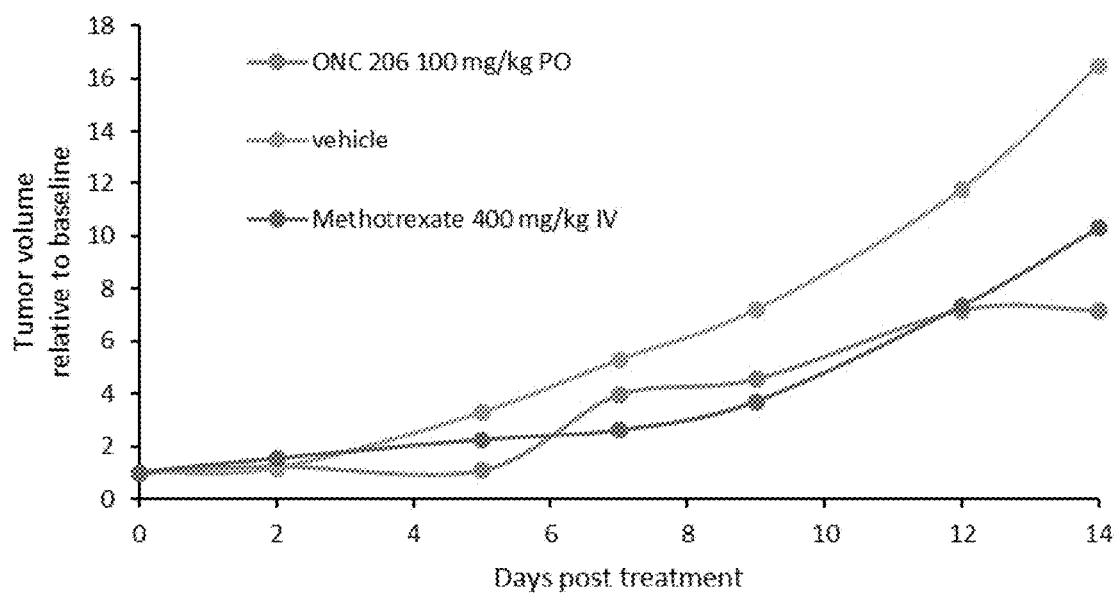
FIG. 16. ONC206 efficacy in Ewing's sarcoma xenograft model (MHH-ES-1 Ewing's sarcoma cells ($5 \times 10^6$) subcutaneously implanted in the flanks of athymic nude mice). ONC206 (PO) and methotrexate (IV) were administered on day 1 and day 13 as indicated. Tumor volume (A) and body weight (B) (n=4) was measured on indicated days.
Figure 16:
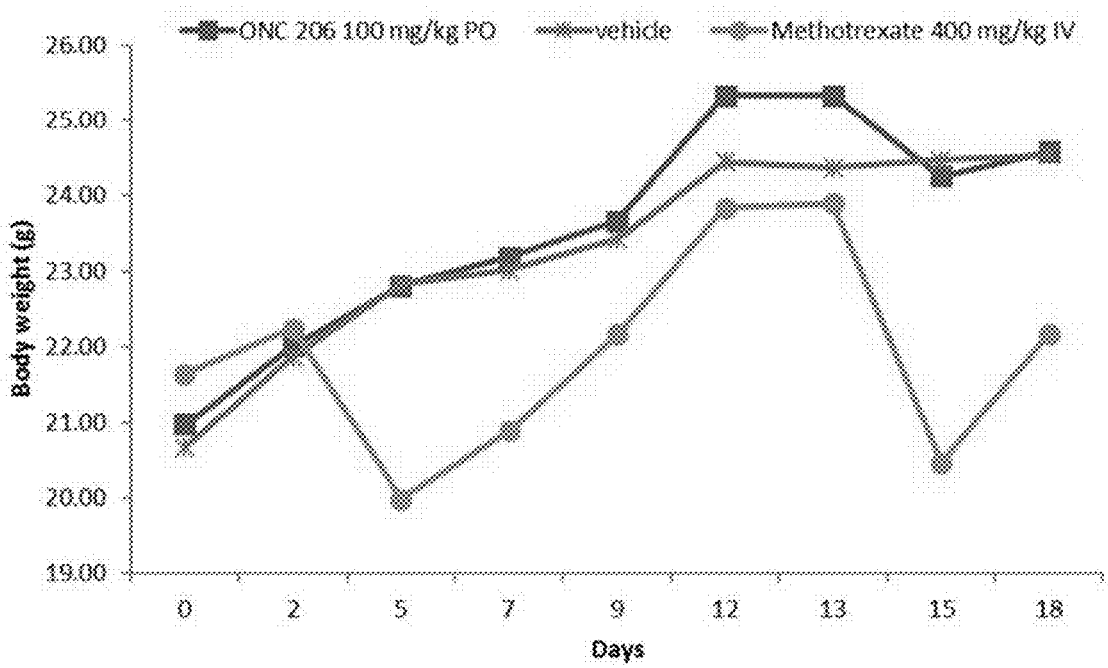

ONC206 showed up to 20 fold improvement compared to ONC201 in in vitro potency with no in vitro toxicity to normal cells at therapeutic doses (Table 5). With ONC206, only 2-fold increased toxicity (NOAEL 125 mg/kg) was noted overall relative to ONC201 (NOAEL 225 mg/kg) in rat non-GLP oral single dose study. In vivo efficacy in Ewing's sarcoma model with no toxicity (FIG. 16). ONC206 efficacy was comparable to chemotherapy methotrexate, but chemotherapy was associated with body weight loss.

ONC213

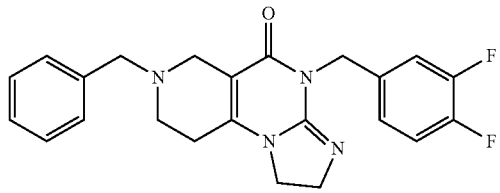

Figure 17:
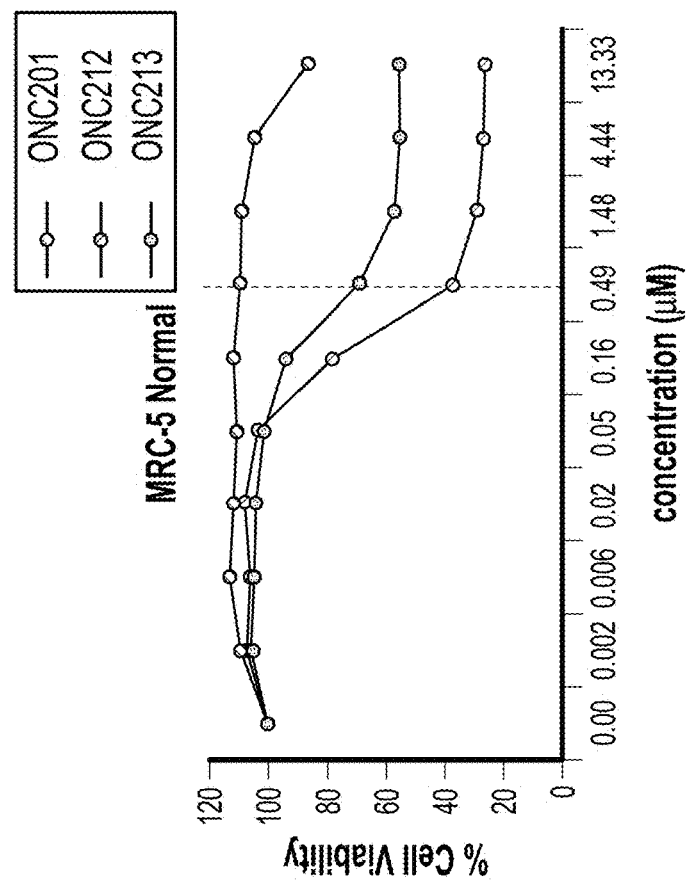
FIG. 17. ONC213 demonstrated in vitro anti-cancer potency in HCT116/RPMI8226 cancer cells similar to ONC212, but in vitro toxicity to normal cells was reduced compared to ONC212.
Figure 17:
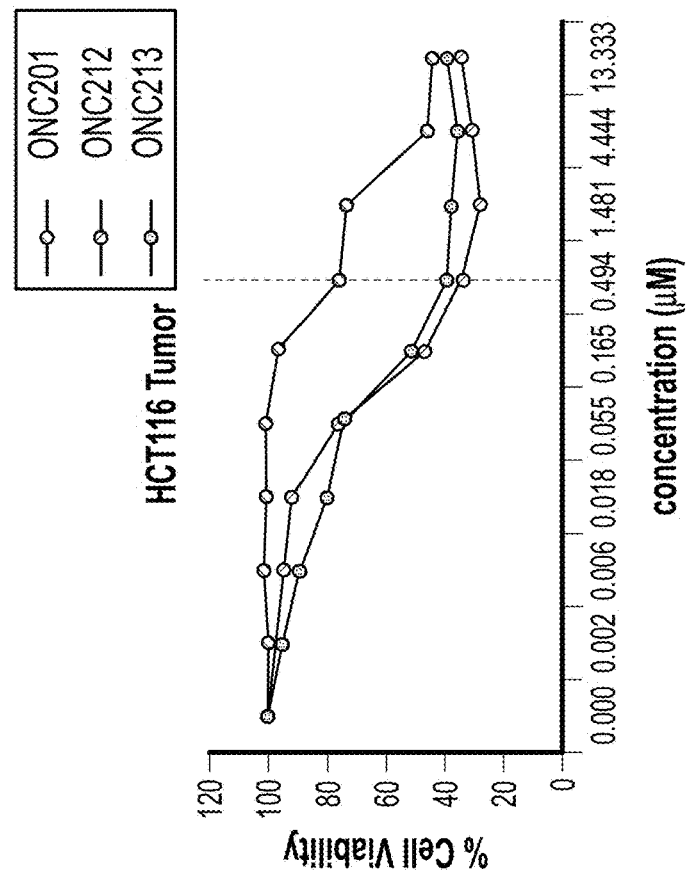

In vitro profiling of GPCR activity using a hetereologous reporter assay for arrestin recruitment, a hallmark of GPCR activation, indicated that ONC213 selectively targets DRD2/3 and GPR132/91. Dual targeting of DRD2/3 and GPR132/91 represents a novel strategy for anti-cancer efficacy without toxicity. ONC213 is a DRD2/3 inhibitor and a GPR132/91 agonist. DRD2/3 potency of ONC213 is more than ONC201 but less than ONC206. GPR132 potency of ONC213 is less than ONC212. Specifically, ONC213 demonstrated in vitro anti-cancer potency in HCT116/RPMI8226 cancer cells similar to ONC212, but in vitro toxicity to normal cells was reduced compared to ONC212 (FIG. 17). The safety profile of ONC213 confirmed in mouse MTD study with NOAEL 75 mg/kg three times that of ONC212 (25 mg/kg). The GPR91 agonist activity of ONC213 provides an opportunity for immunology, immune-oncology and hematopoietic applications (*Nature Immunology* 9:1261 (2008); *J Leukoc Biol.* 85(5):837 (2009)).

ONC237

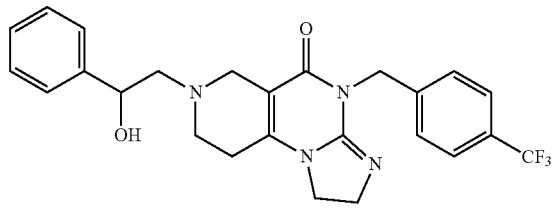

In vitro profiling of GPCR activity using a hetereologous reporter assay for arrestin recruitment, a hallmark of GPCR activation, indicated that ONC237 selectively targets DRD5 and GPR132. ONC237 is a GPR132 agonist and DRD5 antagonist and has reduced anticancer efficacy ($IC_{50}$ 31.2 µM) compared to ONC201. This data show that combining GPR132 agonist activity with DRD5 (D1-like dopamine receptor) antagonist activity results in poor anti-cancer effects compared to ONC213 which combines GPR132 agonist and DRD2/3 antagonist activity.

ONC236

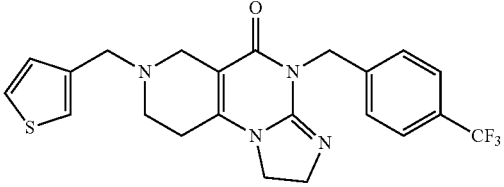

In vitro profiling of GPCR activity using a hetereologous reporter assay for arrestin recruitment, a hallmark of GPCR activation, indicated that ONC236 is a highly selective GPR132 agonist. ONC236 has anticancer efficacy ($IC_{50}$ 88 nM) comparable to ONC212 (10 nM) better than ONC206/ONC201, completeness of response is better than ONC201 but not ONC212 in HCT116 cells.

ONC234

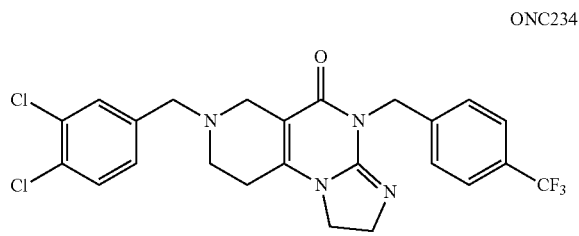 [SMILES: O=C1C2=C(CCN(Cc3ccc(Cl)c(Cl)c3)C2)N2CCN=C2N1Cc1ccc(C(F)(F)F)cc1]

In vitro profiling of GPCR activity using a hetereologous reporter assay for arrestin recruitment, a hallmark of GPCR activation, indicated that ONC234 is a broad spectrum and potent GPCR targeting small molecule. ONC234 hits several GPCRs including antagonist activity for adrenergic, histamine, serotonin, CHRM, CCR, DRD2/5 receptors, as well as CXCR7 agonist activity. ONC236 has anticancer efficacy ($IC_{50}$ 234 nM) similar to ONC206, completeness of response same as ONC212, and better than ONC201 in HCT116 cells.

Example 11. GPCR Antagonism of ONC201

ONC201 was evaluated in a whole cell, functional assay of l3-Arrestin G protein-coupled receptor (GPCR) activity that directly measures dopamine receptor activity by detecting the interaction of l3-Arrestin with the activated GPCR that serves as a reporter. For each dopamine receptor (DRD1, DRD2S, DRD2L, DRD3, DRD4, and DRD5), cell lines overexpressing reporter constructs were expanded from freezer stocks. Cells were seeded in a total volume of 20 µL into white walled, 384-well microplates and incubated at 37° C. prior to testing, with antagonist followed by agonist challenge at the $EC_{50}$ concentration. Intermediate dilution of sample stocks was performed to generate 5× sample in assay buffer. 3.5 µL of 5× sample was added to cells and incubated at 37° C. or room temperature for 30 minutes. Vehicle concentration was 1%. 5 µL of 6× $EC_{50}$ agonist in assay buffer was added to cells and incubated at 37° C. or room temperature for 90 or 180 minutes prior to assay readout. % Antagonism was calculated using the following formula %: Antagonism=100%×(1−(mean RLU of test sample−mean RLU of vehicle control)/(mean RLU of $EC_{50}$ control−mean RLU of vehicle control).

Example 12: Selective Antagonism of DRD2 by ONC201

ONC201 is a first-in-class small molecule discovered in a phenotypic screen for p53-independent inducers of tumor selective proapoptotic pathways. Oral ONC201 is being evaluated as a new therapeutic agent in five early phase clinical trials for select advanced cancers based on pronounced efficacy in aggressive and refractory tumors and excellent safety.

In this Example, the prediction and validation of selective direct molecular interactions between ONC201 and specific dopamine receptor family members are reported. Experimental GPCR profiling indicated that ONC201 selectively antagonizes the D2-like, but not D1-like, dopamine receptor subfamily. Reporter assays in a heterologous expression system revealed that ONC201 selectively antagonizes both short and long isoforms of DRD2 and DRD3, with weaker potency for DRD4 and no antagonism of DRD1 or DRD5. Increased secretion of prolactin is a clinical hallmark of DRD2 antagonism by several psychiatric medications that potently target this receptor. ELISA measurements in peripheral blood of patients treated with ONC201 in the first-in-human trial with advanced solid tumors determined that 10/11 patients evaluated exhibited induction of prolactin (mean of 2-fold).

Using the TCGA database, the D2-like dopamine receptor subfamily, particularly DRD2, was found to be prevalent and selectively overexpressed in several malignancies. Preclinical reports show that DRD2 inhibition imparts antitumor efficacy, without killing normal cells, via induction of ATF4/CHOP and inhibition of Akt and ERK signaling that are all attributes of ONC201.

Methods

ONC201 dihydrochloride was obtained from Oncoceutics. Kinase inhibition assays for the kinome were performed as described (see Anastassiadis et al., Nat Biotech 29:1039 (2011)). GPCR arrestin recruitment and cAMP modulation reporter assays were performed as described (see McGuinness et al., Journal of Biomolecular Screening 14:49 (2009)). PathHunter™ (DiscoveRx) β-arrestin cells expressing one of several GPCR targets were plated onto 384-well white solid bottom assay plates (Corning 3570) at 5000 cells per well in a 20 µL volume in an appropriate cell plating reagent. Cells were incubated at 37° C., 5% $CO_2$ for 18-24 h. Samples were prepared in buffer containing 0.05% fatty-acid free BSA (Sigma). For agonist mode tests, samples (5 µL) were added to pre-plated cells and incubated for 90 minutes at 37° C., 5% $CO_2$. For antagonist mode tests, samples (5 µL) were added to pre-plated cells and incubated for 30 minutes at 37° C., 5% $CO_2$ followed by addition of $EC_{50}$ agonist (5 µL) for 90 minutes at 37° C., 5% $CO_2$. For Schild analysis, samples (5 µL) were added to pre-plated cells and incubated for 30 minutes at 37° C., 5% $CO_2$ followed by addition of serially dliuted agonist (5 µL) for 90 minutes at 37° C., 5% $CO_2$. Control wells defining the maximal and minimal response for each assay mode were tested in parallel. Arrestin recruitment was measured by addition of 15 µL PathHunter Detection reagent and incubated for 1-2 h at room temperature and read on a Perkin Elmer Envision Plate Reader. For agonist and antagonist tests, data was normalized for percent efficacy using the appropriate controls and fitted to a sigmoidal dose-response (variable slope), Y=Bottom+(Top−Bottom)/(1+10^((Log $EC_{50}$−X)*HillSlope)), where X is the log concentration of compound. For Schild analysis, data was normalized for percent efficacy using the appropriate controls and fitted to a Gaddum/Schild $EC_{50}$ shift using global fitting, where Y=Bottom+(Top−Bottom)/(1+10^((Log EC−X)*HillSlope)), Antag=1+(B/(10^(−1*pA2)))^SchildSlope and Log EC=Log($EC_{50}$*Antag). $EC_{50}$/$IC_{50}$ analysis was performed in CBIS data analysis suite (Cheminnovation) and Schild analysis performed in GraphPad Prism 6.0.5.

Results

ONC201 is a small molecule in phase II clinical trials for select advanced cancers. It was discovered in a phenotypic screen for p53-independent inducers of the pro-apoptotic TRAIL pathway. Although the contribution of ONC201-induced ATF4/CHOP upregulation and inactivation of Akt/ERK signaling (Allen et al., Science translational medicine 5, 171ra117-171ra117 (2013)) to its anti-cancer activity has been characterized, its molecular binding target had remained elusive.

In vitro profiling of GPCR activity using a heterologous reporter assay for arrestin recruitment, a hallmark of GPCR activation, indicated that ONC201 selectively antagonizes the D2-like (DRD2/3/4), but not D1-like (DRD1/5), dopamine receptor subfamily (FIG. 1). Antagonism of adrenoceptor alpha receptors or other GPCRs was not observed under the evaluated conditions. Among the DRD2 family, ONC201 antagonized both short and long isoforms of DRD2 and DRD3, with weaker potency for DRD4. Further characterization of ONC201-mediated antagonism of arrestin recruitment to DRD2L was assessed by a Gaddum/Schild $EC_{50}$ shift analysis, which determined a dissociation constant of 2.9 µM for ONC201 that is equivalent to its effective dose in many human cancer cells. Confirmatory results were obtained for cAMP modulation in response to ONC201, which is another measure of DRD2L activation. The ability of dopamine to reverse the dose-dependent antagonism of up to 100 µM ONC201 suggests direct, competitive antagonism of DRD2L. In agreement with the ONC201 specificity predicted by BANDIT, no significant interactions were identified between ONC201 and nuclear hormone receptors, the kinome, or other drug targets of FDA-approved cancer therapies. Interestingly, a biologically inactive constitutional isomer of ONC201 (Wagner et al., Oncotarget 5:12728 (2014)) did not inhibit DRD2L, suggesting that antagonism of this receptor could be linked to its biological activity. In summary, these studies establish that ONC201 selectively antagonizes the D2-like dopamine receptor subfamily, which appears to be a promising therapeutic target in oncology, and ONC201 is the first compound to exploit this treatment paradigm in several ongoing Phase II clinical studies.

Example 13: Preclinical Data in H3 K27M Adult and Pediatric Glioma

The discovery of H3 K27M as an oncogenic mutation occurred in the context of midline gliomas that involve the thalamus, pons, or spinal cord. H3 K27M refers to a specific mutation in histone H3 proteins. Due to the location of these tumors, areas of the brain involved in critical physiological functions, these tumors have historically been inoperable (especially in the brain stem where the pons is located). This means that until recently, midline gliomas such as diffuse intrinsic pontine glioma (DIPG) were diagnosed solely on a radiographic basis. Recent advances in neurosurgical techniques and increased parental consent to post-mortem tumor tissue retrieval led to the availability of sufficient biospecimens that enabled systematic genomic evaluations of DIPG and other midline gliomas. Gliomas in the midline of the brain belong to the most aggressive types of primary malignant brain cancers. The disease arises from glial cells, which are cells that form the tissue that surrounds and protects other nerve cells found within the brain and spinal cord.

Standard therapy for midline gliomas involves neurosurgery, when feasible, followed by fractionated external beam radiotherapy. Due to location in the brain, aggressiveness and low survival time, gliomas in the midline of the brain are considered as part of the most lethal forms of cancer.

There is evidence that H3 K27M predominantly occurs in midline gliomas and in younger patients: ~75% of thalamic brain tumors, ~54% of brainstem tumors and 55% of spinal cord tumors; 24% of pediatric gliomas and 8% of adult gliomas. The H3 K27M mutation occurs in a unique spatiotemporal pattern, with midline gliomas involving the pons (i.e. DIPG) tending to occur in pediatric patients (<18 years of age) while midline gliomas involving the thalamus and spinal cord tending to occur in young adult patients.

The presence of the H3 K27M mutation in midline gliomas is generally thought to confer a worse clinical prognosis. This understanding was incorporated into the World Health Organization 2016 classification of central nervous system tumors that now defines diffuse midline gliomas with the H3 K27M mutation as a new distinct disease entity. This disease is defined as grade IV regardless of histopathological features due to the widely recognized dismal prognosis of brain tumors with this mutation.

Most of the prognostic literature for H3 K27M is derived from DIPG that exhibits a 70-85% prevalence of this mutation. It is clear than the presence of the H3 K27M mutation in tumors of the pons confers a much shorter overall survival relative to the minority of patients who do not have this mutation. For the smaller number of pediatric patients with gliomas outside of the pons, the literature is consistent that those with the H3 K27M mutation have a poorer prognosis. The field looks to DIPG as the most robust body of clinical experience with H3 K27M gliomas based on high prevalence of the mutation in that disease. Decades of DIPG clinical trials have failed to improve outcomes and standard-of-care, a 6-week course of radiation, remains associated with a 9-11-month overall survival. Historically, therapeutic clinical trials in DIPG focused on the evaluation of therapies that were proven effective in adult high-grade gliomas. The recent molecular profiling and emerging preclinical models of H3 K27M midline gliomas have shown that these tumors exhibit vastly different biology and therapeutic sensitivity relative to other adult gliomas, such as glioblastoma.

H3 K27M-mutant gliomas occur at a lower rate in adults compared to pediatric patients. The literature is relatively congruous with pediatric findings and overall seems to confirm the dismal effect of H3 K27M mutations in brain tumors for adults, especially in brainstem gliomas. Overall survival of adult patients with H3 K27M midline gliomas is approximately 16 months with studies indicating that H3 K27M mutations in brainstem locations are associated with significantly shorter survival times.

One of the features in the selection process that identified ONC201 as an anticancer agent was the compound's ability to penetrate the blood-brain barrier to address tumors residing in the CNS, unlike many available therapies. Ensuing animal studies revealed that ONC201 rapidly traverses the blood-brain barrier, achieves 5-fold higher concentrations in the brain relative to plasma and induces downstream signaling (TRAIL induction) in the brain.

The compound is highly bioactive in the brain, shows no evidence of neurotoxicity, and is potently cytotoxic to high grade glioma tumors in vitro, ex vivo, and in vivo. ONC201 has p53-independent activity against high grade glioma cell lines including those with resistance to radiotherapy. In addition to cell lines, ONC201 exerts potent anticancer activity in primary high grade glioma samples resistant to temozolomide.

In vivo, ONC201 shrinks temozolomide-resistant high-grade glioma xenografts and prolongs the survival of mice with orthotopic xenografts as a monoagent and in combination with bevacizumab. Compelling monoagent efficacy of ONC201 has also been observed in radio- and chemo-resistant high-grade glioma cell lines and in 3D neurosphere cultures of newly diagnosed and recurrent patient samples.

Figure 3:
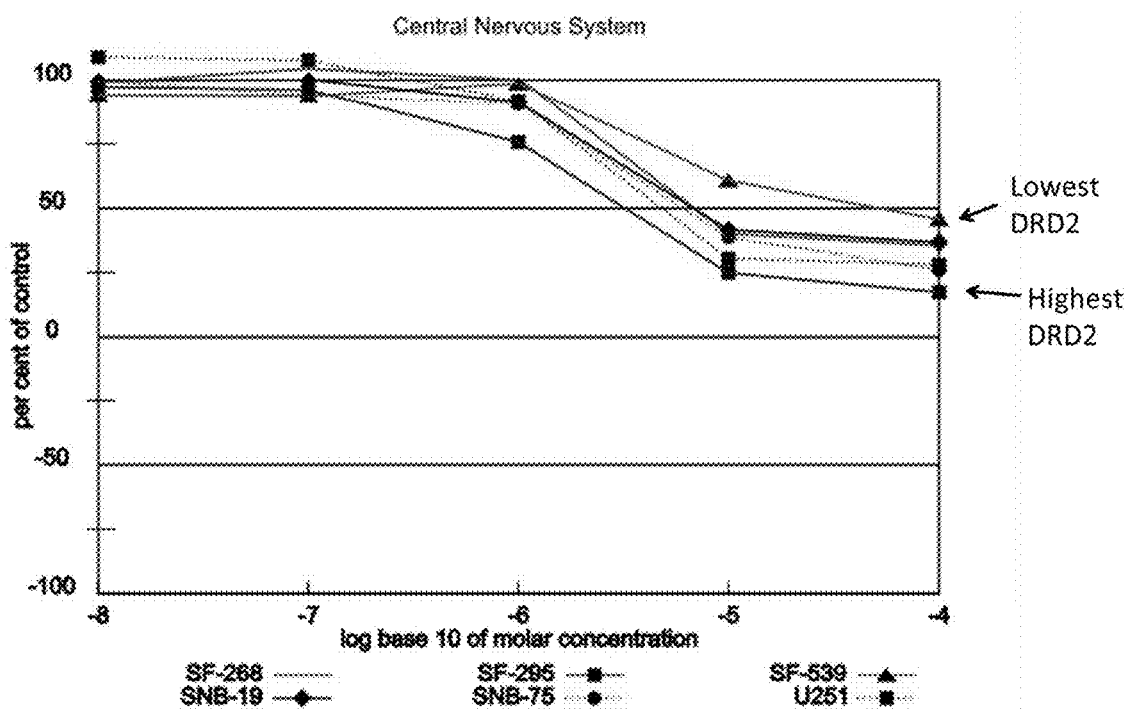
FIG. 3. GBM cell lines with higher DRD2 or lower DRD5 expression are more responsive to ONC201. (A) Inhibition of NCI60 GBM cell lines as a function of ONC201 concentration. (B) Log ONC201 $GI_{50}$ (M) vs DRD2 expression for each GBM cell line. $R^2=0.8707$. (C) Low DRD5 expression significantly correlates with improved ONC201 efficacy in NCI60 panel of cancer cell lines.
Figure 3:
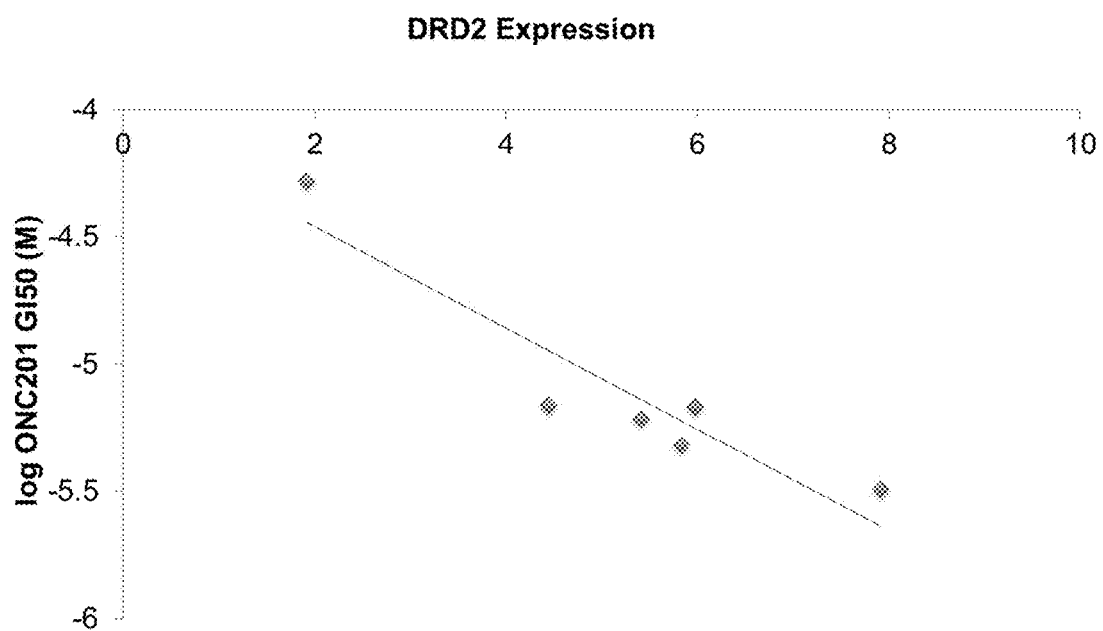
Figure 4:
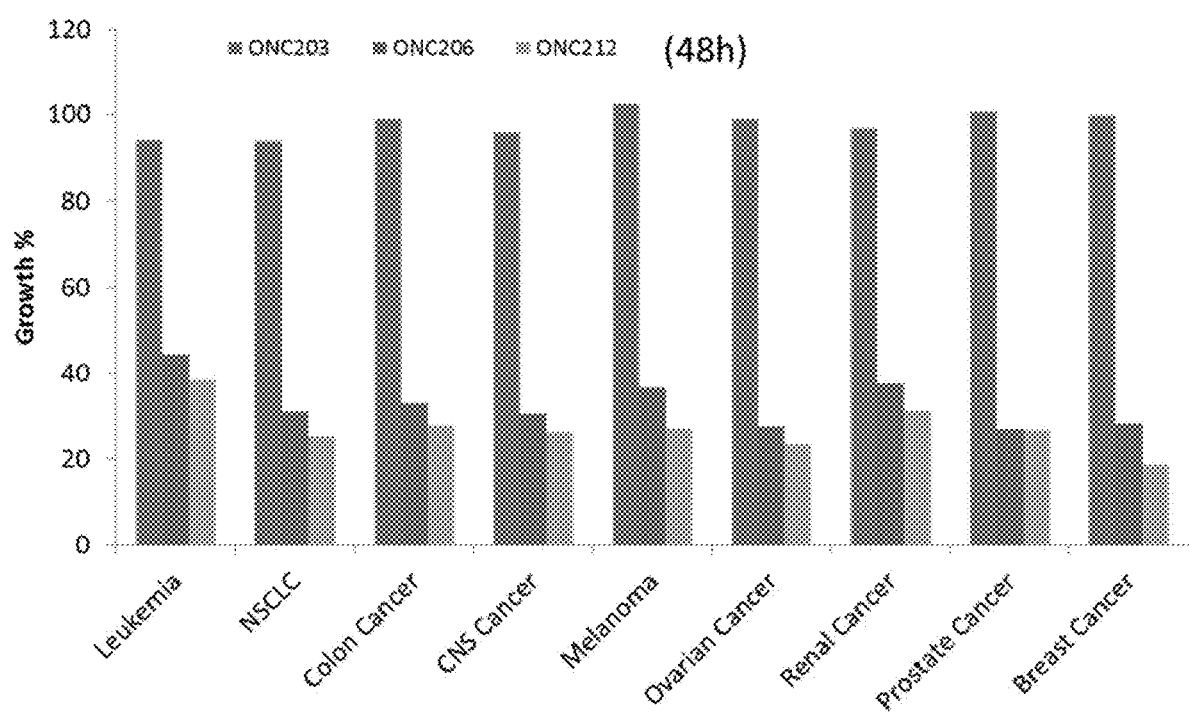
FIG. 4. ONC206 and ONC212 demonstrated anti-cancer efficacy across various tumor types in the NCI60 cancer cell line panel. ONC203 is an inactive negative control.
Figure 5:
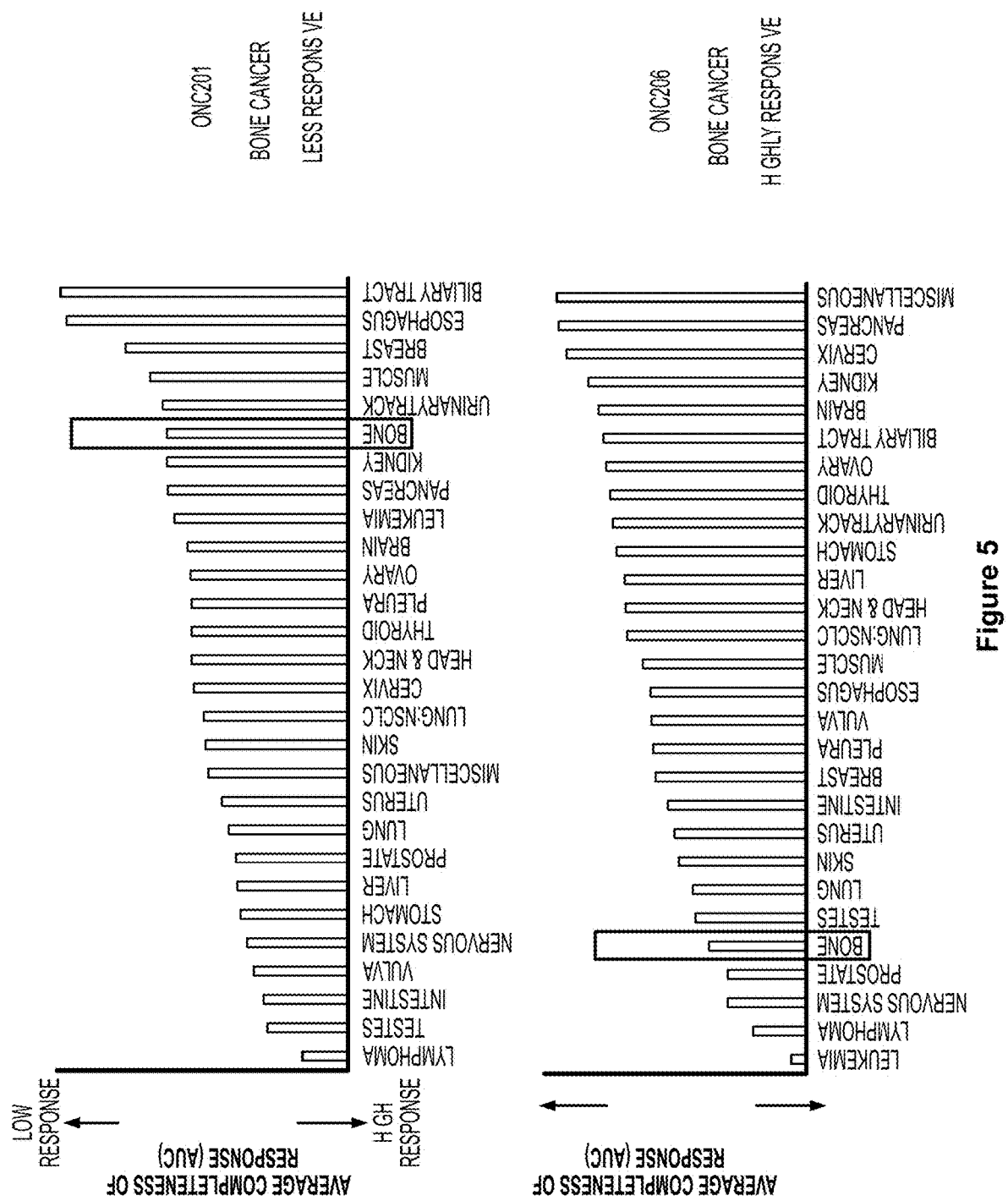
FIG. 5. Bone cancer is more responsive to ONC206 than ONC201.
Figure 6:
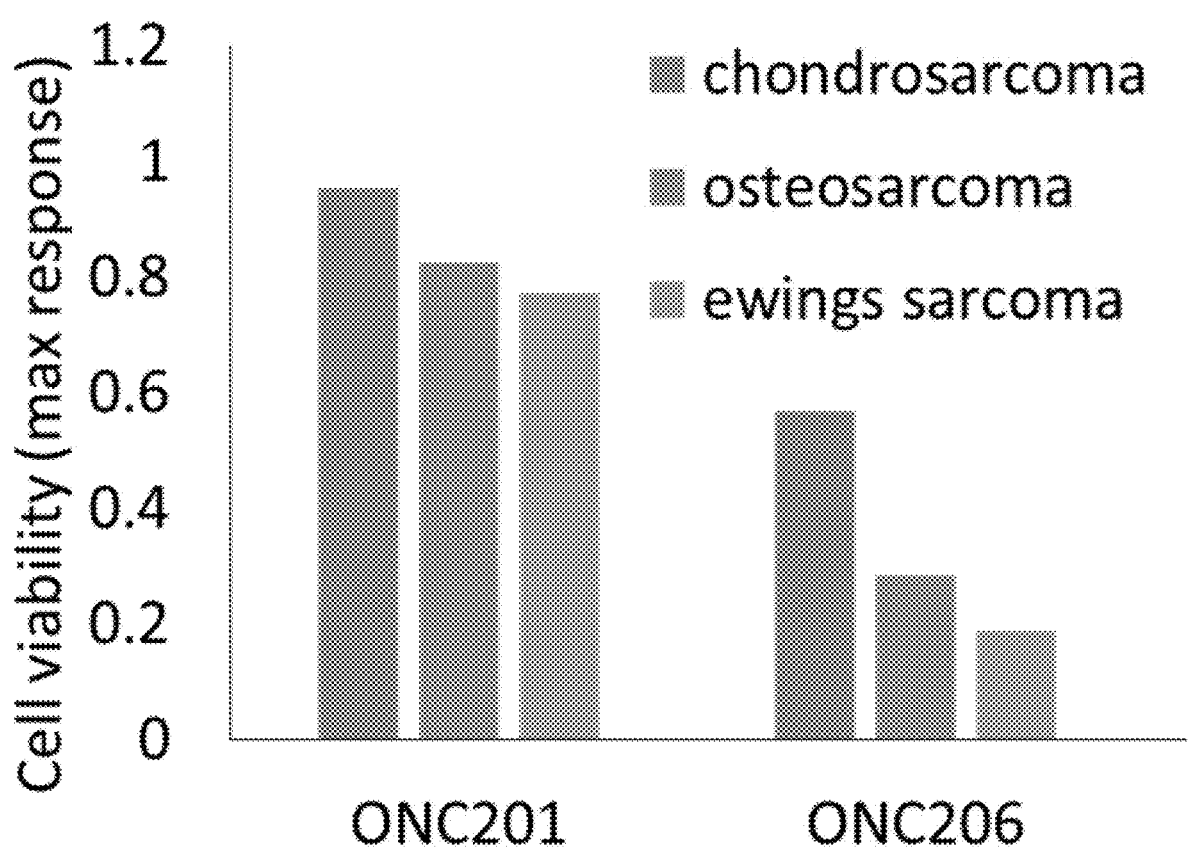
FIG. 6. Ewing's sarcoma is the most ONC206 responsive bone cancer subtype.
Figure 7:
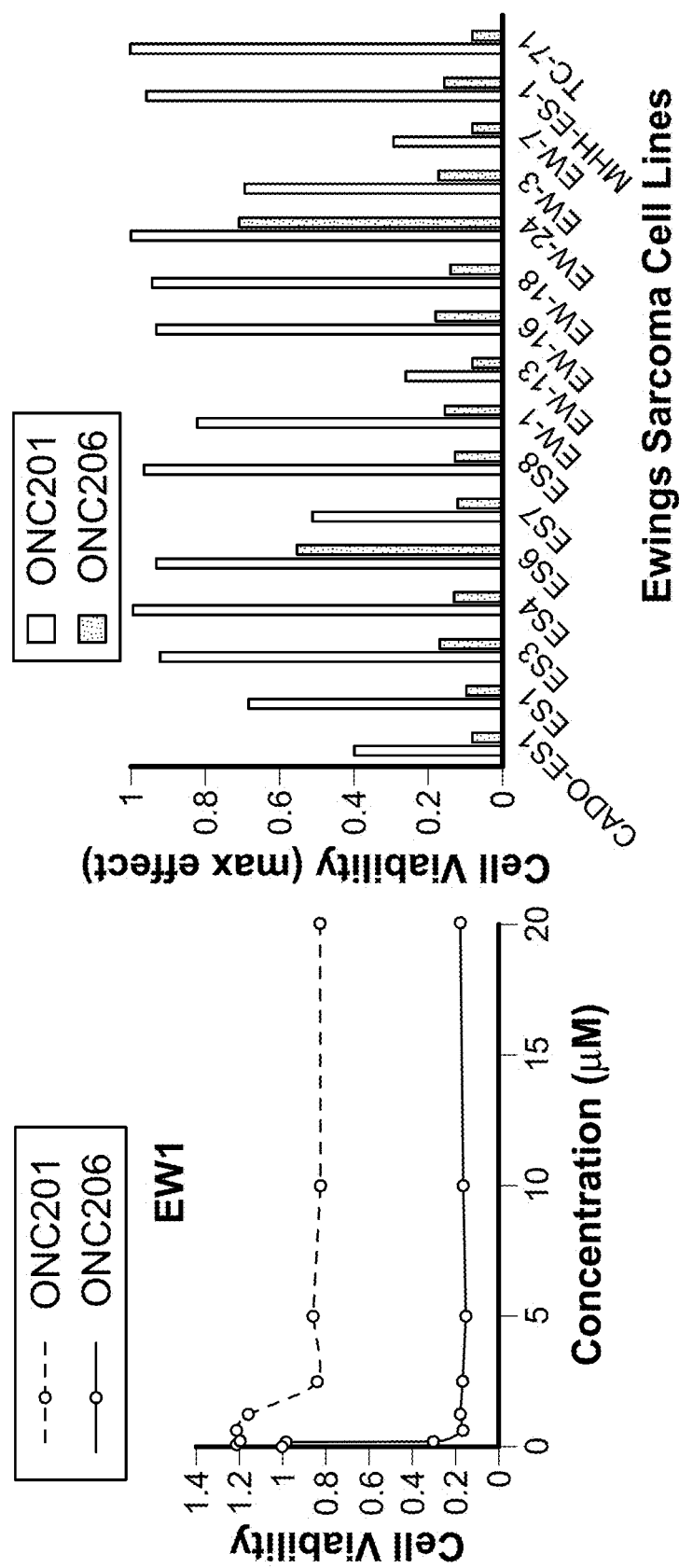
FIG. 7. ONC206 anti-cancer efficacy is in the nanomolar range in 14 out of 16 Ewing's sarcoma cell lines. ONC206 demonstrated superior efficacy compared to ONC201 in all cell lines FIG. 8. ONC212 induced cell death in cancer cells (HCT116) but not normal cells (MRC5) at nanomolar concentrations.
Figure 8:
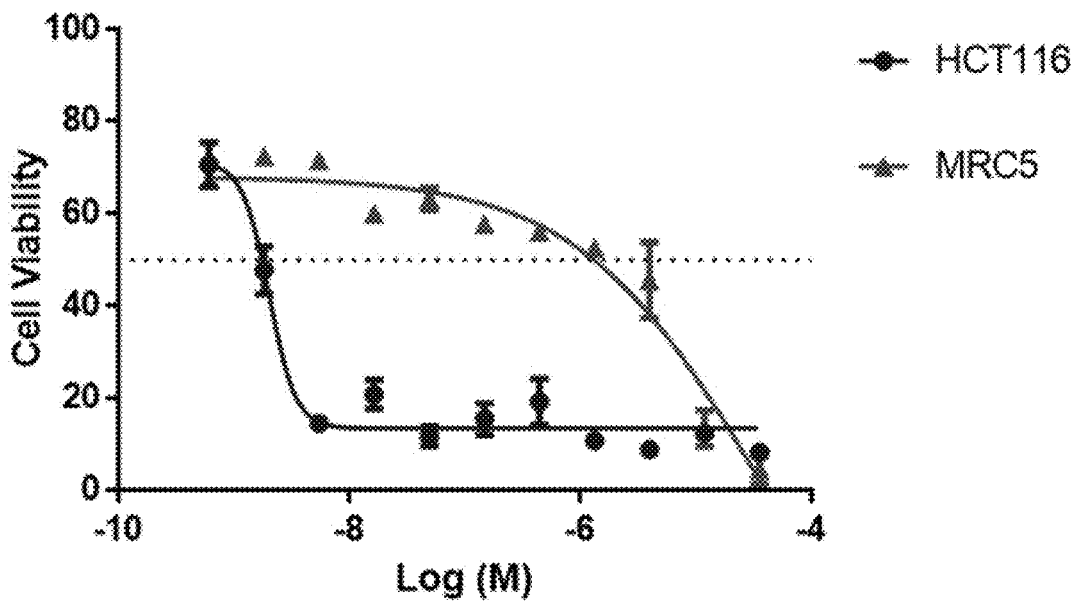
Figure 9:
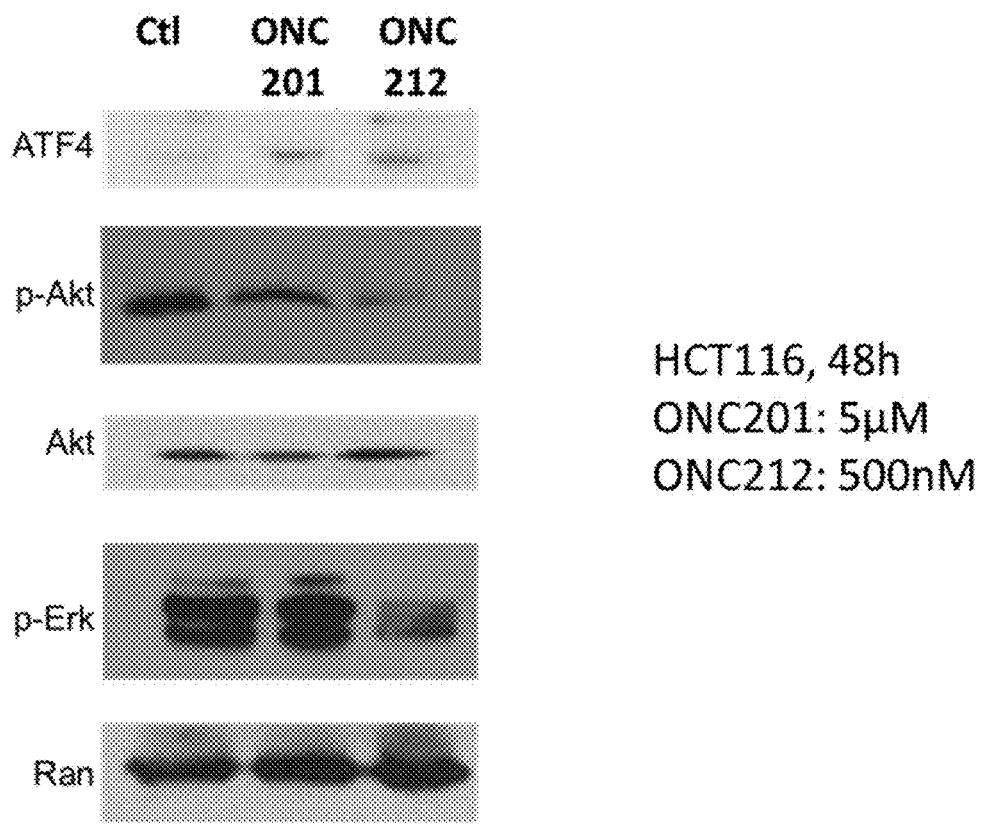
FIG. 9. ONC212 induces the integrated stress response and inhibits Akt/ERK phosphorylation at nanomolar concentrations and at earlier time points compared to ONC201.

DRD2 is overexpressed in high grade glioma. In studies utilizing six human GBM cell lines from the NCI60 panel of cell lines, expression levels of DRD2 correlated with the responsiveness of the cells to ONC201 (FIG. 3). Interestingly, expression of DRD5, a D1-like dopamine receptor that counteracts DRD2 signaling, was significantly inversely correlated with ONC201 potency in the NCI60 and GDSC datasets (P<0.05) (FIG. 3).

In publically available ChIP-Seq databases, H3 and components of the PRC2 methyl transferase complex, which is inhibited by the K27M mutation, were found to each mark both the DRD2 and DRD5 gene in DIPG and isogenic models. While the precise epigenetic mechanisms regulating the balance of the DRD2:DRD5 expression is an active area of investigation, H3 K27M gliomas was hypothesized to foster a chromatin landscape that leads to high DRD2 expression and suppression of DRD5 expression, which in turn may make these tumor cells more sensitive to ONC201. ONC201 was tested against a panel of patient-derived glioma tumorsphere cultures grown in serum-free neural stem cell media. Patient-derived lines included five histone H3 K27M mutant DIPG (two HIST1H3B and three H3F3A mutant), two H3F3A G34 mutant pediatric glioblastoma (one G34V, one G34R), and 7 H3 wild-type (3 pediatric, 4 adult) glioblastoma cell lines. ONC201 was more potently cytotoxic to histone H3 K27M mutant (median $IC_{50}$ ~0.6 µM, n=5 lines) compared to histone H3 wild-type glioma lines (median $IC_{50}$ ~1.5 µM, n=7 lines; p<0.01).

In addition, the expression of DRD2 and DRD5 was analyzed in untreated patient glioma samples. RNASeq was conducted on patient biopsies from H3 K27M mutant glioma (n=8), wild-type pediatric (n=3) and adult glioma (n=25), H3 G34R mutant glioma (n=3). DRD2 expression was significantly increased in histone H3 K27M mutant glioma tumors compared to adult and pediatric H3 wild-type tumors (p=0.02). In contrast, DRD5 expression in all glioma tumors tested were low, however DRD5 expression in histone H3 K27M mutant glioma tumors showed a trend towards lower expression than wild-type glioma. Therefore, DRD2 and DRD5 expression profiles of H3 K27M mutant patient gliomas appear consistent with an expression signature in preclinical models that predicts ONC201 sensitivity.

Cancer stem cells have been shown to express relatively high levels of DRD2 compared to the bulk population, and ONC201 effectively depletes cancer stem cells in numerous malignancies. This effect may contribute to the prolongation of survival in patients in a Phase II GBM study of ONC201 despite the fact that many patients received limited exposure to drug (1 or 2 doses).

NK cells are known to express DRD2 and ONC201 has been reported to increase the pool of circulating and intra-tumoral NK cells. Even more important is activation of NK cell function documented in vivo as well as in patient samples. This significant immune-stimulatory effect likely contributes to the antitumor activity of the compound and is consistent with the response kinetics, i.e. prolonged and late responses, seen in an ongoing clinical trial. The GBM tumor microenvironment has been described as profoundly immune-suppressed and several modalities that stimulate immune function have been shown to affect GBM tumor cell growth.

Example 14: ONC201 Treatment in a 22 Year Old Female with Recurrent H3 K27M Mutant Glioblastoma Histone H3 K27M mutations distinguish a subgroup of midline gliomas in children and young adults with devastating prognosis for which there are no effective medical therapies. The first H3 K27M glioma patient to receive ONC201 was a 22-year-old female with multi-focal disease that included her thalamus who was treated as part of a Phase II recurrent glioblastoma trial in adults (NCT02525692). She had recurrent glioblastoma (unmethylated MGMT, H3.3 K27M mutant) and was treated with 625 mg of ONC201 once every three weeks. She had previously progressed following prior surgery, radiation, and temozolomide.

Figure 13:
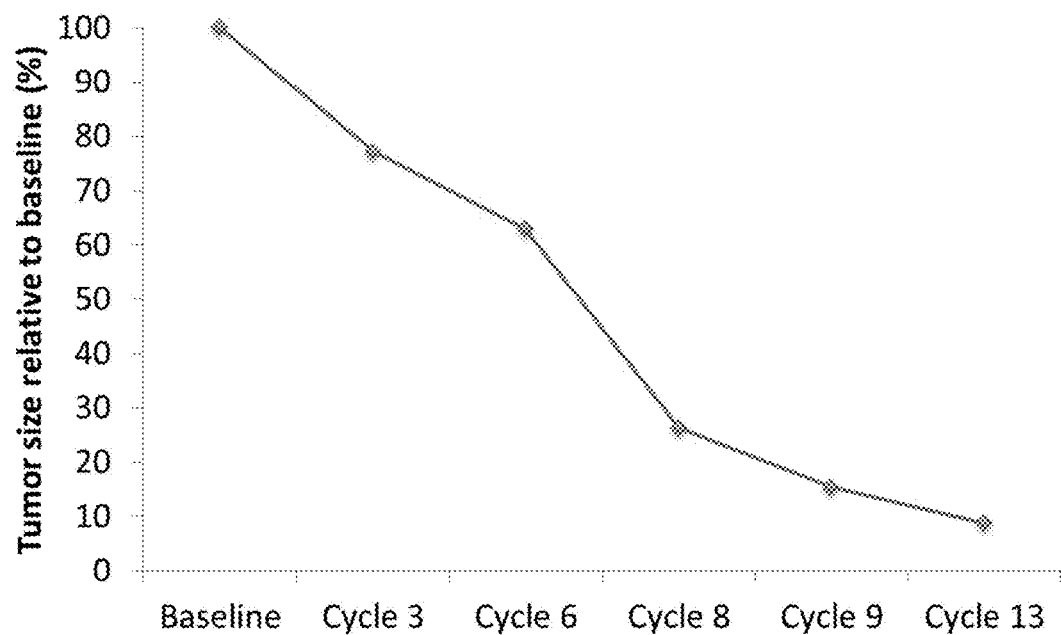
FIG. 13. A subject with recurrent glioblastoma (Example 14). (A) Tumor size relative to baseline (%) of total tumor burden in the subject. One cycle is 3 weeks. (B) Contrast MRI scans at baseline, 21, 27 and 36 weeks post-ONC201 initiation of one of 2 malignant lesions.
Figure 13:
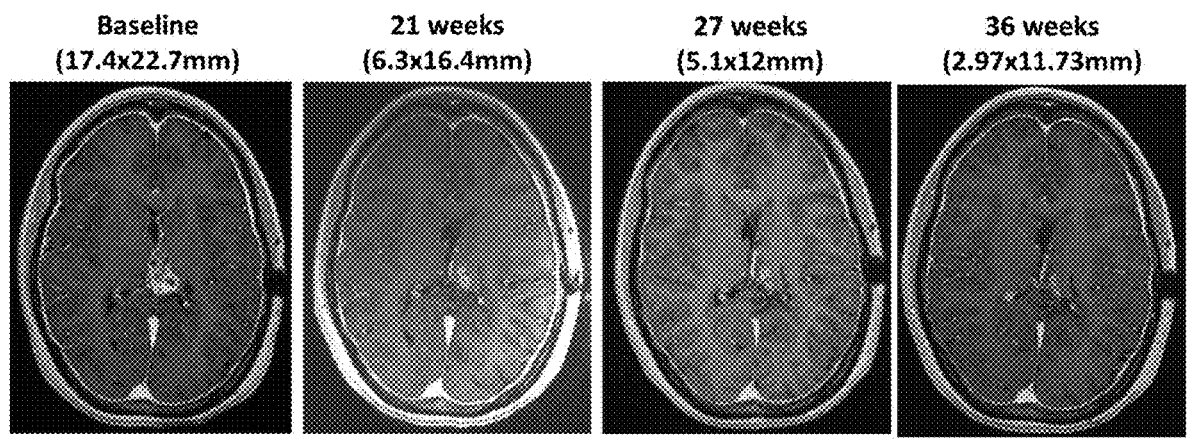

After initiating ONC201 therapy, this subject showed a durable objective response with complete regression of thalamic lesions (FIGS. 13A and 18A). Overall tumor size regressed by 96% after 18 doses (FIGS. 13B and 18B). She no longer takes anti-seizure medication on a regular basis, as she did prior to initiating ONC201. This response remains durable and she continues therapy for >1.5 years with no drug-related adverse events reported. In addition to cytotoxic effects in tumor cells, DRD2 antagonism can induce the activation of NK and other immune cells. Immune induction correlated with tumor shrinkage (FIG. 19). Immune effector levels in the serum was found to correlate with the kinetics of the objective response, which is consistent with a delayed durable response.

Figure 20:
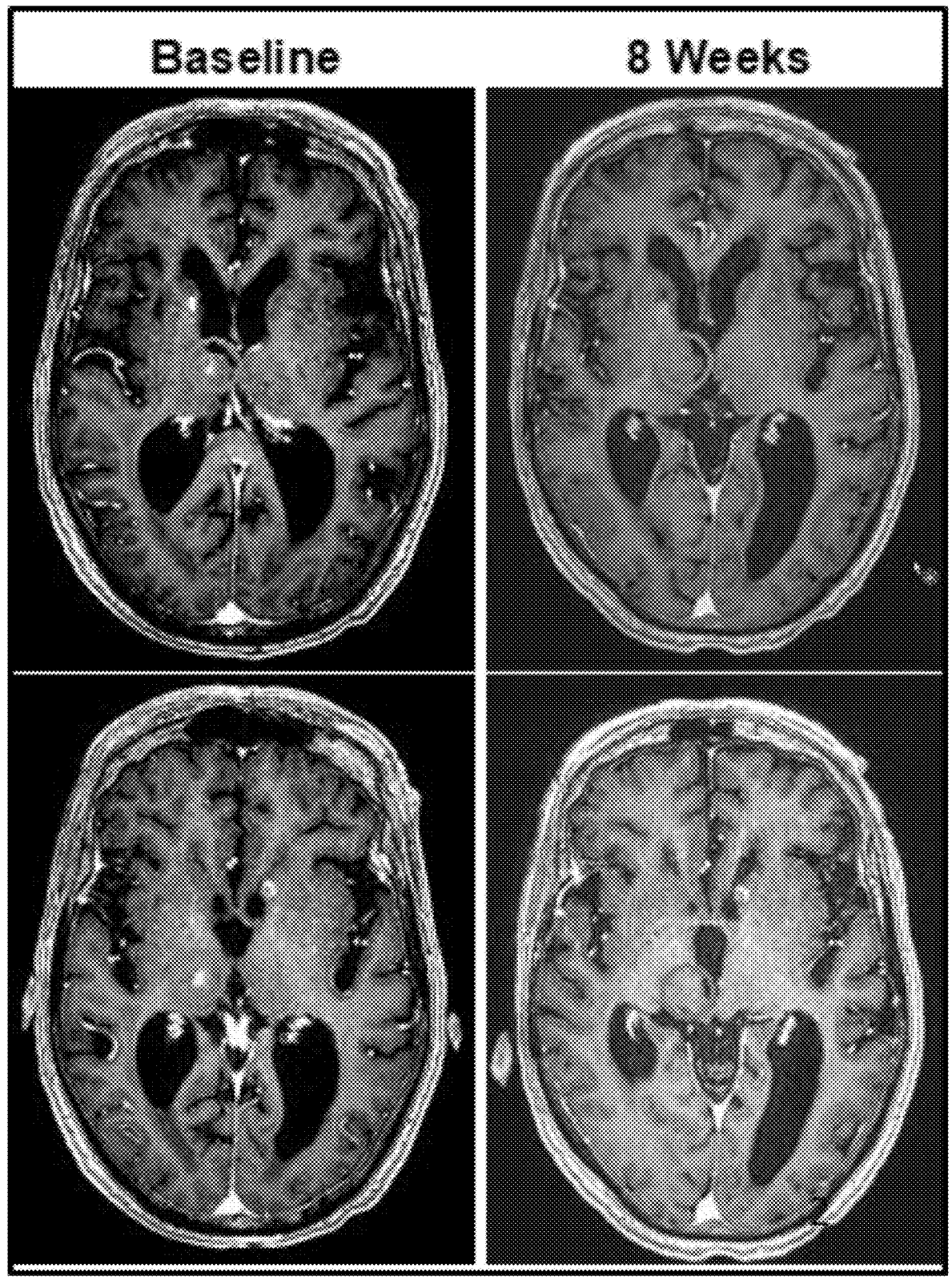
FIG. 20. A 74-year-old woman with recurrent H3 K27M glioblastoma. First on-treatment 8 week MRI shows complete disappearance of tumor lesions.

Example 15: ONC201 Treatment in a 74 Year Old Female with Recurrent H3 K27M Mutant Glioblastoma This Example provides a case study of a 74-year-old female H3 K27M (unknown MGMT status) glioma patient who also participated in the Phase II recurrent glioblastoma trial with ONC201 referenced in the previous Example. She also had multi-focal disease and progressed following first-line surgery, radiation, and temozolomide. She also progressed following subsequent second-line therapy with CCNU. Prior to ONC201 treatment, this subject had three lesions. Her first on-treatment evaluation at 8-weeks following initiation of ONC201 therapy revealed a complete disappearance of malignant lesions (FIG. 20). She also tolerates the therapy well and remains on study after >10 weeks.

Example 16: ONC201 Treatment in a 10 Year Old Girl with H3 K27M Mutant DIPG

Figure 21:
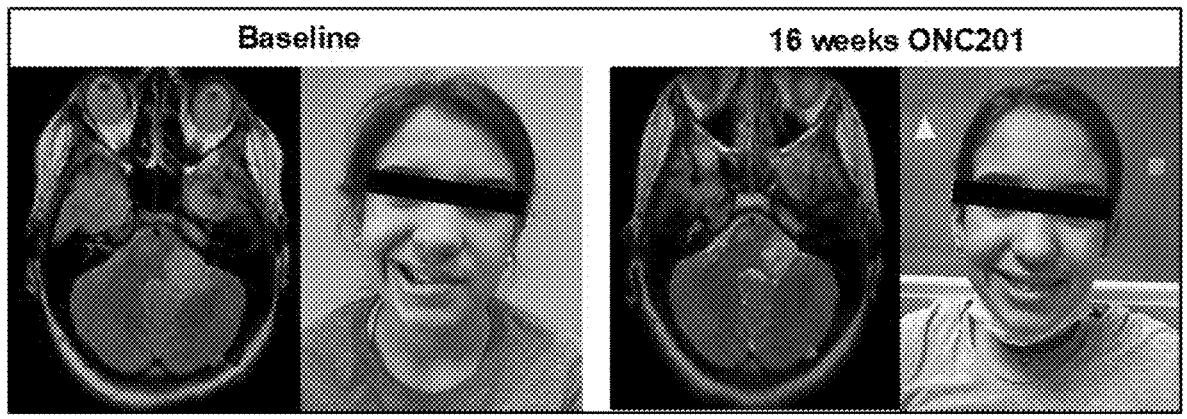
FIG. 21. A 10-year-old girl with H3 K27M diffuse intrinsic pontine glioma has improvement in facial palsy and shrinkage of lesion after 16 doses.

In this Example, a 10 year old girl with H3.3 K27M mutant diffuse intrinsic pontine glioma (DIPG) was treated with 500 mg of ONC201 once weekly. The subject suffered from left facial palsy and decreased hearing in the left ear. Prior therapy included a 6 week course of radation. After 16 weeks of ONC201 therapy, radiographic evaluation of her tumor revealed a significant regression and decreased enhancement of her exophytic cerebral tumor (FIG. 21). She also experienced near-complete resolution of her facial palsy that was associated with a cranial nerve palsy due to her tumor's location. She also tolerates the therapy well and continues on trial.

Example 17: ONC201 Treatment in a 3 Year Old Girl with H3 K27M Mutant DIPG

Figure 22:
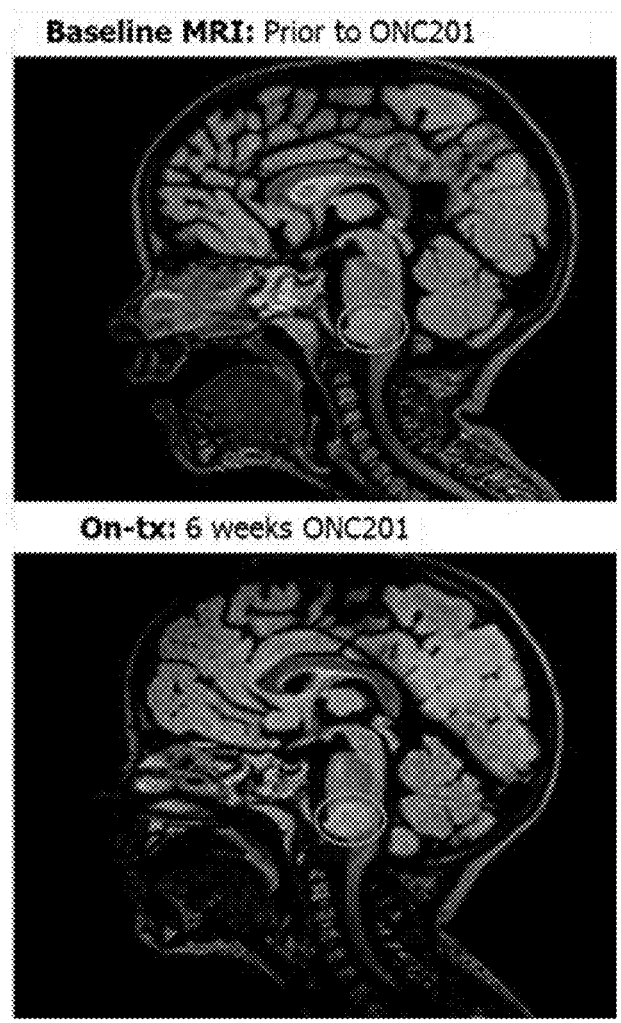
FIG. 22. A 3-year-old girl with H3 K27M diffuse intrinsic pontine glioma. First on-treatment 6 week MRI shows stable tumor lesion.

In this Example, a 3 year old girl with H3.3 K27M mutant diffuse intrinsic pontine glioma (DIPG) was treated with 125 mg of ONC201 once weekly. The subject suffered from right sixth nerve palsy and left arm and hand weakness. Prior therapy included a 6 week course of radation. After 6 weeks of ONC201 therapy, radiographic evaluation of her tumor revealed a stable tumor lesion (FIG. 22). She also experienced a complete resolution of her inability to use her left arm and hand that was associated with a cranial nerve palsy due to her tumor's location. She is fully ambulatory and also tolerates the therapy well and continues on trial.

Figure 23:
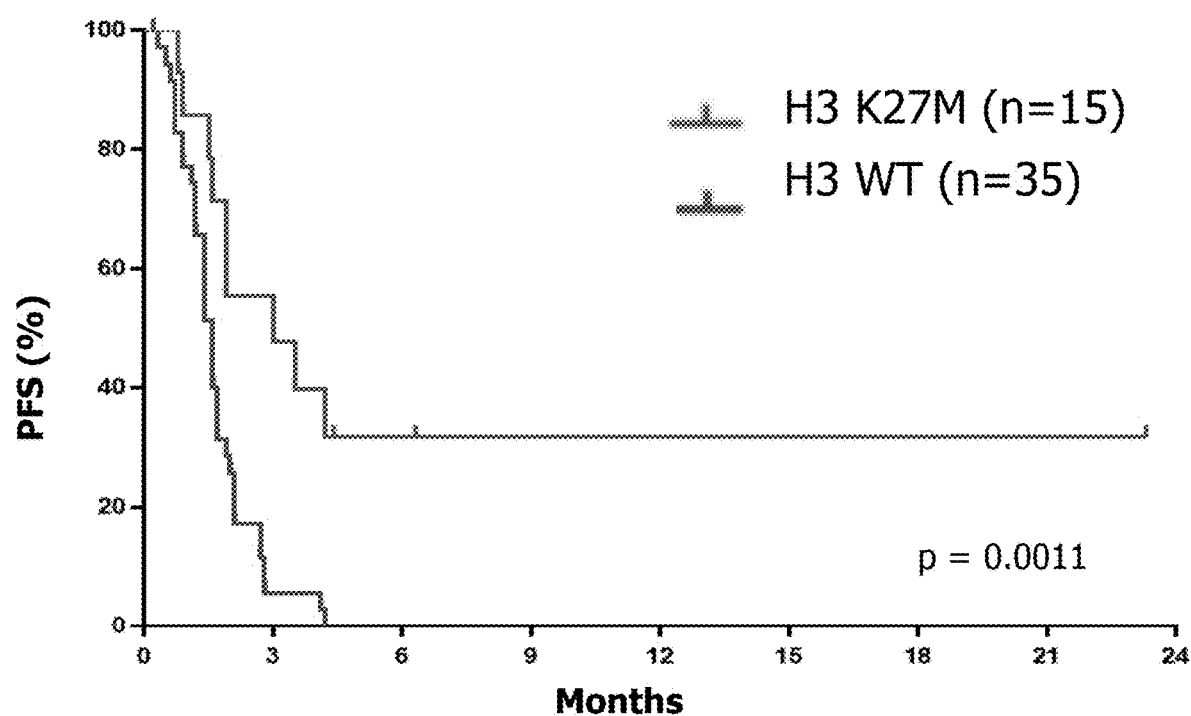
FIG. 23. Progression-free survival of patients with recurrent high grade glioma present at baseline by MRI before initiating ONC201 therapy. The cohort is divided into two groups: one with known H3 K27M mutation (red curve) and the other with wild-type or unknown H3 status (blue curve).

High grade gliomas with the H3 K27M mutation have significantly inferior clinical outcomes relative to patients who do not have the mutation. In one study of thirty-nine pediatric diffuse intrinsic pontine gliomas, DIPG patients carrying the K27M-H3.3 mutation (n=30) have worse overall survival compared to patients wild-type (n=9) for this histone (Khoung-Quang et al., *Acta Neuropathol* (2012) 124:439). Notably, all long-term survivors were H3.3 wild type. Surprisingly, ONC201 treatment confers superior progression-free survival (PFS) in H3 K27M patients. Progression-free survival (PFS) with ONC201 treatment was determined for fifty patients with recurrent high grade glioma present at baseline by MRI before initiating ONC201 therapy (FIG. 23). The cohort is divided into two groups: one with known H3 K27M mutation (n=15) and the other with wild-type or unknown H3 status (n=35). Notably, all long-term progression-free patients treated with ONC201 were H3 K27M patients.

Example 18: Clinical Evaluation of the Imipridone ONC201 in Recurrent Glioblastoma: Predictive and Pharmacodynamic Biomarker Analyses The imipridone ONC201 is the first selective antagonist of the G protein-coupled receptor DRD2 for clinical oncology. ONC201 induces p53-independent apoptosis in newly diagnosed and recurrent glioblastoma in vitro, ex vivo, and in vivo. A Phase II clinical trial was performed that enrolled an initial cohort of 17 patients with recurrent, bevacizumab-naïve, IDH1/2 WT glioblastoma who received 625 mg ONC201 every three weeks. One patient continues to have a durable objective response that has deepened over time, exhibiting an 92% regression by 92% after 15 months of therapy. Another patient remains disease-free 14 months after enrolling on this trial following a re-resection. Median OS was 41.6 weeks with an OS12 of 35%. No drug-related SAEs or treatment discontinuation due to toxicity occurred. Plasma PK at 2 hours post-dose was 2.6 µg/mL and serum prolactin induction was observed as a surrogate marker of target engagement. In addition to cytotoxic effects in tumor cells, DRD2 antagonism can induce the activation of NK and other immune cells. Immune effector levels in the serum correlated with the kinetics of the objective response. Preclinical studies have identified a $DRD2^+DRD5^-$ tumor biomarker signature that is predictive of innate sensitivity to ONC201. Among the 15 available archival tumor tissue specimens, all had expression of DRD2 and 8/17 patients had low expression of DRD5. Patients with PFS>5 month had no detectable expression of DRD5 unlike those with PFS<5 months. In addition, 4/8 $DRD2^+DRD5^-$ and 0/7 $DRD2^+DRD5^+$ patients still alive with a median follow-up of 47.4 weeks. In summary, ONC201 is a well tolerated therapy with potential anti-glioblastoma activity that may be associated with a predictive biomarker signature and immune activation.

Example 19: ONC201 is Active in Glioblastoma with DRD2 Pathway Dysregulation

Figure 2:
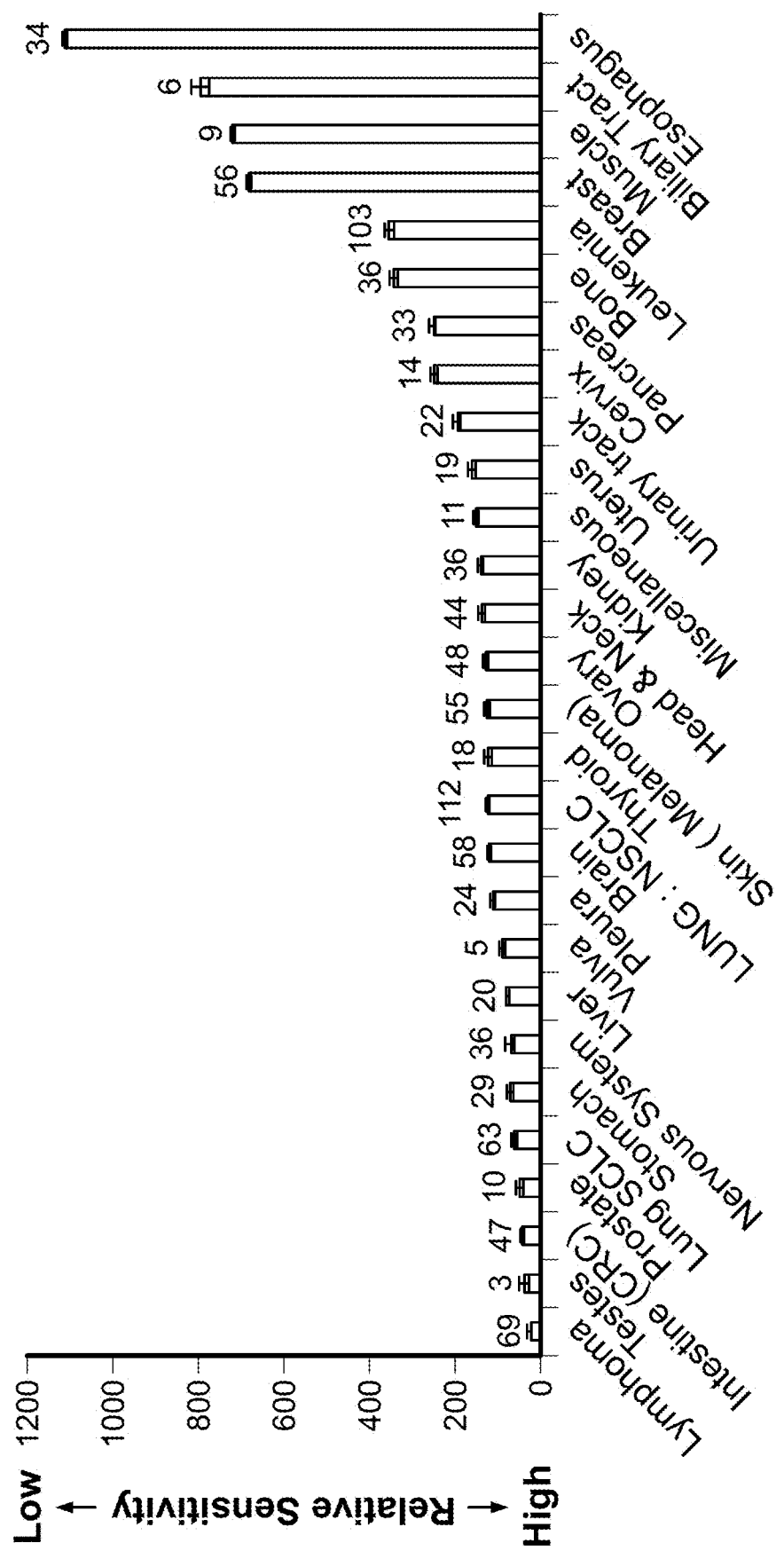
FIG. 2. Tumor type sensitivity of the Genomic of Drug Sensitivity in Cancer program (GDSC) cell line collection. The average sensitivity was determined by average estimated $IC_{50}$ values from cell viability assays conducted at 72 hours post-treatment. Numbers above the bar indicates indicate the number of cell lines per tumor type.

ONC201, an imipridone that is a selective antagonist of the G protein-coupled receptors dopamine receptor D2 (DRD2) and D3 (DRD3), has exhibited tumor shrinkage and an exceptional safety profile in a phase II recurrent glioblastoma clinical trial. In vitro and in vivo studies have demonstrated single agent ONC201 efficacy in glioblastoma models (Allen et al., *Science translational medicine* 5, 171ra117-171ra117 (2013)). In vitro efficacy profiling of ONC201 in the Genomic of Drug Sensitivity in Cancer (GDSC) collection of cell lines confirmed broad anti-cancer efficacy with high sensitivity in human brain cancer cell lines (FIG. 2). DRD2 is overexpressed in glioblastoma and DRD2 antagonism induces tumor cell apoptosis via the same signaling pathways that respond to ONC201. Investigation of The Cancer Genome Atlas (TCGA) revealed that DRD2 is highly expressed in glioblastoma relative to other dopamine receptor family members and that genetic aberrations were rare. High expression of DRD2 occurred in primary, rather than secondary, glioblastoma and was associated with a poor prognosis. Immunohistochemistry analyses of tissue microarrays revealed DRD2 overexpression in glioblastoma relative to normal brain. A linear correlation between DRD2 mRNA and ONC201 $GI_{50}$ was observed among glioblastoma cell lines in the NCI60 panel. A significant induction of serum prolactin, a surrogate biomarker of target engagement, was detected in ONC201-treated glioblastoma patients. Interestingly, expression of DRD5, a D1-like dopamine receptor that counteracts DRD2 signaling, was significantly inversely correlated with ONC201 potency in the NCI60 and GDSC datasets (P<0.05). A missense DRD5 mutation was also identified in cancer cells with acquired resistance to ONC201. Resistance could be recapitulated with overexpression of the mutant DRD5 gene or, to a lesser extent, with the wild-type gene. In conclusion, the DRD2 pathway is a therapeutic target that is dysregulated in glioblastoma and contains biomarkers of tumor sensitivity to ONC201.

Example 20: Differentiated Pharmacology of the Imipridone ONC201, the First Selective DRD2/3 Antagonist in Clinical Neuro-Oncology ONC201, founding member of the imipridone class of compounds, has demonstrated evidence of tumor shrinkage along with exceptional safety in recurrent glioblastoma patients. In this Example, a previously unknown binding target of ONC201 was identified and characterized. BANDIT—a machine learning-based drug target identification platform—predicted that ONC201 would bind with high selectivity to the G-protein coupled receptors (GPCRs) dopamine receptor D2 (DRD2) and D3 (DRD3). DRD2 is overexpressed in glioblastoma, controls pro-survival mechanisms, and its antagonism causes pro-apoptotic effects in malignant cells. PATHHUNTER® β-arrestin and cAMP assays determined that ONC201 selectively antagonizes DRD2 and DRD3. Consistent with BANDIT and in contrast to DRD2 blocking antipsychotics, ONC201 did not antagonize other dopamine receptors or other closely related GPCRs with identified endogenous ligands. Schild analyses and radioligand competition assays revealed DRD2 affinities that were consistent with those identified for ONC201 anticancer activity. In accordance with superior selectivity, ONC201 exhibited a wider therapeutic window compared to other antipsychotics. In support of the hypothesis that selectively targeting D2-like receptors yields superior anti-cancer efficacy, combined DRD2/DRD1 inhibition was found to be inferior to DRD2 inhibition alone. ONC201 exhibited a very slow association rate for DRD2 relative to antipsychotics, whereas the dissociation rate was similar to atypical antipsychotics that are better tolerated clinically. Shotgun mutagenesis across 350 amino acids of DRD2 identified 8 residues critical for ONC201-mediated antagonism of DRD2-induced calcium flux. Several residues were not conserved among other dopamine receptors, suggesting a potential role in conferring ONC201 selectivity. Consistent with competitive inhibition, several mutated residues were within the orthosteric binding site (OBS), however, two distal residues were identified outside of the OBS suggesting a secondary binding pocket. In summary, receptor pharmacology of ONC201, the first selective DRD2/3 antagonist in clinical neuro-oncology, may explain its unique selectivity, safety, and anti-cancer activity in clinical trials.

Example 21: Imipridone Family Member ONC206 Suppresses Glioma Stem Cell Maintenance Imipridones selectively target G protein-coupled receptors (GPCRs) that control critical signaling pathways in various cancer cells. Aberrant GPCR overexpression has been implicated in tumorigenesis. ONC201, a first generation imipridone that directly antagonizes dopamine receptor D2 (DRD2), continues to be evaluated in clinical trials for advanced cancers.

METHODS & RESULTS: Here, ONC206, an ONC201 analog that shares the same imipridone core chemical structure and selective DRD2 antagonism, potently inhibits patient-derived glioma stem cell (GSC) populations. In silico analysis of a glioma patient database led to investigation of DRD2 signaling in glioma; alteration of DRD2 mRNA expression was directly connected to global gene expression change in the glioma patient database. CellTiter-Glo cell viability assay showed that exposure to ONC206 in a dose dependent manner preferentially eliminated GSCs, compared to differentiated glioma cells. Protein array of stem cell markers revealed ONC206 treatment down-regulated protein expression of oncogenic stem cell markers in the GSCs. Further, in vitro limiting dilution assay and sphere formation analysis showed that ONC206 prevented tumor sphere formation and tumor growth. These observations indicate that ONC206 exhibits promising anti-glioma activity and warrant elucidating the downstream effects of antagonizing DRD2 signaling with ONC206 in gliomas.

One skilled in the art will appreciate that changes could be made to the exemplary embodiments shown and described above without departing from the broad inventive concept thereof. It is understood, therefore, that this invention is not limited to the exemplary embodiments shown and described, but it is intended to cover modifications within the spirit and scope of this invention as defined by the claims. For example, specific features of the exemplary embodiments may or may not be part of the claimed invention and features of the disclosed embodiments may be combined. Unless specifically set forth here, the terms "a", "an" and "the" are not limited to one element but instead should be read to mean "at least one."

It is to be understood that the figures and descriptions may have been simplified to focus on elements that are relevant for a clear understanding, while eliminating, for purposes of clarity, other elements that one skilled in the art will appreciate may also comprise a portion of the invention. However, because such elements are well known in the art, and because they do not necessarily facilitate a better understanding of the invention, a description of such elements is not provided herein.

Further, to the extent that a method does not rely on the particular order of steps set forth, the particular order should not be construed as a limitation on the claims. Claims directed to a method should not be limited to performance of the steps in the order written, and one skilled in the art can readily appreciate that they can be varied and still remain within the spirit and scope of this invention.

All references, including publications, patent applications, and patents, cited herein are hereby incorporated by reference to the same extent as if each reference were individually and specifically indicated to be incorporated by reference and were set forth in its entirety here.

What is claimed is:

1. A method of treating cancer in a subject in need thereof, comprising: administering to the subject in need of such treatment a pharmaceutical composition comprising a therapeutically effective amount of a compound having the following structure:

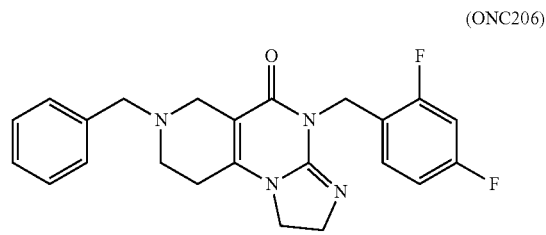 [SMILES: O=C1C2=C(CCN(Cc3ccccc3)C2)N2CCN=C2N1Cc1ccc(F)cc1F]

(ONC206)

or a pharmaceutically acceptable salt thereof, wherein the cancer is a glioma having a histone H3 K27M mutation.

2. The method according to claim 1, wherein the glioma is selected from the group consisting of a diffuse intrinsic pontine glioma, a diffuse midline glioma, a spinal cord glioma, a thalamic glioma, a brainstem glioma, and a cerebellar glioma.

3. The method according to claim 1, wherein the glioma is not a spinal cord tumor.

4. The method according to claim 1, wherein the histone H3 K27M mutation in the glioma is H3.3 K27M or H3.1 K27M.

5. The method according to claim 1, wherein the histone H3 K27M mutation in the glioma is in one or more histone genes selected from H3F3A, H3F3B, HIST1H3A, HIST1H3B, HIST1H3C, HIST1H3D, HIST1H3E, HIST1H3F, HIST1H3G, HIST1H3H, HIST1H3I, or HIST1H3J.

6. The method according to claim 1, wherein in cancerous tissue DRD2 is overexpressed, DRD5 is underexpressed, or both.

7. The method according to claim 1, wherein the subject is a human.

8. The method according to claim 1, wherein the subject is a domesticated pet.

9. The method according to claim 1, wherein the subject is a pediatric subject.

10. A method of treating cancer in a subject in need thereof, comprising: administering to the subject in need of such treatment a pharmaceutical composition comprising a therapeutically effective amount of a compound having the following structure:

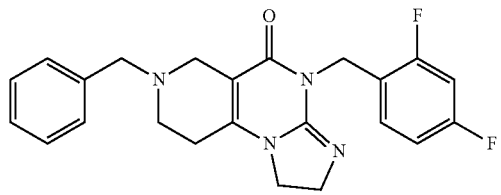

(ONC206)

or a pharmaceutically acceptable salt thereof, wherein the cancer has a histone H3 mutation.

11. The method according to claim 10, wherein the cancer is selected from the group consisting of a central nervous system tumor, a brain tumor, a peripheral nervous system tumor, a pheochromocytoma, a paraganglioma, an adrenal cortical carcinoma, an adrenal tumor, and a neuroendocrine tumor.

12. The method according to claim 10, wherein the cancer is selected from the group consisting of meningioma, ependymoma, glioma, neuroblastoma, and diffuse intrinsic pontine glioma.

13. The method according to claim 10, wherein the cancer is selected from the group consisting of a diffuse midline glioma, a spinal cord glioma, a thalamic glioma, a brainstem glioma, and a cerebellar glioma.

14. The method according to claim 10, wherein the histone H3 mutation is H3.3 K27M or H3.1 K27M.

15. The method according to claim 10, wherein the cancer has a K27M mutation in one or more histone genes selected from H3F3A, H3F3B, HIST1H3A, HIST1H3B, HIST1H3C, HIST1H3D, HIST1H3E, HIST1H3F, HIST1H3G, HIST1H3H, HIST1H3I, or HIST1H3J.

16. The method according to claim 10, wherein DRD2 is overexpressed in cancerous tissue.

17. The method according to claim 10, wherein the subject is a human.

18. The method according to claim 10, wherein the subject is a domesticated pet.

19. The method according to claim 10, wherein the subject is a pediatric subject.

20. A method of treating cancer in a subject in need thereof, comprising: administering to the subject in need of such treatment a pharmaceutical composition comprising a therapeutically effective amount of a compound having the following structure:

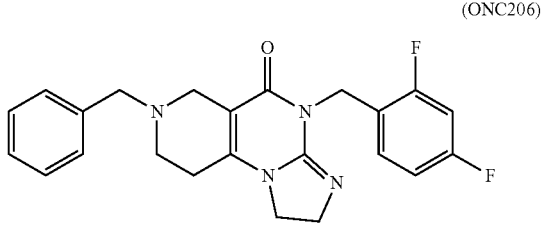 [SMILES: O=C1C2=C(CCN(Cc3ccccc3)C2)N2CCN=C2N1Cc1ccc(F)cc1F]

(ONC206)

or a pharmaceutically acceptable salt thereof, wherein the cancer is a midline glioma.

21. The method according to claim 20, wherein the cancer is selected from the group consisting of a diffuse intrinsic pontine glioma, a diffuse midline glioma, a spinal cord glioma, a thalamic glioma, a brainstem glioma, and a cerebellar glioma.

22. The method according to claim 20, wherein the cancer is not a spinal cord tumor.

23. The method according to claim 20, wherein the cancer has a histone H3 mutation, wherein the histone H3 mutation is H3.3 K27M or H3.1 K27M.

24. The method according to claim 20, wherein the cancer has a histone H3 K27M mutation in one or more histone genes selected from H3F3A, H3F3B, HIST1H3A, HIST1H3B, HIST1H3C, HIST1H3D, HIST1H3E, HIST1H3F, HIST1H3G, HIST1H3H, HIST1H3I, or HIST1H3J.

25. The method according to claim 20, wherein DRD2 is overexpressed in cancerous tissue.

26. The method according to claim 20, wherein the subject is a human.

27. The method according to claim 20, wherein the subject is a domesticated pet.

28. The method according to claim 20, wherein the subject is a pediatric subject.

* * * * *